US008884098B2

(12) United States Patent
Song et al.

(10) Patent No.: US 8,884,098 B2
(45) Date of Patent: Nov. 11, 2014

(54) EXPRESSION CASSETTES FOR REGULATION OF EXPRESSION IN MONOCOTYLEDONOUS PLANTS

(75) Inventors: Hee-Sook Song, Raleigh, NC (US); Marc Morra, Bronx, NY (US); Christian Dammann, Durham, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 1286 days.

(21) Appl. No.: 11/883,996

(22) PCT Filed: Feb. 8, 2006

(86) PCT No.: PCT/EP2006/050781
§ 371 (c)(1),
(2), (4) Date: Aug. 8, 2007

(87) PCT Pub. No.: WO2006/084868
PCT Pub. Date: Aug. 17, 2006

(65) Prior Publication Data
US 2008/0163395 A1   Jul. 3, 2008

Related U.S. Application Data

(60) Provisional application No. 60/651,268, filed on Feb. 9, 2005.

(51) Int. Cl.
*C12N 15/00* (2006.01)
*C12N 15/05* (2006.01)
*C12N 15/63* (2006.01)
*A01H 5/00* (2006.01)
*A01H 15/00* (2006.01)
*C12N 15/82* (2006.01)

(52) U.S. Cl.
CPC ........ *C12N 15/8225* (2013.01); *C12N 15/8237* (2013.01); *C12N 15/8227* (2013.01); *C12N 15/8234* (2013.01); *C12N 15/8216* (2013.01)
USPC ........ 800/278; 800/298; 424/93.2; 435/320.1

(58) Field of Classification Search
None
See application file for complete search history.

(56) References Cited

U.S. PATENT DOCUMENTS

| 5,466,785 A | 11/1995 | de Framond |
| 5,633,363 A | 5/1997 | Colbert et al. |
| 5,837,848 A | 11/1998 | Ely et al. |
| 6,018,099 A | 1/2000 | De Framond |

FOREIGN PATENT DOCUMENTS

| WO | WO 99/43797 | * | 9/1999 | ............. C12N 15/00 |
| WO | WO-99/43797 A2 | | 9/1999 | |
| WO | WO 03/000898 | * | 1/2003 | ............. C12N 15/29 |
| WO | WO-03/000898 A1 | | 1/2003 | |
| WO | WO-03/008540 A2 | | 1/2003 | |
| WO | WO-2004/013169 A1 | | 2/2004 | |
| WO | WO-2004/101741 A2 | | 11/2004 | |

OTHER PUBLICATIONS

Chinese Science Bulletin: Aug. 2004; vol. 49, No. 15, pp. 1602-1606.*
Zhao, H. et al. Chinese Science Bulletin; 2004, vol. 49, No. 15: pp. 1602-1506.*
GenBank Accession GI : 49618874 (Jul. 7, 2004).*
GenBank Accession GI : 55296124 (Nov. 3, 2004).*
Christensen, A.H., et al, "Ubiquitin Promoter-based Vectors for High-level Expression of Selectable and/or Screenable Marker Genes in Monocotyledonous Plants" Transgenic Research, vol. 5 (1996), pp. 213-218.
Chen, C., et al., "Cell-Specific and Conditional Expression of Caffeoyl-Coenzyme A-3-O-Methyltransferase in Poplar", Plant Physiology, vol. 123, (2000), pp. 853-867.
Grimmig, B., et al., "Structure of the Parsley Caffeoyl-CoA O-methyltransferase Gene, Harbouring a Novel Elicitor Responsive cis-Acting Element", Plant Molecular Biology, vol. 33, (1997), pp. 323-341.
Lawton, M.A., et al., "Transcriptional Activation of Plant Defense Genes by Fungal Elicitor, Wounding, and Infection", Molecular and Cellular Biology, vol. 7, No. 1, (1987), pp. 335-341.
Menossi, M., et al., "Analysis of Regulatory Elements of the Promoter and the 3' Untranslated Region of the Maize *Hrgp* Gene Coding for a Cell Wall Protein", Plant Cell Reports, vol. 21, (2003), pp. 916-923.
Odell, J.T., et al., "Identification of DNA Sequences Required for Activity of the Cauliflower Mosaic Virus 35S Promoter", Nature, vol. 313, (1985), pp. 810-812.
Wang, Y., et al., "Characterization of *cis*-Acting Elements Regulating Transcription from the Promoter of a Constitutively Active Rice Actin Gene", Molecular and Cellular Biology, vol. 12, No. 8, (1992), pp. 3399-3406.
"*Oryza sativa* (japonica cultivar-group) genomic DNA, chromosome 6, BAC clone: OSJNBa0015114", Database EMBL Accession No. AP002536, Jul. 1, 2000.
Zhao, H., et al., "Characterization of Three Rice *CCoAOMT* Genes", Chinese Science Bulletin, vol. 49, No. 15, (2004), pp. 1602-1606.
"OGOAH05TH ZM_0.7_1.5_KB *Zea mays* genomic clone ZMMBMa0337B10, genomic survey sequence", Database EBI Accession No. CC626440, Jun. 20, 2003.
European Examination Report for Application No. 09 176 097.5, dated Oct. 10, 2011.

* cited by examiner

*Primary Examiner* — Russell Kallis
*Assistant Examiner* — Jeffrey Bolland
(74) *Attorney, Agent, or Firm* — Drinker Biddle & Reath LLP

(57) ABSTRACT

The present invention relates to expression cassettes comprising at least one transcription regulating nucleotide sequence obtainable from the group of genes of monocotyle-donous plants consisting of caffeoyl-CoA-O-methyltransferase genes, C8,7-sterol isomerase genes, hydroxyproline-rich glycoprotein (HRGP) genes, lactate dehydrogenase genes, and chloroplast protein 12 like genes. More preferably the transcription regulating sequences are obtainable from *Zea mays* or *Oryza sativa*. The transcription regulating sequences are especially useful for root/kernel-preferential, leaf/endosperm-preferential, root/silk/kernel-preferential, or constitutive expression.

13 Claims, 13 Drawing Sheets

```
        +    +   ++
1)   MKKAT SLS---ELGFD AGDASSGFFRPVSGDS-STPTSQ-HHRRRLTKVS
2)   MKKAS SLS---ELGFD AEGASSGFFRPVADGG-STPTS---HRRRLTKIS
3)   MHKAS SLS---ELGFD AGGASSGFFRPVADGCPATPTSSAVPHRRLTKIS
4)   MKKAS SLS---ELGFD ADGPS--FFRHLTLTDGDDGTLP---RRRLIKIS
5)   MEKNASTSSLKDLGPSGLDLTSAFFKPIHNSDPSLPSN------RRTKVS
6)   MEKNASTSSLKDLGPSGLDLTSAFFKPIHNSDPSLPSN------RRTKVS
7)   MQNSSSSS---SLGPGGLDLTQAFFKSISNAAPPSPTK------RHTKIS
8)   MSSSS------PLSLDGLDLNQVFFKSISNADPPSQTN------HHTKIS
         :* *    *. ... ** : :        :      : *:*
         +
1)   VIGAGNVGM AIAQTILTRDLADEIALVDAVPDKLRGEMLDLQHAAAFLPR
2)   VIGAGNVGM AIAQTILTRDMADEIALVDAVPDKLRGEMLDLQHAAAFLPR
3)   VIGAGNVGM AIAQTILTQNLADEIALVDALPDKLRGEALDLQHAAAFLPR
4)   VIGAGNVGM AIAQTILTQDLADEIVLIDAVADKVRGEMLDLQHAAAFLPR
5)   VVGVGNVGMAIAQTILTQDLADEIALVDAKPDKLRGEMLDLQHAAAFLPR
6)   VVGVGNVGMAIAQTILTQDLADEIALVDAKPDKLRGEMLDLQHAAAFLPR
7)   VIGVGNVGMAIAQTILTQDLVDELALVDAKSDKLRGEMLDLQHAAAFLPR
8)   VIGVGNVGMAIAQTILTQDLVDELALVDNSDKLRGEMLDLQHAAAFLPR
     *:*.************:::.**:.*:*. .**:*** ************
                             +                +
1)   TRLVSGTDMSVTRGSDL VIVTAGARQ IQGETRLDLLQRN VALFRKI VPPL
2)   VRLVSDTDLAVTRGSDL AIVTAGARQ IPGESRLNLLQRN VALFRKI VPAL
3)   VR-ISGTDAAVTKNSDL VIVTAGARQ IPGETRLNLLQRN VALYRKI VPPV
4)   VNIVSGTEVSLTRSSDL VIVTAGARQ IPGETRLNLLQRN VSLFRKI VPAA
5)   TKITASVDYEVTAGSDLCIVTAGARQNPGESRLNLLQRNVALFRHIIPPL
6)   TKITASVDYEVTAGSDLCIVTAGARQNPGESRLNLLQRNVALFRHIIPPL
7)   TKIHASIDYSVTAGSDLCIVTAGARQNPGESRLNLLQRNMALFRSIIPPL
8)   TKIVASVDYTVTAGSDLCIVTAGARQNPGESRLNLLQRNLAMYKSIVPEL
     ..  :.  : :.***  ******* **:**:*****::::: *:*
                                    ++
1)   AEQSHDALLLVVSNPVDVLTYVAWK LSGFPAS RVIGSGTNLDS SRFRI
2)   AEHSPEALLLIVSNPVDVLTYVAWK LSGFPAS RVIGSGTNLDS SRFRI
3)   AEHSPDALLLVVSNPVDVLTYVAWK LSGFPAS RVIGSGTNLDS SRFRI
4)   AEASPESVLVIVSNPVDVLTYVAWKLSGFPASRVIGSGTNLDSSRFRI LL
5)   AKASPDSILIVVSNPVDVLTYVAWKLSGFPNRVLGSGTNLDSSRFRFLI
6)   AKASPDSILIIVSNPVDVLTYVAWKLSGFPNRVLGSGTNLDSSRFRFLI
7)   VKYSPETTLLVVSNPVDVLTYVAWKLSGFPANRVIGSGTNLDSSRFRFLI
8)   VKYSPECILLIVSNPVDVLTYVAWK-SGFPNRVIGSGTNLDSSRFRFLI
     + .: *  :   *::.*************  ****  + **:*************:
1)   AEHL DVNAQD VQAYMVGE HGDSSVAVWSSVSVAGMPVLKSLQESHRC---
2)   AEHL QVNAQD VQAYMVGE HGDSSVAIWSSMSVAGMPVLKSLRESHQS---
3)   AEHL DVNAQD VQAYMVGE HGDSSVAIWSSISVGGMPAFKSLRDSHRS---
4)   AEHLEVSAQDVQAYMVGEHGDSSVALWSSISVGGMPVLAHLQKNHRSAAT
5)   ADHLDVNAQDVQAFIVGEHGDSSVALWSSISVGGIPVLSFLEKNQIA---
6)   ADHLDVNAQDVQAFIVGEHGDSSVALWSSISVGGIPVLSFLEKNQIA---
7)   ADHLDVNAQDVQAYIVGEHGDSSVALWSGISVGGVPVLSFLERQQIA---
8)   ADHLDVNAQDVQAYIVGEHGDSSVALWSSISVGGIPVLSFLERQQIA---
     *:**:*.******::*************:**.:**.*:  *. .: .
```

Fig. 10-A

```
            + ++ +                        +
1)  ---FDEEALEGIRRAVVDSAYEVISLKGYTSWAIGYSVASLAASLLRDQR
2)  ---FDEEALEGIRRAVVDSAYEVISLKGYTSWAIGYSVASLAASLLRDQH
3)  ---FDEAALEGIRRAVVGGAYEVIGLKGYTSWAIGYSVASLAASLLRDQR
4)  AKKFDEAALEGIRRAVVGSAYEVIKLKGYTSWAIGYSVASIAWSLLRDQR
5)  ---YEKQTLEDIHQAVVGSAYEVIGLKGYTSWAIGYSVANLARTILRDQR
6)  ---YEKQTLEDIHQAVVGSAYEVIGLKGYTSWAIGYSVANLARTILRDQR
7)  ---LEKETLEKIHQEVVHSAYEVISLKGYTSWAIGYSVANLARTILRDQR
8)  ---FEKDTLEKIHKQVVQSAYEVINLKGYTSWAIGYSVANLAFSIIRDQR
         ::  :** *:: ** .***** **************.:* :::***:

1)  RIHPVSVLARG-FHGIPDGTTSSSACPPRRPRR-RPGRR-EMELTEEEAK
2)  RIHPVSVLASG-FHGIPQDHEVFLSLPARLGRAGVLGVA-EMELTEEEAR
3)  RVHPVSVLASG-FHGISDGHEVFLSLPARLGRGGILGVA-EMDLTEAEAA
4)  RIHPVSVLAKGLVRGVPADRELFLSLPARLGRAGVLGVAAELVLTDEEER
5)  KIHPVTVLARG-FYGVDGG-DVFLSLPALLGRNGVVAVT-NVHMTDEEAE
6)  KIHPVTVLARG-FYGVDGG-DVFLSLPALLGRNGVVAVT-NVHMTDEEAE
7)  RIHPVSVLAKG-FYGIDGG-DVFLSLPAQLGRSGVLGVT-NVHLTDEEIE
8)  RIHPVSILVKG-FYGIDGG-DVFLSLPAQLGRSGVLGVT-NVHLTDEEIQ
    ::***::*. * . *:  .      : *.   *   .  :: :*: *

1)  RLRRSAKTIWENCQLLGL
2)  RLRRSAKTLWENCQLLDL
3)  QLRRSAKTLWENCQLLDL
4)  RLRISAETLWGYCHALGL
5)  KLQKSAKTILEMQSQLGL
6)  KLQKSAKTILEMQSQLGL
7)  QLRNSAKTILEVQSQLGI
8)  QLRNSAETILEVQNQLGI
    :*: **:*:       *.:
```

Fig. 10-B

```
1)                              -----------------------------M-EELAHPYVPRDLNLPGYV
2)                              -----------------------------M-KELAHPYVPRDLNLPGYV
3)                              -----------------------------M-EELAHPYVPRDLNLPGYV
4)                              -----------------------------MGHPHPHPYAPAELHLPGFV

1)      PISMSMSSIVSIYLGSSLLVVSLVWLLFG---RKKAKLDKLLMCWWTFTG
2)      PISMSMSSIVSIYLGSSLLVVSLVWLLFG---RKKAKLDKLLMCWWTFTG
3)      PISMSMSSIVSIYLGSSLLVVSLVWLLFG---RKKAKLDKLLMCWWTFTG
4)      PLQLSQAQILVPYLATSLFLLLAVWLISGRCSRRLSDTDRWLMCWWAFTG

1)      LTHVILEGYFVFSPEFFKDNTSAYLAEVWKEYSKGDSRYVGRDSAVVSVE
2)      LTHVILEGYFVFSPEFFKDNTSAYLAEVWKEYSKGDSRYVGRDSAVVSVE
3)      LTHVILEGYFVFSPEFFKDNTSAYLAEVWKEYSKGDSRYVGRDSAVVSVE
4)      LTHIIIEGTFVFAPNFFSNQNPSYFDEVWKEYSKGDSRYVARDPATVTVE

1)      GITAVIVGPASLLAIYAIAKEKSYSYVLQLAISVCQLYGCLVYFITAILE
2)      GITAVIVGPASLLAIYAIAKEKSYSYVLQLAISVCQLYGCLVYFITAILE
3)      GITAVIVGPASLLAIYAIAKEKSYSYVLQLAISVCQLYGCVVYFITAILE
4)      GITAVLEGPASLLAVYAIASGKSYSHILQFTVCLGQLYGCLVYFITAYLD

1)      GD--NFATNSFYYYSYYIGANCWWVLIPSLISFRCWKKICAAAAIANNNV
2)      GD--NFATNSFYYYSYYIGANCWWVLIPSLISFRCWKKICAAAAIANNNV
3)      GD--NFATNSFYYYSYYIGANCWWVLIPSLISFRCWKKICAAAAIANNNV
4)      GF--NFWTSPFYFWAYFIGANSSWVVIPTMIAIRSWKKICA--AFQGEKV

1)      ETKTKKKTR
2)      ETKTKKKTR
3)      ETKTKKKTR
4)      KTK------
```

Fig. 11

```
1)    MAENG------------------------------IKHQEVGHKSLLQSDALYQ
2)    MAANAEPQQ---------------------TQPAKHSEVGHKSLLQSDALYQ
3)    MATNGEEQQ-----------------SQAGRHQEVGHKSLLQSDALYQ
4)    MATTATEA----APAQEQQANGNG---EQKTRHSEVGHKSLLKSDDLYQ
5)    MATTATEATKTTAPAQEQQANGNGNG--EQKTRHSEVGHKSLLKSDDLYQ
6)    MATTATEATKTTAPAQEQQANGNGNGNGEQKTRHSEVGHKSLLKSDDLYQ
7)    MAEAASAA----AAATTEQANGSSGG--EQKTRHSEVGHKSLLKSDDLYQ
       **   .                    ++++ +:*.********:** ***

1)    YILETSVYPREPESMKELREVTAKHPWNLMTTSADEGQFLNMLLKLINAK
2)    YILETSVYPREPESMKELREITAKHPWNLMTTSADEGQFLNMLLKLINAK
3)    YILETSVYPREPECMKELREVTAKHPWNIMTTSADEGQFLNMLLKLVNAK
4)    YILDTSVYPREPESMKELREVTAKHPWNLMTTSADEGQFLNMLIKLIGAK
5)    YILDTSVYPREPESMKELREITAKHPWNLMTTSADEGQFLNMLIKLIGAK
6)    YILDTSVYPREPESMKELREITAKHPWNLMTTSADEGQFLNMLIKLIGAK
7)    YILETSVYPREHECMKELREVTANHPWNLMTTSADEGQFLNLLLKLIGAK
       ***:******* *.******:**:****:*************:**::**
                                                +

1)    NTMEIGVYTGYSLLATALAIPDDGKILAMDINRENYEIGLPIIEKAGVAH
2)    NTMEIGVYTGYSLLATALALPDDGKILAMDINRENFEIGLPVIEKAGLAH
3)    NTMEIGVYTGYSLLATALAIPEDGKILAMDINRENYELGLPVIQKAGVAH
4)    KTMEIGVYTGYSLLATALALPEDGTILAMDINRENYELGLPCIEKAGVAH
5)    KTMEIGVYTGYSLLATALALPEDGTILAMDINRENYELGLPCINKAGVGH
6)    KTMEIGVYTGYSLLATALALPEDGTILAMDINRENYELGLPCINKAGVAH
7)    KTMEIGVYTGYSLLATALAIPDDGTILAMDINRENYELGLPSIEKAGVAH
      +:******.**********:*:**.**********:*:*** *:***:.*

1)    KIEFREGPALPVLDQLVEDKKNHGTYDFIFVDADKDNYINYHKRIIDLVK
2)    KIDFREGPALPLLDQLVQDEKNHGTYDFIFVDADKDNYINYHKRLIDLVK
3)    KIDFKEGPALPVLDQMIEDGKCHGSFDFIFVDADKDNYINYHKRLIELVK
4)    KIDFREGPALPVLDDLIAEEKNHGSFDFVFVDADKDNYINYHERLLKLVK
5)    KIDFREGPALPVLDDLVADKEQHGSFDFAFVDADKDNYINYHERLLKLVR
6)    KIDFREGPALPVLDDLVADKEQHGSFDFAFVDADKDNYISYHERLLKLVR
7)    KIDFREGPALPVLDQLVEEEGNHGSFDFVFVDADKDNYINYHERLMKLVK
      **:*:******:**::: :   **::** *********:+**:4:..**:

1)    VGGLIGYDNTLWNGSVVAPPDAPMRKYVRYYRDFVLELNKALAADPRIEI
2)    VGGLIGYDNTLWNGSVVAPADAPLRKYVRYYRDFVLELNKALAVDPRVEI
3)    VGGLIGYDNTLWNGSVVAPPDAPMRKYVRYYRDFVLELNKALAADPRIEI
4)    LGGLIGYDNTLWNGSVVLPDDAPMRKYIRFYRDFVLVLNKALAADDRVEI
5)    PGGLIGYDNTLWNGSVVLPDDAPMRKYIRFYRDFVLALNSALAADDRVEI
6)    PGGLIGYDNTLWNGSVVLPDDAPMRKYIRFYRDFVLALNSALAADDRVEI
7)    VGGLVGYDNTLWNGSVVLPADAPMRKYIRYYRDFVLELNKALAADHRVEI
       ***:*********** * ***:***:*:****** **.***.* :***

1)    CMLPVGDGITLCRRIT
2)    CMLPVGDGITLCRRVS
3)    CMLPVGDGITLCRRIQ
4)    CQLPVGDGVTLCRRVK
5)    CQLPVGDGVTLCRRVK
6)    CQLPVGDGVTLCRRVK
7)    CQLPVGDGITLCRRVK
      + ******:*****.+
```

Fig. 12

EXPRESSION CASSETTES FOR REGULATION OF EXPRESSION IN MONOCOTYLEDONOUS PLANTS

RELATED APPLICATIONS

This application is a national stage application (under 35 U.S.C. 371) of PCT/EP2006/050781 filed Feb. 8, 2006, which claims benefit of U.S. application 60/651,268 filed Feb. 9, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is Revised Sequence Listing 13987 00064 US. The size of the text file is 174 KB, and the text file was created on Apr. 22, 2011.

FIELD OF THE INVENTION

The present invention relates to expression cassettes comprising at least one transcription regulating nucleotide sequence obtainable from the group of genes of monocotyledonous plants consisting of caffeoyl-CoA-O-methyltransferase genes, C8,7-sterol isomerase genes, hydroxyproline-rich glycoprotein (HRGP) genes, lactate dehydrogenase genes, and chloroplast protein 12 like genes. More preferably the transcription regulating sequences are obtainable from Zea mays or Oryza sativa. The transcription regulating sequences are especially useful for root/kernel-preferential, leaf/endosperm-preferential, root/silk/kernel-preferential, or constitutive expression.

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

Constitutive promoters are favored in situations where expression in all (or most) tissues during all (or most) times of the plant development is required. The number of constitutive promoters functional in monocotyledonous plants is limited and include the rice actin 1 (Wang 1992; U.S. Pat. No. 5,641, 876), CaMV 35S (Odell 1985), CaMV 19S (Lawton 1987), and the maize ubiquitin promoters (Christensen 1996). While several constitutive and tissue-specific promoters from dicotyledonous plants are described by sequence (e.g., the promoter from the caffeoyl-CoA-O-methyltransferase gene from parsley (Grimmig 1997), poplar (Chen 1998) and pine (Li 1999)) only a very limited number has been characterized in heterogenous gene expression. In comparison with dicotyledonous promoters, promoters from monocotyledonous plants are still very limited. It is advantageous to have the choice of a variety of different promoters so that the most suitable promoter may be selected for a particular gene, construct, cell, tissue, plant, or environment. Moreover, the increasing interest in cotransforming plants with multiple plant transcription units (PTU) and the potential problems associated with using common regulatory sequences for these purposes merit having a variety of promoter sequences available.

Root-preferential or root-specific promoters are useful for alteration of the function of root tissue, modification of growth rate, improvement of resistance to root preferred pathogens, pests, herbicides or adverse weather conditions, for detoxification of soil as well as for broadening the range of soils or environments in which said plant may grow. Root abundant or root specific gene expression would provide a mechanism according to which morphology and metabolism may be altered to improve the yield and to produce useful proteins in greater amounts. In particular, root specific promoters may be useful for expressing defense-related genes, including those conferring insectical resistance and stress tolerance, e.g. salt, cold or drought tolerance, and genes for altering nutrient uptake. The number of root preferential and root-specific promoters functional in monocotyledonous plants is very limited. These include the MR7 promoter from Zea mays (U.S. Pat. No. 5,837,848), the ZRP2 promoter of Zea mays (U.S. Pat. No. 5,633,363), and the MTL promoter from Zea mays (U.S. Pat. Nos. 5,466,785 and 6,018,099). Many of these examples disclose promoters with expression patterns confined to a limited number of root tissues. Other fail to provide the root specificity needed for expression of selected genes. It is advantageous to have the choice of a variety of different promoters so that the most suitable promoter may be selected for a particular gene, construct, cell, tissue, plant, or environment. Moreover, the increasing interest in cotransforming plants with multiple plant transcription units (PTU) and the potential problems associated with using common regulatory sequences for these purposes merit having a variety of promoter sequences available.

There is, therefore, a great need in the art for the identification of novel sequences that can be used for expression of selected transgenes in the economically most important monocotyledonous plants, especially in rice and maize. It is thus an objective of the present invention to provide new and alternative expression cassettes for expression of transgenes in monocotyledonous plants, more preferably with the opportunity to modulate the tissue specificity of expression

The plasmid comprises an expression construct containing an Os.CCoAMT1 promoter operably linked to Zm.ubiquitin intron, a β-glucuronidase gene (GUS including the potato invertase [PIV]2 intron), and 3' untranslated region and transcriptional termination region of the Os.CCoAMT1. SM cassette is representing a selection marker (ahas) cassette.

Figure 1:
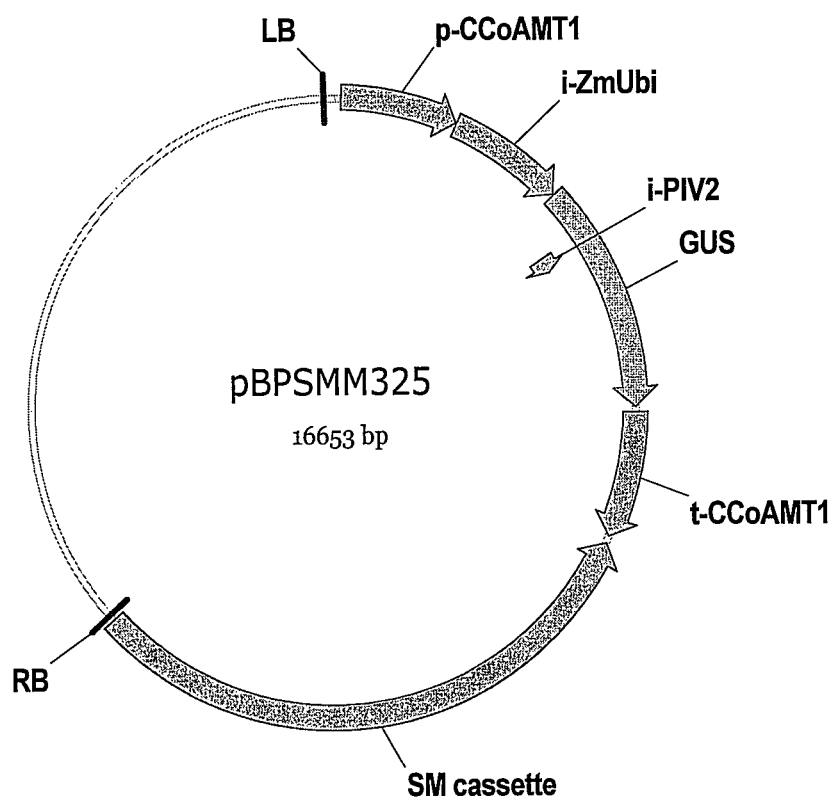
FIG. 1 Map of Os.CCoAMT1 promoter::Zm.ubiquitin intron::GUS (PIV2)::CCoAMT1 terminator chimeric construct (pBPSMM325).
Figure 2:
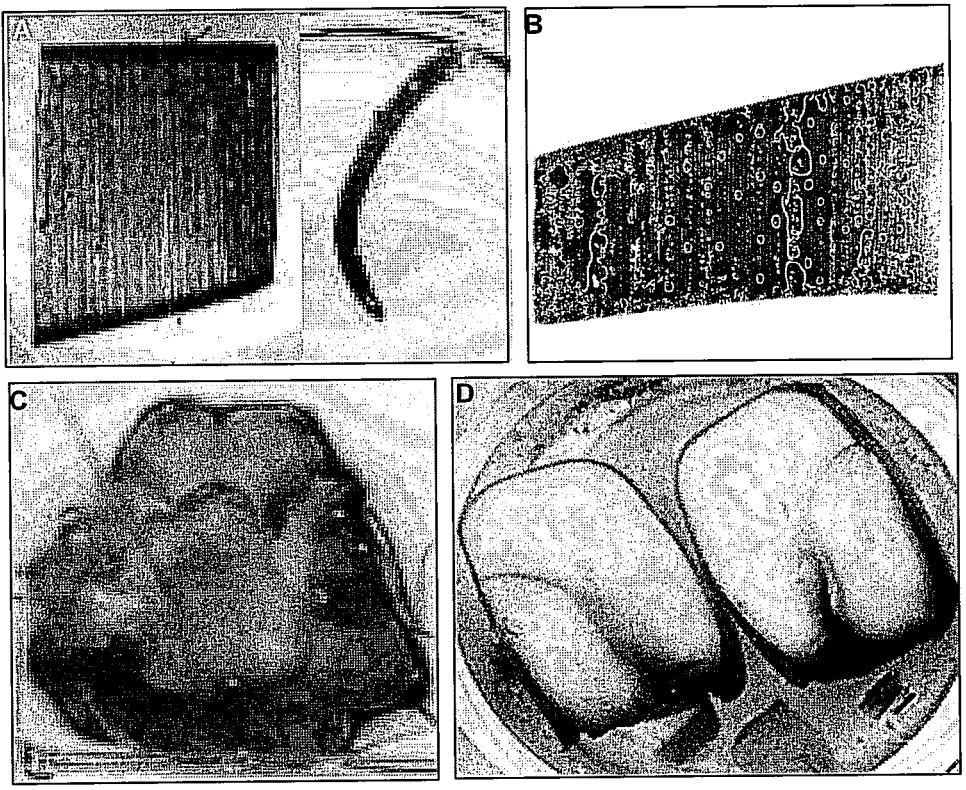
Figure 2:
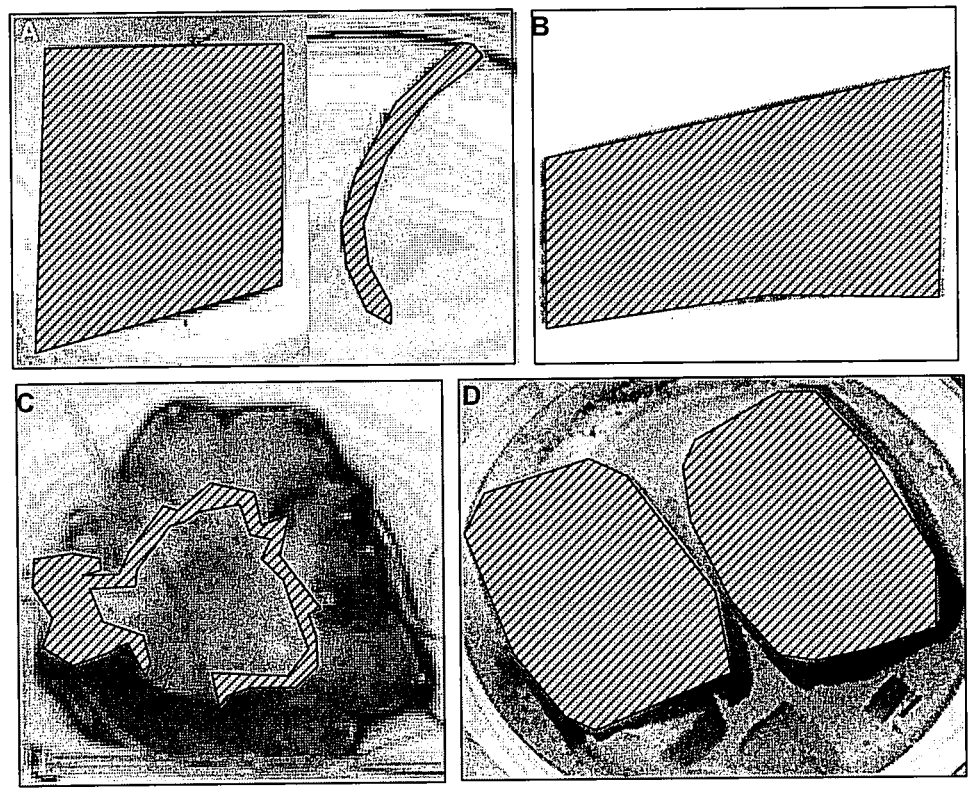

FIG. 2 GUS expression controlled by Oryza sativa (Os) CCoAMT1 promoter construct (pBPSMM325) in maize. The upper panel (I) represents the original photos with the GUS staining, while the lower panel (II) indicates areas distinctly stained blue by overlaid shaded areas.

(A) Leaf+root at the 5 leaf stage
    (B) Leaf at flowering stage
    (C) Kernel (prepollination)
    (D) Kernel 30 DAP
    Pictures represent reproducible expression patterns from 15 $T_1$ single copy lines.

Figure 3:
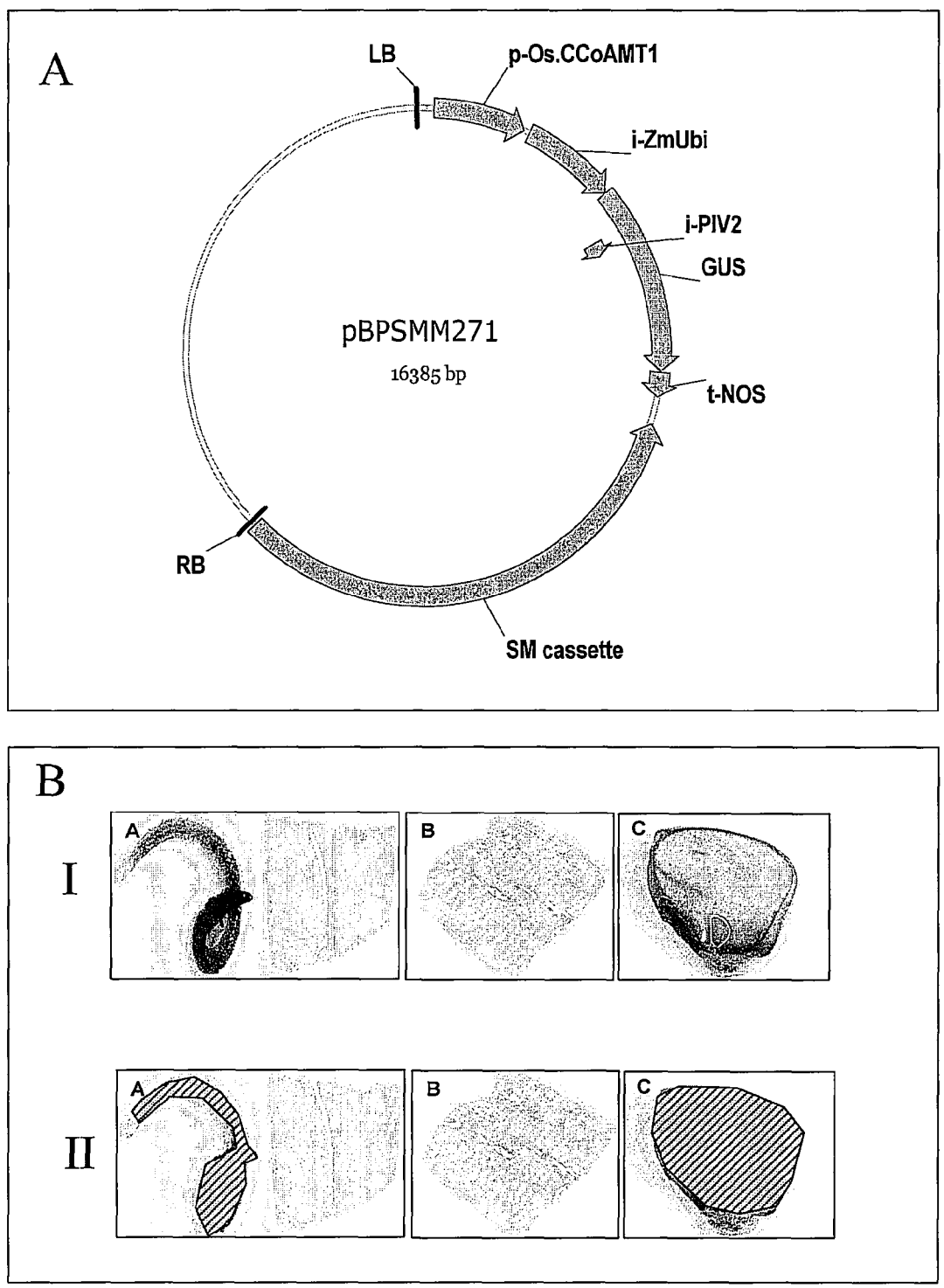

FIG. 3 A: Map of Os.CCoAMT1 promoter::Zm.ubiquitin intron::GUS (PIV2)::NOS terminator fusion construct (PBPSM M271).

The plasmid comprises an expression construct containing an Os.CCoAMT1 promoter operably linked to Zm.ubiquitin intron, a β-glucuronidase gene (GUS including the potato invertase [PIV]2 intron), and nopaline synthase (NOS) terminator. The SM cassette is representing a selection marker (ahas) cassette.

B: GUS expression controlled by Os.CCoAMT1 promoter construct (pBPSMM271) in maize. The upper panel (I) represents the original photos with the GUS staining, while the lower panel (II) indicates areas distinctly stained blue by overlaid shaded areas.

(A) Leaves and roots at the 5 leaf stage
(B) Leaf at the flowering stage
(C) Kernel (30 d after pollination: DAP)

Pictures represent reproducible expression patterns from 15 T₁ single copy lines.

Figure 4:
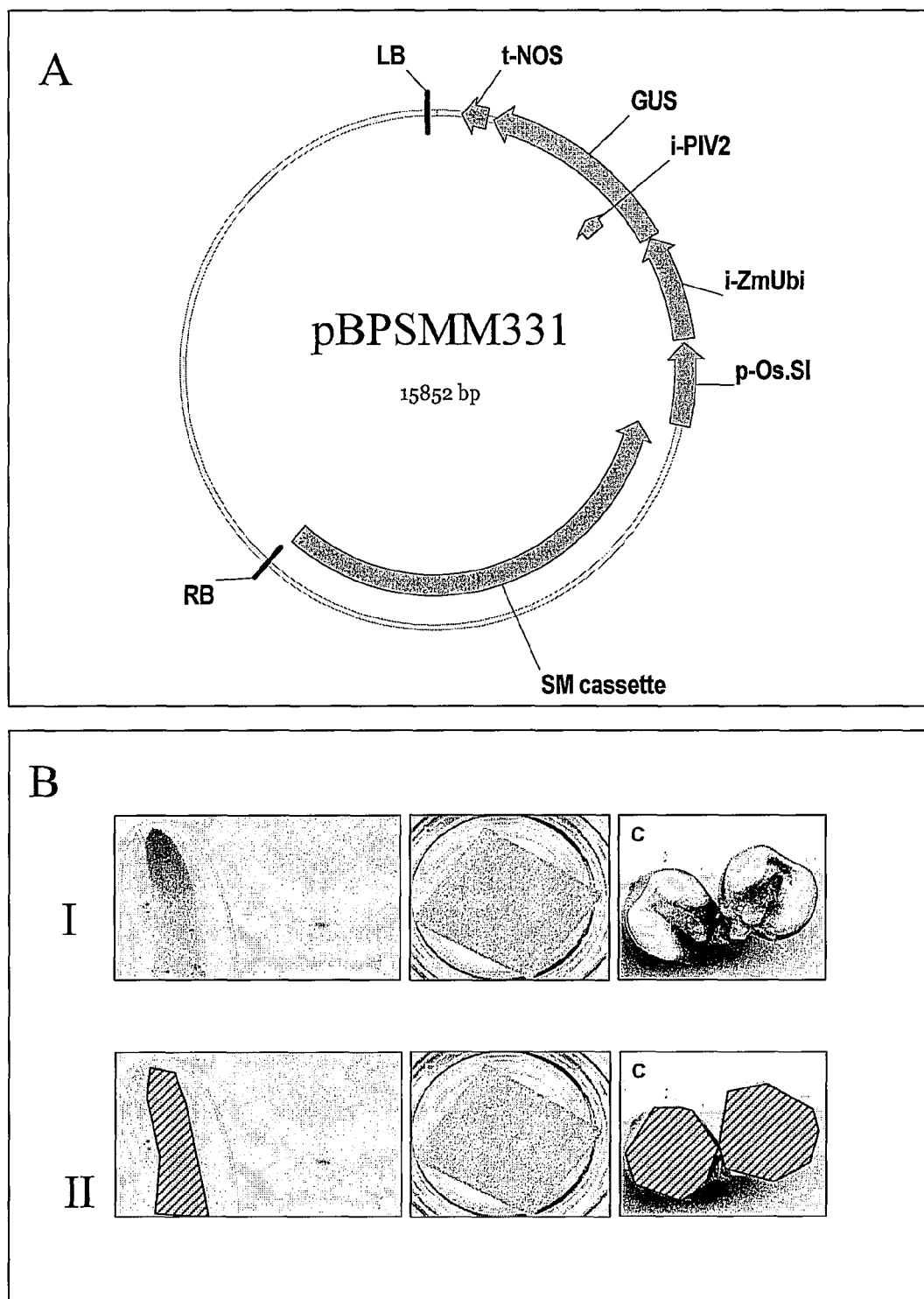

FIG. 4 A: Map of Os.SI::Zm.ubiquitin intron::GUS (PIV2)::NOS terminator fusion construct (pBPSMM331).

The plasmid comprises an expression construct containing an Os.SI promoter operably linked to Zm.ubiquitin intron, a β-glucuronidase gene (GUS including the potato invertase [PIV]2 intron), and NOS terminator. The SM cassette is representing a selection marker cassette.

B: GUS expression controlled by Os.SI promoter construct (pBPSMM331) in maize. The upper panel (I) represents the original photos with the GUS staining, while the lower panel (II) indicates areas distinctly stained blue by overlaid shaded areas.

(A) Leaves and roots at the 5 leaf stage
(B) Leaf at the 5 leaf stage Leaf at the flowering stage
(C) Kernel (30 d after pollination: DAP)

Pictures represent reproducible expression patterns from 15 T₁ single copy lines.

Figure 5:
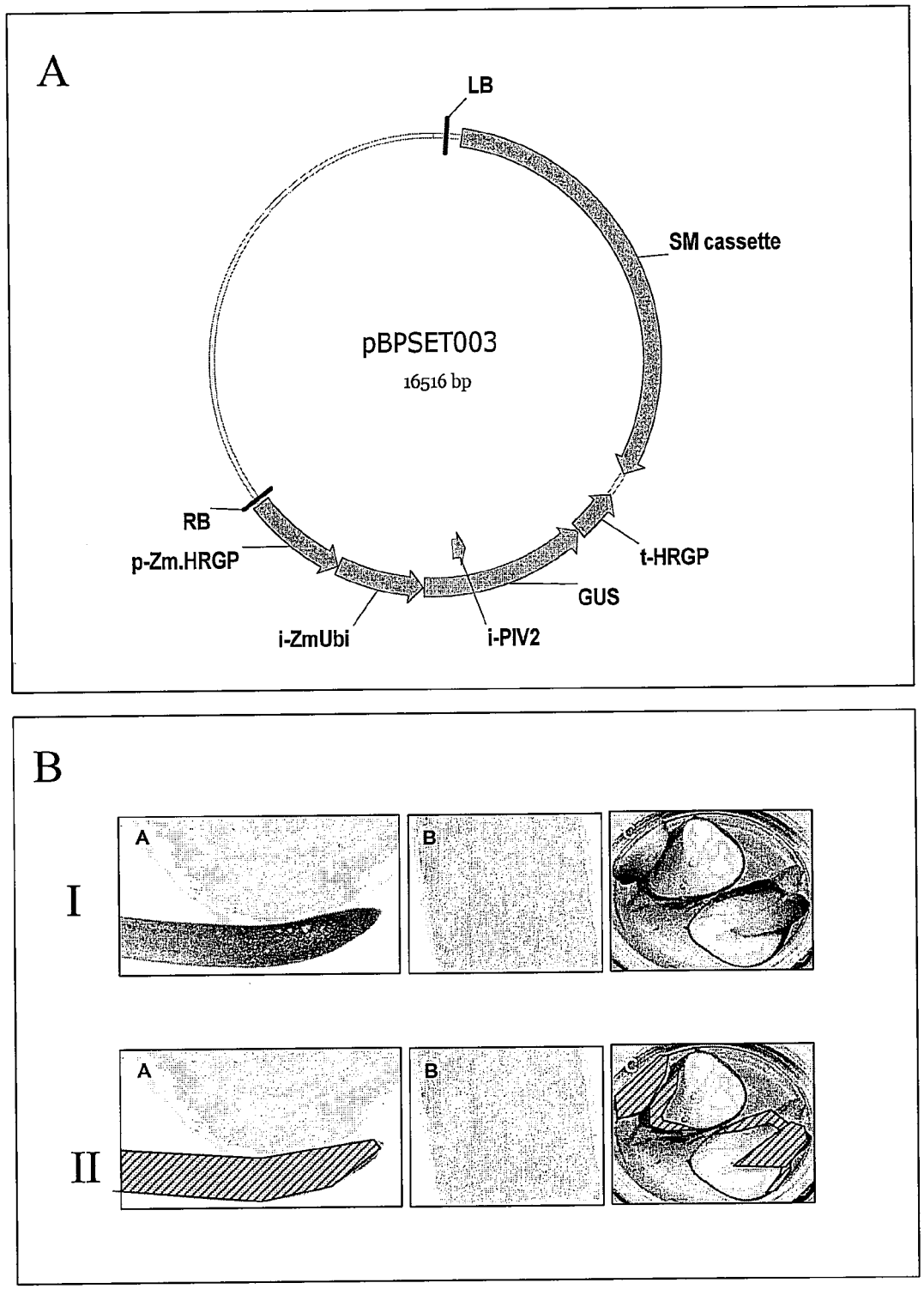

FIG. 5 A: Map of Zm.HRGP::Zm.ubiquitin intron::GUS (PIV2)::Zm.HRGP terminator fusion construct (pBPSET003).

The plasmid comprises an expression construct containing a Zm.HRGP promoter operably linked to Zm.ubiquitin intron, a β-glucuronidase gene (GUS including the potato invertase [PIV]2 intron), and HRGP terminator. The SM cassette is representing a selection marker (ahas) cassette.

B: GUS expression controlled by maize Zm.HRGP promoter construct (pBPSET003) in maize. The upper panel (I) represents the original photos with the GUS staining, while the lower panel (II) indicates areas distinctly stained blue by overlaid shaded areas.

(A) Leaves and roots at the 5 leaf stage
(B) Leaf at the 5 leaf stage Leaf at the flowering stage
(C) Kernel (30 d after pollination: DAP)

Pictures represent reproducible expression patterns from 15 T₁ single copy lines.

Figure 6:
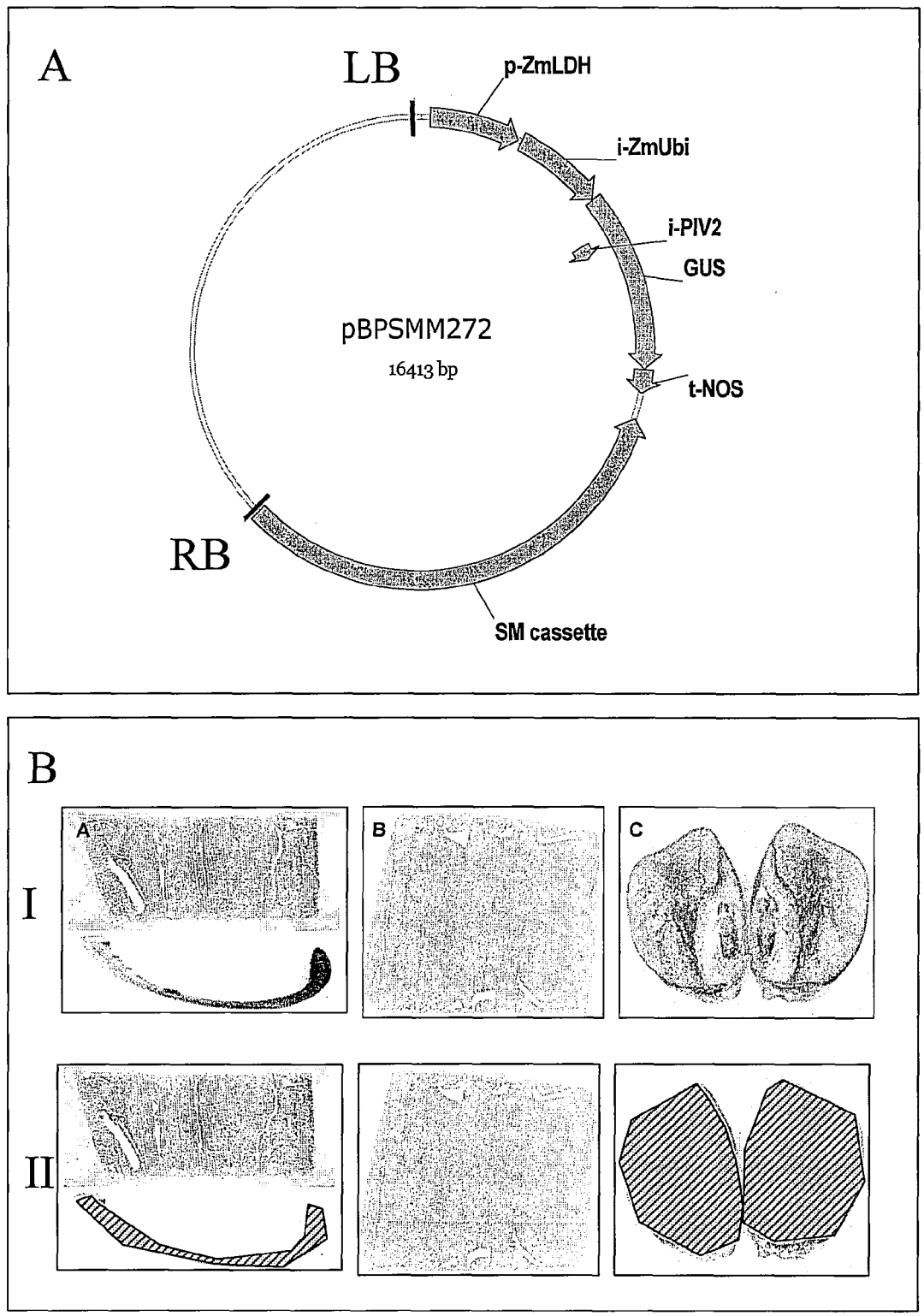

FIG. 6 A: Map of Zm.LDH::Zm.ubiquitin intron::GUS (PIV2)::NOS terminator fusion construct (pBPSMM272).

The plasmid comprises an expression construct containing a Zm.LDH promoter operably linked to Zm.ubiquitin intron, a β-glucuronidase gene (GUS including the potato invertase [PIV]2 intron), and NOS terminator. The SM cassette is representing a selection marker (ahas) cassette.

B: GUS expression controlled by maize Zm.LDH promoter construct (pBPSMM272) in maize. The upper panel (I) represents the original photos with the GUS staining, while the lower panel (II) indicates areas distinctly stained blue by overlaid shaded areas. The transgenic plants containing either pBPSMM272 or pBPSET007 showed the same expression patterns.

(A) Leaves and roots at the 5 leaf stage
(B) Leaf at the 5 leaf stage Leaf at the flowering stage
(C) Kernel (30 d after pollination: DAP)

Pictures represent reproducible expression patterns from 8 T₁ single copy lines.

Figure 7:
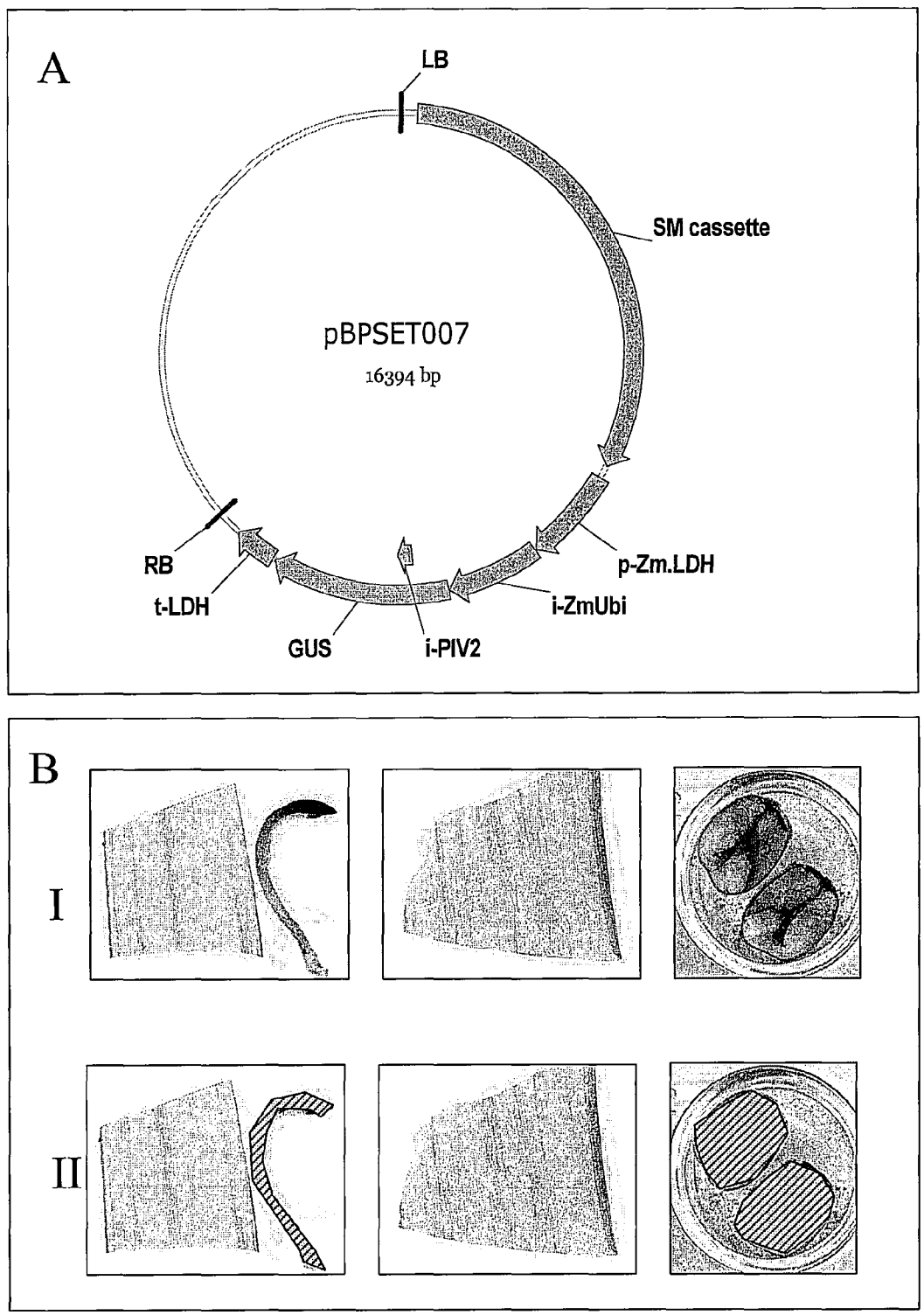

FIG. 7 A: Map of Zm.LDH::Zm.ubiquitin intron::GUS (PIV2)::Zm.LDH terminator fusion construct (pBPSET007).

The plasmid comprises an expression construct containing a Zm.LDH promoter operably linked to Zm.ubiquitin intron, a β-glucuronidase gene (GUS including the potato invertase [PIV]2 intron), and LDH terminator. The SM cassette is representing a selection marker (ahas) cassette.

B: GUS expression controlled by maize Zm.LDH promoter construct (pBPSET007) in maize. The upper panel (I) represents the original photos with the GUS staining, while the lower panel (II) indicates areas distinctly stained blue by overlaid shaded areas.

(A) Leaves and roots at the 5 leaf stage
(B) Leaf at the flowering stage
(C) Kernel (30 d after pollination: DAP)

Pictures represent reproducible expression patterns from 15 T₁ single copy lines.

Figure 8:
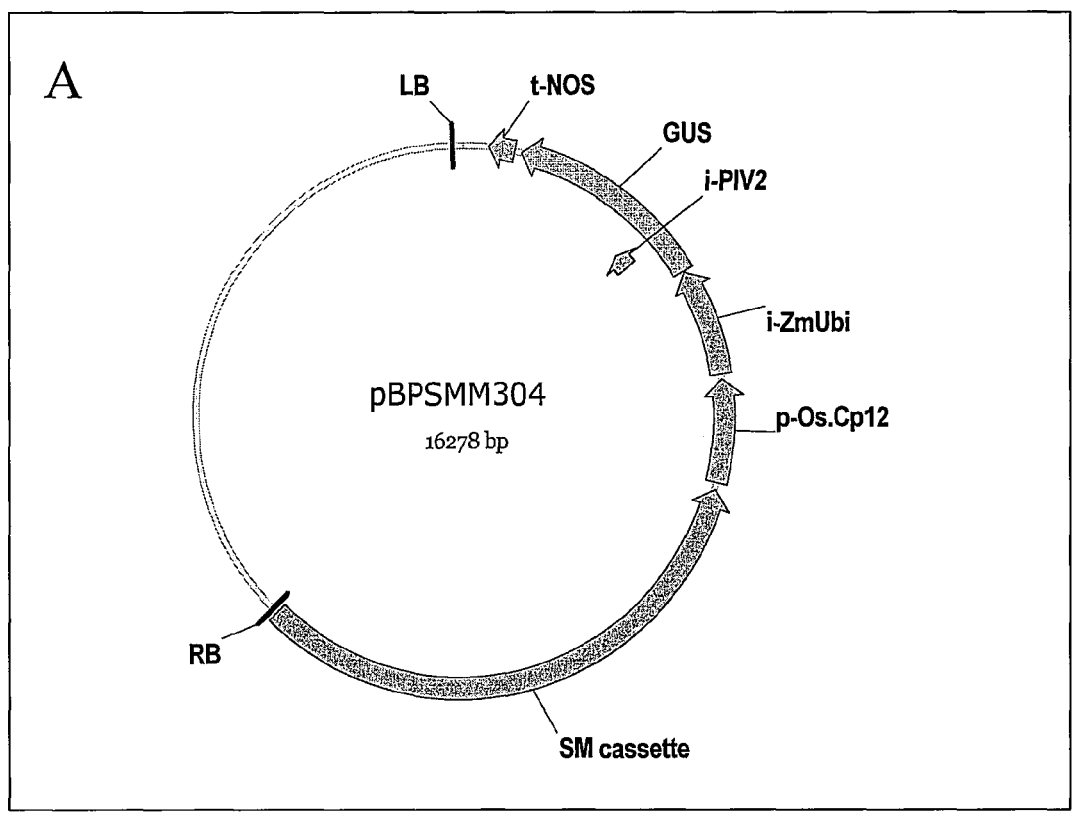
Figure 8:
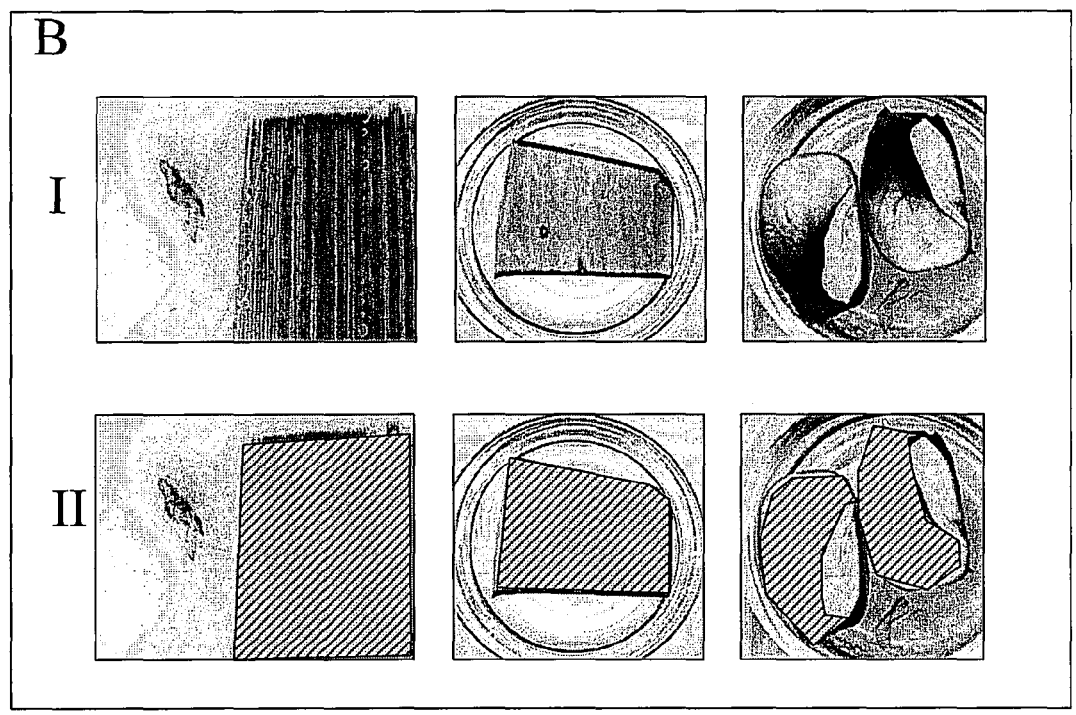

FIG. 8 A: Map of Os.CP12::Zm.ubiquitin intron::GUS (PIV2)::NOS terminator fusion construct (pBPSMM304).

The plasmid comprises an expression construct containing a Os.CP12 promoter operably linked to Zm.ubiquitin intron, a β-glucuronidase gene (GUS including the potato invertase [PIV]2 intron), and NOS terminator. SM cassette is representing a selection marker cassette.

B: GUS expression controlled by maize Os.CP12 promoter construct (pBPSMM304) in maize. The upper panel (I) represents the original photos with the GUS staining, while the lower panel (II) indicates areas distinctly stained blue by overlaid shaded areas.

(A) Leaves and roots at the 5 leaf stage
(B) Leaf at the flowering stage
(C) Kernel (30 d after pollination: DAP)

Pictures represent reproducible expression patterns from 15 T₁ single copy lines.

Figure 9:
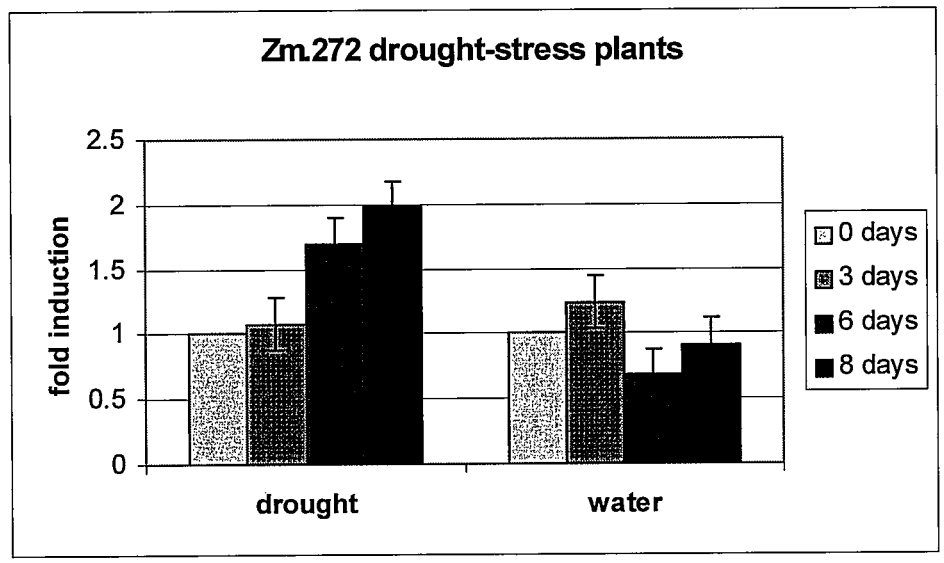

FIG. 9 Drought-stress-induced expression of Zm.LDH promoter construct (pBPSMM272) in maize. Transgenic plants at 5-leaf stage were drought-stressed by withholding water. Samples were taken from leaves at the indicated time points. RNA was isolated from leaf samples and analyzed with quantitative RT-PCR. GUS expression was normalized against an internal control gene in each sample. Results are shown as fold increase of expression levels compared to the 0-timepoint, which is set as 1.

FIG. 10A-B Protein alignment of rice lactate dehydrogenase (LDH) protein with the LDH proteins from maize (1) (SEQ ID NO: 26), rice (2) (SEQ ID NO: 65), barley (3) (SEQ ID NO: 95), rice (4) (SEQ ID NO: 60), Arabidopsis (5, 6) (SEQ ID NO: 96 and SEQ ID NO: 97), tomato (7) (SEQ ID NO: 98), potato (8) (SEQ ID NO: 99).

The sequences motifs distinguishing monocotyledonous LDH proteins from other dicotyledonous LDH proteins are boxed (relevant different amino acids are marked with a "+"). Further such sequences motifs may be readily identified by the person skilled in the art based on the present alignment.

FIG. 11. Protein alignment of rice C8,7 sterol isomerase (SI) protein with the SI proteins from *Arabidopsis* (1-3) (SEQ ID NO: 100, SEQ ID NO: 101, SEQ ID NO: 102) and rice (4) (SEQ ID NO: 10).

FIG. 12. Protein alignment of rice Caffeoyl CoA-O-methyltransferase 1 (CCoAMT1) with the CCoAMT1 proteins from tobacco (1) (SEQ ID NO: 103), eucalyptus (2) (SEQ ID NO: 104), popular (3) (SEQ ID NO: 105), maize (4, 5, 6) (SEQ ID NO: 106, SEQ ID NO: 107, SEQ ID NO: 70) and rice (7) (SEQ ID NO: 5).

SUMMARY OF THE INVENTION

Accordingly, a first embodiment of the invention relates to expression cassettes for regulating expression in monocotyledonous plants comprising
i) at least one transcription regulating nucleotide sequence of a monocotyledonous plant gene, said monocotyledonous plant gene selected from the group of genes consisting of caffeoyl-CoA-O-methyltransferase genes, C8,7-sterol isomerase genes, hydroxyproline-rich glycoprotein (HRGP) genes, lactate dehydrogenase genes, and chloroplast protein like 12 genes, and functionally linked thereto
ii) at least one nucleic acid sequence which is heterologous in relation to said transcription regulating sequence.

Preferably, the transcription regulating nucleotide sequence is obtainable from monocotyledonous plant genomic DNA from a gene encoding a polypeptide which
a1) comprises at least one sequence motif of a monocotyledonous plant lactate dehydrogenase protein selected from the group consisting of the amino acid sequences

| | | |
|---|---|---|
| i) | SLSELGFDA, | (SEQ ID NO: 76) |
| ii) | VIGAGNVGMA, | (SEQ ID NO: 77) |
| iii) | IVTAGARQI, | (SEQ ID NO: 78) |
| iv) | L(F/Y)RKIVP, | (SEQ ID NO: 79) |
| v) | GFPASRV, | (SEQ ID NO: 80) |
| vi) | RF(L/I)AEHL, | (SEQ ID NO: 81) |
| vii) | QAYMVGEH, | (SEQ ID NO: 82) |
| viii) and | ALEGIRRAV, | (SEQ ID NO: 83) |
| ix) or | GYSVAS(L/I)A, | (SEQ ID NO: 84) | b1) is encoding a lactate dehydrogenase protein from a monocotyledonous plant having an amino acid sequence identity of at least 90% to a polypeptide selected from the group described by SEQ ID NO: 26, 60 and 65, or
a2) comprises at least one sequence motif of a monocotyledonous plant caffeoyl-CaA-O-methyltransferase protein selected from the group consisting of the amino acid sequences

| | | |
|---|---|---|
| x) | EQKTRHSE, | (SEQ ID NO: 85) |
| xi) | L(I/L)KLIGAK, | (SEQ ID NO: 86) |
| xii) | KTMEIGVY, | (SEQ ID NO: 87) |
| xiii) | HERL(L/M)KLV, | (SEQ ID NO: 88) |
| xiv) | CQLPVGDG, | (SEQ ID NO: 89) |
| xv) and or | TLCRRVK, | (SEQ ID NO: 90) | b2) is encoding a caffeoyl-CaA-O-methyltransferase protein from a monocotyledonous plant having an amino acid sequence identity of at least 90% to a polypeptide selected from the group described by SEQ ID NO: 5, and 70, or
b3) is encoding a hydroxyproline-rich glycoprotein from a monocotyledonous plant having an amino acid sequence identity of at least 90% to a polypeptide selected from the group described by SEQ ID NO: 18, and 75, or
b4) is encoding a C-8,7-stereol-isomerase protein from a monocotyledonous plant having an amino acid sequence identity of at least 90% to a polypeptide selected described by SEQ ID NO: 10, or
b5) is encoding a Chloroplast protein 12 like protein from a monocotyledonous plant having an amino acid sequence identity of at least 90% to a polypeptide described by SEQ ID NO: 31.

Preferably, the transcription regulating nucleotide sequence is from a corn (*Zea mays*) or rice (*Oryza sativa*) plant. Even more preferably the transcription regulating nucleotide sequence is from a plant gene selected from the group of genes consisting of *Oryza sativa* caffeoyl-CoA-O-methyltransferase genes, *Oryza sativa* C8,7-sterol isomerase genes, *Zea may* hydroxyproline-rich glycoprotein (HRGP) genes, *Zea mays* lactate dehydrogenase genes, *Oryza sativa* chloroplast protein 12 like genes and functional equivalents thereof. The functional equivalent gene is preferably encoding a polypeptide which has at least 90% amino acid sequence identity to a polypeptide selected from the group described by SEQ ID NO: 5, 10, 18, 26, 31, 60, 65, 70, and 75.

In a more preferred embodiment the transcription regulating nucleotide sequence is selected from the group of sequences consisting of
i) the sequences described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, and
ii) a fragment of at least 50 consecutive bases of a sequence under i); and
iii) a nucleotide sequence having substantial similarity (preferably with a sequence identity of at least 60%; more preferably measured by the BLASTN program with the default parameters wordlength (W) of 11, an expectation (E) of 10, a cutoff of 100, M=5, N=-4, and a comparison of both strands) to a transcription regulating nucleotide sequence described by SEQ ID NO: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73; and
iv) a nucleotide sequence capable of hybridizing to a transcription regulating nucleotide sequence described by SEQ ID NO: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof; and
v) a nucleotide sequence capable of hybridizing to a nucleic acid comprising 50 to 200 or more consecutive nucleotides of a transcription regulating nucleotide sequence described by SEQ ID NO: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof (preferably in 7% sodium dodecyl sulfate (SDS), 0.5 M NaPO$_4$, 1 mM EDTA at 50° C. with washing in 2×SSC, 0.1% SDS at 50° C.; more preferably in 7% sodium dodecyl sulfate (SDS), 0.5 M NaPO$_4$, 1 mM EDTA at 50° C. with washing in 1×SSC, 0.1% SDS at 50° C., still more preferably in 7% sodium dodecyl sulfate (SDS), 0.5 M NaPO$_4$, 1 mM EDTA at 50° C. with washing in 0.5×SSC, 0.1% SDS at 50° C., even more preferably in 7% sodium dodecyl sulfate (SDS), 0.5 M NaPO$_4$, 1 mM EDTA at 50° C. with washing in 0.1× SSC, 0.1% SDS at 50° C., most preferably in 7% sodium dodecyl sulfate (SDS), 0.5 M NaPO$_4$, 1 mM EDTA at 50° C. with washing in 0.1×SSC, 0.1% SDS at 65° C.); and vi) a nucleotide sequence which is the complement or reverse complement of any of the previously mentioned nucleotide sequences under i) to v).

Another preferred embodiment relates to an expression cassette for regulating expression in monocotyledonous plants comprising a) at least one transcription regulating nucleotide sequence functional in a monocotyledonous plant comprising at least one sequence selected from the group of sequences consisting of
   i) the sequences described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, and
   ii) a fragment of at least 50 consecutive bases of a sequence under i); and
   iii) a nucleotide sequence having substantial similarity (preferably with a sequence identity of at least 60%; more preferably measured by the BLASTN program with the default parameters wordlength (W) of 11, an expectation (E) of 10, a cutoff of 100, M=5, N=−4, and a comparison of both strands) to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73; and
   iv) a nucleotide sequence capable of hybridizing to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof (preferably in 7% sodium dodecyl sulfate (SDS), 0.5 M NaPO$_4$, 1 mM EDTA at 50° C. with washing in 2×SSC, 0.1% SDS at 50° C.; more preferably in 7% sodium dodecyl sulfate (SDS), 0.5 M NaPO$_4$, 1 mM EDTA at 50° C. with washing in 1×SSC, 0.1% SDS at 50° C., still more preferably in 7% sodium dodecyl sulfate (SDS), 0.5 M NaPO$_4$, 1 mM EDTA at 50° C. with washing in 0.5× SSC, 0.1% SDS at 50° C., even more preferably in 7% sodium dodecyl sulfate (SDS), 0.5 M NaPO$_4$, 1 mM EDTA at 50° C. with washing in 0.1×SSC, 0.1% SDS at 50° C., most preferably in 7% sodium dodecyl sulfate (SDS), 0.5 M NaPO$_4$, 1 mM EDTA at 50° C. with washing in 0.1×SSC, 0.1% SDS at 65° C.); and
   v) a nucleotide sequence capable of hybridizing to a nucleic acid comprising 50 to 200 or more consecutive nucleotides of a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof; and
   vi) a nucleotide sequence which is the complement or reverse complement of any of the previously mentioned nucleotide sequences under i) to v), and b) at least one nucleic acid sequence which is heterologous in relation to said transcription regulating sequence.

Preferably, the sequences specified under ii), iii), iv) v) and vi) in the paragraphs above are capable to modify transcription in a monocotyledonous plant cell or organism. More preferably said sequences specified under ii), iii), iv) v) and vi) have substantially the same transcription regulating activity as the transcription regulating nucleotide sequence described by SEQ ID NO: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73.

Also preferably the sequences specified under iii) above have a sequence identity of at least 60%, preferably 70% or 80%, more preferably 90% or 95% to a sequence described by SEQ ID NO: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73, wherein the identity is preferably measured by the BLASTN program with the default parameters wordlength (W) of 11, an expectation (E) of 10, a cutoff of 100, M=5, N=−4, and a comparison of both strands.

Further preferably, the sequences specified under iv) or v) above are hybridizing under stringent conditions, preferably under medium stringent conditions, most preferably under high stringent conditions (such as in 7% sodium dodecyl sulfate (SDS), 0.5 M NaPO$_4$, 1 mM EDTA at 50° C. with washing in 0.1×SSC, 0.1% SDS at 65° C.) with the specified target sequence.

In one preferred embodiment of the expression cassette of the invention, the expression of the nucleic acid sequence results in expression of a protein, or expression of an antisense RNA, sense or double-stranded RNA.

The expression profile of the expression cassettes of the invention may be modulated depending on the combination of the transcription regulating nucleotide sequence with expression enhancing introns and/or transcriptions termination sequences. This in a preferred embodiment the expression cassette of the inventions comprises at least one additional element selected from the group consisting of
a) 5'-untranslated regions, and
b) intron encoding sequences, and
c) transcription termination sequences.

The intron encoding sequences are preferably encoding an expression enhancing intron from a monocotyledonous plant. More preferably the intron sequence is an intron from an ubiquitin, actin or alcohol dehydrogenase gene. Preferably, this intron is inserted in the expression construct in the 5'-untranslated region of the nucleic acid sequence, which should be expressed (i.e., between the transcription regulating nucleotide sequence and the protein coding sequence (open reading frame) or the nucleic acid sequence to be expressed).

Preferably, the 5'-untranslated region is from the same gene as the transcription regulating sequences.

The transcription terminating sequence preferably also comprises a sequence inducing polyadenylation. The transcription terminating sequence may be heterologous with respect to the transcription regulating nucleotide sequence and/or the nucleic acid sequence to be expressed, but may also be the natural transcription regulating nucleotide sequence of the gene of said transcription regulating nucleotide sequence and/or said nucleic acid sequence to be expressed. In one preferred embodiment of the invention the transcription regulating nucleotide sequence is the natural transcription regulating nucleotide sequence of the gene of the transcription regulating sequence. Preferably the transcription termination sequence is selected from the group of sequences described by SEQ ID NO: 32, 34, and 35.

The transcription regulating sequences of the invention are especially useful for constitutive or root/kernel-preferential or root/kernel-specific expression in monocotyledonous plants. However, a use in other plants (e.g., dicotyledonous or gymnosperm plants) and other tissues cannot be ruled out. It has been shown that the tissue specificity of the transcription regulating sequences of the invention can be advantageously modulated by the combination with introns and/or transcription termination sequences.

The expression cassette may be employed for numerous expression purposes such as for example expression of a protein, or expression of an antisense RNA, sense or double-stranded RNA. Preferably, expression of the nucleic acid sequence confers to the plant an agronomically valuable trait.

Some of the transcription regulating sequences of the invention are novel even as such (i.e. as isolated nucleotide sequences). Accordingly another embodiment of the invention relates to an isolated nucleic acid sequence comprising at least one transcription regulating nucleotide sequence as described by SEQ ID NO: 6, 7, 8, 11, 12, 13, 19, 20, or 21.

Other embodiments of the invention relate to vectors comprising an expression cassette of the invention, and transgenic host cell or non-human organism comprising an expression cassette or a vector of the invention. Preferably the organism is a plant, more preferably a monocotyledonous plant, most preferably selected form the group consisting of *Zea mays* (corn), *Oryza sativa* (rice), *Triticum aestivum* (wheat), *Hordeum vulgare* (barley), and *Avena sativa* (oats).

Another embodiment of the invention relates to a method for identifying and/or isolating transcription regulating nucleotide sequence from a monocotyledonous plant characterized that said identification and/or isolation utilizes a nucleic acid sequence encoding an amino acid sequence as described by SEQ ID NOs: 5, 10, 18, 26, 31, 60, 65, 70, or 75, or a part of at least 15 bases of said nucleic acid sequence. Preferably the employed nucleic acid sequences is described by SEQ ID NOs: 4, 9, 17, 25, 30, 59, 64, 69, or 74 or a part of at least 15 bases of said nucleic acid sequence. Preferably said identification and/or isolation is realized by a method selected from polymerase chain reaction, hybridization, and database screening.

Still another embodiment of the invention relates to a method for providing a transgenic expression cassette for heterologous expression in monocotyledonous plants comprising the steps of:

I. isolating of a transcription regulating nucleotide sequence from a monocotyledonous plant utilizing at least one nucleic acid sequence or a part thereof, wherein said sequence is encoding a polypeptide described by SEQ ID NOs: 5, 10, 18, 26, 31, 60, 65, 70, or 75, or a part of at least 15 bases of said nucleic acid sequence, and II. functionally linking said transcription regulating nucleotide sequence to another nucleotide sequence of interest, which is heterologous in relation to said transcription regulating nucleotide sequence.

For both of the above mentioned methods preferably the nucleotide sequence utilized for isolation of said transcription regulating nucleotide sequence is encoding a polypeptide comprising a1) at least one sequence motif of a monocotyledonous plant lactate dehydrogenase protein selected from the group consisting of the amino acid sequences

| i) | SLSELGFDA, | (SEQ ID NO: 76) |
|---|---|---|
| ii) | VIGAGNVGMA, | (SEQ ID NO: 77) |
| iii) | IVTAGARQI, | (SEQ ID NO: 78) |
| iv) | L(F/Y)RKIVP, | (SEQ ID NO: 79) |
| v) | GFPASRV, | (SEQ ID NO: 80) |

-continued

| vi) | RF(L/I)AEHL, | (SEQ ID NO: 81) |
|---|---|---|
| vii) | QAYMVGEH, | (SEQ ID NO: 82) |
| viii) and | ALEGIRRAV, | (SEQ ID NO: 83) |
| ix) or | GYSVAS(L/I)A, | (SEQ ID NO: 84) | a2) at least one sequence motif of a monocotyledonous plant caffeoyl-CaA-O-methyltransferase protein selected from the group consisting of the amino acid sequences

| x) | EQKTRHSE, | (SEQ ID NO: 85) |
|---|---|---|
| xi) | L(I/L)KLIGAK, | (SEQ ID NO: 86) |
| xii) | KTMEIGVY, | (SEQ ID NO: 87) |
| xiii) | HERL(L/M)KLV, | (SEQ ID NO: 88) |
| xiv) and | CQLPVGDG, | (SEQ ID NO: 89) |
| xv) | TLCRRVK. | (SEQ ID NO: 90) |

DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "intron" refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: intron 14 of the RecA-like protein gene and intron 7 of the G5 gene from *Arabidopsis thaliana* are AT-AC introns, Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branchpoint The branchpoint sequence is important in splicing and splice-site selection in plants. The branchpoint sequence is usually located 10-60 nucleotides upstream of the 3' splice site. Plant sequences exhibit sequence deviations in the branchpoint, the consensus sequences being CURAY or YURAY.

The term "native" or "wild type" gene refers to a gene that is present in the genome of an untransformed cell, i.e., a cell not having a known mutation.

A "marker gene" encode a selectable or screenable trait.

The term "chimeric gene" refers to any gene that contains
1) DNA sequences, including regulatory and coding sequences, that are not found together in nature, or
2) sequences encoding parts of proteins not naturally adjoined, or
3) parts of promoters that are not naturally adjoined.

Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1,000's of nucleotides in length.

The terms "protein," "peptide" and "polypeptide" are used interchangeably herein.

The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *Agrobacterium tumefaciens*, such, as the octopine synthase and nopaline synthase termination regions (see also, Guerineau 1991; Proudfoot 1991; Sanfacon 1991; Mogen 1990; Munroe 1990; Ballas 1989; Joshi 1987).

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, double-stranded-RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating sequence" is not limited to promoters. However, preferably a transcription regulating nucleotide sequence of the invention comprises at least one promoter sequence (e.g., a sequence localized up-stream of the transcription start of a gene capable to induce transcription of the down-stream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of an expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence, which can stimulate promoter activity and may be an innate element of the promoter or a heterologous element inserted to enhance the level or tissue specificity of a promoter. It is capable of operating in both orientations (normal or flipped), and is capable of functioning even when moved either upstream or down-stream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors, which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter.

By "tissue-independent," "tissue-general," or "constitutive" is intended expression in the cells throughout a plant at most times and in most tissues. As with other promoters classified as "constitutive" (e.g., ubiquitin), some variation in absolute levels of expression can exist among different tissues or stages. However, constitutive promoters generally are expressed at high or moderate levels in most, and preferably all, tissues and most, and preferably all, developmental stages. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

The term "root" in the context of the inventions means the usually underground organ of a plant that lacks buds or leaves or nodes, absorbs water and mineral salts and usually it anchors the plant to the ground. The plant root consists of many cell types such as epidermal, root cap, columella, cortex, pericycle, vascular and root hair forming trichoblasts, organized into tissues or regions of the root, for example, the root tip, root epidermis, meristematic zone, primary root, lateral root, root hair, and vascular tissue. Transcription regulating sequences isolated as root-specific or root-preferred may regulate expression in one or a few of these cell types. This cell-specific activity can be useful for specific applications such as regulating meristematic activity in only meristematic cell zone or expression of a nematicidal gene in only the cell type that are contacted by the nematode pest.

The term "tissue-specific transcription" in the context of this invention in relation to a certain tissue or a group of tissue (e.g., root and kernel) means the transcription of a nucleic acid sequence by a transcription regulating element in a way that transcription of said nucleic acid sequence in said tissue or group of tissues contribute to more than 90%, preferably more than 95%, more preferably more than 99% of the entire quantity of the RNA transcribed from said nucleic acid sequence in the entire plant during any of its developmental stage.

"Tissue-preferential transcription" in the context of this invention in relation to a certain tissue or a group of tissue (e.g., root and kernel) means the transcription of a nucleic acid sequence by a transcription regulating element in a way that transcription of said nucleic acid sequence in said tissue or group of tissues contribute to more than 50%, preferably more than 70%, more preferably more than 80% of the entire quantity of the RNA transcribed from said nucleic acid sequence in the entire plant during any of its developmental stage.

"Inducible promoter" refers to those regulated promoters that can be turned on in one or more cell types by an external stimulus, such as a chemical, light, hormone, stress, or a pathogen.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products, which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way, techniques available to those skilled in the art are hybridization S1-RNAse analysis, Northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequences of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of the transcription regulating sequences from maize or rice specifically disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences, which simply reflect the degeneracy of the genetic code but nonetheless encode amino acid sequences that are identical to a particular amino acid sequence, are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is a polypeptide encoded by a gene with a promoter having any one of SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73, a nucleotide sequence comprising an open reading frame having any one of SEQ ID NOs: 4, 9, 17, 25, 30, 59, 64, 69, or 74, which encodes one of SEQ ID NOs: 5, 10, 18, 26, 31, 60, 65, 70, or 75. One indication that two polypeptides are substantially similar to each other, besides having substantially the same function, is that an agent, e.g., an antibody, which specifically binds to one of the polypeptides, specifically binds to the other.

Sequence comparisons maybe carried out using a Smith-Waterman sequence alignment algorithm (see e.g., Waterman (1995) or http://wwwhto.usc.edu/software/seqaln/index.html). The locals program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include Agrobacterium-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as Agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein, which encodes a polypeptide, also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid, which encodes a polypeptide, is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,793 and 5,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., root/kernel specific or preferential).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from *Actinomycetes* and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bifunctional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information (http://www.ncbi.nim.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See http://www.ncbi.nim.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5° C. + 16.6(\log_{10} M) + 0.41(\% GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point 1. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacilladophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species max (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others. Further preferred are trees such as apple, pear, quince, plum, cherry, peach, nectarine, apricot, papaya, mango, and other woody species including coniferous and deciduous trees such as poplar, pine, *sequoia*, cedar, oak, etc.

Most preferably, the transgenic plants according to the invention may be selected among monocotyledonous crop plants. The term "monocotyledonous plant" when referring to a transgenic plant according to the invention or to the source of the transcription regulating sequences of the invention is intended to comprise all genera, families and species of monocotyledonous plants. Preferred are Gramineae plants such as, for example, cereals such as maize, rice, wheat, barley, sorghum, millet, rye, triticale, or oats, and other non-cereal monocotyledonous plants such as sugarcane or banana. Especially preferred are corn (maize), rice, barley, wheat, rye, and oats. Most preferred are all varieties of the specie *Zea mays* and *Oryza sativa*.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention provides for isolated nucleic acid molecules comprising a plant nucleotide sequence that directs transcription of an operably linked nucleic acid fragment in a plant cell, preferably in monocotyledonous plants. Specifically, the present invention provides expression cassettes for regulating expression in monocotyledonous plants comprising i) at least one transcription regulating nucleotide sequence of a monocotyledonous plant gene, said monocotyledonous plant gene selected from the group of genes consisting of caffeoyl-CoA-O-methyltransferase genes, C8,7-sterol isomerase genes, hydroxyproline-rich glycoprotein (HRGP) genes, lactate dehydrogenase genes, and chloroplast protein like 12 genes, and functionally linked thereto ii) at least one nucleic acid sequence which is heterologous in relation to said transcription regulating sequence.

Preferably a transcription regulating nucleotide sequence of the invention comprises at least one promoter sequence of the respective gene (e.g., a sequence localized upstream of the transcription start of the respective gene capable to induce transcription of the downstream sequences). The transcription regulating nucleotide sequence of the invention may comprise the promoter sequence of said genes but may further comprise other elements such as the 5'-untranslated sequence, enhancer, introns etc. Preferably, said promoter sequence directs transcription of an operably linked nucleic acid segment in a plant or plant cell e.g., a linked plant DNA comprising an open reading frame for a structural or regulatory gene.

The transcription regulating sequences of the inventions can be combined with various 5'-untranslated regions, intron (preferably expression enhancing introns), and transcription terminations sequences (as described below in more detail). It has been shown that the tissue specificity of the transcription regulating sequences of the invention can be advantageously modulated by the combination with introns and/or transcription termination sequences. In most combinations the resulting expression cassettes exhibit a preferential or specific expression in root and kernel. However other expression specificities (e.g., constitutive expression) can be achieved. The transcription regulating sequences with expression activity in roots may be useful for alteration of the function of root tissue, modification of growth rate, improvement of resistance to root preferred pathogens, pests, herbicides or adverse weather conditions, for detoxification of soil as well as for broadening the range of soils or environments in which said plant may grow. Root abundant or root specific gene expression would provide a mechanism according to which morphology and metabolism may be altered to improve the yield and to produce useful proteins in greater amounts.

However, in some combinations, the transcriptions regulating sequence may exhibit a strong constitutive expression profile. Constitutive promoters are favored in situations where expression in all (or most) tissues during all (or most) times of the plant development is required. Other tissue specificities may be possible depending on the regulatory elements used in combination with the transcription regulating sequences of the invention.

The following Table 1 illustrates the genes from which the promoters of the invention are preferably isolated, the function of said genes, the cDNA encoded by said genes, and the protein (ORF) encoded by said genes.

TABLE 1

Genes from which the promoters of the invention are preferably isolated, putative function of said genes, cDNA and the protein encoded by said genes.

| Gene Product | Preferred Specie | Promotor SEQ ID | mRNA locus ID cDNA SEQ ID | Proteine ID Protein SEQ ID |
|---|---|---|---|---|
| Caffeoyl-CoA-O-methyltransferase | *Oryza sativa* | SEQ ID NO: 1, 2, 3 | AB023482.2 SEQ ID NO: 4 | BAA78733 SEQ ID NO: 5 |
| Caffeoyl-CoA-O-methyltransferase | *Zea mays* | SEQ ID NO: 66, 67, 68 | SEQ ID NO: 69 | SEQ ID NO: 70 |
| C-8,7-sterol-isomerase | *Oryza sativa* | SEQ ID NO: 6, 7, 8 | NM_183458 SEQ ID NO: 9 | NP_908347 SEQ ID NO: 10 |
| Hydroxyproline-rich glycoprotein | *Zea mays* | SEQ ID NO: 11, 12, 13, 14, 15, 16 | S45164 SEQ ID NO: 17 | AAB23539 SEQ ID NO: 18 |
| Hydroxyproline-rich glycoprotein | *Zea diploperennis* | SEQ ID NO: 71, 72, 73 | SEQ ID NO: 74 | SEQ ID NO: 75 |
| Lactate-dehydrogenase | *Zea mays* | SEQ ID NO: 19, 20, 21, 22, 23, 24 | Z11754 SEQ ID NO: 25 | CAA77808 SEQ ID NO: 26 |
| Lactate-dehydrogenase | *Oryza sativa* | SEQ ID NO: 56, 57, 58, 61, 62, 63 | Os06g01590 SEQ ID NO: 59 Os02g01510 SEQ ID NO: 64 | Os06g01590 SEQ ID NO: 60 Os02g01510 SEQ ID NO: 65 |
| Chloroplast protein 12 lie protein | *Oryza sativa* | SEQ ID NO: 27, 28, 29 | AP002881 SEQ ID NO: 30 | BAB19776 SEQ ID NO: 31 |

Preferably, the transcription regulating nucleotide sequence is obtainable from monocotyledonous plant genomic DNA from a gene encoding a polypeptide which a1) comprises at least one (preferably at least 2 or 3, more preferably at least 4 or 5, most preferably all) sequence motif of a monocotyledonous plant lactate dehydrogenase protein selected from the group consisting of the amino acid sequences

| i) | SLSELGFDA, | (SEQ ID NO: 76) |
|---|---|---|
| ii) | VIGAGNVGMA, | (SEQ ID NO: 77) |
| iii) | IVTAGARQI, | (SEQ ID NO: 78) |
| iv) | L(F/Y)RKIVP, | (SEQ ID NO: 79) |
| v) | GFPASRV, | (SEQ ID NO: 80) |
| vi) | RF(L/I)AEHL, | (SEQ ID NO: 81) |
| vii) | QAYMVGEH, | (SEQ ID NO: 82) |
| viii) and | ALEGIRRAV, | (SEQ ID NO: 83) |
| ix) or | GYSVAS(L/I)A, | (SEQ ID NO: 84) | b1) is encoding a lactate dehydrogenase protein from a monocotyledonous plant having an amino acid sequence identity of at least 90%, preferably at least 95%, more preferably at least 98% to a polypeptide selected from the group described by SEQ ID NO: 26, 60 and 65, or a2) comprises at least one (preferably at least 2 or 3, more preferably at least 4 or 5, most preferably all) sequence motif of a monocotyledonous plant caffeoyl-CaA-O-methyltransferase protein selected from the group consisting of the amino acid sequences

| x) | EQKTRHSE, | (SEQ ID NO: 85) |
|---|---|---|
| xi) | L(I/L)KLIGAK, | (SEQ ID NO: 86) |
| xii) | KTMEIGVY, | (SEQ ID NO: 87) |
| xiii) | HERL(L/M)KLV, | (SEQ ID NO: 88) |
| xiv) and | CQLPVGDG, | (SEQ ID NO: 89) |
| xv) or | TLCRRVK, | (SEQ ID NO: 90) | b2) is encoding a caffeoyl-CaA-O-methyltransferase protein from a monocotyledonous plant having an amino acid sequence identity of at least 90%, preferably at least 95%, more preferably at least 98% to a polypeptide selected from the group described by SEQ ID NOs: 5 and 70, or b3) is encoding a hydroxyproline-rich glycoprotein from a monocotyledonous plant having an amino acid sequence identity of at least 90%, preferably at least 95%, more preferably at least 98% to a polypeptide selected from the group described by SEQ ID NOs: 18 and 75, or b4) is encoding a C-8,7-stereol-isomerase protein from a monocotyledonous plant having an amino acid sequence identity of at least 90%, preferably at least 95%, more preferably at least 98% to a polypeptide selected described by SEQ ID NO: 10, or b5) is encoding a Chloroplast protein 12 like protein from a monocotyledonous plant having an amino acid sequence identity of at least 90%, preferably at least 95%, more preferably at least 98% to a polypeptide described by SEQ ID NO: 31.

Preferably functional equivalent of the transcription regulating nucleotide sequence can be obtained or is obtainable from plant genomic DNA from a gene expressing a mRNA described by a cDNA which is substantially similar and preferably has at least 70%, preferably 80%, more preferably 90%, most preferably 95% sequence identity to a sequence described by any one of SEQ ID NOs: 4, 9, 17, 25, 30, 59, 64, 69, or 74, respectively, or a fragment of said transcription regulating nucleotide sequence which exhibits the same promoter activity (e.g., root/kernel-preferential or root/kernel-specific or constitutive expression activity).

Preferably, the transcription regulating nucleotide sequence is from a corn (Zea mays) or rice (Oryza sativa) plant. Even more preferably the transcription regulating nucleotide sequence is from a plant gene selected from the group of genes consisting of Oryza sativa caffeoyl-CoA-O-methyltransferase genes, Oryza sativa C8,7-sterol isomerase genes, Zea may hydroxyproline-rich glycoprotein (HRGP) genes, Zea mays lactate dehydrogenase genes, Oryza sativa chloroplast protein 12 like genes and functional equivalents thereof. The functional equivalent gene is preferably encoding a polypeptide which has at least 90% amino acid sequence identity, preferably at least 95% amino acid sequence identity, more preferably at least 98% amino acid sequence identity to a polypeptide selected from the group described by SEQ ID NOs: 5, 10, 18, 26, 31, 60, 65, 70, and 75.

Some of the transcription regulating sequences of the invention provided herein are novel as such (i.e. as isolated nucleotide sequences). Accordingly another embodiment of the invention relates to an isolated nucleic acid sequence comprising at least one transcription regulating nucleotide sequence as described by SEQ ID NOs: 6, 7, 8, 11, 12, 13, 19, 20, or 21.

In a more preferred embodiment the transcription regulating nucleotide sequence is selected from the group of sequences consisting of i) the sequences described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, and ii) a fragment of at least 50 (preferably at least 70 or 100, more preferably at least 150 or 200, even more preferably at least 300 or 400, most preferably at least 500 or 700) consecutive bases of a sequence under i); and iii) a nucleotide sequence having substantial similarity (preferably with a sequence identity of at least 60%; more preferably measured by the BLASTN program with the default parameters wordlength (W) of 11, an expectation (E) of 10, a cutoff of 100, M=5, N=−4, and a comparison of both strands) to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73; and iv) a nucleotide sequence capable of hybridizing to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof (preferably in 7% sodium dodecyl sulfate (SDS), 0.5 M NaPO$_4$, 1 mM EDTA at 50° C. with washing in 2×SSC, 0.1% SDS at 50° C.; more preferably in 7% sodium dodecyl sulfate (SDS), 0.5 M NaPO$_4$, 1 mM EDTA at 50° C. with washing in 1×SSC, 0.1% SDS at 50° C., still more preferably in 7% sodium dodecyl sulfate (SDS), 0.5 M NaPO$_4$, 1 mM EDTA at 50° C. with washing in 0.5×SSC, 0.1% SDS at 50° C., even more preferably in 7% sodium dodecyl sulfate (SDS), 0.5 M NaPO$_4$, 1 mM EDTA at 50° C. with washing in 0.1× SSC, 0.1% SDS at 50° C., most preferably in 7% sodium dodecyl sulfate (SDS), 0.5 M NaPO$_4$, 1 mM EDTA at 50° C. with washing in 0.1×SSC, 0.1% SDS at 65° C.); and v) a nucleotide sequence capable of hybridizing to a nucleic acid comprising 50 to 200 or more ((preferably at least 70 or 100, more preferably at least 150 or 200, even more preferably at least 300 or 400, most preferably at least 500 or 700) consecutive nucleotides of a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof; and vii) a nucleotide sequence which is the complement or reverse complement of any of the previously mentioned nucleotide sequences under i) to v).

Another preferred embodiment relates to an expression cassette for regulating expression in monocotyledonous plants comprising a) at least one transcription regulating nucleotide sequence functional in a monocotyledonous plant comprising at least one sequence selected from the group of sequences consisting of i) the sequences described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, and ii) a fragment of at least 50 (preferably at least 70 or 100, more preferably at least 150 or 200, even more preferably at least 300 or 400, most preferably at least 500 or 700) consecutive bases of a sequence under i); and iii) a nucleotide sequence having substantial similarity (preferably with a sequence identity of at least 60%; more preferably measured by the BLASTN program with the default parameters wordlength (W) of 11, an expectation (E) of 10, a cutoff of 100, M=5, N=−4, and a comparison of both strands) to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73; and iv) a nucleotide sequence capable of hybridizing to a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof (preferably in 7% sodium dodecyl sulfate (SDS), 0.5 M NaPO$_4$, 1 mM EDTA at 50° C. with washing in 2×SSC, 0.1% SDS at 50° C.; more preferably in 7% sodium dodecyl sulfate (SDS), 0.5 M NaPO$_4$, 1 mM EDTA at 50° C. with washing in 1×SSC, 0.1% SDS at 50° C., still more preferably in 7% sodium dodecyl sulfate (SDS), 0.5 M NaPO$_4$, 1 mM EDTA at 50° C. with washing in 0.5× SSC, 0.1% SDS at 50° C., even more preferably in 7% sodium dodecyl sulfate (SDS), 0.5 M NaPO$_4$, 1 mM EDTA at 50° C. with washing in 0.1×SSC, 0.1% SDS at 50° C., most preferably in 7% sodium dodecyl sulfate (SDS), 0.5 M NaPO$_4$, 1 mM EDTA at 50° C. with washing in 0.1×SSC, 0.1% SDS at 65° C.); and v) a nucleotide sequence capable of hybridizing to a nucleic acid comprising 50 to 200 or more (preferably at least 70 or 100, more preferably at least 150 or 200, even more preferably at least 300 or 400, most preferably at least 500 or 700) consecutive nucleotides of a transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 or the complement thereof; and vi) a nucleotide sequence which is the complement or reverse complement of any of the previously mentioned nucleotide sequences under i) to v), and b) at least one nucleic acid sequence which is heterologous in relation to said transcription regulating sequence.

Preferably, the sequences specified under ii), iii), iv) v) and vi) in the paragraphs above are capable to modify transcription in a monocotyledonous plant cell or organism. More preferably said sequences specified under ii), iii), iv) v) and vi) have substantially the same transcription regulating activity as the transcription regulating nucleotide sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73.

Also preferably the sequences specified under iii) above have a sequence identity of at least 60%, preferably 70% or 80%, more preferably 90% or 95% to a sequence described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73, wherein the identity is preferably measured by the BLASTN program with the default parameters wordlength (W) of 11, an expectation (E) of 10, a cutoff of 100, M=5, N=−4, and a comparison of both strands.

Further preferably, the sequences specified under iv) or v) above are hybridizing under stringent conditions, preferably under medium stringent conditions, most preferably under high stringent conditions (such as in 7% sodium dodecyl sulfate (SDS), 0.5 M NaPO$_4$, 1 mM EDTA at 50° C. with washing in 0.1×SSC, 0.1% SDS at 65° C.) with the specified target sequence.

The activity of a specific transcription regulating nucleotide sequence is considered substantially the same or equivalent if transcription is initiated preferentially or specifically in the same tissue than the original promoter (e.g., in root and kernel or constitutive in all or most tissues) under otherwise identical conditions (i.e. in combination with the set of additional regulatory elements (e.g., introns, transcription terminator sequences and 5'-untranslated regions) and the same nucleic acid sequence to be expressed in the same plant expression system). Such expression profile is preferably demonstrated using reporter genes operably linked to said transcription regulating sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987). With respect to promoters with constitutive expression activity, the term "at most times" means a transcription regulating activity (as demonstrated by an β-glucuronidase assays as described in the examples below) preferably during at least 50%, preferably at least 70%, more preferably at least 90% of the development cycle of a plant comprising the respective expression cassette stably integrated into its chromosomal DNA.

With respect to a constitutive transcription regulating nucleotide sequence (e.g., a constitutive promoter), the term "in most tissues" means a transcription regulating activity (as demonstrated by an β-glucuronidase assays as described in the examples below) in tissues which together account to preferably at least 50%, preferably at least 70%, more preferably at least 90% of the entire biomass of the a plant comprising the respective expression cassette stably integrated into its chromosomal DNA.

Beside this the transcription regulating activity of a function equivalent may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences which—in comparison with its parent sequence—does not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Such functional equivalent of the transcription regulating nucleotide sequence may be obtained from other monocotyledonous plant species by using the transcription regulating sequences described herein as probes to screen for homologous structural genes in other plants by hybridization under low, moderate or stringent hybridization conditions. Regions of the transcription regulating sequences of the present invention, which are conserved among species, can also be used as PCR primers to amplify a segment from a species other than rice or maize, and that segment used as a hybridization probe (the latter approach permitting higher stringency screening) or in a transcription assay to determine promoter activity. Moreover, the transcription regulating sequences could be employed to identify structurally related sequences in a database using computer algorithms.

More specifically, based on the transcription regulating sequences of the present invention, orthologs may be identified or isolated from the genome of any desired organism, preferably from another plant, according to well known techniques based on their sequence similarity to the transcription regulating sequences of the invention, e.g., hybridization, PCR or computer generated sequence comparisons. For example, all or a portion of a particular transcription regulating nucleotide sequence of the invention is used as a probe that selectively hybridizes to other gene sequences present in a population of cloned genomic DNA fragments (i.e., genomic libraries) from a chosen source organism. Further, suitable genomic libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the transcription regulating sequences of the invention as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the transcription regulating sequences disclosed herein, i.e., the corresponding nucleotide sequences in other (i.e. other than the host organism where the specific sequences disclosed herein are derived from) monocotyledonous plant organisms, preferably, e.g., cereal plants such as corn, wheat, rye, barley, oats, turfgrass, sorghum, millet, or other monocotyledonous plants such as sugarcane or banana. An ortholog or orthologous gene is a gene from a different species that encodes a product having the same or similar function, e.g., catalyzing the same reaction as a product encoded by a gene from a reference organism. Thus, an ortholog includes polypeptides having less than, e.g., 90% amino acid sequence identity, but which ortholog encodes a polypeptide having the same or similar function. Databases such GenBank may be employed to identify sequences related to the maize or rice sequences disclosed herein, e.g., orthologs in other monocotyledonous plants such as wheat, barley, oats and others. Alternatively, recombinant DNA techniques such as hybridization or PCR may be employed to identify sequences related to the maize and rice sequences or to clone the equivalent sequences from different maize or rice DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another embodiment of the invention relates to a method for identifying and/or isolating a transcription regulating nucleotide sequence from a monocotyledonous plant characterized that said identification and/or isolation utilizes a nucleic acid sequence encoding an amino acid sequence as described by SEQ ID NOs: 5, 10, 18, 26, 31, 60, 65, 70, or 75, or a parts of said nucleic acid sequence. Preferred are nucleic acid sequences described by SEQ ID NOs: 4, 9, 17, 25, 30, 59, 64, 69, or 74 or parts thereof. "Part" in this context means a nucleic acid sequence of at least 15 bases preferably at least 25 bases, more preferably at least 50 bases. The method can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Still another embodiment of the invention relates to a method for providing a transgenic expression cassette for heterologous expression in monocotyledonous plants comprising the steps of:
I. isolating of a transcription regulating nucleotide sequence from a monocotyledonous plant utilizing at least one nucleic acid sequence or a part thereof, wherein said sequence is encoding a polypeptide described by SEQ ID NOs: 5, 10, 18, 26, 31, 60, 65, 70, or 75, or a part of at least 15 bases of said nucleic acid sequence, and
III. functionally linking said transcription regulating nucleotide sequence to another nucleotide sequence of interest, which is heterologous in relation to said transcription regulating nucleotide sequence.

Preferably, the nucleic acid sequence employed for the isolation comprises at least 15 base, preferably at least 25 bases, more preferably at least 50 bases of a sequence described by SEQ ID NOs: 4, 9, 17, 25, 30, 59, 64, 69, or 74 Preferably, the isolation of the transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

For both of the above mentioned methods preferably the nucleotide sequence utilized for isolation of said transcription regulating nucleotide sequence is encoding a polypeptide comprising
a1) at least one sequence motif of a monocotyledonous plant lactate dehydrogenase protein selected from the group consisting of the amino acid sequences

| | | |
|---|---|---|
| i) | SLSELGFDA, | (SEQ ID NO: 76) |
| ii) | VIGAGNVGMA, | (SEQ ID NO: 77) |
| iii) | IVTAGARQI, | (SEQ ID NO: 78) |
| iv) | L(F/Y)RKIVP, | (SEQ ID NO: 79) |
| v) | GFPASRV, | (SEQ ID NO: 80) |
| vi) | RF(L/I)AEHL, | (SEQ ID NO: 81) |
| vii) | QAYMVGEH, | (SEQ ID NO: 82) |
| viii) and | ALEGIRRAV, | (SEQ ID NO: 83) |
| ix) or | GYSVAS(L/I)A, | (SEQ ID NO: 84) | a2) at least one sequence motif of a monocotyledonous plant caffeoyl-CaA-O-methyltransferase protein selected from the group consisting of the amino acid sequences

| | | |
|---|---|---|
| x) | EQKTRHSE, | (SEQ ID NO: 85) |
| xi) | L(I/L)KLIGAK, | (SEQ ID NO: 86) |
| xii) | KTMEIGVY, | (SEQ ID NO: 87) |
| xiii) | HERL(L/M)KLV, | (SEQ ID NO: 88) |
| xiv) and | CQLPVGDG, | (SEQ ID NO: 89) |
| xv) | TLCRRVK. | (SEQ ID NO: 90) |

Preferably, the transcription regulating nucleotide sequences and promoters of the invention include a consecutive stretch of about 25 to 2,000, including 50 to 500 or 100 to 250, and up to 1,000 or 1,500, contiguous nucleotides, e.g., 40 to about 743, 60 to about 743, 125 to about 743, 250 to about 743, 400 to about 743, 600 to about 743, of any one of SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, or the promoter orthologs thereof, which include the minimal promoter region.

In a particular embodiment of the invention said consecutive stretch of about 25 to 2,000, including 50 to 500 or 100 to 250, and up to 1,000 or 1,500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95%, nucleic acid sequence identity with a corresponding consecutive stretch of about 25 to 2,000, including 50 to 500 or 100 to 250, and up to 1,000 or 1,500, contiguous nucleotides, e.g., 40 to about 743, 60 to about 743, 125 to about 743, 250 to about 743, 400 to about 743, 600 to about 743, of any one of SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, and 73, or the promoter orthologs thereof, which include the minimal promoter region. The above defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving expression in monocotyledonous plants of a coding sequence in a target cell, particularly in a plant cell. The promoter sequences and methods disclosed herein are useful in regulating expression in monocotyledonous plants, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. The term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted inbetween the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73) into the plant genome. Such insertion will result in an operable linkage to a nucleic acid sequence of interest which as such already existed in the genome. By the insertion the nucleic acid of interest is expressed in the desired way (e.g., root/kernel-preferentially or root/kernel-specific or constitutive) due to the transcription regulating properties of the transcription regulating sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide sequence in its natural genomic environment (i.e. linked to its natural gene) in a way that the inserted sequence becomes operably linked to the transcription regulating sequence, thereby forming an expression cassette of the invention.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant which exhibits substantially no phenotypic changes as a consequence of agent administration, infection with a pathogen, or exposure to stress. By "tolerant" is meant a plant which, although it may exhibit some phenotypic changes as a consequence of infection, does not have a substantially decreased reproductive capacity or substantially altered metabolism.

The transcription regulating sequences of the invention with a constitutive expression profile may be advantageously used for expressing a wide variety of genes including those which alter metabolic pathways, confer disease resistance, for protein production, e.g., antibody production, or to improve nutrient uptake and the like. Constitutive promoters may be modified so as to be regulatable, e.g., inducible. The genes and promoters described hereinabove can be used to identify orthologous genes and their promoters which are also likely expressed in a particular tissue and/or development manner. Moreover, the orthologous promoters are useful to express linked open reading frames. In addition, by aligning the promoters of these orthologs, novel cis elements can be identified that are useful to generate synthetic promoters.

The expression regulating nucleotide sequences specified above may be optionally operably linked to other suitable regulatory sequences, e.g., a transcription terminator sequence, operator, repressor binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating sequences of the invention further comprise sequences which are complementary to one (hereinafter "test" sequence) which hybridizes under stringent conditions with a nucleic acid molecule as described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73 as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors which may be employed in conjunction with the present invention will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof which is introduced into the plant genome is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phages are readily commercially available and their use is generally well known to those skilled in the art. Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the B10BASE database "Transfac" (Biologische Datenbanken GmbH, Braunschweig; Wingender 2001) or the database PlantCARE (Lescot 2002).

Preferably, functional equivalent fragments of one of the transcription regulating sequences of the invention comprises at least 100 base pairs, preferably, at least 200 base pairs, more preferably at least 500 base pairs of a transcription regulating nucleotide sequence as described by SEQ ID NOs: 1, 2, 3, 6, 7, 8, 11, 12, 13, 14, 15, 16, 19, 20, 21, 22, 23, 24, 27, 28, 29, 56, 57, 58, 61, 62, 63, 66, 67, 68, 71, 72, or 73. More preferably this fragment is starting from the 3'-end of the indicated sequences.

Especially preferred are equivalent fragments of transcription regulating sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating sequences of the invention are equivalent fragments of other sequences (see Table 2 below).

TABLE 2

Relationship of transcription regulating sequences of the invention

| Transcription regulating sequence | Equivalent sequence | Equivalent fragment |
|---|---|---|
| SEQ ID NO: 1 (1034 bp) | SEQ ID NO: 66 (997 bp) | SEQ ID NO: 2 (992 bp) |
| | | SEQ ID NO: 3 (301 bp) |
| | | SEQ ID NO: 67 (900 bp) |
| | | SEQ ID NO: 68 (301 bp) |
| SEQ ID NO: 6 (797 bp) | | SEQ ID NO: 7 (766 bp) |
| | | SEQ ID NO: 8 (301 bp) |
| SEQ ID NO: 11 (1182 bp) | SEQ ID NO: 14 (1270 bp) | SEQ ID NO: 12 (1111 bp) |
| | SEQ ID NO: 71 (1028 bp) | SEQ ID NO: 13 (301 bp) |
| | | SEQ ID NO: 15 (1191 bp) |
| | | SEQ ID NO: 16 (301 bp) |
| | | SEQ ID NO: 72 (954 bp) |
| | | SEQ ID NO: 73 (301 bp) |
| SEQ ID NO: 19 (1060 bp) | SEQ ID NO: 22 (1093 bp) | SEQ ID NO: 20 (946 bp) |
| | SEQ ID NO: 56 (1000 bp) | SEQ ID NO: 21 (301 bp) |
| | SEQ ID NO: 61 (1000 bp) | SEQ ID NO: 23 (948 bp) |
| | | SEQ ID NO: 24 (301 bp) |
| | | SEQ ID NO: 57 (945 bp) |
| | | SEQ ID NO: 58 (301 bp) |
| | | SEQ ID NO: 62 (719 bp) |
| | | SEQ ID NO: 63 (301 bp) |
| SEQ ID NO: 27 (998 bp) | | SEQ ID NO: 28 (948 bp) |
| | | SEQ ID NO: 29 (301 bp) |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct, which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette of the invention may comprise further regulatory elements. The term in this context is to be understood in the broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating sequence).

The expression profile of the expression cassettes of the invention may be modulated depending on the combination of the transcription regulating nucleotide sequence with expression enhancing introns and/or transcriptions termination sequences. This in a preferred embodiment the expression cassette of the inventions comprises at least one additional element selected from the group consisting of
a) 5'-untranslated regions, and
b) intron encoding sequences, and
c) transcription termination sequences.

The intron encoding sequences are preferably encoding an expression enhancing intron from a monocotyledonous plant. More preferably the intron sequence is an intron from an ubiquitin, actin or alcohol dehydrogenase gene. Preferably, this intron is inserted in the expression construct in the 5'-untranslated region of the nucleic acid sequence, which should be expressed (i.e., between the transcription regulating nucleotide sequence and the protein coding sequence (open reading frame) or the nucleic acid sequence to be expressed).

Preferably, the 5'-untranslated region is from the same gene as the transcription regulating sequences.

The transcription terminating sequence preferably also comprises a sequence inducing polyadenylation. The transcription terminating sequence may be heterologous with respect to the transcription regulating nucleotide sequence and/or the nucleic acid sequence to be expressed, but may also be the natural transcription regulating nucleotide sequence of the gene of said transcription regulating nucleotide sequence and/or said nucleic acid sequence to be expressed. In one preferred embodiment of the invention the transcription regulating nucleotide sequence is the natural transcription regulating nucleotide sequence of the gene of the transcription regulating sequence. Preferably the transcription termination sequence is selected from the group of sequences described by SEQ ID NOs: 32, 34, and 35.

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realized expression in other organisms (such as *E. coli* or *Agrobacterium*). Such regulatory elements can be find in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, New York (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired.

Especially preferred are the 5'-untranslated region, introns and the 3'-untranslated region from genes selected from the group of genes consisting of caffeoyl-CoA-O-methyltransferase genes, C8,7-sterol isomerase genes, hydroxyproline-rich glycoprotein (HRGP) genes, lactate dehydrogenase genes, chloroplast protein 12 like genes. More preferably, the 5'-untranslated region, introns and the 3'-untranslated region utilized in an expression cassette of the invention is from a plant gene selected from the group of genes consisting of *Oryza sativa* caffeoyl-CoA-O-methyltransferase genes, *Oryza sativa* C8,7-sterol isomerase genes, *Zea may* hydroxyproline-rich glycoprotein (HRGP) genes, *Zea mays* lactate dehydrogenase genes, *Oryza sativa* chloroplast protein 12 like genes and functional equivalents thereof.

Most preferred are the 5'-untranslated regions comprised at the 3'-end of the sequences described by SEQ ID NOs: 1, 6, 11, 14, 19, 22, and 27. Especially preferred are the sequences described by nucleotide 993 to 1034 of SEQ ID NO: 1, nucleotide 767 to 797 of SEQ ID NO: 6, nucleotide 1112 to 1182 of SEQ ID NO 11, nucleotide 1192 to 1270 of SEQ ID NO 14, nucleotide 947 to 1060 of SEQ ID NO: 19, nucleotide 949 to 1093 of SEQ ID NO: 22, and nucleotide 949 to 998 of SEQ ID NO: 27.

The intron encoding sequences is preferably encoding an expression enhancing intron from a monocotyledonous plant. Preferably, this intron is inserted in the expression construct in the 5'-untranslated region of the nucleic acid sequence, which should be expressed (i.e., between the transcription regulating nucleotide sequence and the protein coding sequence (open reading frame) or the nucleic acid sequence to be expressed). Most preferred as intron sequences are:

a) the introns of the *Zea mays* ubiquitin gene, preferably intron I thereof, most preferably the intron sequence as described by nucleotide 1,082 to 2,091 of SEQ ID NO: 36,
b) the introns of the rice actin gene, preferably intron I thereof, most preferably the intron sequence as described by nucleotide 121 to 568 of the sequence described by GenBank Acc. No.: X63830,
c) the introns of the *Zea mays* alcohol dehydrogenase (adh) gene, preferably intron 6 thereof, most preferably the intron sequence as described by nucleotide 3,135 to 3,476 of the sequence described by GenBank Acc.-No.: X04049, The transcription terminating sequence preferably also comprises a sequence inducing polyadenylation. The transcription terminating sequence may be heterologous with respect to the transcription regulating nucleotide sequence and/or the nucleic acid sequence to be expressed, but may also be the natural transcription regulating nucleotide sequence of the gene of said transcription regulating nucleotide sequence and/or said nucleic acid sequence to be expressed. In one preferred embodiment of the invention the transcription regulating nucleotide sequence is the natural transcription regulating nucleotide sequence of the gene of the transcription regulating sequence. Preferred as transcription termination sequences are the transcription termination sequences from a plant gene selected from the group of genes consisting of *Oryza sativa* caffeoyl-CoA-O-methyltransferase genes, *Oryza sativa* C8,7-sterol isomerase genes, *Zea may* hydroxyproline-rich glycoprotein (HRGP) genes, *Zea mays* lactate dehydrogenase genes, *Oryza sativa* chloroplast protein 12 like genes and functional equivalents thereof. Most preferred are the transcription termination sequence of the *Zea mays* lactate dehydrogenase gene as described by SEQ ID NO: 32, of the *Oryza sativa* caffeoyl-CoA-O-methyltransferase gene as described by SEQ ID NO: 34, and of the *Zea may* hydroxyproline-rich glycoprotein (HRGP) gene as described by SEQ ID NO: 35. By the combination of the transcription regulating sequences with specific 5'-untranslated regions, introns, and/or transcription termination sequences it is possible to modulate the expression specificity, especially tissue specificity.

| Promoter | 5'-UTR | Intron | Terminator | Tissue Specificity |
|---|---|---|---|---|
| *Oryza sativa* Caffeoyl-CoA-O-methyltransferase | own | *Zea mays* Ubiquitin | Own | all (constitutive) |
| *Oryza sativa* Caffeoyl-CoA-O-methyltransferase | own | *Zea mays* Ubiquitin | NOS | root (kernel, pollen) |
| *Oryza sativa* C-8,7-sterol-isomerase | own | *Zea mays* Ubiquitin | NOS | root, kernel |
| *Zea* maize Hydroxyproline-rich glycoprotein (HRGP) | own | *Zea mays* Ubiquitin | Own | root, silk (kernel: embryo) |
| *Zea* maize Lactate-dehydrogenase | own | *Zea mays* Ubiquitin | NOS or own | root, kernel |
| Chloroplast protein 12 lie protein | own | *Zea mays* Ubiquitin | NOS | Leaf, endosperm | own: element of the same gene to which the promoter naturally belongs;
NOS: nopaline synthase.

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a monocotyledonous genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a constitutive manner or a root/kernel-preferential or root/kernel-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest, which encodes a polypeptide, are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Exemplary Transgenes

The transcription regulating sequences of the invention are especially useful for expression (preferably constitutive or root/kernel-preferential or root/kernel-specific expression) in monocotyledonous plants (as defined above in the DEFINITION section), especially in cereal plants such as corn, rice, wheat, rye, barley and oats. However, a use in other plants (e.g., dicotyledonous or gymnosperm plants) and other tissues cannot be ruled out.

The transcription regulating nucleotide sequences and expression cassettes of the invention may be employed for numerous expression purposes such as for example expression of a protein, or expression of an antisense RNA, sense or double-stranded RNA. Preferably, expression of the nucleic acid sequence confers to the plant an agronomically valuable trait.

1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes which can be introduced include Bacillus thuringiensis crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA (c) genes. Endotoxin genes from other species of B. thuringiensis which affect insect growth or development may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by cystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a nontoxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol-0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or root/kernel-preferential or root/kernel-specific expression of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltrans-ferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have anti-fungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode *lepidoptera*-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

1.6 Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, B.sub.12, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

1.7 Tuber or Seed Composition or Quality

Various traits can be advantageously expressed especially in seeds or tubers to improve composition or quality. Such traits include but are not limited to:

Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.

Expression of genes which bring about an accumulation of fine chemicals such as of tocopherols, tocotrienols or carotenoids. An example which may be mentioned is phytoene desaturase. Preferred are nucleic acids which encode the *Narcissus pseudonarcissus* photoene desaturase (GenBank Acc. No.: X78815) or functional equivalents thereof.

Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the *Bertholletia excelsa* high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella alpina* Δ6-desaturase (Sakuradani et al. 1999 Gene 238:445-453), the *Caenorhabditis elegans* Δ5-desaturase (Michaelson et al. 1998, FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.

Production of high-quality proteins and enzymes for industrial purposes (for example enzymes, such as lipases) or as pharmaceuticals (such as, for example, antibodies, blood clotting factors, interferons, lymphokines, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial β-glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those which encode the *Medicago sativa* acetyl-CoA carboxylase (ACCase) (GenBank Acc. No.: L25042), or functional equivalents thereof.

Reducing levels of α-glucan L-type tuber phosphorylase (GLTP) or α-glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an α-glucan phosphorylase selected from the group consisting of α-glucan L-type tuber phosphorylase (GLTP) and α-glucan H-type phosphorylase (GHTP).

Further examples of advantageous genes are mentioned for example in Dunwell J M, Transgenic approaches to crop improvement, J Exp Bot. 2000; 51 Spec No; pages 487-96.

1.7 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plants of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.8 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.9 Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani 1990). For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

1.10. Non-Protein-Expressing Sequences 1.10.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the art and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.10.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., seed-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline-rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. Especially preferred negative selection markers are those which confer resistance to herbicides. Examples which may be mentioned are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A10 218 571).

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)

Bromoxynil® degrading nitrilases (bxn; Stalker 1988)

Kanamycin- or geneticin (G418) resistance genes (NPTII; NPT or neo; Potrykus 1985) coding e.g., for neomycin phosphotransferases (Fraley 1983; Nehra 1994)

2-Desoxyglucose-6-phosphate phosphatase (DOG$^R$1-Gene product; WO 98/45456; EP 0 807 836) conferring resistance against 2-desoxyglucose (Randez-Gil 1995).

hygromycin phosphotransferase (HPT), which mediates resistance to hygromycin (Vanden Elzen 1985).

altered dihydrofolate reductase (Eichholtz 1987) conferring resistance against methotrexat (Thillet 1988);

mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4.3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3.1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/L may be included in the medium. For example, with the daol gene as the selective marker, D-serine or D-alanine at a concentration of from about 3 to 100 mg/L may be included in the medium. Typical concentrations for selection are 20 to 40 mg/L. For example, with the mutated ahas genes as the selective marker, PUR-SUIT™ at a concentration of from about 3 to 100 mg/L may be included in the medium. Typical concentrations for selection are 20 to 40 mg/L.

2.1.2 Positive Selection Marker

Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or α-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is carries dominant .quadrature.ultila for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P. S. Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue (e.g., roots and kernel) or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and air-borne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive, tissue-independent promoter operably linked to an antisense nucleotide sequence, such that constitutive expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), β-glucuronidase (GUS), green fluorescent protein (GFP), β-galactosidase (β-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter, an actin cl promoter, a sucrose synthetase promoter, an INOPS promoter, an EXM5 promoter, a globulin2 promoter, a b-32, ADPG-pyrophosphorylase promoter, an LtpI promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapetum-specific gene promoter, tapetum-specific gene RAB24 promoter, an anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as nptII) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, Brassica, canola, soybean, barley, soybean, sugarbeet, cotton, safflower, peanut, sorghum, wheat, millet, tobacco, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to transgenic cells or non-human, transgenic organisms comprising an expression cassette of the invention. Preferred are prokaryotic and eukaryotic organism. Both microorganism and higher organisms are comprised. Preferred microorganisms are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11).

Especially preferred are microorganisms capable to infect plants and to transfer DNA into their genome, especially bacteria of the genus *Agrobacterium*, preferably *Agrobacterium tumefaciens* and *rhizogenes*. Preferred yeasts are *Candida, Saccharomyces, Hansenula* and *Pichia*. Preferred Fungi are *Aspergillus, Trichoderma, Ashbya, Neurospora, Fusarium*, and *Beauveria*. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Agrobacterium tumefaciens cells containing a vector comprising an expression cassette of the present invention, wherein the vector comprises a Ti plasmid, are useful in methods of making transformed plants. Plant cells are infected with an Agrobacterium tumefaciens as described above to produce a transformed plant cell, and then a plant is regenerated from the transformed plant cell. Numerous Agrobacterium vector systems useful in carrying out the present invention are known.

Various Agrobacterium strains can be employed, preferably disarmed Agrobacterium tumefaciens or rhizogenes strains. In a preferred embodiment, Agrobacterium strains for use in the practice of the invention include octopine strains, e.g., LBA4404 or agropine strains, e.g., EHA101 or EHA105. Suitable strains of A. tumefaciens for DNA transfer are for example EHA101[pEHA101] (Hood 1986), EHA105 [pEHA105] (Li 1992), LBA4404[pAL4404] (Hoekema 1983), C58C1[pMP90] (Koncz & Schell 1986), and C58C1 [pGV2260] (Deblaere 1985). Other suitable strains are Agrobacterium tumefaciens C58, a nopaline strain. Other suitable strains are A. tumefaciens C58C1 (Van Larebeke 1974), A136 (Watson 1975) or LBA4011 (Klapwijk 1980). In another preferred embodiment the soil-borne bacterium is a disarmed variant of Agrobacterium rhizogenes strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the Agrobacterium strain used to transform the plant tissue pre-cultured with the plant phenolic compound contains a L,L-succinamopine type Ti-plasmid, preferably disarmed, such as pEHA101. In another preferred embodiment, the Agrobacterium strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular Agrobacterium strains, to further increase the transformation efficiency, such as Agrobacterium strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of Agrobacterium tumefaciens strain LBA4404 (Hiei 1994) with super-virulent plasmids. These are preferably pTOK246-based vectors (Ishida 1996).

A binary vector or any other vector can be modified by common DNA recombination techniques, multiplied in E. coli, and introduced into Agrobacterium by e.g., electroporation or other transformation techniques (Mozo & Hooykaas 1991).

Agrobacterium is grown and used in a manner similar to that described in Ishida (1996). The vector comprising Agrobacterium strain may, for example, be grown for 3 days on YP medium (5 g/L yeast extract, 10 g/L peptone, 5 g/L NaCl, 15 g/L agar, pH 6.8) supplemented with the appropriate antibiotic (e.g., 50 mg/L spectinomycin). Bacteria are collected with a loop from the solid medium and resuspended. In a preferred embodiment of the invention, Agrobacterium cultures are started by use of aliquots frozen at −80° C. The concentration of Agrobacterium used for infection and co-cultivation may need to be varied. For example, a cell suspension of the Agrobacterium having a population density of approximately from $10^5$ to $10^{11}$, preferably $10^6$ to $10^{10}$, more preferably about $10^8$ cells or cfu/mL is prepared and the target tissue is immersed in this suspension for about 3 to 10 minutes. The bacteria are resuspended in a plant compatible co-cultivation medium. Supplementation of the co-culture medium with anti-oxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defense responses (like phenolic oxidation) may further improve the efficiency of Agrobacterium-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 µM to about 10 µM of silver nitrate and from about 50 mg/L to about 1,000 mg/L of L-Cystein. This results in a highly reduced vulnerability of the target tissue against Agrobacterium-mediated damage (such as induced necrosis) and highly improves overall transformation efficiency.

Various vector systems can be used in combination with Agrobacteria. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences, which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants (R.sub.0) was suggested by germline transmission and the identical Southern blot hybridization patterns and intensities of the transforming DNA in callus, R.sub.0 plants and R.sub.1 progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantification of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding, which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products, which were not able to tolerate comparable adverse developmental conditions.

SEQUENCES

1. SEQ ID NO: 1 Nucleic acid sequence encoding the transcription regulating nucleotide sequence of *Oryza sativa* (rice) caffeoyl CoA-O-methyltransferase (Os.CCoAMT1) gene including 5'-untranslated region
2. SEQ ID NO: 2 Nucleic acid sequence encoding the transcription regulating nucleotide sequence of *Oryza sativa* (rice) caffeoyl CoA-O-methyltransferase (Os.CCoAMT1) gene
3. SEQ ID NO: 3 Nucleic acid sequence encoding the core promoter region of the transcription regulating nucleotide sequence of *Oryza sativa* (rice) caffeoyl CoA-O-methyltransferase (Os.CCoAMT1) gene comprising clusters of promoter elements.

4. SEQ ID NO: 4 Nucleic acid sequence encoding *Oryza sativa* (rice) caffeoyl CoA-O-methyltransferase (Os.CCoAMT1)

5. SEQ ID NO: 5 Amino acid sequence encoding *Oryza sativa* (rice) caffeoyl CoA-O-methyltransferase (Os.CCoAMT1)

6. SEQ ID NO: 6 Nucleic acid sequence encoding a transcription regulating nucleotide sequence from the *Oryza sativa* (rice) C8,7-sterol isomerase gene (Os.SI) including the 5' untranslated region of the gene.

7. SEQ ID NO: 7 Nucleic acid sequence encoding a transcription regulating nucleotide sequence from the *Oryza sativa* (rice) C8,7-sterol isomerase gene (Os.SI).

8. SEQ ID NO: 8 Nucleic acid sequence encoding the core promoter region of the transcription regulating nucleotide sequence from the *Oryza sativa* (rice) C8,7-sterol isomerase gene (Os.SI) comprising clusters of promoter elements.

9. SEQ ID NO: 9 Nucleic acid sequence encoding *Oryza sativa* (rice) C8,7-sterol isomerase gene (Os.SI)

10. SEQ ID NO: 10 Amino acid sequence encoding *Oryza sativa* (rice) C8,7-sterol isomerase gene (Os.SI)

11. SEQ ID NO: 11 Nucleic acid sequence encoding a transcription regulating nucleotide sequence from a *Zea mays* hydroxyproline-rich glycoprotein (HRGP) (Zm.HRGP) including the 5' untranslated region of the gene.

12. SEQ ID NO: 12 Nucleic acid sequence encoding a transcription regulating nucleotide sequence from a *Zea mays* hydroxyproline-rich glycoprotein (HRGP) (Zm.HRGP).

13. SEQ ID NO: 13 Nucleic acid sequence encoding the core promoter region of the transcription regulating nucleotide sequence from a *Zea mays* hydroxyproline-rich glycoprotein (HRGP) (Zm.HRGP) comprising clusters of promoter elements.

14. SEQ ID NO: 14 Nucleic acid sequence encoding a function equivalent of the transcription regulating nucleotide sequence from a *Zea mays* hydroxyproline-rich glycoprotein (HRGP) (Zm.HRGP) including the 5' untranslated region of the gene.

15. SEQ ID NO: 15 Nucleic acid sequence encoding a function equivalent of the transcription regulating nucleotide sequence from a *Zea mays* hydroxyproline-rich glycoprotein (HRGP) (Zm.HRGP).

16. SEQ ID NO: 16 Nucleic acid sequence encoding the core promoter region of a function equivalent of the transcription regulating nucleotide sequence from a *Zea mays* hydroxyproline-rich glycoprotein (HRGP) (Zm.HRGP) comprising clusters of promoter elements.

17. SEQ ID NO: 17 Nucleic acid sequence encoding the *Zea mays* hydroxyproline-rich glycoprotein (HRGP)

18. SEQ ID NO: 18 Amino acid sequence encoding the *Zea mays* hydroxyproline-rich glycoprotein (HRGP)

19. SEQ ID NO: 19 Nucleic acid sequence encoding a transcription regulating nucleotide sequence from a *Zea mays* lactate dehydrogenase (Zm.LDH) including the 5' untranslated region of the gene.

20. SEQ ID NO: 20 Nucleic acid sequence encoding a transcription regulating nucleotide sequence from a *Zea mays* lactate dehydrogenase (Zm.LDH).

21. SEQ ID NO: 21 Nucleic acid sequence encoding the core promoter region of the transcription regulating nucleotide sequence from a *Zea mays* lactate dehydrogenase (Zm.LDH) comprising clusters of promoter elements.

22. SEQ ID NO: 22 Nucleic acid sequence encoding a function equivalent of the transcription regulating nucleotide sequence from a *Zea mays* lactate dehydrogenase (Zm.LDH) including the 5' untranslated region of the gene.

23. SEQ ID NO: 23 Nucleic acid sequence encoding a function equivalent of the transcription regulating nucleotide sequence from a *Zea mays* lactate dehydrogenase (Zm.LDH).

24. SEQ ID NO: 24 Nucleic acid sequence encoding the core promoter region of a function equivalent of the transcription regulating nucleotide sequence from a *Zea mays* lactate dehydrogenase (Zm.LDH) comprising clusters of promoter elements.

25. SEQ ID NO: 25 Nucleic acid sequence encoding the *Zea mays* lactate dehydrogenase (Zm.LDH)

26. SEQ ID NO: 26 Amino acid sequence encoding the *Zea mays* lactate dehydrogenase (Zm.LDH)

27. SEQ ID NO: 27 Nucleic acid sequence encoding a function equivalent of the transcription regulating nucleotide sequence from an *Oryza sativa* (rice) choroplast 12 (CP12) protein including the 5' untranslated region of the gene.

28. SEQ ID NO: 28 Nucleic acid sequence encoding a function equivalent of the transcription regulating nucleotide sequence from an *Oryza sativa* (rice) choroplast 12 (CP12) protein.

29. SEQ ID NO: 29 Nucleic acid sequence encoding the core promoter region of a function equivalent of the transcription regulating nucleotide sequence from an *Oryza sativa* (rice) choroplast 12 (CP12) protein comprising clusters of promoter elements.

30. SEQ ID NO: 30 Nucleic acid sequence encoding the *Oryza sativa* (rice) choroplast 12 (CP12) protein.

31. SEQ ID NO: 31 Amino acid sequence encoding the *Oryza sativa* (rice) choroplast 12 (CP12) protein.

32. SEQ ID NO: 32 Nucleic acid sequence encoding the intergenic sequence comprising 3'-untranslated region of *Zea mays* lactate dehydrogenase gene with the transcription termination and polyadenylation sequence.

33. SEQ ID NO: 33 Nucleic acid sequence encoding construct pBPSMM304 [Os.CP12 promoter::Zm.ubiquitin intron::GUS (PIV2)::NOS terminator]

34. SEQ ID NO: 34 Nucleic acid sequence encoding the intergenic sequence including the 3' untranslated region of caffeoyl CoA-O-methyltransferase with the transcription termination and polyadenylation sequence.

35. SEQ ID NO: 35 Nucleic acid sequence encoding the intergenic sequence including the 3' untranslated region of hydroxyproline-rich glyco-protein gene with the transcription termination and polyadenylation sequence.

36. SEQ ID NO: 36 Nucleic acid sequence encoding construct pBPS325 [Os.CCoAMT1 promoter::Zm.ubiquitin intron::GUS (PIV2)::Os.CCoAMT1 terminator]

37. SEQ ID NO: 37 Nucleic acid sequence encoding construct pBPS331 [Os.SI promoter::Zm.ubiquitin intron::GUS (PIV2)::NOS terminator]

38. SEQ ID NO: 38 Nucleic acid sequence encoding construct pBPSET003 [Zm.HRGP promoter::Zm.ubiquitin intron::GUS (PIV2)::Zm.HRGP terminator]

39. SEQ ID NO: 39 Nucleic acid sequence encoding construct pBPSET007 [Zm.LDH promoter::Zm.ubiquitin intron::GUS (PIV2)::Zm.LDH terminator]

40. SEQ ID NO: 40 Forward Primer Os.CCoAMT1 promoter-5'
5'-CAACTACTGCACGGTAAAAGTGATAGG-3'

41. SEQ ID NO: 41 Reverse Primer Os.CCoAMT1 promoter-3'
5'-GCAGCTTGCTTCGATCTCTCGCTCGCC-3'

42. SEQ ID NO: 42 Forward Primer Os.CCoAMT1 3'UTR-5'
5'-GCCGATGCCCAAGAACTAGTCATTTTAA-3'

43. SEQ ID NO: 43 Reverse Primer Os.CCoAMT1 3'UTR-3'
    5'-ATTAACACGTCAACCAAACCGCCGTCC-3'
44. SEQ ID NO: 44 Forward Primer Os.SI promoter-5'
    5'-TGCCTCGATTCGACCGTGTAATGGAAT-3'
45. SEQ ID NO: 45 Reverse Primer Os.SI promoter-3'
    5'-ACTCCTGGCTTCCTTCCGATCTGGACT-3'
46. SEQ ID NO: 46 Forward Primer Zm.HRGP promoter-5'
    5'-CCGGTGACCTTCTTGCTTCTTCGATCG-3'
47. SEQ ID NO: 47 Reverse Primer Zm.HRGP promoter-3'
    5'-CCTCTCTCTCACACACACTCTCAGTAA-3'
48. SEQ ID NO: 48 Forward Primer ZmDLH promoter-5'
    5'-AACAAATGGCGTACTTATATAACCACA-3'
49. SEQ ID NO: 49 Reverse Primer ZmDLH promoter-3'
    5'-CGGGCGGAATGGGATGGGATTACGTGT-3'
50. SEQ ID NO: 50 Forward Primer Zm.HRGP 3'UTR-5'
    5'-AAAGCGATGCCTACCATACCACACTGC-3'
51. SEQ ID NO: 51 Reverse Primer Zm.HRGP 3'UTR-3'
    5'-TGCCCACATTTATTATGGTTTTACACCC-3'
52. SEQ ID NO: 52 Forward Primer Zm.LDH 3'UTR-5'
    5'-TGATCACATCACCGTCTCTCTTCATTAA-3'
53. SEQ ID NO: 53 Reverse Primer Zm.LDH 3'UTR-3'
    5'-TATCCCAGTCTCGATATTGTCATCCGCT-3'
54. SEQ ID NO: 54 Forward Primer Os.CP12-p FP
    5'-TTTGTATTTAGGTCCCTAACGCCCTC-3'
55. SEQ ID NO: 55 Reverse Primer Os.CP12-p RP
    5'-TGTTGATGCGGATTTCTGCGTGTGAT-3'
56. SEQ ID NO: 56 Nucleic acid sequence encoding a transcription regulating nucleotide sequence from a *Oryza sativa* lactate dehydrogenase (Os.LDH) including the 5' untranslated region of the gene.
57. SEQ ID NO: 57 Nucleic acid sequence encoding a transcription regulating nucleotide sequence from a *Oryza sativa* lactate dehydrogenase (Os.LDH).
58. SEQ ID NO: 58 Nucleic acid sequence encoding the core promoter region of the transcription regulating nucleotide sequence from a *Oryza sativa* lactate dehydrogenase (Os.LDH) comprising clusters of promoter elements.
59. SEQ ID NO: 59 Nucleic acid sequence encoding a *Oryza sativa* lactate dehydrogenase (Os.LDH)
60. SEQ ID NO: 61 Amino acid sequence encoding a *Oryza sativa* lactate dehydrogenase (Os.LDH)
61. SEQ ID NO: 61 Nucleic acid sequence encoding a transcription regulating nucleotide sequence from a *Oryza sativa* lactate dehydrogenase (Os.LDH) including the 5' untranslated region of the gene.
62. SEQ ID NO: 62 Nucleic acid sequence encoding a transcription regulating nucleotide sequence from a *Oryza sativa* lactate dehydrogenase (Os.LDH).
63. SEQ ID NO: 63 Nucleic acid sequence encoding the core promoter region of the transcription regulating nucleotide sequence from a *Oryza sativa* lactate dehydrogenase (Os.LDH) comprising clusters of promoter elements.
64. SEQ ID NO: 64 Nucleic acid sequence encoding a *Oryza sativa* lactate dehydrogenase (Os.LDH)
65. SEQ ID NO: 65 Amino acid sequence encoding a *Oryza sativa* lactate dehydrogenase (Os.LDH)
66. SEQ ID NO: 66 Nucleic acid sequence encoding the transcription regulating nucleotide sequence of *Zea mays* caffeoyl CoA-O-methyltransferase (Zm.CCoAMT1) gene including 5'-untranslated region
67. SEQ ID NO: 67 Nucleic acid sequence encoding the transcription regulating nucleotide sequence of *Zea mays* caffeoyl CoA-O-methyltransferase (Zm.CCoAMT1) gene
68. SEQ ID NO: 68 Nucleic acid sequence encoding the core promoter region of the transcription regulating nucleotide sequence of *Zea mays* caffeoyl CoA-O-methyltransferase (Zm.CCoAMT1) gene comprising clusters of promoter elements.
69. SEQ ID NO: 69 Nucleic acid sequence encoding *Zea mays* caffeoyl CoA-O-methyltransferase (Zm.CCoAMT1)
70. SEQ ID NO: 70 Amino acid sequence encoding *Zea mays* caffeoyl CoA-O-methyltransferase (Zm.CCoAMT1)
71. SEQ ID NO: 71 Nucleic acid sequence encoding a function equivalent of the transcription regulating nucleotide sequence from a *Zea diploperennis* hydroxyproline-rich glycoprotein (HRGP) including the 5' untranslated region of the gene.
72. SEQ ID NO: 72 Nucleic acid sequence encoding a function equivalent of the transcription regulating nucleotide sequence from a *Zea diploperennis* hydroxyproline-rich glycoprotein (HRGP).
73. SEQ ID NO: 73 Nucleic acid sequence encoding the core promoter region of a function equivalent of the transcription regulating nucleotide sequence from a *Zea diploperennis* hydroxyproline-rich glycoprotein (HRGP) comprising clusters of promoter elements.
74. SEQ ID NO: 74 Nucleic acid sequence encoding the *Zea diploperennis* hydroxyproline-rich glycoprotein (HRGP)
75. SEQ ID NO: 75 Amino acid sequence encoding the *Zea diploperennis* hydroxyproline-rich glycoprotein (HRGP)
76. SEQ ID NO: 76-84 Amino acid sequence motif of a monocotyledonous plant lactate dehydrogenase protein
77. SEQ ID NO: 85-90 Amino acid sequence motif of a monocotyledonous plant caffeoyl-CaA-O-methyltransferase protein
91. SEQ ID NO: 91 Oligonucleotide primer GUS-forward
    5'-ttacgtggcaaaggattcgat-3'
92. SEQ ID NO: 92 Oligonucleotide primer GUS-reverse
    5'-gccccaatccagtccattaa-3'
93. SEQ ID NO: 93 Oligonucleotide primer Control gene forward
    5'-tctgccttgcccttgctt-3'
94. SEQ ID NO: 94 Oligonucleotide primer Control gene reverse
    5'-caattgcttggcaggtcttattt-3'

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

For generating transgenic plants *Agrobacterium tumefaciens* (strain C58C1[pMP90]) is transformed with the various promoter::GUS vector constructs (see below). Resulting *Agrobacterium* strains are subsequently employed to obtain transgenic plants. For this purpose a isolated transformed *Agrobacterium* colony is incubated in 4 mL culture (Medium: YEB medium with 50 µg/mL Kanamycin and 25 µg/mL Rifampicin) over night at 28° C. With this culture a 400 ml culture of the same medium is inoculated and incubated over night (28° C., 220 rpm). The bacteria a precipitated by centrifugation (GSA-Rotor, 8,000 U/min, 20 min) and the pellet is resuspended in infiltration medium (½ MS-Medium; 0.5 g/L MES, pH 5.8; 50 g/L sucrose). The suspension is placed in a plant box (Duchefa) and 100 mL SILVET L-77 (Osi Special-ties Inc., Cat. P030196) are added to a final concentration of 0.02%. The plant box with 8 to 12 Plants is placed into a desiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

Example 1

Isolation of Promoters

Genomic DNA from maize and rice is extracted using the Qiagen DNAeasy Plant Mini Kit (Qiagen). The promoter regions were isolated from genomic DNA using conventional PCR. Approximately 0.1 µg of digested genomic DNA was uses for the regular PCR reaction (see below). The primers were designed based on the maize or rice genomic DNA sequences upstream of the EST candidates, maize genomic sequences, or promoter sequences disclosed in the public database (e.g. rice caffeoyl CoA-O-methyltransferase [CCoAMT1], GenBank accession number AB023482; rice unknown protein, GenBank accession number AP002818; maize hydroxyproline-rich glycoprotein [HRGP], GenBank accession number AJ131535; maize lactate dehydrogenase [LDH], GenBank accession number Z11754). One µL of the diluted digested genomic DNA was used as the DNA template in the primary PCR reaction. The reaction comprised forward (5') and reverse (3') primers in a mixture containing Buffer 3 following the protocol outlined by an Expand Long PCR kit (Cat #1681-842, Roche-Boehringer Mannheim). The isolated DNA is employed as template DNA in a PCR amplification reaction using the following primers:

TABLE 3

Primer sequences for isolation of the promoter or terminator region

| Promoter or Terminator* | Size (bp) | Primer Sequences Forward Primer (F) & Reverse Primer (R) |
|---|---|---|
| *Oryza sativa* Caffeoyl-CoA-O-methyltransferase Promoter (Os.CCoAMT1-p) | 1,035 | F: 5'-CAACTACTGCACGGTAAAAGTGATAGG-3' (SEQ ID NO: 40) <br> R: 5'-GCAGCTTGCTTCGATCTCTCGCTCGCC-3' (SEQ ID NO: 41) |
| *Oryza sativa* Caffeoyl-CoA-O-methyltransferase Terminator (Os.CCoAMT1-t) | 1,092 | FP: 5'-GCCGATGCCCAAGAACTAGTCATTTTA-3' (SEQ ID NO: 42) <br> RP: 5'-ATTAACACGTCAACCAAACCGCCGTCC-3' (SEQ ID NO: 43) |
| *Oryza sativa* C-8,7-sterol-isomerase Promoter (Os.Sl-p) | 813 | FP: 5'-TGCCTCGATTCGACCGTGTAATGGAAT-3' (SEQ ID NO: 44) <br> RP: 5'-ACTCCTGGCTTCCTTCCGATCTGGACT-3' (SEQ ID NO: 45) |
| *Zea maize* Hydroxyproline-rich glycoprotein Promoter (Zm.HRGP-p) | 1,263 | FP: 5'-CCGGTGACCTTCTTGCTTCTTCGATCG-3' (SEQ ID NO: 46) <br> RP: 5'-CCTCTCTCTCACACACACTCTCAGTAA-3' (SEQ ID NO: 47) |
| *Zea maize* Hydroxyproline-rich glycoprotein Terminator (Zm.HRGP-t) | 541 | FP: 5'-AAAGCGATGCCTACCATACCACACTGC-3' (SEQ ID NO: 50) <br> RP: 5'-TGCCCACATTTATTATGGTTTTACACCC-3' (SEQ ID NO: 51) |
| *Zea maize* Lactate-dehydrogenase | 1,061 | FP: 5'-AACAAATGGCGTACTTATATAACCACA-3' (SEQ ID NO: 48) <br> RP: 5'-CGGGCGGAATGGGATGGGATTACGTGT-3' |

TABLE 3-continued

Primer sequences for isolation of the
promoter or terminator region

| Promoter or Terminator* | Size (bp) | Primer Sequences Forward Primer (F) & Reverse Primer (R) |
|---|---|---|
| promoter (Zm.LDH-p) | | (SEQ ID NO: 49) |
| Zea maize Lactate-dehydrogenase terminator (Zm.LDH-t) | 475 | FP: 5'-TGATCACATCACCGTCTCTCTTCATTAA-3' (SEQ ID NO: 52) RP: 5'-TATCCCAGTCTCGATATTGTCATCCGCT-3' (SEQ ID NO: 53) |
| Oryza sativa Chloroplast protein 12 Promoter (Os.CP12-p) | 998 | FP: 5'-TTTGTATTTAGGTCCCTAACGCCCTC-3' (SEQ ID NO: 54) RP: 5'-TGTTGATGCGGATTTCTGCGTGTGAT-3' (SEQ ID NO: 55) |

*terminator including 3'UTR

The promoter regions are amplified in the reaction solution [1×PCR reaction buffer (Roche Diagnostics), 5 µL genomic DNA (corresponds to approximately 80 ng, 2.5 mM of each dATP, dCTP, dGTP and dTTP (Invitrogen: dNTP mix), 1 µL 5' primer (100 µM) 1 µL 3' primer (100 µM), 1 µL Taq DNA polymerase 5 U/µL (Roche Diagnostics), in a final volume of 100 µL] under the optimized PCR thermocycler program (T3 Thermocycler Biometra; 1 cycle with 180 sec at 95° C., 30 cycles with 40 sec at 95° C., 60 sec at 53° C. and 2 min at 72° C., and 1 cycle with 5 min at 72° C. before stop the reaction at 4° C.).

The PCR product was applied to a 1% (w/v) agarose gel and separated at 80V followed by excising from the gel and purified with the aid of the Qiagen Gel Extraction Kit (Qiagen, Hilden, Germany). If appropriate, the eluate of 50 µL can be evaporated. The PCR product was cloned directly into vector pCR4-TOPO (Invitrogen) following the manufacturer's instructions, i.e. the PCR product obtained is inserted into a vector having T overhangs with its A overhangs and a topoisomerase.

Example 2

Isolation of Terminator of Interest Including the 3' Untranslated Region

Rice genomic DNA fragment (1,092 bp) containing the 3' untranslated region of caffeoyl CoA-O-methyltransferase (Os.CCoAMT1) was isolated using sequence specific primers based on the sequences that disclosed in the public database (GenBank accession number AB023482). The protocols for plant genomic DNA isolation and conventional PCR amplification was described in the Example 1.

```
Forward Primer OsCCoAMT1 3'UTR-5':
                                    (SEQ ID NO: 42)
5'-GCCGATGCCCAAGAACTAGTCATTTTA-3'

Reverse primer OsCCoAMT1 3'UTR-3':
                                    (SEQ ID NO: 43)
5'-ATTAACACGTCAACCAAACCGCCGTCC-3'
```

SacI for the forward primer and PmeI for the reverse primer were added to the sequence-specific primers for the further cloning purpose. (The illustrated primer sequences do not include restriction enzyme sites.)

Rice genomic DNA fragment, 519 bp or 473 bp, containing the 3' untranslated region of HRGP or LDH gene was isolated, respectively using sequence specific primers based on the sequences that disclosed in the public database (GenBank accession number AJ131535; Z11754). The protocols for plant genomic DNA isolation and conventional PCR amplification using sequence specific primers was described in the Example 1.

SacI for the forward primer and PmeI for the reverse primer were added to the sequence-specific primers for the further cloning purpose. (The illustrated primer sequences do not include restriction enzyme sites.)

Example 3

Vector Construction 3.1 pUC Based Vector (Promoter of Interest::Intron (IME):: GUS::NOS or Terminator of Interest)

The base vector to which the intron candidates were cloned in was pBPSMM270 at BglI and XmaI. This vector comprises multiple cloning sites (MCS) followed by Zm.ubiquitin intron, the GUSint ORF (including the potato invertase [PIV]2 intron to prevent bacterial expression), and nopaline synthase (NOS) terminator in order (5' to 3'). Maize ubiquitin intron can be replaced with an intron of interest that functions in intron-mediated enhancement.

The PCR fragment containing terminator of interest (e.g. 1,092 bp rice genomic DNA including CCoAMT1 terminator; 558 bp maize genomic DNA including HRGP terminator, 477 bp maize genomic DNA including LDH terminator) was digested with SacI and PmeI enzymes. Nopaline synthase terminator region in pBPSMM270 was replaced with the CCoAMT1 terminator, HRGP terminator or LDH terminator resulting in pBPSMM270a, pBPSMM270-HRGP3' or pBPSMM270-LDH3', respectively.

The genomic DNA fragment containing Os.CCoAMT1 or Os.SI promoter in the Topo vector (Invitrogen) was digested with PacI and AscI followed by subcloned upstream of the Zm.ubiquitin intron in pBPSMM270, respectively.

The genomic DNA fragment containing CCoAMT1 promoter in the Topo vector (Invitrogen) was digested with PacI and AscI followed by subcloned upstream of the Zm.ubiquitin intron in pBPSMM270-CCoAMT1 3', respectively.

The genomic DNA fragment containing Zm.HRGP or Zm.LDH promoter in the Topo vector (Invitrogen) was digested with PacI and AscI followed by subcloned upstream of the Zm.ubiquitin intron in pBPSMM270-HRGP3' or pBPSMM270-LDH3', respectively.

3.2 Transformation Binary Vector (Promoter of Interest::Intron (IME)::GUS::NOS or Terminator of Interest)

The GUS chimeric cassette (Os.CCoAMT1 promoter::Zm.ubiquitin intron::GUS (PIV2)::CCoAMT1 terminator, Zm.CCoAMT1 promoter::Zm.ubiquitin intron::GUS (PIV2)::NOS, Os.SI promoter::Zm.ubiquitin intron::GUS (PIV2)::NOS, Zm.HRGP promoter::Zm.ubiquitin intron::GUS (PIV2)::Zm.HRGP terminator, or Zm.LDH promoter::Zm.ubiquitin intron::GUS (PIV2)::Zm.LDH terminator) in pUC-based vector were digested with AscI or PacI (5') and PmeI (3') and subcloned into a monocot binary vector containing a plant selectable marker cassette (pBPSMM344) at AscI or PacI (5') and PmlI (3') sites to generate pBPSMM325, pBPSMM271, pBPSMM331, pBPSET003, or pBPSET007, respectively.

Example 4

Agrobacterium-Mediated Transformation in Monocotyledonous Plants

The Agrobacterium-mediated plant transformation using standard transformation and regeneration techniques may also be carried out for the purposes of transforming crop plants (Gelvin 1995; Glick 1993).

The transformation of maize or other monocotyledonous plants can be carried out using, for example, a technique described in U.S. Pat. No. 5,591,616.

The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag N.Y.).

Example 5

Detection of Reporter Gene Expression

To identify the characteristics of the promoter and the essential elements of the latter, which bring about its tissue specificity, it is necessary to place the promoter itself and various fragments thereof before what is known as a reporter gene, which allows the determination of the expression activity. An example, which may be mentioned, is the bacterial β-glucuronidase (Jefferson 1987a). The β-glucuronidase activity can be detected in-planta by means of a chromogenic substrate such as 5-bromo-4-chloro-3-indolyl-β-D-glucuronic acid in an activity staining (Jefferson 1987b). To study the tissue specificity, the plant tissue is cut, embedded, stained and analyzed as described (for example Bäumlein 1991b).

A second assay permits the quantitative determination of the GUS activity in the tissue studied. For the quantitative activity determination, MUG (4-methylumbelliferyl-β-D-glucuronide) is used as substrate for β-glucuronidase, and the MUG is cleaved into MU (methylumbelliferone) and glucuronic acid.

To do this, a protein extract of the desired tissue is first prepared and the substrate of GUS is then added to the extract. The substrate can be measured fluorimetrically only after the GUS has been reacted. Samples which are subsequently measured in a fluorimeter are taken at various points in time. This assay may be carried out for example with linseed embryos at various developmental stages (21, 24 or 30 days after flowering). To this end, in each case one embryo is ground into a powder in a 2 mL reaction vessel in liquid nitrogen with the aid of a vibration grinding mill (Type: Retsch MM 2000). After addition of 100 µL of EGL buffer (0.1 M $KPO_4$, pH 7.8; 1 mM EDTA; 5% glycerol; 1 M DTT), the mixture is centrifuged for 10 minutes at 25° C. and 14,000×g. The supernatant is removed and recentrifuged. Again, the supernatant is transferred to a new reaction vessel and kept on ice until further use. 25 µL of this protein extract are treated with 65 µL of EGL buffer (without DTT) and employed in the GUS assay. 10 µL of the substrate MUG (10 mM 4-methylumbelliferyl-β-D-glucuronide) are now added, the mixture is vortexed, and 30 µL are removed immediately as zero value and treated with 470 µL of Stop buffer (0.2 M $Na_2CO_3$). This procedure is repeated for all of the samples at an interval of 30 seconds. The samples taken were stored in the refrigerator until measured. Further readings were taken after 1 h and after 2 h. A calibration series which contained concentrations from 0.1 mM to 10 mM MU (4-methylumbelliferone) was established for the fluorimetric measurement. If the sample values were outside these concentrations, less protein extract was employed (10 µL, 1 µL, 1 µL from a 1:10 dilution), and shorter intervals were measured (0 h, 30 min, 1 h). The measurement was carried out at an excitation of 365 nm and an emission of 445 nm in a Fluoroscan II apparatus (Labsystem). As an alternative, the substrate cleavage can be monitored fluorimetrically under alkaline conditions (excitation at 365 nm, measurement of the emission at 455 nm; Spectro Fluorimeter BMG Polarstar+) as described in Bustos (1989). All the samples were subjected to a protein concentration determination by the method of Bradford (1976), thus allowing an identification of the promoter activity and promoter strength in various tissues and plants.

Example 6

Constitutive Expression in Maize 6.1 Rice CCoAMT1-Promoter::Zmubiquitin-Intron::GUS::CCoAMT1 Terminator (pBPSMM325)

CCoAMT1 promoter in combination with CCoAMT1 terminator shows strong constitutive and ubiquitous expression in all tissues and organs at different developmental stages. Strong ubiquitous expression can also be detected in in vitro plants.

TABLE 4

GUS expression controlled by monocot constitutive promoter candidates

| Tissues/Developmental stages | Promoter (GUS expression levels) | | | |
|---|---|---|---|---|
| | pBPSMM232* | pBPSMM247* | pBPSMM272 | pBPSMM325 |
| 3 days after co-cultivation | ++++ | +++ | ++ | +++ |
| Leaves at 5-leaf stage | +++++ | +++++ | ++++ | ++++ |
| Roots at 5-leaf stage | +++++ | +++++ | ++++ | ++++ |

TABLE 4-continued

GUS expression controlled by monocot constitutive promoter candidates

| Tissues/Developmental stages | pBPSMM232* | pBPSMM247* | pBPSMM272 | pBPSMM325 |
|---|---|---|---|---|
| Leaves at flowering stage | +++++ | +++++ | ++++ | +++ |
| Stem | +++ | +++ | ++ | +++ |
| Pre-pollination | +++++ | +++++ | +++ | ++ |
| 5 days after pollination [DAP] | +++++ | +++ (7 DAP) | ++++ (7 DAP) | ND |
| 30 DAP | +++++ | +++++ | ++++ | ++ |
| Dry seeds | ND | +++ | ND | ++ |
| Imbibition/germination | +++++ | ++++ | +++ | ND |

*Positive controls as a constitutive promoter (pBPSMM232 = Zm.ubiquitin promoter::Zm.ubiquitin intron::GUS (PIV2):: NOS terminator; pBPSMM247 = sugarcane bacilliform virus promoter::GUS (PIV2)::NOS terminator); a range of GUS expression levels measured by histochemical assay (− to +++++), ND: not determined yet

Example 7

Root and Kernel Preferable Expression in Maize

7.1 Rice Os.CCoAMT1 Promoter::Zm.Ubiquitin Intron:: GUS (PIV2)::NOS Terminator Caffeoyl-CoA-O-methyltransferase (CCoAMT1) promoter::ubiquitin-intron::NOS terminator (pBPSMM271) showed low expression in leaves and stem of T1 plants but strong expression in roots. GUS stain was also detected in kernel and pollen.

7.2 Rice SI Promoter::Zm.Ubiquitin Intron::GUS (PIV2):: NOS Terminator

OsC-8,7-sterol-isomerase promoter::Zm.ubiquitinintron:: NOS terminator (pBPSMM331) showed weak expression in most parts of the plants but good expression in roots and kernels.

7.3 Maize HRGP Promoter::Zm.Ubiquitin Intron::GUS (PIV2)::HRGP Terminator

HRGP promoter containing the ubiquitin intron and the HRGP terminator (pBPSET003) showed no expression in leaves but strong expression in roots and silk. In kernels expression is predominantly in the embryo and only weak in the endosperm.

7.4 Maize LDH Promoter::Zm.Ubiquitin Intron::GUS (PIV2)::NOS or LDH Terminator Lactate-dehydrogenase (LDH) promoter::Zm.ubiquitinintron::NOS or LDH terminator (pBPSMM272 or pBPSET007, respectively) showed weak expression in leaves but good expression in roots and kernels.

TABLE 5

GUS expression controlled by monocot root and kernel-preferable promoter candidates

| Tissues & Developmental stages | pBPSMM232* | pBPSMM271 | pBPSMM331 | pBPSET003 | pBPSMM272 or pBPSET007 |
|---|---|---|---|---|---|
| 3 days after co-cultivation | ++++ | + | ND | ND | +++ |
| Leaves at 5-leaf stage | +++++ | + | + | − | ++ |
| Roots at 5-leaf stage | +++++ | ++++ | +++ | ++++ | ++++ |
| Leaves at flowering stage | +++++ | + | ++ | − | ++ |
| Stem | +++ | + | ND | ND | + |
| Pre-pollination | +++++ | +++ | ++++ | ND | +++ |
| 5 days after pollination [DAP] | +++++ | +++ | ND | ND | +++ |
| 30 DAP | ++++ | +++ | ++ | ++ | +++ |
| Dry seeds | ND | ND | ND | ND | ND |
| Imbibition/germination | +++++ | +++ | ND | ND | +++ |

*positive control as a constitutive promoter (pBPSMM232 = Zm.ubiquitin promoter::Zm.ubiquitin intron::GUS (PIV2)::NOS terminator); a range of GUS expression levels measured by histochemical assay (− to +++++), ND: not determined yet

Example 8

Leaf and Endosperm Preferable Expression in Maize

Os.CP12 promoter::Zm.ubiquitin intron::GUS (PIV2):: NOS terminator (pBPSMM304) showed strong expression in leaves and endosperm, but not in roots or embryo.

TABLE 6

GUS expression controlled by leaf and endosperm-preferable monocot promoter

| Tissues/Developmental stages | pBPSMM232* | pBPSMM304 |
|---|---|---|
| 3 days after co-cultivation | ++++ | + |
| In vitro leaves | +++++ | ++++ |
| In vitro roots | +++++ | − |
| Leaves | +++++ | ++++ |
| Roots | +++++ | − |
| Kernel pre-pollination | +++++ | + |
| Kernel 30 DAP - Endosperm | +++++ | ++++ |

TABLE 6-continued

GUS expression controlled by leaf and
endosperm-preferable monocot promoter

| | Promoter (GUS expression levels) | |
|---|---|---|
| Tissues/Developmental stages | pBPSMM232* | pBPSMM304 |
| Kernel 30 DAP - Embryo | +++++ | – |
| Dry seeds | ++++ | ND |

*positive control as a constitutive promoter (pBPSMM232 = Zm.ubiquitin promoter::Zm.u-biquitin intron::GUS (PIV2)::NOS terminator); a range of GUS expression levels measured by histochemical assay (– to +++++), ND: not determined yet Example 9

Analysis of Drought-Inducible Expression Using Real Time RT PCR Analysis

Young maize plants were grown from seeds in the greenhouse under standard conditions. When plants had five true leaves (5-leaf stage) water was withheld from the drought-stress plants while watering continued for the water control plants. The 0-timepoint is taken at the last watering day. After that the first time point is taken when the soil is dry but plants don't show symptoms of drought yet (approximately 3 days), the second time point is taken when at least one leaf of every plant shows "rolling" (mild symptoms, approximately 5 days) and the last time point is taken when all leaves show "rolling" (severe symptoms, approximately 7 days).

Expression levels of the reporter gene was measured at the mRNA levels using a GeneAmp 5700 Sequence Detection System (Applied Biosystems). Total nucleic acids were extracted from maize leaf samples taken at various time points during the drought stress experiments using the Wizard Magnetic 96 DNA plant System kit (Promega, FF3661). Subsequently, DNA was removed from the samples using the DNA-free kit (Ambion, #1906). The resulting DNA-free RNA solution was used in subsequent PCR reactions. The one-batch RT/quantitative PCR reactions for expression analysis contained:

| | |
|---|---|
| 10 µL | RNA solution |
| 15 µL | SYBR Green master Mix (2×; Eurogentec #RTSNRT032X-1) |
| 0.15 µL | reverse transcriptase + inhibitor1 mix (Eurogentec #RTSNRT032X-1) |
| 0.6 µL | forward primer (10 pmol/µL) |
| 0.6 µL | reverse primer (10 pmol/µL) |
| 3.65 µL | sterile water |

The PCR program was:
1 cycle 48° C. for 30 min (RT reaction)
40 cycles 90° C. for 10 min; 95° C. for 15 sec and 60° C. for 1 min
The amplification was followed by a dissociation protocol:
95° C. for 15 sec, 60° C. for 20 sec
20 min slow ramp from 60° C. to 95° C.

TABLE 7

Primer sequences of the GUS gene and control gene encoding microtubule-associated protein 1 light chain 3

| Gene | Primers | | SEQ ID |
|---|---|---|---|
| GUS | Fwd: | 5'-ttacgtggcaaaggattcgat | SEQ ID NO: 91 |
| | Rev: | 5'-gccccaatccagtccattaa | SEQ ID NO: 92 |

TABLE 7-continued

Primer sequences of the GUS gene and control gene encoding microtubule-associated protein 1 light chain 3

| Gene | Primers | | SEQ ID |
|---|---|---|---|
| Control gene | Fwd: | 5'-tctgccttgcccttgctt | SEQ ID NO: 93 |
| | Rev: | 5'-caattgcttggcaggtcttatt | SEQ ID NO: 94 |

For each timepoint of the drought-stress experiment RNA solution of each sample was used in two qPCR reactions that were run at the same time on the same plate. One reaction contained the GUS primers the second reaction contained primers for an endogenous control gene from maize. This endogenous control gene shows stable expression under stress conditions in a variety of tissues.

The preset baseline and threshold of the GeneAmp 5700 software were used in all experiments to generate raw data (cycle numbers). In order to normalize the values obtained with the GeneAmp 5700 Sequence Detection System the values of the endogenous primer reactions were subtracted from the values of the GUS primer reactions. The difference in cycle numbers was then used to calculate the change of expression levels. As templates are exponentially amplified during PCR one cycle difference equals a two-fold difference in template levels. Results are shown as an x-fold induction compared to the 0-timepoint that is set to 1.

9.1 Drought-Inducible Expression Controlled by Maize LDH Promoter

In T1 plants containing a single copy shows strong constitutive expression in roots and in kernels. Expression in leaves and stem at different developmental stages was weak. Upon drought-stress expression in leaves was induced two-fold compared to well-watered control.

Example 10

Utilization of Transgenic Crops

A reporter gene in pBPSMM325 can be replaced with gene of interest to express in a constitutive and ubiquitous manner, a reporter gene in pBPSMM271, pBPSMM331, pBPSET003, and pBPSET007 can be replaced with gene of interest to express mostly in roots and kernel, a reporter gene in pBPSMM304 can be replaced with gene of interest to express mostly in leaves and endosperm (e.g., by antisense or double-stranded RNA), thereby improving—for example—biomass and/or yield, or tolerant to biotic and abiotic environmental stresses. The chimeric constructs are transformed into monocotyledonous plants. Standard methods for transformation in the art can be used if required. Transformed plants are regenerated using known methods. Various phenotypes are measured to determine improvement of biomass, yield, fatty acid composition, high oil, disease tolerance, or any other phenotypes that link yield enhancement or stability. Gene expression levels are determined at different stages of development and at different generations ($T_0$ to $T_2$ plants or further generations). Results of the evaluation in plants lead to determine appropriate genes in combination with this promoter to increase yield, improve disease tolerance, and/or improve abiotic stress tolerance.

Example 11

Expression of Selectable Marker Gene in Monocotyledonous Plants

A reporter gene in pBPSMM325 can be replaced with a selectable marker gene and transformed into monocotyledonous plants such as rice, barley, maize, wheat, or ryegrass but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations ($T_0$ to $T_2$ plants or further generations). Results of the evaluation in plants lead to determine appropriate genes in combination with this promoter.

Example 12

Expression of Transgene for Root Vigor in Monocotyledonous Plants

A reporter gene in pBPSMM271, pBPSMM331, pBPSET003, pBPSMM272, and pBPSET007 can be replaced with gene of interest to express mostly in roots, which affects root architecture and transformed into monocotyledonous plants such as rice, barley, maize, wheat, or ryegrass but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations ($T_0$ to $T_2$ plants or further generations). Results of the evaluation in plants lead to determine appropriate genes in combination with this promoter.

Example 13

Expression of Transgene for Feed and Food in Monocotyledonous Plants

A reporter gene in pBPSMM271, pBPSMM331, pBPSET003, pBPSMM272, pBPSET007, and pBPSMM304 can be replaced with gene of interest to express mostly in kernel, which improve nutrition in embryo and endosperm and transformed into monocotyledonous plants such as rice, barley, maize, wheat, or ryegrass but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations ($T_0$ to $T_2$ plants or further generations). Results of the evaluation in plants lead to determine appropriate genes in combination with this promoter.

Example 14

Deletion Analysis

The cloning method is described by Rouster (1997) and Sambrook (1989). Detailed mapping of these promoters (i.e., narrowing down of the nucleic acid segments relevant for its specificity) is performed by generating various reporter gene expression vectors which firstly contain the entire promoter region and secondly various fragments thereof. Firstly, the entire promoter region or fragments thereof are cloned into a binary vector containing GUS or other reporter gene. To this end, fragments are employed firstly, which are obtained by using restriction enzymes for the internal restriction cleavage sites in the full-length promoter sequence. Secondly, PCR fragments are employed which are provided with cleavage sites introduced by primers. The chimeric GUS constructs containing various deleted promoters are transformed into Zea mays, Arabidopsis and other plant species using transformation methods in the current art. Promoter activity is analyzed by using GUS histochemical assays or other appropriate methods in various tissues and organs at the different developmental stages. Modification of the promoter sequences can eliminate leakiness based on our needs.

Example 15

In Vivo Mutagenesis

The skilled worker is familiar with a variety of methods for the modification of the promoter activity or identification of important promoter elements. One of these methods is based on random mutation followed by testing with reporter genes as described above. The in vivo mutagenesis of microorganisms can be achieved by passage of the plasmid (or of another vector) DNA through E. coli or other microorganisms (for example Bacillus spp. or yeasts such as Saccharomyces cerevisiae) in which the ability of maintaining the integrity of the genetic information is disrupted. Conventional mutator strains have mutations in the genes for the DNA repair system (for example mutHLS, mutD, mutT and the like; for reference, see Rupp 1996). The skilled worker is familiar with these strains. The use of these strains is illustrated for example by Greener (1994). The transfer of mutated DNA molecules into plants is preferably effected after selection and testing of the microorganisms. Transgenic plants are generated and analyzed as described above.

Example 16

PLACE Analysis for Os.CCoAMT1 Promoter (SEQ ID NO: 1)

Based on the below given PLACE results are potential TATA box is localized at base pair 952 to base pair 958 of SEQ ID NO: 1. In consequence the 5' untranslated region starts at about base pair 993 and extends to base pair 1,035 of SEQ ID NO: 1. The sequence described by SEQ ID NO: 2 ends 17 base pairs before the ATG start codon.

The following clusters of promoter elements were identified in the Os.CCoAMT1 promoter as described by SEQ ID NO: 1:

| IUPAC | Position from-to | Str. | Sequence |
|---|---|---|---|
| LTRECOREATCOR15 | 33-39 | (−) | TCCGACC |
| TATABOX3 | 45-51 | (+) | TATTAAT |
| CCAATBOX1 | 86-90 | (−) | CCAAT |
| SEF1MOTIF | 99-107 | (+) | ATATTTATA |

-continued

| IUPAC | Position from-to | Str. | Sequence |
|---|---|---|---|
| TATAPVTRNALEU | 101-113 | (+) | ATTTATATATTAA |
| TATABOX2 | 101-107 | (-) | TATAAAT |
| TATABOX4 | 103-109 | (-) | TATATAA |
| WBOXATNPR1 | 132-146 | (-) | ATTGACGTCGAATTG |
| HEXMOTIFTAH3H4 | 135-147 | (+) | TTCGACGTCAATA |
| TGACGTVMAMY | 137-149 | (-) | TCTATTGACGTCG |
| CGACGOSAMY3 | 137-141 | (+) | CGACG |
| ACGTCBOX | 138-143 | (+) | GACGTC |
| ACGTCBOX | 138-143 | (-) | GACGTC |
| BOXIINTPATPB | 145-150 | (+) | ATAGAA |
| SP8BFIBSP8AIB | 169-176 | (-) | ACTGTGTA |
| CIACADIANLELHC | 190-199 | (-) | CAATAATATC |
| S1FBOXSORPS1L21 | 221-226 | (+) | ATGGTA |
| ABRELATERD1 | 226-238 | (+) | ATCAACGTGATCG |
| CIACADIANLELHC | 228-237 | (+) | CAACGTGATC |
| BP5OSWX | 228-234 | (+) | CAACGTG |
| MYBST1 | 267-273 | (+) | GGGATAT |
| ABRELATERD1 | 307-319 | (-) | TAAAACGTGTGCT |
| QARBNEXTA | 310-316 | (-) | AACGTGT |
| CCAATBOX1 | 325-329 | (+) | CCAAT |
| SEF3MOTIFGM | 333-338 | (+) | AACCCA |
| TATABOXOSPAL | 360-366 | (+) | TATTTAA |
| TATABOX2 | 366-372 | (-) | TATAAAT |
| QELEMENTZMZM13 | 375-389 | (-) | CAGGTCACGAATTCA |
| WBOXHVISO1 | 386-400 | (+) | CCTGACTCACTCACA |
| GCN4OSGLUB1 | 387-395 | (-) | GTGAGTCAG |
| WBOXHVISO1 | 413-427 | (-) | GGTGACTGAGACAAA |
| SEBFCONSSTPR10A | 414-420 | (+) | TTGTCTC |
| ARFAT | 415-420 | (+) | TGTCTC |
| IBOXCORENT | 449-455 | (+) | GATAAGG |
| IBOXCORE | 456-462 | (-) | GATAAAC |
| MYBST1 | 458-464 | (-) | AGGATAA |
| CGACGOSAMY3 | 471-475 | (+) | CGACG |
| HEXAMERATH4 | 471-476 | (-) | CCGTCG |
| IBOXCORE | 475-481 | (-) | GATAACC |
| IBOXCORE | 527-533 | (+) | GATAAG |
| TAAAGSTKST1 | 527-533 | (+) | GATAAG |
| NTBBF1ARROLB | 528-534 | (-) | ACTTTAT |
| MYB2AT | 543-553 | (+) | GTTTTAACTGC |
| PALBOXLPC | 576-586 | (+) | CCTCACCAACC |
| MYBPLANT | 579-589 | (+) | CACCAACCTTC |
| MYBPZM | 581-586 | (+) | CCAACC |
| ARFAT | 608-613 | (+) | TGTCTC |
| AGCBOXNPGLB | 623-629 | (+) | AGCCGCC |
| RAV1BAT | 653-665 | (+) | ACGCACCTGGCGG |
| ABRELATERD1 | 689-701 | (+) | GAAGACGTGGAGG |
| CCAATBOX1 | 730-734 | (+) | CCAAT |
| PALBOXAPC | 737-742 | (+) | CCGTCC |
| MYB1AT | 768-773 | (+) | AAACCA |
| PALBOXLPC | 774-784 | (+) | CCTCACCAACC |
| MYBPLANT | 777-787 | (+) | CACCAACCCAA |
| MYBPZM | 779-784 | (+) | CCAACC |
| SEF3MOTIFGM | 781-786 | (+) | AACCCA |
| CAREOSREP1 | 785-790 | (+) | CAACTC |
| BOXCPSAS1 | 816-822 | (+) | CTCCCAC |
| GCBP2ZMGAPC4 | 831-839 | (-) | GTGGGCCCG |
| RAV1BAT | 834-846 | (+) | GCCCACCTGTCGG |
| DRECRTCOREAT | 841-847 | (-) | GCCGACA |
| CCA1ATLHCB1 | 880-887 | (-) | AAAAATCT |
| PYRIMIDINEBOXHVEPB | 883-890 | (+) | TTTTTTCC |
| MYCATERD1 | 920-926 | (-) | CATGTGA |
| MYCATRD22 | 921-927 | (+) | CACATGC |
| BOXCPSAS1 | 932-938 | (+) | CTCCCAC |
| TATAPVTRNALEU | 948-960 | (-) | GTTTATATAGCGC |
| TATABOX4 | 952-958 | (+) | TATATAA |
| CGACGOSAMY3 | 970-974 | (-) | CGACG |
| DRECRTCOREAT | 981-987 | (-) | GCCGACG |
| CGACGOSAMY3 | 981-985 | (-) | CGACG |
| WBOXATNPR1 | 982-996 | (-) | ATTGACTTCGCCGAC |

Example 17

PLACE Analysis for Os.SI Promoter (SEQ ID NO: 6)

Based on the below given PLACE results, no conventional TATA box has been found in this promoter region (797 bp). The following clusters of promoter elements were identified in the Zm.SI promoter as described by SEQ ID NO: 6:

| IUPAC | Position From-to | Str. | Sequence |
|---|---|---|---|
| TBOXATGAPB | 66-71 | (+) | ACTTTG |
| RAV1AAT | 96-100 | (+) | CAACA |
| CATATGGMSAUR | 113-118 | (+) | CATATG |
| CATATGGMSAUR | 113-118 | (-) | CATATG |
| -300ELEMENT | 127-135 | (+) | TGCAAAATC |
| POLLEN2LELAT52 | 159-167 | (-) | TCCACCATA |
| CGACGOSAMY3 | 259-263 | (+) | CGACG |
| HEXAMERATH4 | 259-264 | (-) | CCGTCG |
| CGACGOSAMY3 | 288-292 | (+) | CGACG |
| HEXAMERATH4 | 288-293 | (-) | CCGTCG |
| GCCCORE | 384-390 | (-) | CGCCGCC |
| GCCCORE | 387-393 | (-) | CGCCGCC |
| GCCCORE | 390-396 | (-) | TGCCGCC |
| GRAZMRAB28 | 390-398 | (-) | CATGCCGCC |
| DRECRTCOREAT | 397-403 | (-) | GCCGACA |
| GCCCORE | 401-407 | (-) | CGCCGCC |
| BS1EGCCR | 422-427 | (+) | AGCGGG |
| CGACGOSAMY3 | 434-438 | (+) | CGACG |
| HEXAMERATH4 | 434-439 | (-) | CCGTCG |
| GCCCORE | 450-456 | (-) | CGCCGCC |
| DRECRTCOREAT | 456-462 | (-) | GCCGACC |
| MYBPZM | 552-557 | (-) | CCAACC |
| CGACGOSAMY3 | 559-563 | (+) | CGACG |
| SEF3MOTIFGM | 593-598 | (-) | AACCCA |
| LRENPCABE | 607-619 | (-) | GCCGACGTGGCAT |
| ABREOSRAB21 | 608-620 | (+) | TGCCACGTCGGCC |
| DRECRTCOREAT | 613-619 | (-) | GCCGACG |
| CGACGOSAMY3 | 613-617 | (-) | CGACG |
| TAAAGSTKST1 | 634-640 | (-) | GTTAAAG |
| MYBGAHV | 637-643 | (+) | TAACAAA |
| QELEMENTZMZM13 | 672-686 | (-) | TAGGTCAATGCCTCA |
| ELRECOREPCRP1 | 678-692 | (+) | ATTGACCTACCTTGG |
| MYBPZM | 683-688 | (+) | CCTACC |
| LTRECOREATCOR15 | 733-739 | (+) | CCCGACG |
| CGACGOSAMY3 | 735-739 | (+) | CGACG |
| CCAATBOX1 | 756-760 | (+) | CCAAT |

Example 18

PLACE Analysis for Zm.HRGP Promoter (SEQ ID NO: 11)

Based on the below given PLACE results are potential TATA box is localized at base pair 1,071 to base pair 1,077 of SEQ ID NO: 11. In consequence the 5' untranslated region starts at about base pair 1,112 and extends to base pair 1,182 of SEQ ID NO: 11. The sequence described by SEQ ID NO: 11 end just before the ATG start codon.

The following clusters of promoter elements were identified in the Zm.HRGP promoter as described by SEQ ID NO: 11:

| IUPAC | Position from-to | Str. | Sequence |
|---|---|---|---|
| ACGTCBOX | 30-35 | (+) | GACGTC |
| ACGTCBOX | 30-35 | (-) | GACGTC |
| CGACGOSAMY3 | 32-36 | (-) | CGACG |
| BOXIINTPATPB | 95-100 | (+) | ATAGAA |
| CGACGOSAMY3 | 138-142 | (+) | CGACG |
| HEXAMERATH4 | 138-143 | (-) | CCGTCG |
| MYBPZM | 146-151 | (+) | CCAACC |
| GT1CORE | 167-177 | (+) | CGGTTAAATAG |
| TATABOXOSPAL | 170-176 | (-) | TATTTAA |
| CGACGOSAMY3 | 179-183 | (+) | CGACG |
| HEXAMERATH4 | 179-184 | (-) | CCGTCG |
| MYCATERD1 | 223-229 | (-) | CATGTGC |
| MYCATRD22 | 224-230 | (+) | CACATGC |
| NTBBF1ARROLB | 238-244 | (+) | ACTTTAT |
| TAAAGSTKST1 | 239-245 | (-) | TATAAAG |
| TATABOX2 | 242-248 | (+) | TATAAAT |
| IBOXCORE | 276-282 | (-) | GATAATA |
| REBETALGLHCB21 | 291-297 | (+) | CGGATAG |
| IBOXCORE | 296-302 | (-) | GATAACT |
| IBOXCORE | 325-331 | (+) | GATAACT |
| NTBBF1ARROLB | 329-335 | (+) | ACTTTAT |
| TAAAGSTKST1 | 330-336 | (-) | TATAAAG |
| TATABOX2 | 333-339 | (+) | TATAAAT |
| GCCCORE | 358-364 | (-) | TGCCGCC |
| ABRELATERD1 | 366-378 | (-) | GCAGACGTGTGCG |
| BOXIINTPATPB | 409-414 | (+) | ATAGAA |
| LTRECOREATCOR15 | 429-435 | (+) | TCCGACC |
| ASF1MOTIFCAMV | 447-459 | (+) | GACATTGACGGAT |
| WBOXATNPR1 | 450-464 | (+) | ATTGACGGATCCAGA |
| ELRECOREPCRP1 | 466-480 | (-) | TTTGACCGGATCGCC |

-continued

| IUPAC | Position from-to | Str. | Sequence |
|---|---|---|---|
| CGACGOSAMY3 | 485-489 | (+) | CGACG |
| RAV1AAT | 537-541 | (-) | CAACA |
| TATABOX2 | 560-566 | (+) | TATAAAT |
| IBOXCORE | 595-601 | (-) | GATAATA |
| IBOXCORE | 615-621 | (-) | GATAACG |
| SV40COREENHAN | 643-650 | (-) | GTGGATCG |
| ABRELATERD1 | 644-656 | (-) | AACGACGTGGATC |
| CGACGOSAMY3 | 650-654 | (-) | CGACG |
| MYCATERD1 | 672-678 | (-) | CATGTGC |
| MYCATRD22 | 673-679 | (+) | CACATGG |
| AGCBOXNPGLB | 678-684 | (-) | AGCCGCC |
| DPBFCOREDCDC3 | 688-694 | (-) | ACACAAG |
| ABRELATERD1 | 744-756 | (+) | AATAACGTGAGTA |
| RAV1BAT | 791-803 | (+) | ATCCACCTGCTCC |
| MYBST1 | 823-829 | (-) | TGGATAG |
| AMYBOX2 | 824-830 | (+) | TATCCAT |
| TATCCAOSAMY | 824-830 | (+) | TATCCAT |
| WBOXATNPR1 | 829-843 | (-) | GTTGACGAATGGAAT |
| ASF1MOTIFCAMV | 834-846 | (-) | CATGTTGACGAAT |
| RAV1AAT | 840-844 | (+) | CAACA |
| RYREPEATBNNAPA | 841-851 | (+) | AACATGCAGGT |
| INTRONLOWER | 845-850 | (+) | TGCAGG |
| CCAATBOX1 | 895-899 | (+) | CCAAT |
| MYCATERD1 | 944-950 | (-) | CATGTGG |
| MYCATRD22 | 945-951 | (+) | CACATGG |
| HEXAMERATH4 | 1006-1011 | (+) | CCGTCG |
| CGACGOSAMY3 | 1007-1011 | (-) | CGACG |
| ASF1MOTIFCAMV | 1014-1026 | (-) | TCTCGTGACGCCC |
| TATABOX4 | 1071-1077 | (+) | TATATAA |
| CCAATBOX1 | 1121-1125 | (-) | CCAAT |
| MYBPZM | 1136-1141 | (+) | CCAACC |
| MYB2AT | 1152-1162 | (-) | TCAGTAACTGC |

Example 19

PLACE Analysis for Zm.LDH Promoter (SEQ ID NO: 19)

Based on the below given PLACE results are potential TATA box is localized at base pair 906 to base pair 912 of SEQ ID NO: 19. In consequence the 5' untranslated region starts at bout base pair 947 and extends to base pair 1,060 of SEQ ID NO: 19. The sequence described by SEQ ID NO: 19 ends 31 base pairs before the ATG start codon.

The following clusters of promoter elements were identified in the Zm.LDH promoter as described by SEQ ID NO: 19.

| IUPAC | Position from-to | Str. | Sequence |
|---|---|---|---|
| TATABOX4 | 15-21 | (-) | TATATAA |
| 5256BOXLELAT5256 | 16-27 | (-) | TGTGGTTATATA |
| TATABOX4 | 16-22 | (+) | TATATAA |
| MYB1AT | 20-25 | (+) | TAACCA |
| ASF1MOTIFCAMV | 39-51 | (-) | AATAATGACGCAG |
| MYB1AT | 93-98 | (+) | AAACCA |
| AACACOREOSGLUB1 | 114-120 | (-) | AACAAAC |
| LTRE1HVBLT49 | 119-124 | (-) | CCGAAA |
| REALPHALGLHCB21 | 144-154 | (-) | AACCAACGATA |
| WBOXHVISO1 | 172-186 | (-) | GATGACTCGTACGGC |
| IBOXCORE | 201-207 | (-) | GATAAAA |
| DRE2COREZMRAB17 | 208-214 | (+) | ACCGACT |
| RAV1AAT | 238-242 | (+) | CAACA |
| ASF1MOTIFCAMV | 254-266 | (-) | GTTCGTGACGCTT |
| TAAAGSTKST1 | 339-345 | (+) | ATTAAAG |
| NTBBF1ARROLB | 340-346 | (-) | ACTTTAA |
| RAV1AAT | 361-365 | (+) | CAACA |
| CATATGGMSAUR | 378-383 | (+) | CATATG |
| CATATGGMSAUR | 378-383 | (-) | CATATG |
| -10PEHVPSBD | 397-402 | (-) | TATTCT |
| TAAAGSTKST1 | 419-425 | (+) | GTTAAAG |
| RAV1AAT | 435-439 | (-) | CAACA |
| CAREOSREP1 | 448-453 | (-) | CAACTC |
| CGACGOSAMY3 | 456-460 | (+) | CGACG |
| IBOXCORE | 476-482 | (+) | GATAAAA |
| TBOXATGAPB | 489-494 | (-) | ACTTTG |
| IBOXCORE | 561-567 | (+) | GATAAAA |
| TATABOXOSPAL | 574-580 | (+) | TATTTAA |
| TATABOXOSPAL | 583-589 | (-) | TATTTAA |
| GT1CORE | 597-607 | (-) | AGGTTAAAACT |
| S1FBOXSORPS1L21 | 667-672 | (+) | ATGGTA |
| PROLAMINBOXOSGLUB1 | 678-686 | (+) | TGCAAAGAG |
| MYB2AT | 732-742 | (+) | TGGGTAACTGT |
| WBOXATNPR1 | 735-749 | (-) | GTTGACGACAGTTAC |
| ASF1MOTIFCAMV | 740-752 | (-) | CCGGTTGACGACA |

| IUPAC | Position from-to | Str. | Sequence |
|---|---|---|---|
| CCA1ATLHCB1 | 810-817 | (-) | AAAAATCT |
| GT1CORE | 831-841 | (-) | TGGTTAAAATT |
| MYB1AT | 836-841 | (+) | TAACCA |
| SV40COREENHAN | 861-868 | (+) | GTGGTTTG |
| MYB1AT | 862-867 | (-) | AAACCA |
| TATABOX3 | 890-896 | (+) | TATTAAT |
| WUSATAg | 892-898 | (+) | TTAATGG |
| TATAPVTRNALEU | 902-914 | (-) | CTTTATATATTCA |
| TATABOX4 | 906-912 | (+) | TATATAA |
| TAAAGSTKST1 | 908-914 | (+) | TATAAAG |
| BOXCPSAS1 | 937-943 | (+) | CTCCCAC |
| OCTAMERMOTIFTAH3H4 | 998-1005 | (-) | CGCGGATC |
| ELRECOREPCRP1 | 1010-1024 | (+) | TTTGACCCAACCAGA |
| MYBPZM | 1016-1021 | (+) | CCAACC |
| CIACADIANLELHC | 1017-1026 | (+) | CAACCAGATC |
| ABRELATERD1 | 1031-1043 | (-) | GATTACGTGTGTG |
| DPBFCOREDCDC3 | 1032-1038 | (+) | ACACACG |

Example 20

PLACE Analysis for Os.Cp12 Promoter (SEQ ID NO: 27)

Based on the below given PLACE results are potential TATA box is localized at base pair 908 to base pair 914 of SEQ ID NO:27. In consequence the 5' untranslated region starts at about base pair 960 and extends to base pair 998 of SEQ ID NO:27.

The following clusters of promoter elements were identified in the Os.Cp12 promoter as described by SEQ ID NO:27:

| IUPAC | Position from-to | Str. | Sequence |
|---|---|---|---|
| AMMORESIIUDCRNIA1 | 28-35 | (+) | GGAAGGGT |
| ABRELATERD1 | 57-69 | (+) | GAGGACGTGAGGC |
| LTRE1HVBLT49 | 88-93 | (-) | CCGAAA |
| -300ELEMENT | 96-104 | (+) | TGAAAATT |
| SEF1MOTIF | 108-116 | (-) | ATATTTAAA |
| TATABOXOSPAL | 109-115 | (-) | TATTTAA |
| WBOXATNPR1 | 173-187 | (-) | GTTGACTGGGCCTTA |
| MYB2AT | 213-223 | (+) | GCTGTAACTGG |
| RAV1AAT | 244-248 | (-) | CAACA |
| CIACADIANLELHC | 286-295 | (+) | CAAGGCCATC |
| MYB1AT | 296-301 | (-) | AAACCA |
| SV40COREENHAN | 310-317 | (-) | GTGGTAAG |
| CCAATBOX1 | 352-356 | (+) | CCAAT |
| -300ELEMENT | 362-370 | (-) | TGTAAAGTT |
| NTBBF1ARROLB | 363-369 | (+) | ACTTTAC |
| -300CORE | 364-370 | (-) | TGTAAAG |
| TAAAGSTKST1 | 364-370 | (-) | TGTAAAG |
| CCAATBOX1 | 392-396 | (-) | CCAAT |
| -300ELEMENT | 403-411 | (+) | TGAAAATA |
| RAV1BAT | 443-455 | (+) | CTGCACCTGTACA |
| MYBPLANT | 519-529 | (+) | CACCAAACTTT |
| EVENINGAT | 543-551 | (-) | AAAATATCT |
| LTRE1HVBLT49 | 557-562 | (+) | CCGAAA |
| RAV1AAT | 620-624 | (+) | CAACA |
| MYBST1 | 645-651 | (-) | TGGATAC |
| TATCCAOSAMY | 646-652 | (+) | TATCCAA |
| MYBPZM | 649-654 | (+) | CCAACC |
| WBOXHVISO1 | 676-690 | (-) | GATGACTGTGGGTGT |
| ELRECOREPCRP1 | 698-712 | (-) | TTTGACCGTGAAAAC |
| ABREAZMRAB28 | 807-819 | (-) | TGCCACGTGGGCT |
| GBOXLERBCS | 808-820 | (+) | GCCCACGTGGCAC |
| UPRMOTIFIIAT | 813-831 | (-) | CCAATCGTCGTGTGCCACG |
| CGACGOSAMY3 | 822-826 | (+) | CGACG |
| CCAATBOX1 | 827-831 | (-) | CCAAT |
| IBOXCORENT | 842-848 | (+) | GATAAGA |
| ABRELATERD1 | 853-865 | (-) | GACGACGTGCACT |
| CGACGOSAMY3 | 859-863 | (-) | CGACG |
| CGACGOSAMY3 | 862-866 | (-) | CGACG |
| UPRMOTIFIIAT | 879-897 | (+) | CCTTCTCCCCCACCCCACG |
| TATAPVTRNALEU | 904-916 | (-) | GTTTATATATATA |
| TATABOX4 | 908-914 | (+) | TATATAA |
| CGACGOSAMY3 | 948-952 | (-) | CGACG |
| RAV1AAT | 953-957 | (+) | CAACA |
| RAV1AAT | 994-998 | (+) | CAACA |

Example 21

Vector Construction for Overexpression and Gene "Knockout" Experiments 21.1 Overexpression Vectors used for expression of full-length "candidate genes" of interest in plants (overexpression) are designed to overexpress the protein of interest and are of two general types, biolistic and binary, depending on the plant transformation method to be used.

For biolistic transformation (biolistic vectors), the requirements are as follows:
1. a backbone with a bacterial selectable marker (typically, an antibiotic resistance gene) and origin of replication functional in *Escherichia coli* (*E. coli*; e.g., ColE1), and
2. a plant-specific portion consisting of:
    a. a gene expression cassette consisting of a promoter (e.g. ZmUBIint MOD), the gene of interest (typically, a full-length cDNA) and a transcriptional terminator (e.g., *Agrobacterium tumefaciens* nos terminator);
    b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:
1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by *A. tumefaciens* right and left border sequences which mediate transfer of the DNA flanked by these two sequences to the plant.

21.2 Gene Silencing Vectors

Vectors designed for reducing or abolishing expression of a single gene or of a family or related genes (gene silencing vectors) are also of two general types corresponding to the methodology used to downregulate gene expression: antisense or double-stranded RNA interference (dsRNAi).

(a) Anti-Sense

For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter; thus, mRNA will be made from the non-coding (antisense) strand in planta.

(b) dsRNAi

For dsRNAi vectors, a partial gene fragment (typically, 300 to 500 base pairs long) is used in the gene expression cassette, and is expressed in both the sense and antisense orientations, separated by a spacer region (typically, a plant intron, e.g. the OsSH1 intron 1, or a selectable marker, e.g. conferring kanamycin resistance). Vectors of this type are designed to form a double-stranded mRNA stem, resulting from the basepairing of the two complementary gene fragments in planta.

Biolistic or binary vectors designed for overexpression or knockout can vary in a number of different ways, including e.g. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzer et al., Nucleic Acid Res., 19:5081 (1991).
10. Bäumlein et al. Mol Gen Genet. 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110 (1989).
24. Bustos et al. (1989) Plant Cell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed. Ivermectin and Abamectin, Springer-Verlag, New York, 1989.
29. Chee et al. Plant Physiol., 91:1212 (1989).
30. Chen and Winans (1991) J. Bacteriol. 173: 1139-1144
31. Christensen A H, Quail P H (1996) Transgenic Res 5: 213-218.
32. Christou et al. Proc. Natl. Acad. Sci. USA, 86:7500 (1989).
33. Christou et al., Biotechnology, 9:957 (1991).
34. Christou et al., Plant Physiol., 87:671 (1988).
35. Chui et al. (1996) Curr Biol 6:325-330
36. Coe et al., In: Corn and Corn Improvement, Sprague et al. (eds.) pp. 81-258 (1988).
37. Corpet et al. Nucleic Acids Res., 16:10881 (1988).
38. Coxson et al., Biotropica, 24:121 (1992).
39. Crameri et al., Nature Biotech., 15:436 (1997).
40. Crameri et al., Nature, 391:288 (1998).
41. Crossway et al., BioTechniques, 4:320 (1986).
42. Cuozzo et al., Bio/Technology, 6:549 (1988).
43. Cutler et al., J. Plant Physiol., 135:351 (1989).
44. Czapla and Lang, J. Econ. Entomol., 83:2480 (1990).
45. Datta et al., Bio/Technology, 8:736 (1990).
46. Davies et al., Plant Physiol., 93:588 (1990).
47. Dayhoff et al., Atlas of Protein Sequence and Structure, Natl. Biomed. Res. Found., Washington, D.C. (1978).
48. De Blaere et al., Meth. Enzymol., 143:277 (1987).
49. De Block et al. Plant Physiol., 91:694 (1989).
50. De Block et al., EMBO Journal, 6:2513 (1987).
51. Deblaere et al. Nucl Acids Res 13:4777-4788 (1985)

52. Della-Cioppa et al. Bio/Technology 5:579-584 (1987)
53. Della-Cioppa et al., Plant Physiology, 84:965-968 (1987).
54. Dellaporta et al., in Chromosome Structure and Function, Plenum Press, 263-282 (1988).
55. Depicker et al., Plant Cell Reports, 7:63 (1988).
56. Dunn et al., Can. J. Plant Sci., 61:583 (1981).
57. Dure et al., Plant Mol. Biol., 12:475 (1989).
58. Ebinuma et al. Proc Natl Acad Sci USA 94:2117-2121 (2000a)
59. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b)
60. Eichholtz et al. Somatic Cell and Molecular Genetics 13, 67-76 (1987)
61. Ellis et al., EMBO Journal, 6:3203 (1987).
62. Elroy-Stein et al., Proc. Natl. Acad. Sci. U.S.A., 86:6126 (1989).
63. English et al., Plant Cell, 8:179 (1996).
64. Erdmann et al., J. Gen. Microbiol., 138:363 (1992).
65. Erikson et al. Nat. Biotechnol. 22(4):455-8 (2004)
66. Everett et al., Bio/Technology, 5:1201 (1987).
67. Fedoroff & Smith Plant J 3:273-289 (1993)
68. Fire et al., Nature 391:806-811 (1998)
69. Fitzpatrick, Gen. Engineering News, 22:7 (1993).
70. Fraley et al. Proc Natl Acad Sci USA 80:4803 (1983)
71. Fromm et al., Bio/Technology, 8:833 (1990).
72. Fromm et al., Nature (London), 319:791 (1986).
73. Galbiati et al. Funct. Integr Genozides 2000, 201:25-34
74. Gallie et al. Nucl Acids Res 15:8693-8711 (1987)
75. Gallie et al., Nucleic Acids Res., 15:3257 (1987).
76. Gallie et al., The Plant Cell, 1:301 (1989).
77. Gan et al., Science, 270:1986 (1995).
78. Gatehouse et al., J. Sci. Food Agric., 35:373 (1984).
79. Gelfand, eds., PCR Strategies Academic Press, New York (1995).
80. Gelvin et al., Plant Molecular Biology Manual, (1990).
81. Gleave et al. Plant Mol. Biol. 40(2):223-35 (1999)
82. Gordon-Kamm et al., Plant Cell, 2:603 (1990).
83. Goring et al, PNAS, 88:1770 (1991).
84. Gruber et al., Vectors for Plant Transformation, in: Methods in Plant Molecular Biology & Biotechnology" in Glich et al., (Eds. pp. 89-119, CRC Press, 1993).
85. Guerineau et al., Mol. Gen. Genet., 262:141 (1991).
86. Guerrero et al., Plant Mol. Biol., 15:11 (1990).
87. Gupta et al., PNAS, 90:1629 (1993).
88. Haines and Higgins (eds.), Nucleic Acid Hybridization, IRL Press, Oxford, U.K.
89. Hajdukiewicz et al. Plant Mol Biol 25:989-994 (1994)
90. Hammock et al., Nature, 344:458 (1990).
91. Hansen et al., Proc. Natl. Acad. Sci. USA 91:7603-7607 (1994)
92. Hayford et al., Plant Physiol. 86:1216 (1988)
93. Hemenway et al., EMBO Journal, 7:1273 (1988).
94. Henikoff & Henikoff, Proc. Natl. Acad. Sci. USA, 89:10915 (1989).
95. Hiei et al., Plant J 6: 271-282 (1994)
96. Higgins et al., Gene, 73:237 (1988).
97. Higo et al., Nucl Acids Res 27(1): 297-300 (1999).
98. Hilder et al., Nature, 330:160 (1987).
99. Hille et al., Plant Mol. Biol. 7:171 (1986)
100. Hinchee et al., Bio/Technology 6:915 (1988).
101. Hoekema et al., Nature 303:179-181 (1983).
102. Hoekema, In: The Binary Plant Vector System. Offset-drukkerij Kanters B. V.; Alblasserdam (1985).
103. Hood et al. J Bacteriol 168:1291-1301 (1986)
104. Huang et al., CABIOS, 8:155 (1992).
105. Ikeda et al., J. Bacteriol., 169:5612 (1987).
106. Ikuta et al., Biotech., 8:241 (1990).
107. Ingelbrecht et al., Plant Cell, 1:671 (1989).
108. Innis and Gelfand, eds., PCR Methods Manual (Academic Press, New York) (1999).
109. Innis et al., eds., PCR Protocols: A Guide to Methods and Applications (Academic Press, New York (1995).
110. Innis et al., PCR Protocols: A Guide to Methods and Applications, Academic Press, Inc., San Diego, Calif. (1990).
111. Ishida et al., Nature Biotech 745-750 (1996).
112. Jefferson et al., EMBO J. 6:3901-3907 (1987).
113. Jefferson et al., Plant Mol Biol Rep 5:387-405 (1987).
114. Jenes et al., Techniques for Gene Transfer, in: Recombinant Plants, Vol. 1, Engineering and Utilization, edited by S D Kung and R Wu, Academic Press, pp. 128-143 (1993).
115. Jobling et al., Nature, 325:622 (1987).
116. Johnson et al., PNAS USA, 86:9871 (1989).
117. Jones et al., Mol. Gen. Genet., 210:86 (1987).
118. Joshi et al., Nucleic Acid Res., 15:9627 (1987).
119. Kaasen et al., J. Bacteriol., 174:889 (1992).
120. Karlin and Altschul, Proc. Natl. Acad. Sci. USA, 87:2264 (1990).
121. Karlin and Altschul, Proc. Natl. Acad. Sci. USA, 90:5873 (1993).
122. Karsten et al., Botanica Marina, 35:11 (1992).
123. Katz et al., J. Gen. Microbiol., 129:2703 (1983).
124. Keller et al., EMBO Journal, 8:1309 (1989).
125. Keller et al., Genes Dev., 3:1639 (1989).
126. Klapwijk et al., J. Bacteriol., 141, 128-136 (1980.)
127. Klein et al., Bio/Technology, 6:559 (1988).
128. Klein et al., Plant Physiol., 91:440 (1988).
129. Klein et al., Proc. Natl. Acad. Sci. USA, 85:4305 (1988).
130. Knauf et al., Genetic Analysis of Host Range Expression by *Agrobacterium* In: Molecular Genetics of the Bacteria-Plant Interaction, Puhler, A. ed., Springer-Verlag, New York, 1983.
131. Koncz & Schell Mol Gen Genet. 204:383-396 (1986)
132. Koprek et al., Plant J 19(6): 719-726 (1999)
133. Koster and Leopold, Plant Physiol., 88:829 (1988).
134. Koziel et al., Biotechnology, 11:194 (1993).
135. Kunkel et al., Methods in Enzymol., 154:367 (1987).
136. Kunkel, Proc. Natl. Acad. Sci. USA, 82:488 (1985).
137. Lam and Chua, J Biol Chem; 266(26):17131-17135 (1991)
138. Laufs et al., PNAS, 87:7752 (1990).
139. Lawton et al., Mol. Cell. Biol., 7:335 (1987).
140. Lee and Saier, J. Bacteriol., 153 (1982).
141. Leffel et al. Biotechniques 23(5):912-8 (1997)
142. Lescot et al., Nucleic Acids Res 30(1):325-7 (2002)
143. Levings, Science, 250:942 (1990).
144. Li et al. Plant Mol Biol 20:1037-1048 (1992)
145. Lindsey et al., Transgenic Research, 2:3347 (1993).
146. Liu et al., Plant J. 8, 457-463 (1995)
147. Lommel et al., Virology, 181:382 (1991).
148. Loomis et al., J. Expt. Zool., 252:9 (1989).
149. Lorz et al., Mol. Gen. Genet., 199:178 (1985).
150. Ma et al., Nature, 334:631 (1988).
151. Macejak et al., Nature, 353:90 (1991).
152. Maki et al., Methods in Plant Mol. Biol. & Biotechn., Glich et al., 67-88 CRC Press, (1993).
153. Maniatis et al., Molecular Cloning: A Laboratory Manual, Cold Spring Harbor Laboratory, Cold Spring Harbor (N.Y.), (1989)
154. Mariani et al, Nature, 347:737 (1990).
155. Matzke et al. Plant Mol Biol 43:401-415 (2000).

156. McBride et al., PNAS USA, 91:7301 (1994).
157. McCabe et al., Bio/Technology, 6:923 (1988).
158. Meinkoth and Wahl, Anal. Biochem., 138:267 (1984).
159. Messing and Vierra, Gene, 19:259 (1982).
160. Michael et al., J. Mol. Biol., 26: 585 (1990). (im Text steht: Michael et al. 1994)
161. Millar et al., Plant Mol Biol Rep 10:324-414 (1992)
162. Mogen et al., Plant Cell, 2:1261 (1990).
163. Moore et al., J. Mol. Biol., 272:336 (1997).
164. Mozo & Hooykaas Plant Mol. Biol. 16:917-918 (1991).
165. Mundy and Chua, EMBO J., 7:2279 (1988).
166. Munroe et al., Gene, 91:151 (1990).
167. Murakami et al., Mol. Gen. Genet., 205:42 (1986).
168. Murata et al., FEBS Lett., 296:187 (1992).
169. Murdock et al., Phytochemistry, 29:85 (1990).
170. Murray et al., Nucleic Acids Res., 17:477 (1989).
171. Myers and Miller, CABIOS, 4:11 (1988).
172. Naested, Plant J 18:571-576 (1999).
173. Napoli et al., Plant Cell, 2:279 (1990).
174. Needleman and Wunsch, J. Mol. Biol., 48:443-453 (1970).
175. Nehra et al. Plant J. 5:285-297 (1994)
176. Niedz et al., Plant Cell Reports, 14:403 (1995).
177. Odell et al., Mol. Gen. Genet., 113:369 (1990).
178. Odell et al., Nature, 313:810 (1985).
179. Ohtsuka et al., J. Biol. Chem., 260:2605 (1985)
180. Olhoft et al. Plant Cell Rep 20: 706-711 (2001)
181. Ow et al., Science, 234:856 (1986).
182. Pacciotti et al., Bio/Technology, 3:241 (1985).
183. Park et al., J. Plant Biol., 38:365 (1985).
184. Paszkowski et al., EMBO J., 3:2717 (1984).
185. Pearson and Lipman, Proc. Natl. Acad. Sci., 85:2444 (1988).
186. Pearson et al., Meth. Mol. Biol., 24:307 (1994).
187. Perera et al. Plant Mol. Biol. 23(4): 793-799 (1993).
188. Perlak et al., Proc. Natl. Acad. Sci. USA, 88:3324 (1991).
189. Phillips et al., In Corn & Corn Improvement, 3rd Edition Sprague et al. (Eds. pp. 345-387) (1988).
190. Phi-Van et al., Mol. Cell. Biol., 10:2302 (1990).
191. Piatkowski et al., Plant Physiol., 94:1682 (1990).
192. Potrykus et al., Mol. Gen. Genet., 199:183 (1985).
193. Potrykus, Trends Biotech., 7:269 (1989).
194. Prasher et al., Biochem. Biophys. Res. Comm., 126: 1259 (1985).
195. Proudfoot, Cell, 64:671 (1991).
196. Reed et al., J. Gen. Microbiol., 130:1 (1984).
197. Riggs et al., Proc. Natl. Acad. Sci. USA, 83:5602 (1986).
198. Rossolini et al., Mol. Cell. Probes, 8:91 (1994).
199. Ruiz, Plant Cell, 10:937 (1998).
200. Sambrook et al., Molecular Cloning: A Laboratory Manual (2d ed., Cold Spring Harbor Laboratory Press, Plainview, N.Y.) (1989).
201. Sanfacon et al., Genes Dev., 5:141 (1991).
202. Sanford et al., Particulate Science and Technology, 5:27 (1987).
203. Scheeren-Groot et al. J. Bacteriol 176: 6418-6426 (1994).
204. Schenborn and Groskreutz Mol Biotechnol 13(1): 29-44 (1999).
205. Schlaman and Hooykaas Plant J 11:1377-1385 (1997).
206. Schoffl et al. Mol Gen Genetics 217(2-3):246-53 (1989).
207. Shagan et al., Plant Physiol., 101:1397 (1993).
208. Shah et al., Science 233: 478 (1986).
209. Shapiro, Mobile Genetic Elements, Academic Press, N.Y. (1983).
210. Shimamoto et al., Nature, 338:274 (1989).
211. Silhavy et al., Experiments with Gene Fusions, Cold Spring Harbor Laboratory Press, Cold Spring Harbor (N.Y.), (1984).
212. Skuzeski et al., Plant Molec. Biol. 15: 65-79 (1990).
213. Smith et al., Adv. Appl. Math., 2:482. (1981).
214. Smith et al., Mol. Gen. Genet., 224:447 (1990).
215. Spencer et al., Theor. Appl. Genet, 79:625 (1990). Spencer 1992 Referenz fehlt
216. Stalker et al., Science, 242:419 (1988).
217. Staub et al., EMBO J., 12:601 (1993).
218. Staub et al., Plant Cell, 4:39 (1992).
219. Steifel et al., The Plant Cell, 2:785 (1990).
220. Stemmer, Nature, 370:389 (1994).
221. Stemmer, Proc. Natl. Acad. Sci. USA, 91:10747 (1994).
222. Stief et al., Nature, 341:343 (1989).
223. Stougaard, Plant J 3:755-761 (1993)
224. Sukhapinda et al., Plant Mol. Biol., 8:209 (1987).
225. Sundaresan et al. Gene Develop 9: 1797-1810 (1995)
226. Sutcliffe, PNAS USA, 75:3737 (1978).
227. Svab et al., Plant Mol. Biol. 14:197 (1990)
228. Svab et al., Proc. Natl. Acad. Sci. USA, 87:8526 (1990).
229. Svab et al., Proc. Natl. Acad. Sci. USA, 90:913 (1993).
230. Tarczynski et al., PNAS USA, 89:2600 (1992).
231. Thillet et al., J. Biol. Chem., 263:12500 (1988).
232. Tijssen, Laboratory Techniques in Biochemistry and Molecular Biology-Hybridization with Nucleic Acid Probes, Elsevier, N.Y. (1993).
233. Tomes et al., Plant Cell, Tissue and Organ Culture: Fundamental Methods, Springer Verlag, Berlin (1995).
234. Tomic et al., NAR, 12:1656 (1990).
235. Turner et al., Molecular Biotechnology, 3:225 (1995).
236. Twell et al., Plant Physiol., 91:1270 (1989).
237. Ugaki et al., Nucl. Acids Res., 19:371 (1991).
238. Ulmasov et al., Plant Mol. Biol., 35:417 (1997).
239. Upender et al., Biotechniques, 18:29 (1995).
240. van der Krol et al., Plant Cell, 2:291 (1990).
241. Vanden Elzen et al., Plant Mol. Biol. 5:299 (1985)
242. Vasil et al. Bio/Technology, 10:667-674 (1992)
243. Vasil et al., Bio/Technology, 11:1153-1158 (1993)
244. Vasil et al., Mol. Microbiol., 3:371 (1989).
245. Vasil et al., Plant Physiol., 91:1575 (1989).
246. Vernon and Bohnert, EMBO J., 11:2077 (1992).
247. Walker and Gaastra, eds., Techniques in Molecular Biology, MacMillan Publishing Company, New York (1983).
248. Wan & Lemaux, Plant Physiol., 104:3748 (1994).
249. Wang et al., Mol. Cell. Biol., 12:3399 (1992).
250. Waterman, Introduction to Computational Biology: Maps, sequences and genomes. Chapman & Hall. London (1995).
251. Watrud et al., in Engineered Organisms and the Environment (1985).
252. Watson et al. J. Bacteriol 123, 255-264 (1975)
253. Watson et al., Corn: Chemistry and Technology (1987).
254. Weeks et al. Plant Physiol 102:1077-1084 (1993)
255. Weissinger et al., Annual Rev. Genet., 22:421 (1988).
256. White et al., Nucl Acids Res, 18, 1062 (1990).
257. Wingender et al., Nucleic Acids Res 29(1):281-3 (2001)
258. Wolter et al., EMBO Journal, 11:4685 (1992).
259. Wyn-Jones and Storey, Physiology and Biochemistry of Drought Resistance in Plants, Paleg et al. (eds.), pp. 171-204 (1981).
260. Yamaguchi-Shinozaki et al., Plant Cell Physiol., 33:217 (1992).
261. Zhang et al., Proc. Natl. Acad. Sci. USA, 94:4504 (1997).
262. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An expression cassette for regulating expression in a monocotyledonous plant, said expression cassette comprising:
   i) a promoter nucleotide sequence sharing at least 98% sequence identity to the nucleotide sequence of SEQ ID NO:1;
   ii) at least one nucleic acid sequence which is heterologous in relation to said promoter; and
   iii) a terminator comprising a nucleotide sequence sharing at least 98% sequence identity to the nucleotide sequence of SEQ ID NO:34;
   wherein the expression of the at least one nucleic acid sequence is constitutive.

2. The expression cassette of claim 1, further comprising the 5'-untranslated region of a plant expressed gene, or an intron from a plant expressed gene.

3. The expression cassette of claim 2, wherein the intron is from ubiquitin, actin, or alcohol dehydrogenase gene.

4. The expression cassette of claim 1, wherein the terminator comprises the nucleotide sequence of SEQ ID NO: 34.

5. A vector comprising the expression cassette of claim 1.

6. A transgenic host cell or non-human organism comprising:
   i) the expression cassette of claim 1; or
   ii) a vector comprising the expression cassette.

7. A transgenic plant comprising:
   i) the expression cassette of claim 1; or
   ii) a vector comprising the expression cassette.

8. A method for providing a transgenic expression cassette for heterologous expression in a monocotyledonous plant, said method comprising:
   I. isolating a promoter nucleotide sequence from a monocotyledonous plant, wherein the promoter nucleotide sequence shares at least 98% sequence identity to the nucleotide sequence of SEQ ID NO:1;
   II. functionally linking said promoter nucleotide sequence to another nucleotide sequence of interest, which is heterologous in relation to said promoter nucleotide sequence; and
   III. functionally linking said another nucleotide sequence of interest to a terminator comprising a nucleotide sequence sharing at least 98% sequence identity to the nucleotide sequence of SEQ ID NO:34.

9. The method of claim 8, wherein said terminator comprises the nucleotide sequence of SEQ ID NO: 34.

10. A cell culture, part, organ, tissue or transgenic propagation material derived from the non-human organisms of claim 6, wherein said cell culture, part, organ, tissue or transgenic propagation material comprises the expression cassette.

11. A method for the transgenic expression of a nucleic acid, said method comprising growing or culturing the non-human organisms of claim 6 or cell cultures, parts, organs, tissues or transgenic propagation material derived therefrom, wherein said cell cultures, parts, organs, tissues or transgenic propagation material comprise the expression cassette.

12. A method for identifying and/or isolating a sequence with constitutive expression activity, said method comprising:
   a) obtaining a polynucleotide sequence sharing at least 98% sequence identity with the nucleic acid sequence of SEQ ID NO:1;
   b) preparing an expression cassette comprising the polynucleotide operably linked to a reporter gene or marker and to a terminator sharing at least 98% sequence identity with the nucleic acid sequence of SEQ ID NO: 34;
   c) testing the expression cassette for constitutive expression; and
   d) identifying and/or isolating the polynucleotide with constitutive expression activity.

13. A method for directing expression in a monocotyledonous plant, said method comprising:
   I. introducing into a plant cell the expression cassette of claim 1,
   II. selecting a transgenic cell which comprises said expression cassette, and
   III. regenerating a plant from the transgenic cell, wherein the promoter nucleotide sequence directs constitutive expression of the nucleic acid sequence which is heterologous in relation to said promoter in the plant.

* * * * *

SEQUENCE LISTING

```
<160> NUMBER OF SEQ ID NOS: 107

<210> SEQ ID NO 1
<211> LENGTH: 1035
<212> TYPE: DNA
<213> ORGANISM: Oryza sativa
<220> FEATURE:
<221> NAME/KEY: promoter
<222> LOCATION: (1)..(1035)
<223> OTHER INFORMATION: transcription regulating sequence of caffeoyl
      CoA-O-methyltransferase gene including 5'-untranslated region
<220> FEATURE:
<221> NAME/KEY: misc_feature
<222> LOCATION: (692)..(992)
<223> OTHER INFORMATION: Potential core region of the promoter
      comprising clusters of promoter elements
<220> FEATURE:
<221> NAME/KEY: TATA_signal
<222> LOCATION: (952)..(958)
<220> FEATURE:
<221> NAME/KEY: 5'UTR
<222> LOCATION: (993)..(1035)
<223> OTHER INFORMATION: potential 5'-untranslated region

<400> SEQUENCE: 1
gcaactactg cacggtaaaa gtgataggaa tcggtcggaa acagtattaa tgtttttatt      60
atttttacaa aaacgaattg aaataattgg aaattttcat atttatatat taaactattc     120
agtatcaact tcaattcgac gtcaatagaa attagaaaag cataattata cacagtaata     180
ggcgttcaag atattattgt tattatttag ttttgtggaa atggtatcaa cgtgatcgga     240
aaattttgta catgttttca ccctgcggga tatctcaatt ccttctcctc cctctaccgc     300
catatcagca cacgttttag agcaccaatc ataacccata aatccgtggg ctactcactt     360
atttaattta tatgtgaatt cgtgacctga ctcactcaca tactatcaaa aatttgtctc     420
agtcacccat ctccttcttt cctggtccga taagggttta tcctacggtt cgacggttat     480
cacgatagtc gtgcggttac tgaggtatac cgtgatttaa aaatatgata aagttaccgc     540
aggttttaac tgcgcggttt ggtaaacctg ttcctcctca ccaaccttct cctccggtct     600
ccttatgtgt ctcaccgagg cgagccgccg cgagaccgca tggacgcggt ccacgcacct     660
ggcggtgcac ctcctcctcc ccggcgaaga agacgtggag gagagtaaat gagcaatcag     720
gcccacggcc caatcgccgt ccaccaccca ccaccctcag cgacccaaaa ccacctcacc     780
aacccaactc tgtaccgtac tgtacccgcc ctcccctccc actgacactc cgggcccacc     840
tgtcggcgcg actcttccac ggtcccttc tctcctcaga gattttttcc acgcatttt     900 taattttttt ttctgcagtt cacatgctct tctcccactc ttccgccgcg ctatataaac     960
cgcgcgaggc gtcgttgcct cgtcggcgaa gtcaatccgg cgatccccgg cgagcgagag    1020
atcgaagcaa gctgc                                                     1035

<210> SEQ ID NO 2
<211> LENGTH: 992
<212> TYPE: DNA
<213> ORGANISM: Oryza sativa
<220> FEATURE:
<221> NAME/KEY: promoter
<222> LOCATION: (1)..(992)
<223> OTHER INFORMATION: transcription regulating sequence from caffeoyl
```

```
        CoA-O-methyltransferase gene
<220> FEATURE:
<221> NAME/KEY: misc_feature
<222> LOCATION: (692)..(992)
<223> OTHER INFORMATION: Potential core region of the promoter
      comprising clusters of promoter elements
<220> FEATURE:
<221> NAME/KEY: TATA_signal
<222> LOCATION: (952)..(958)

<400> SEQUENCE: 2
gcaactactg cacggtaaaa gtgataggaa tcggtcggaa acagtattaa tgtttttatt      60
atttttacaa aaacgaattg aaataattgg aaattttcat atttatatat taaactattc     120
agtatcaact tcaattcgac gtcaatagaa attagaaaag cataattata cacagtaata     180
ggcgttcaag atattattgt tattatttag ttttgtggaa atggtatcaa cgtgatcgga     240
aaattttgta catgttttca ccctgcggga tatctcaatt ccttctcctc cctctaccgc     300
catatcagca cacgttttag agcaccaatc ataacccata aatccgtggg ctactcactt     360
atttaattta tatgtgaatt cgtgacctga ctcactcaca tactatcaaa aatttgtctc     420
agtcacccat ctccttcttt cctggtccga taagggttta tcctacggtt cgacggttat     480
cacgatagtc gtgcggttac tgaggtatac cgtgatttaa aaatatgata aagttaccgc     540
aggttttaac tgcgcggttt ggtaaacctg ttcctcctca ccaaccttct cctccggtct     600
ccttatgtgt ctcaccgagg cgagccgccg cgagaccgca tggacgcggt ccacgcacct     660
ggcggtgcac ctcctcctcc ccggcgaaga agacgtggag gagagtaaat gagcaatcag     720
gcccacggcc caatcgccgt ccaccaccca ccacccctcag cgacccaaaa ccacctcacc     780
aacccaactc tgtaccgtac tgtacccgcc ctcccctccc actgacactc cgggcccacc     840
tgtcggcgcg actcttccac ggtccccttc tctcctcaga gatttttttcc acgcatttttt     900 taattttttt ttctgcagtt cacatgctct tctcccactc ttccgccgcg ctatataaac     960
cgcgcgaggc gtcgttgcct cgtcggcgaa gt                                   992

<210> SEQ ID NO 3
<211> LENGTH: 301
<212> TYPE: DNA
<213> ORGANISM: Oryza sativa
<220> FEATURE:
<221> NAME/KEY: promoter
<222> LOCATION: (1)..(301)
<223> OTHER INFORMATION: Potential core region of the transcription
      regulating sequence of caffeoyl CoA-O-methyltransferase gene
      comprising clusters of promoter elements
<220> FEATURE:
<221> NAME/KEY: TATA_signal
<222> LOCATION: (260)..(266)

<400> SEQUENCE: 3
acgtggagga gagtaaatga gcaatcaggc ccacggccca atcgccgtcc accacccacc      60
accctcagcg acccaaaacc acctcaccaa cccaactctg taccgtactg tacccgccct     120
cccctcccac tgacactccg ggcccacctg tcggcgcgac tcttccacgg tccccttctc     180
tcctcagaga ttttttccac gcattttta atttttttt ctgcagttca catgctcttc     240
tcccactctt ccgccgcgct atataaaccg cgcgaggcgt cgttgcctcg tcggcgaagt     300
c                                                                     301

<210> SEQ ID NO 4
<211> LENGTH: 783
<212> TYPE: DNA
```

<213> ORGANISM: Oryza sativa
<220> FEATURE:
<221> NAME/KEY: CDS
<222> LOCATION: (1)..(780)
<223> OTHER INFORMATION: coding for caffeoyl CoA-O-methyltransferase

<400> SEQUENCE: 4

| | | | | | | | | | | | | | | | | |
|---|---|---|---|---|---|---|---|---|---|---|---|---|---|---|---|---|
| atg | gcc | gag | gcg | gcg | tcg | gcg | gcg | gcg | gcg | acg | acg | gag | cag | gcg | | 48 |
| Met | Ala | Glu | Ala | Ala | Ser | Ala | Ala | Ala | Ala | Thr | Thr | Glu | Gln | Ala | | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aat | ggg | agc | agc | ggc | ggc | gag | cag | aag | acg | cgg | cac | tcg | gag | gtc | ggc | 96 |
| Asn | Gly | Ser | Ser | Gly | Gly | Glu | Gln | Lys | Thr | Arg | His | Ser | Glu | Val | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| cac | aag | agc | ctc | ctc | aag | agc | gac | gat | ctc | tac | cag | tac | atc | ctc | gag | 144 |
| His | Lys | Ser | Leu | Leu | Lys | Ser | Asp | Asp | Leu | Tyr | Gln | Tyr | Ile | Leu | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| acg | agc | gtg | tac | ccg | cgc | gag | cac | gag | tgc | atg | aag | gag | ctc | cgc | gag | 192 |
| Thr | Ser | Val | Tyr | Pro | Arg | Glu | His | Glu | Cys | Met | Lys | Glu | Leu | Arg | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| gtc | acc | gcc | aac | cac | cca | tgg | aac | ctg | atg | acg | acg | tcg | gcg | gac | gag | 240 |
| Val | Thr | Ala | Asn | His | Pro | Trp | Asn | Leu | Met | Thr | Thr | Ser | Ala | Asp | Glu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggg | caa | ttc | ctg | aac | ctg | ctg | ctg | aag | ctc | atc | ggc | gcc | aag | aag | acc | 288 |
| Gly | Gln | Phe | Leu | Asn | Leu | Leu | Leu | Lys | Leu | Ile | Gly | Ala | Lys | Lys | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | gag | atc | ggc | gtc | tac | acc | ggc | tac | tcc | ctc | ctc | gcc | acc | gcc | ctc | 336 |
| Met | Glu | Ile | Gly | Val | Tyr | Thr | Gly | Tyr | Ser | Leu | Leu | Ala | Thr | Ala | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gcc | atc | ccc | gac | gac | ggc | acg | atc | ttg | gcg | atg | gac | atc | aac | cgg | gag | 384 |
| Ala | Ile | Pro | Asp | Asp | Gly | Thr | Ile | Leu | Ala | Met | Asp | Ile | Asn | Arg | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| aac | tac | gag | ctg | ggg | ctc | ccg | tcg | atc | gag | aag | gcg | gga | gtg | gcg | cac | 432 |
| Asn | Tyr | Glu | Leu | Gly | Leu | Pro | Ser | Ile | Glu | Lys | Ala | Gly | Val | Ala | His | |
| | 130 | | | | | 135 | | | | | 140 | | | | | |

| | | | | | | | | | | | | | | | | |
|---|---|---|---|---|---|---|---|---|---|---|---|---|---|---|---|---|
| aag | atc | gac | ttc | cgg | gag | gga | ccc | gcg | ctg | ccg | gtg | ctg | gac | cag | ctg | 480 |
| Lys | Ile | Asp | Phe | Arg | Glu | Gly | Pro | Ala | Leu | Pro | Val | Leu | Asp | Gln | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gtg | gag | gag | gag | ggc | aac | cat | ggg | tcg | ttc | gac | ttc | gtg | ttc | gtc | gac | 528 |
| Val | Glu | Glu | Glu | Gly | Asn | His | Gly | Ser | Phe | Asp | Phe | Val | Phe | Val | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| gcc | gac | aag | gac | aac | tac | ctc | aac | tac | cac | gag | cgg | ctg | atg | aag | ctg | 576 |
| Ala | Asp | Lys | Asp | Asn | Tyr | Leu | Asn | Tyr | His | Glu | Arg | Leu | Met | Lys | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | aag | gtc | ggc | ggc | ctc | gtc | ggc | tac | gac | aac | acg | ctc | tgg | aac | ggc | 624 |
| Val | Lys | Val | Gly | Gly | Leu | Val | Gly | Tyr | Asp | Asn | Thr | Leu | Trp | Asn | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | gtc | gtg | ctc | ccc | gcc | gac | gcc | ccc | atg | cgc | aag | tac | atc | cgc | tac | 672 |
| Ser | Val | Val | Leu | Pro | Ala | Asp | Ala | Pro | Met | Arg | Lys | Tyr | Ile | Arg | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| tac | cgc | gac | ttc | gtg | ctc | gag | ctc | aac | aag | gcc | ctc | gcc | gcc | gac | cac | 720 |
| Tyr | Arg | Asp | Phe | Val | Leu | Glu | Leu | Asn | Lys | Ala | Leu | Ala | Ala | Asp | His | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| cgc | gtc | gag | atc | tgc | cag | ctc | ccc | gtc | ggc | gac | ggc | atc | acc | ctc | tgc | 768 |
| Arg | Val | Glu | Ile | Cys | Gln | Leu | Pro | Val | Gly | Asp | Gly | Ile | Thr | Leu | Cys | |
| | | | | 245 | | | | | 250 | | | | | 255 | | |

| | | | | |
|---|---|---|---|---|
| cgc | cgc | gtc | aag | tga | 783 |
| Arg | Arg | Val | Lys | | |
| | | | 260 | | |

<210> SEQ ID NO 5
<211> LENGTH: 260

<212> TYPE: PRT
<213> ORGANISM: Oryza sativa

<400> SEQUENCE: 5

```
Met Ala Glu Ala Ala Ser Ala Ala Ala Ala Thr Thr Glu Gln Ala
1               5                   10                  15

Asn Gly Ser Gly Gly Glu Gln Lys Thr Arg His Ser Glu Val Gly
            20                  25                  30

His Lys Ser Leu Leu Lys Ser Asp Asp Leu Tyr Gln Tyr Ile Leu Glu
        35                  40                  45

Thr Ser Val Tyr Pro Arg Glu His Glu Cys Met Lys Glu Leu Arg Glu
    50                  55                  60

Val Thr Ala Asn His Pro Trp Asn Leu Met Thr Thr Ser Ala Asp Glu
65                  70                  75                  80

Gly Gln Phe Leu Asn Leu Leu Leu Lys Leu Ile Gly Ala Lys Lys Thr
                85                  90                  95

Met Glu Ile Gly Val Tyr Thr Gly Tyr Ser Leu Leu Ala Thr Ala Leu
            100                 105                 110

Ala Ile Pro Asp Asp Gly Thr Ile Leu Ala Met Asp Ile Asn Arg Glu
        115                 120                 125

Asn Tyr Glu Leu Gly Leu Pro Ser Ile Glu Lys Ala Gly Val Ala His
    130                 135                 140

Lys Ile Asp Phe Arg Glu Gly Pro Ala Leu Pro Val Leu Asp Gln Leu
145                 150                 155                 160

Val Glu Glu Glu Gly Asn His Gly Ser Phe Asp Phe Val Phe Val Asp
                165                 170                 175

Ala Asp Lys Asp Asn Tyr Leu Asn Tyr His Glu Arg Leu Met Lys Leu
            180                 185                 190

Val Lys Val Gly Gly Leu Val Gly Tyr Asp Asn Thr Leu Trp Asn Gly
        195                 200                 205

Ser Val Val Leu Pro Ala Asp Ala Pro Met Arg Lys Tyr Ile Arg Tyr
    210                 215                 220

Tyr Arg Asp Phe Val Leu Glu Leu Asn Lys Ala Leu Ala Ala Asp His
225                 230                 235                 240

Arg Val Glu Ile Cys Gln Leu Pro Val Gly Asp Gly Ile Thr Leu Cys
                245                 250                 255

Arg Arg Val Lys
            260
```

<210> SEQ ID NO 6
<211> LENGTH: 797
<212> TYPE: DNA
<213> ORGANISM: Oryza sativa
<220> FEATURE:
<221> NAME/KEY: promoter
<222> LOCATION: (1)..(797)
<223> OTHER INFORMATION: transcription regulating sequence of C8,7-
      sterol isomerase gene comprising 5'untranslated region
<220> FEATURE:
<221> NAME/KEY: promoter
<222> LOCATION: (1)..(766)
<223> OTHER INFORMATION: transcription regulating sequence of C8,7-
      sterol isomerase gene
<220> FEATURE:
<221> NAME/KEY: misc_feature
<222> LOCATION: (466)..(766)
<223> OTHER INFORMATION: potential core region of promoter comprising
      clusters of promoer elements
<220> FEATURE:
<221> NAME/KEY: 5'UTR
<222> LOCATION: (767)..(797)

<223> OTHER INFORMATION: potential 5'-UTR

<400> SEQUENCE: 6

| | | | | | |
|---|---|---|---|---|---|
| gcctcgattc | gaccgtgtaa | tggaatgaag | gtggtgggcc | cccaccccca | caagccactc | 60 |
| tccacacttt | ggtgttcctg | gtatgtcacc | tagaccaaca | actatgttaa | gccatatgtt | 120 |
| ccacagtgca | aaatctacaa | gaccacgata | caagtaggta | tggtggacta | ccacattttc | 180 |
| acttctcttt | cactttcccc | tctctctccc | ccctctcttc | ctttccccca | ccgcagagag | 240 |
| cctggcgcgc | ggagacggcg | acggcgccgg | accaagcagt | ggtggagcga | cggcagggcg | 300 |
| acagcgccga | gcggcgggat | gcgctcgccg | gcgcaccacc | cctcctctc | cccccgagc | 360 |
| ggcggggctg | ctcggagcag | cagggcggcg | gcggcatgtc | ggcggcgggc | agacgacttg | 420 |
| gagcgggaga | cggcgacggg | cggatgcgag | gcggcggtcg | gcgccctcct | ccctggagt | 480 |
| tcggctgctt | cgcccctct | cctctctcct | ctagcggtgg | tgtgggtccc | actgagctga | 540 |
| ggagggcgcg | cggttggacg | acgaggcaaa | ggaatactag | tcttcgcttt | tttgggttga | 600 |
| ggctgaatgc | cacgtcggcc | cattgtgaat | gccctttaac | aaaacaaggg | tttatggcta | 660 |
| tgggatctgg | ctgaggcatt | gacctacctt | ggtccttggc | agagagagag | agagactccc | 720 |
| cctcactcct | tccccgacga | cctgctcgat | ccgatccaat | cagctcctct | ccagtccaga | 780 |
| tcggaaggaa | gccagga | | | | | 797 |

<210> SEQ ID NO 7
<211> LENGTH: 766
<212> TYPE: DNA
<213> ORGANISM: Oryza sativa
<220> FEATURE:
<221> NAME/KEY: promoter
<222> LOCATION: (1)..(766)
<223> OTHER INFORMATION: transcription regulating sequence from C8,7-
   sterol isomerase gene
<220> FEATURE:
<221> NAME/KEY: misc_feature
<222> LOCATION: (466)..(766)
<223> OTHER INFORMATION: potential core region of promoter comprising
   clusters of promoer elements

<400> SEQUENCE: 7

| | | | | | |
|---|---|---|---|---|---|
| gcctcgattc | gaccgtgtaa | tggaatgaag | gtggtgggcc | cccaccccca | caagccactc | 60 |
| tccacacttt | ggtgttcctg | gtatgtcacc | tagaccaaca | actatgttaa | gccatatgtt | 120 |
| ccacagtgca | aaatctacaa | gaccacgata | caagtaggta | tggtggacta | ccacattttc | 180 |
| acttctcttt | cactttcccc | tctctctccc | ccctctcttc | ctttccccca | ccgcagagag | 240 |
| cctggcgcgc | ggagacggcg | acggcgccgg | accaagcagt | ggtggagcga | cggcagggcg | 300 |
| acagcgccga | gcggcgggat | gcgctcgccg | gcgcaccacc | cctcctctc | cccccgagc | 360 |
| ggcggggctg | ctcggagcag | cagggcggcg | gcggcatgtc | ggcggcgggc | agacgacttg | 420 |
| gagcgggaga | cggcgacggg | cggatgcgag | gcggcggtcg | gcgccctcct | ccctggagt | 480 |
| tcggctgctt | cgcccctct | cctctctcct | ctagcggtgg | tgtgggtccc | actgagctga | 540 |
| ggagggcgcg | cggttggacg | acgaggcaaa | ggaatactag | tcttcgcttt | tttgggttga | 600 |
| ggctgaatgc | cacgtcggcc | cattgtgaat | gccctttaac | aaaacaaggg | tttatggcta | 660 |
| tgggatctgg | ctgaggcatt | gacctacctt | ggtccttggc | agagagagag | agagactccc | 720 |
| cctcactcct | tccccgacga | cctgctcgat | ccgatccaat | cagctc | | 766 |

<210> SEQ ID NO 8
<211> LENGTH: 301

<212> TYPE: DNA
<213> ORGANISM: Oryza sativa
<220> FEATURE:
<221> NAME/KEY: promoter
<222> LOCATION: (1)..(301)
<223> OTHER INFORMATION: potential core region of promoter from C8,7-
sterol isomerase gene comprising clusters of promoer elements

<400> SEQUENCE: 8

```
ctcctcccct ggagttcggc tgcttcgccc cctctcctct ctcctctagc ggtggtgtgg      60
gtcccactga gctgaggagg gcgcgcggtt ggacgacgag gcaaaggaat actagtcttc     120
gcttttttgg gttgaggctg aatgccacgt cggcccattg tgaatgccct ttaacaaaac     180
aagggtttat ggctatggga tctggctgag gcattgacct accttggtcc ttggcagaga     240
gagagagaga ctccccctca ctccttcccc gacgacctgc tcgatccgat ccaatcagct     300
c                                                                     301
```

<210> SEQ ID NO 9
<211> LENGTH: 660
<212> TYPE: DNA
<213> ORGANISM: Oryza sativa
<220> FEATURE:
<221> NAME/KEY: CDS
<222> LOCATION: (1)..(657)
<223> OTHER INFORMATION: coding for C8,7-sterol isomerase

<400> SEQUENCE: 9

```
atg ggg cac ccc cac ccc cac cct tac gcg ccg gcg gag ctt cac ctc      48
Met Gly His Pro His Pro His Pro Tyr Ala Pro Ala Glu Leu His Leu
1               5                   10                  15 ccg ggc ttc gtg cct ctc caa ctg tcc cag gcc caa atc ctc gtg ccc      96
Pro Gly Phe Val Pro Leu Gln Leu Ser Gln Ala Gln Ile Leu Val Pro
            20                  25                  30 tac ctc gcc acc tcc ctc ttc ctc ctc ctc gcc gtc tgg ctc atc tcc     144
Tyr Leu Ala Thr Ser Leu Phe Leu Leu Leu Ala Val Trp Leu Ile Ser
        35                  40                  45 ggg aga tgc agt cgt agg ctt tcc gac acc gac cgc tgg ctc atg tgc     192
Gly Arg Cys Ser Arg Arg Leu Ser Asp Thr Asp Arg Trp Leu Met Cys
    50                  55                  60 tgg tgg gcc ttc acc ggc ctc acc cac att atc atc gag gga acc ttt     240
Trp Trp Ala Phe Thr Gly Leu Thr His Ile Ile Ile Glu Gly Thr Phe
65                  70                  75                  80 gtc ttt gct cct aat ttc ttc tcc aac caa aac cct tct tac ttc gat     288
Val Phe Ala Pro Asn Phe Phe Ser Asn Gln Asn Pro Ser Tyr Phe Asp
                85                  90                  95 gaa gtt tgg aaa gag tac agc aaa ggt gac tcc aga tat gtc gcc aga     336
Glu Val Trp Lys Glu Tyr Ser Lys Gly Asp Ser Arg Tyr Val Ala Arg
            100                 105                 110 gac cct gct act gtt aca gtt gaa gga att aca gct gtc ttg gaa ggc     384
Asp Pro Ala Thr Val Thr Val Glu Gly Ile Thr Ala Val Leu Glu Gly
        115                 120                 125 cct gct tca ctc ctt gct gtc tat gcc atc gca tcg ggc aag tcc tac     432
Pro Ala Ser Leu Leu Ala Val Tyr Ala Ile Ala Ser Gly Lys Ser Tyr
    130                 135                 140 agc cat atc ctc cag ttc act gtc tgt ctt ggt cag ctc tat gga tgc     480
Ser His Ile Leu Gln Phe Thr Val Cys Leu Gly Gln Leu Tyr Gly Cys
145                 150                 155                 160 ctg gtg tac ttt att aca gcc tac ttg gat ggc ttc aac ttc tgg act     528
Leu Val Tyr Phe Ile Thr Ala Tyr Leu Asp Gly Phe Asn Phe Trp Thr
                165                 170                 175 agc ccg ttc tac ttc tgg gct tat ttc att ggt gca aac agc tcg tgg     576
Ser Pro Phe Tyr Phe Trp Ala Tyr Phe Ile Gly Ala Asn Ser Ser Trp
```

```
Ser Pro Phe Tyr Phe Trp Ala Tyr Phe Ile Gly Ala Asn Ser Ser Trp
        180                 185                 190 gtt gtt ata cca act atg atc gcc ata agg agc tgg aag aag att tgt    624
Val Val Ile Pro Thr Met Ile Ala Ile Arg Ser Trp Lys Lys Ile Cys
        195                 200                 205 gca gca ttt caa ggt gaa aag gtg aag act aaa tag                    660
Ala Ala Phe Gln Gly Glu Lys Val Lys Thr Lys
        210                 215

<210> SEQ ID NO 10
<211> LENGTH: 219
<212> TYPE: PRT
<213> ORGANISM: Oryza sativa

<400> SEQUENCE: 10

Met Gly His Pro His Pro His Pro Tyr Ala Pro Ala Glu Leu His Leu
1               5                   10                  15

Pro Gly Phe Val Pro Leu Gln Leu Ser Gln Ala Gln Ile Leu Val Pro
            20                  25                  30

Tyr Leu Ala Thr Ser Leu Phe Leu Leu Ala Val Trp Leu Ile Ser
        35                  40                  45

Gly Arg Cys Ser Arg Arg Leu Ser Asp Thr Asp Arg Trp Leu Met Cys
50                  55                  60

Trp Trp Ala Phe Thr Gly Leu Thr His Ile Ile Ile Glu Gly Thr Phe
65                  70                  75                  80

Val Phe Ala Pro Asn Phe Phe Ser Asn Gln Asn Pro Ser Tyr Phe Asp
                85                  90                  95

Glu Val Trp Lys Glu Tyr Ser Lys Gly Asp Ser Arg Tyr Val Ala Arg
            100                 105                 110

Asp Pro Ala Thr Val Thr Val Glu Gly Ile Thr Ala Val Leu Glu Gly
        115                 120                 125

Pro Ala Ser Leu Leu Ala Val Tyr Ala Ile Ala Ser Gly Lys Ser Tyr
    130                 135                 140

Ser His Ile Leu Gln Phe Thr Val Cys Leu Gly Gln Leu Tyr Gly Cys
145                 150                 155                 160

Leu Val Tyr Phe Ile Thr Ala Tyr Leu Asp Gly Phe Asn Phe Trp Thr
                165                 170                 175

Ser Pro Phe Tyr Phe Trp Ala Tyr Phe Ile Gly Ala Asn Ser Ser Trp
            180                 185                 190

Val Val Ile Pro Thr Met Ile Ala Ile Arg Ser Trp Lys Lys Ile Cys
        195                 200                 205

Ala Ala Phe Gln Gly Glu Lys Val Lys Thr Lys
    210                 215

<210> SEQ ID NO 11
<211> LENGTH: 1182
<212> TYPE: DNA
<213> ORGANISM: Zea mays
<220> FEATURE:
<221> NAME/KEY: promoter
<222> LOCATION: (1)..(1182)
<223> OTHER INFORMATION: transcription regulating sequence from Zea mays
      hydroxyproline-rich glycoprotein (HRGP) gene including
      5'-untranslated region
<220> FEATURE:
<221> NAME/KEY: misc_feature
<222> LOCATION: (811)..(1111)
<223> OTHER INFORMATION: Potential core region of the promoter
      comprising clusters of promoter elements
<220> FEATURE:
<221> NAME/KEY: TATA_signal
```

<222> LOCATION: (1071)..(1077)
<220> FEATURE:
<221> NAME/KEY: 5'UTR
<222> LOCATION: (1112)..(1182)
<223> OTHER INFORMATION: Potential 5'UTR

<400> SEQUENCE: 11

| | | |
|---|---|---|
| ggtgaccttc ttgcttcttc gatcgtctgg acgtcgagga gccccgcggc agcgcacgcg | 60 | |
| tctgcaccgt tatggtggcc gcgctcgcga tggaatagaa ggggtaatga tggatccggc | 120 | |
| caggaaggcc acgacatcga cggatccaac cggcaagacg gcgatccggt taaatagacg | 180 | |
| acggatctag ctgggaaggt agactctaca ttaaatgagg ttgcacatgc cctaataact | 240 | |
| ttataaatct aatttattca gaggcaaggt agtagtatta tctttcccaa cggatagtta | 300 | |
| tctgatctgc cgttcagctt gatcgataac tttataaatc taatttattc agaggccggc | 360 | |
| ggcagcgcac acgtctgcac cagtaatgtt agccgcgcct gtggcgtaat agaaggggta | 420 | |
| acgatggatc cgaccagaaa ggcctcgaca ttgacggatc cagacggcga tccggtcaaa | 480 | |
| gagacgacga atctagccga aaggtagat ctctcgagag agttcatatt aaatgatgtt | 540 | |
| gtacatgcca taataactct ataaatctaa tttattcata ggcgaaggta gtagtattat | 600 | |
| ctttcccagc ggatcgttat ctgatctgcc gttcagcttg atcgatccac gtcgtttgat | 660 | |
| ctcggcgagc agcacatggc ggctcttctt gtgtacaggt ctcactctct gctacttcag | 720 | |
| tgcaaggcgg agtgaatgca cacaataacg tgagtattgt gggaactact tgtagatgca | 780 | |
| aacgatgtaa atccacctgc tccaccaagt gcccgcccgg ctctatccat tccattcgtc | 840 | |
| aacatgcagg ttcagactgg cccgtgctgg accagtgagc ggtgccggtg aaccccaatg | 900 | |
| caagcgaagc gagtgaccat cggggaagcc tcccgtgctg ccccacatg gcttgcctga | 960 | |
| atgcctctct ctcgccgcag tgccctctct ctctcctcct cctctccgtc gaagggcgtc | 1020 | |
| acgagagccc agagggcatc cgaggccccc accccacccc ttcctccgtg tatataagca | 1080 | |
| gtggcagggt gagcgtctct cctcagacca ccactgcgcc attggccagc tagagccaac | 1140 | |
| cagaagagct tgcagttact gagagtgtgt gtgagagaga gg | 1182 | |

<210> SEQ ID NO 12
<211> LENGTH: 1111
<212> TYPE: DNA
<213> ORGANISM: Zea mays
<220> FEATURE:
<221> NAME/KEY: promoter
<222> LOCATION: (1)..(1111)
<223> OTHER INFORMATION: transcription regulating sequence from Zea mays hydroxyproline-rich glycoprotein (HRGP) gene
<220> FEATURE:
<221> NAME/KEY: TATA_signal
<222> LOCATION: (1071)..(1077)

<400> SEQUENCE: 12

| | | |
|---|---|---|
| ggtgaccttc ttgcttcttc gatcgtctgg acgtcgagga gccccgcggc agcgcacgcg | 60 | |
| tctgcaccgt tatggtggcc gcgctcgcga tggaatagaa ggggtaatga tggatccggc | 120 | |
| caggaaggcc acgacatcga cggatccaac cggcaagacg gcgatccggt taaatagacg | 180 | |
| acggatctag ctgggaaggt agactctaca ttaaatgagg ttgcacatgc cctaataact | 240 | |
| ttataaatct aatttattca gaggcaaggt agtagtatta tctttcccaa cggatagtta | 300 | |
| tctgatctgc cgttcagctt gatcgataac tttataaatc taatttattc agaggccggc | 360 | |
| ggcagcgcac acgtctgcac cagtaatgtt agccgcgcct gtggcgtaat agaaggggta | 420 | |
| acgatggatc cgaccagaaa ggcctcgaca ttgacggatc cagacggcga tccggtcaaa | 480 | |

```
gagacgacga atctagccga gaaggtagat ctctcgagag agttcatatt aaatgatgtt      540
gtacatgcca taataactct ataaatctaa tttattcata ggcgaaggta gtagtattat      600
ctttcccagc ggatcgttat ctgatctgcc gttcagcttg atcgatccac gtcgtttgat      660
ctcggcgagc agcacatggc ggctcttctt gtgtacaggt ctcactctct gctacttcag      720
tgcaaggcgg agtgaatgca cacaataacg tgagtattgt gggaactact tgtagatgca      780
aacgatgtaa atccacctgc tccaccaagt gcccgcccgg ctctatccat tccattcgtc      840
aacatgcagg ttcagactgg cccgtgctgg accagtgagc ggtgccggtg aaccccaatg      900
caagcgaagc gagtgaccat cggggaagcc tcccgtgctg cccccacatg gcttgcctga      960
atgcctctct ctcgccgcag tgccctctct ctctcctcct cctctccgtc gaagggcgtc     1020
acgagagccc agagggcatc cgaggccccc accccacccc ttcctccgtg tatataagca     1080
gtggcagggt gagcgtctct cctcagacca c                                     1111

<210> SEQ ID NO 13
<211> LENGTH: 301
<212> TYPE: DNA
<213> ORGANISM: Zea mays
<220> FEATURE:
<221> NAME/KEY: promoter
<222> LOCATION: (1)..(301)
<223> OTHER INFORMATION: Potential core region of the promoter from the
      Zea mays hydroxyproline-rich glycoprotein (HRGP) gene comprising
      clusters of promoter elements
<220> FEATURE:
<221> NAME/KEY: TATA_signal
<222> LOCATION: (261)..(267)

<400> SEQUENCE: 13
gcccgcccgg ctctatccat tccattcgtc aacatgcagg ttcagactgg cccgtgctgg       60
accagtgagc ggtgccggtg aaccccaatg caagcgaagc gagtgaccat cggggaagcc      120
tcccgtgctg cccccacatg gcttgcctga atgcctctct ctcgccgcag tgccctctct      180
ctctcctcct cctctccgtc gaagggcgtc acgagagccc agagggcatc cgaggccccc      240
accccacccc ttcctccgtg tatataagca gtggcagggt gagcgtctct cctcagacca      300
c                                                                      301

<210> SEQ ID NO 14
<211> LENGTH: 1270
<212> TYPE: DNA
<213> ORGANISM: Zea mays
<220> FEATURE:
<221> NAME/KEY: promoter
<222> LOCATION: (1)..(1270)
<223> OTHER INFORMATION: transcription regulating sequence from Zea mays
      hydroxyproline-rich glycoprotein (HRGP) gene including
      5'-untranslated region
<220> FEATURE:
<221> NAME/KEY: misc_feature
<222> LOCATION: (891)..(1191)
<223> OTHER INFORMATION: Potential core region of the promoter
      comprising clusters of promoter elements
<220> FEATURE:
<221> NAME/KEY: TATA_signal
<222> LOCATION: (1151)..(1157)
<220> FEATURE:
<221> NAME/KEY: 5'UTR
<222> LOCATION: (1192)..(1270)
<223> OTHER INFORMATION: potential 5'UTR

<400> SEQUENCE: 14
ggtgaccttc ttgcttcttc gatcgtctgg acgtcgagga gcccgcggca gcgcacgcgt       60
```

```
ctgcaccggt aatggtggtc gcgcccgcga cggaatagaa ggggtaacga tggatcgggc    120
caggaaggcc acgacatcga cggatccaac cggcaagacg gcgatctggt caaatagacg    180
acagatctag ctgggaaggt agatccctcg agagactcta tattaaatga ggttgtacat    240
gctctaataa ctctataaat ataatttatt cagaggcgaa ggtagtagcc cttgatgccg    300
agatagtcga agtcgaggtg gtcgtggtcg ggagacatgc ggcaatagcc tattattcgg    360
taggggtcga tgttcaagcg tcaatggtcg gctgggcgac ataaaaatta gcaccagggt    420
gaccttcttg cttcttcgat cgtctggaca tcgaggagcc cgtggcaacg cacgcgtctg    480
cacaggtaat ggtggtcgcg cacaggtaat ggcggaatag aagggggcaac gatggatccg    540 gccaggaagg tcacgacatc gacggatcca accggcaaga cggcgatccg gttaaataga    600
cgacggatct tgctggaaag gtagatccct cgagaaactc tatattaaat gaggttgtac    660 atacccctaat aactttataa atctaattta ttcagaggca aaggtagtaa gtattatctt    720
tcccagcgga tcgttatctg atctgccgtt cagcttgatc gatccacgtc gtttgatctc    780
gtcgagcagc acatggcggc acttcttgtg tacagggctc actctctgct acttcagtgc    840
aaggcggagt gaatgcgcac aataacgtga gtattgtggg aactacttgt agatgcaaac    900
gatgtaaatc cacctatgcc cgcccggctc tatccattcc attcgtcaac acgcaagttc    960
agactggacc agtgagcggt gccggtgaac ccagcccaag cgagtgacca tcggggaagc    1020
ctcccgtgct gcccccacat ggcttgcctg aatgcctctc gccgcagtgc cctctctcct    1080
cctctccgtc gaagggcgtc acgagagccc agagggcatc cgaggccccc accccacccc    1140
ttcctccgtg tatataagca gtggcagggt gagcgtctct cctcagacca ccactgcgcc    1200
attggccagc tagagccaac cagaagagct tgcagttact gagagtgtgt gtgagagaga    1260
ggatgggtgg                                                           1270
```

<210> SEQ ID NO 15
<211> LENGTH: 1191
<212> TYPE: DNA
<213> ORGANISM: Zea mays
<220> FEATURE:
<221> NAME/KEY: promoter
<222> LOCATION: (1)..(1191)
<223> OTHER INFORMATION: transcription regulating sequence from Zea mays
      hydroxyproline-rich glycoprotein (HRGP) gene
<220> FEATURE:
<221> NAME/KEY: misc_feature
<222> LOCATION: (891)..(1191)
<223> OTHER INFORMATION: Potential core region of the promoter
      comprising clusters of promoter elements
<220> FEATURE:
<221> NAME/KEY: TATA_signal
<222> LOCATION: (1151)..(1157)

<400> SEQUENCE: 15

```
ggtgaccttc ttgcttcttc gatcgtctgg acgtcgagga gcccgcggca gcgcacgcgt     60
ctgcaccggt aatggtggtc gcgcccgcga cggaatagaa ggggtaacga tggatcgggc    120
caggaaggcc acgacatcga cggatccaac cggcaagacg gcgatctggt caaatagacg    180
acagatctag ctgggaaggt agatccctcg agagactcta tattaaatga ggttgtacat    240
gctctaataa ctctataaat ataatttatt cagaggcgaa ggtagtagcc cttgatgccg    300
agatagtcga agtcgaggtg gtcgtggtcg ggagacatgc ggcaatagcc tattattcgg    360
taggggtcga tgttcaagcg tcaatggtcg gctgggcgac ataaaaatta gcaccagggt    420
gaccttcttg cttcttcgat cgtctggaca tcgaggagcc cgtggcaacg cacgcgtctg    480
```

```
cacaggtaat ggtggtcgcg cacaggtaat ggcggaatag aagggggcaac gatggatccg     540
gccaggaagg tcacgacatc gacggatcca accggcaaga cggcgatccg gttaaataga     600
cgacggatct tgctggaaag gtagatccct cgagaaactc tatattaaat gaggttgtac     660
atacccctaat aactttataa atctaattta ttcagaggca aaggtagtaa gtattatctt    720
tcccagcgga tcgttatctg atctgccgtt cagcttgatc gatccacgtc gtttgatctc    780
gtcgagcagc acatggcggc acttcttgtg tacagggctc actctctgct acttcagtgc    840
aaggcggagt gaatgcgcac aataacgtga gtattgtggg aactacttgt agatgcaaac    900
gatgtaaatc cacctatgcc cgcccggctc tatccattcc attcgtcaac acgcaagttc    960
agactggacc agtgagcggt gccggtgaac ccagcccaag cgagtgacca tcggggaagc   1020
ctcccgtgct gccccccacat ggcttgcctg aatgcctctc gccgcagtgc cctctctcct   1080
cctctccgtc gaagggcgtc acgagagccc agagggcatc cgaggcccc accccacccc    1140
ttcctccgtg tatataagca gtggcagggt gagcgtctct cctcagacca c             1191
```

<210> SEQ ID NO 16
<211> LENGTH: 301
<212> TYPE: DNA
<213> ORGANISM: Zea mays
<220> FEATURE:
<221> NAME/KEY: promoter
<222> LOCATION: (1)..(301)
<223> OTHER INFORMATION: Potential core region of the promoter from Zea mays hydroxyproline-rich glycoprotein (HRGP) gene comprising clusters of promoter elements
<220> FEATURE:
<221> NAME/KEY: TATA_signal
<222> LOCATION: (261)..(267)

<400> SEQUENCE: 16

```
agatgcaaac gatgtaaatc cacctatgcc cgcccggctc tatccattcc attcgtcaac      60
acgcaagttc agactggacc agtgagcggt gccggtgaac ccagcccaag cgagtgacca    120
tcggggaagc ctcccgtgct gccccccacat ggcttgcctg aatgcctctc gccgcagtgc   180
cctctctcct cctctccgtc gaagggcgtc acgagagccc agagggcatc cgaggcccc     240
accccacccc ttcctccgtg tatataagca gtggcagggt gagcgtctct cctcagacca   300
c                                                                    301
```

<210> SEQ ID NO 17
<211> LENGTH: 987
<212> TYPE: DNA
<213> ORGANISM: Zea mays
<220> FEATURE:
<221> NAME/KEY: CDS
<222> LOCATION: (1)..(984)
<223> OTHER INFORMATION: coding for Zea mays hydroxyproline-rich glycoprotein (HRGP)

<400> SEQUENCE: 17

```
atg ggt ggc agc ggc agg gct gct ctg ctg ctg gcc ctg gtg gtg gtg      48
Met Gly Gly Ser Gly Arg Ala Ala Leu Leu Leu Ala Leu Val Val Val
1               5                   10                  15 gcc gtg agc ctg gcc gtg gag atc cag gcc gac gcc ggg tac ggt tac      96
Ala Val Ser Leu Ala Val Glu Ile Gln Ala Asp Ala Gly Tyr Gly Tyr
            20                  25                  30 ggc ggc ggg tac acc ccg acg ccg acg ccg gcc acc ccg acc ccg aag     144
Gly Gly Gly Tyr Thr Pro Thr Pro Thr Pro Ala Thr Pro Thr Pro Lys
        35                  40                  45
```

```
ccc gag aag ccc ccc acc aag ggg ccg aag ccg gac aag ccg ccc aag      192
Pro Glu Lys Pro Pro Thr Lys Gly Pro Lys Pro Asp Lys Pro Pro Lys
    50                  55                  60 gag cac ggg ccc aag ccg gag aag ccg ccc aag gag cac aag ccg acg      240
Glu His Gly Pro Lys Pro Glu Lys Pro Pro Lys Glu His Lys Pro Thr
65                  70                  75                  80 ccg ccc acg tac acc ccg agc ccc aaa ccc acg ccg acg tac act          288
Pro Pro Thr Tyr Thr Pro Ser Pro Lys Pro Thr Pro Thr Tyr Thr
                85                  90                  95 ccc acc ccg acg ccc ccc aag ccg acg cca ccc aca tac act ccc gcc      336
Pro Thr Pro Thr Pro Pro Lys Pro Thr Pro Pro Thr Tyr Thr Pro Ala
                100                 105                 110 cct acg ccc cac aaa ccc aca cca aaa ccc act ccc act cct ccg acg      384
Pro Thr Pro His Lys Pro Thr Pro Lys Pro Thr Pro Thr Pro Pro Thr
        115                 120                 125 tac acc ccg acc ccc aag cct ccg aca cct aag ccg acc ccg acg          432
Tyr Thr Pro Thr Pro Lys Pro Pro Thr Pro Lys Pro Thr Pro Thr
        130                 135                 140 tac act cca agc ccc aaa cct ccg acg ccc aag ccg acc cca ccg acg      480
Tyr Thr Pro Ser Pro Lys Pro Pro Thr Pro Lys Pro Thr Pro Pro Thr
145                 150                 155                 160 tac acc cct tcc ccc aag cct ccg aca cct aag ccg acc ccg cct acg      528
Tyr Thr Pro Ser Pro Lys Pro Pro Thr Pro Lys Pro Thr Pro Pro Thr
                165                 170                 175 tac act cca agc cct aag cca ccg gct acc aag cct ccc acg ccc aag      576
Tyr Thr Pro Ser Pro Lys Pro Pro Ala Thr Lys Pro Pro Thr Pro Lys
                180                 185                 190 ccg acc ccg cca acg tac acc cct tcg cca aag cct ccg aca ccc aag      624
Pro Thr Pro Pro Thr Tyr Thr Pro Ser Pro Lys Pro Pro Thr Pro Lys
        195                 200                 205 ccg acc ccg ccg acg tac acc cct tct ccc aag cct ccg acg ccc aag      672
Pro Thr Pro Pro Thr Tyr Thr Pro Ser Pro Lys Pro Pro Thr Pro Lys
210                 215                 220 ccg acc ccg ccg acg tac act cca agc ccc aag cct ccc aca cac ccg      720
Pro Thr Pro Pro Thr Tyr Thr Pro Ser Pro Lys Pro Pro Thr His Pro
225                 230                 235                 240 acg ccc aag ccg acc cca ccg acg tac acc cct tcc cca aag cct ccg      768
Thr Pro Lys Pro Thr Pro Pro Thr Tyr Thr Pro Ser Pro Lys Pro Pro
            245                 250                 255 acg ccc aag ccg acc cca ccg acg tac acc cct tcc cca aag cct ccg      816
Thr Pro Lys Pro Thr Pro Pro Thr Tyr Thr Pro Ser Pro Lys Pro Pro
            260                 265                 270 aca ccc aag ccg acc cca ccg acg tac acc cct tcc cca aag cct ccg      864
Thr Pro Lys Pro Thr Pro Pro Thr Tyr Thr Pro Ser Pro Lys Pro Pro
        275                 280                 285 aca ccc aag ccg acc cca ccg acg tac act ccc aca ccg aag ccg ccg      912
Thr Pro Lys Pro Thr Pro Pro Thr Tyr Thr Pro Thr Pro Lys Pro Pro
        290                 295                 300 gcc acc aag ccg ccc acc tac act ccg acg ccg ccg gtg tct cac acc      960
Ala Thr Lys Pro Pro Thr Tyr Thr Pro Thr Pro Pro Val Ser His Thr
305                 310                 315                 320 ccc agc ccg ccg cca cca tac tac tag                                  987
Pro Ser Pro Pro Pro Pro Tyr Tyr
                325
```

<210> SEQ ID NO 18
<211> LENGTH: 328
<212> TYPE: PRT
<213> ORGANISM: Zea mays

<400> SEQUENCE: 18

```
Met Gly Gly Ser Gly Arg Ala Ala Leu Leu Ala Leu Val Val Val
1               5                   10                  15

Ala Val Ser Leu Ala Val Glu Ile Gln Ala Asp Ala Gly Tyr Gly Tyr
            20                  25                  30

Gly Gly Gly Tyr Thr Pro Thr Pro Thr Pro Ala Thr Pro Thr Pro Lys
            35                  40                  45

Pro Glu Lys Pro Pro Thr Lys Gly Pro Lys Pro Asp Lys Pro Pro Lys
        50                  55                  60

Glu His Gly Pro Lys Pro Glu Lys Pro Pro Lys Glu His Lys Pro Thr
65                  70                  75                  80

Pro Pro Thr Tyr Thr Pro Ser Pro Lys Pro Thr Pro Pro Thr Tyr Thr
                85                  90                  95

Pro Thr Pro Thr Pro Pro Lys Pro Thr Pro Pro Thr Tyr Thr Pro Ala
            100                 105                 110

Pro Thr Pro His Lys Pro Thr Pro Lys Pro Thr Pro Thr Pro Pro Thr
            115                 120                 125

Tyr Thr Pro Thr Pro Lys Pro Thr Pro Lys Pro Thr Pro Pro Thr
130                 135                 140

Tyr Thr Pro Ser Pro Lys Pro Thr Pro Lys Pro Thr Pro Pro Thr
145                 150                 155                 160

Tyr Thr Pro Ser Pro Lys Pro Thr Pro Lys Pro Thr Pro Pro Thr
                165                 170                 175

Tyr Thr Pro Ser Pro Lys Pro Ala Thr Lys Pro Pro Thr Pro Lys
                180                 185                 190

Pro Thr Pro Pro Thr Tyr Thr Pro Ser Pro Lys Pro Pro Thr Pro Lys
            195                 200                 205

Pro Thr Pro Pro Thr Tyr Thr Pro Ser Pro Lys Pro Pro Thr Pro Lys
210                 215                 220

Pro Thr Pro Pro Thr Tyr Thr Pro Ser Pro Lys Pro Pro Thr His Pro
225                 230                 235                 240

Thr Pro Lys Pro Thr Pro Pro Thr Tyr Thr Pro Ser Pro Lys Pro Pro
                245                 250                 255

Thr Pro Lys Pro Thr Pro Pro Thr Tyr Thr Pro Ser Pro Lys Pro Pro
                260                 265                 270

Thr Pro Lys Pro Thr Pro Pro Thr Tyr Thr Pro Ser Pro Lys Pro Pro
                275                 280                 285

Thr Pro Lys Pro Thr Pro Pro Thr Tyr Thr Pro Thr Pro Lys Pro Pro
                290                 295                 300

Ala Thr Lys Pro Pro Thr Tyr Thr Pro Thr Pro Val Ser His Thr
305                 310                 315                 320

Pro Ser Pro Pro Pro Tyr Tyr
                325
```

<210> SEQ ID NO 19
<211> LENGTH: 1060
<212> TYPE: DNA
<213> ORGANISM: Zea mays
<220> FEATURE:
<221> NAME/KEY: promoter
<222> LOCATION: (1)..(1060)
<223> OTHER INFORMATION: transcription regulating sequence from Zea mays
      lactate dehydrogenase gene including 5'-untranslated region
<220> FEATURE:
<221> NAME/KEY: misc_feature
<222> LOCATION: (646)..(946)
<223> OTHER INFORMATION: Potential core region of the promoter
      comprising clusters of promoter elements

```
<220> FEATURE:
<221> NAME/KEY: TATA_signal
<222> LOCATION: (906)..(912)
<220> FEATURE:
<221> NAME/KEY: 5'UTR
<222> LOCATION: (947)..(1060)
<223> OTHER INFORMATION: potential 5'UTR

<400> SEQUENCE: 19
aacaaatggc gtacttatat aaccacaatg tactggtgct gcgtcattat tttatactac    60
gcatatatta ttataagtag agaaagctca caaaaccatg cgcgcgcccc cctgtttgtt   120
tcggtcgcta attacaccct ttgtatcgtt ggttgatgat ggtctccacc ggccgtacga   180
gtcatcgatc gttgatttat ttttatcacc gacttgcacg cctttcgaac aaagacgcaa   240
caaaggaaag cgaaagcgtc acgaacgagg ttgttccctg acagttgttc gactaataca   300
actgcaagac actgaataag cagtaaaaat caatatagat taaagttaaa cgaacatgct   360
caacatcgaa tactactcat atgtgttatt attaagagaa taccaccaag gtagaaaagt   420
taaaggacct aaactgttgt gccgggagag ttgtgcgacg aacagatgta aatatgataa   480
aataagttca aagttcatat agatagcacg atcacactta gggctagttt gaagccataa   540
aaatggaaga gattaaatga gataaaattc acttatttaa tttttaaataa gaagagagtt   600
ttaacctcta attctctcca gtattttagc tcctaaacta gctcttacag cagtaaaaga   660
cccttgatgg tagcgtatgc aaagagaagg aactattcaa tgaattgttt ttttaatcac   720
tagtagtatg gtgggtaact gtcgtcaacc ggccctatct acttcagttt agtgaagcac   780
taaaccgcac cttggtatgt tcaaatttaa gattttttttt gaaacgaaac aattttaacc   840
agcggctcca aaccggtgaa gtggtttggt ctttggtgtg gggccagggt attaatggaa   900
ttgaatatat aaagagcagg gtggtggacc tttcccctcc cacgagtcga gtagccattg   960
cccattgcca ttccttcctt cctccacaga gaaatccgat ccgcggagat ttgacccaac  1020
cagatcatat cacacacgta atcccatccc attccgcccg                        1060

<210> SEQ ID NO 20
<211> LENGTH: 946
<212> TYPE: DNA
<213> ORGANISM: Zea mays
<220> FEATURE:
<221> NAME/KEY: promoter
<222> LOCATION: (1)..(946)
<223> OTHER INFORMATION: transcription regulating sequence from Zea mays
      lactate dehydrogenase gene
<220> FEATURE:
<221> NAME/KEY: misc_feature
<222> LOCATION: (646)..(946)
<223> OTHER INFORMATION: Potential core region of the promoter
      comprising clusters of promoter elements
<220> FEATURE:
<221> NAME/KEY: TATA_signal
<222> LOCATION: (906)..(912)

<400> SEQUENCE: 20
aacaaatggc gtacttatat aaccacaatg tactggtgct gcgtcattat tttatactac    60
gcatatatta ttataagtag agaaagctca caaaaccatg cgcgcgcccc cctgtttgtt   120
tcggtcgcta attacaccct ttgtatcgtt ggttgatgat ggtctccacc ggccgtacga   180
gtcatcgatc gttgatttat ttttatcacc gacttgcacg cctttcgaac aaagacgcaa   240
caaaggaaag cgaaagcgtc acgaacgagg ttgttccctg acagttgttc gactaataca   300
actgcaagac actgaataag cagtaaaaat caatatagat taaagttaaa cgaacatgct   360
```

| | | |
|---|---|---|
| caacatcgaa tactactcat atgtgttatt attaagagaa taccaccaag gtagaaaagt | 420 | |
| taaaggacct aaactgttgt gccgggagag ttgtgcgacg aacagatgta aatatgataa | 480 | |
| aataagttca aagttcatat agatagcacg atcacactta gggctagttt gaagccataa | 540 | |
| aaatggaaga gattaaatga gataaaattc acttatttaa ttttaaataa gaagagagtt | 600 | |
| ttaacctcta attctctcca gtattttagc tcctaaacta gctcttacag cagtaaaaga | 660 | |
| cccttgatgg tagcgtatgc aaagagaagg aactattcaa tgaattgttt ttttaatcac | 720 | |
| tagtagtatg gtgggtaact gtcgtcaacc ggccctatct acttcagttt agtgaagcac | 780 | |
| taaaccgcac cttggtatgt tcaaatttaa gattttttt gaaacgaaac aattttaacc | 840 | |
| agcggctcca aaccggtgaa gtggtttggt ctttggtgtg gggccagggt attaatggaa | 900 | |
| ttgaatatat aaagagcagg gtggtggacc tttcccctcc cacgag | 946 | |

<210> SEQ ID NO 21
<211> LENGTH: 301
<212> TYPE: DNA
<213> ORGANISM: Zea mays
<220> FEATURE:
<221> NAME/KEY: promoter
<222> LOCATION: (1)..(301)
<223> OTHER INFORMATION: Potential core region of the promoter from Zea mays lactate dehydrogenase gene comprising clusters of promoter elements
<220> FEATURE:
<221> NAME/KEY: TATA_signal
<222> LOCATION: (261)..(267)

<400> SEQUENCE: 21

| | | |
|---|---|---|
| tacagcagta aaagacccctt gatggtagcg tatgcaaaga gaaggaacta ttcaatgaat | 60 | |
| tgttttttta atcactagta gtatggtggg taactgtcgt caaccggccc tatctacttc | 120 | |
| agtttagtga agcactaaac cgcaccttgg tatgttcaaa tttaagatt ttttgaaac | 180 | |
| gaaacaattt taaccagcgg ctccaaaccg gtgaagtggt ttggtctttg gtgtggggcc | 240 | |
| agggtattaa tggaattgaa tatataaaga gcagggtggt ggacctttcc cctcccacga | 300 | |
| g | 301 | |

<210> SEQ ID NO 22
<211> LENGTH: 1093
<212> TYPE: DNA
<213> ORGANISM: Zea mays
<220> FEATURE:
<221> NAME/KEY: promoter
<222> LOCATION: (1)..(1093)
<223> OTHER INFORMATION: transcription regulating sequence from Zea mays lactate dehydrogenase gene including 5'-untranslated region
<220> FEATURE:
<221> NAME/KEY: misc_feature
<222> LOCATION: (648)..(1093)
<223> OTHER INFORMATION: Potential core region of the promoter comprising clusters of promoter elements
<220> FEATURE:
<221> NAME/KEY: TATA_signal
<222> LOCATION: (908)..(914)
<220> FEATURE:
<221> NAME/KEY: 5'UTR
<222> LOCATION: (949)..(1093)
<223> OTHER INFORMATION: potential 5'UTR

<400> SEQUENCE: 22

| | | |
|---|---|---|
| aacaaatggc gtacttatat aaccacaatg tactggtgct gcgtcattat tttatactac | 60 | |
| gcatatatta ttataagtag agaaagctca caaaaccatg cgcgcgcccc cctgtttgct | 120 | |
| ttcggtcgct aattacaccc tttgtatcgt tggttgatga tggtctccac cggccgtacg | 180 | |

```
agtcatcgat cgttgattta tttttatcac cgacttgcac gcctttcgaa caaagacgca    240
acaaaggaaa gcgaaagcac gaacgaggtt gttccctgac agttgggcga ctaatacaac    300
tgcaagacac tgaataagca gtaaaaatca atatagatta aagttaaacg aacatgctca    360
acatcgaata ctactcatat gtgttattat taagagaata ccaccaaggt agaaaagtta    420
aaggacctaa actgttgtgc cgggagagtt gtgcgacgaa cagatgtaaa tatgataaaa    480
taagttcaaa gttcatatag atagcacgat cacacttagg gctagtttga agccataaaa    540
atggaagaga ttaaatgaga taaaattcac ttatttaatt ttaaataaga agagagttttt   600 aacccctcta attctctcca gtattttagc tcctaaacta gctcttacag cagtaaaaga    660
cccttgatgg tagcgtatgc aaagagaagg aactattcaa tgaattgttt ttttaatcac    720
tagtagtatg gtgggtaacg tgttcgtcaa ccggccctat ctacttcagt ttagtgaagc    780
actaaaccgc accttggtat gttcaaattt aagatttttt ttgaaacgaa acaattttaa    840
ccagcggctc caaccggtg  aagtggtttg gtctttggtg tggggccagg gtattaatgg    900
aattgaatat ataaagagca gggtggtgga cctttcccca cccacgagtc gagtagccat    960
tgcccattgc cattccttcc ttcctccaca gagaaatccg atccgcggag atttgaccca   1020
accagatcat atcacacacg taatcccatc ccattccgcc cgcaacagca gcaccaccgg   1080
tgggaagaag aag                                                     1093
```

<210> SEQ ID NO 23
<211> LENGTH: 948
<212> TYPE: DNA
<213> ORGANISM: Zea mays
<220> FEATURE:
<221> NAME/KEY: promoter
<222> LOCATION: (1)..(948)
<223> OTHER INFORMATION: transcription regulating sequence from Zea mays
      lactate dehydrogenase gene
<220> FEATURE:
<221> NAME/KEY: misc_feature
<222> LOCATION: (648)..(948)
<223> OTHER INFORMATION: Potential core region of the promoter
      comprising clusters of promoter elements
<220> FEATURE:
<221> NAME/KEY: TATA_signal
<222> LOCATION: (908)..(914)

<400> SEQUENCE: 23

```
aacaaatggc gtacttatat aaccacaatg tactggtgct gcgtcattat tttatactac     60
gcatatatta ttataagtag agaaagctca caaaaccatg cgcgcgcccc cctgtttgct    120
ttcggtcgct aattacaccc tttgtatcgt tggttgatga tggtctccac cggccgtacg    180
agtcatcgat cgttgattta tttttatcac cgacttgcac gcctttcgaa caaagacgca    240
acaaaggaaa gcgaaagcac gaacgaggtt gttccctgac agttgggcga ctaatacaac    300
tgcaagacac tgaataagca gtaaaaatca atatagatta aagttaaacg aacatgctca    360
acatcgaata ctactcatat gtgttattat taagagaata ccaccaaggt agaaaagtta    420
aaggacctaa actgttgtgc cgggagagtt gtgcgacgaa cagatgtaaa tatgataaaa    480
taagttcaaa gttcatatag atagcacgat cacacttagg gctagtttga agccataaaa    540
atggaagaga ttaaatgaga taaaattcac ttatttaatt ttaaataaga agagagtttt    600
aacccctcta attctctcca gtattttagc tcctaaacta gctcttacag cagtaaaaga    660
cccttgatgg tagcgtatgc aaagagaagg aactattcaa tgaattgttt ttttaatcac    720
tagtagtatg gtgggtaacg tgttcgtcaa ccggccctat ctacttcagt ttagtgaagc    780
```

```
actaaaccgc accttggtat gttcaaattt aagattttt ttgaaacgaa acaattttaa    840
ccagcggctc caaaccggtg aagtggtttg gtctttggtg tggggccagg gtattaatgg    900
aattgaatat ataaagagca gggtggtgga cctttcccca cccacgag                 948
```

```
<210> SEQ ID NO 24
<211> LENGTH: 301
<212> TYPE: DNA
<213> ORGANISM: Zea mays
<220> FEATURE:
<221> NAME/KEY: misc_feature
<222> LOCATION: (1)..(301)
<223> OTHER INFORMATION: Potential core region of the promoter from Zea
      mays lactate dehydrogenase gene  comprising clusters of promoter
      elements
<220> FEATURE:
<221> NAME/KEY: TATA_signal
<222> LOCATION: (261)..(267)

<400> SEQUENCE: 24
```

```
cagcagtaaa agacccttga tggtagcgta tgcaaagaga aggaactatt caatgaattg    60
tttttttaat cactagtagt atggtgggta acgtgttcgt caaccggccc tatctacttc   120
agtttagtga agcactaaac cgcaccttgg tatgttcaaa tttaagattt tttttgaaac   180
gaaacaattt taaccagcgg ctccaaaccg gtgaagtggt ttggtctttg gtgtggggcc   240
agggtattaa tggaattgaa tatataaaga gcagggtggt ggaccttcc ccacccacga   300 g                                                                   301
```

```
<210> SEQ ID NO 25
<211> LENGTH: 1065
<212> TYPE: DNA
<213> ORGANISM: Zea mays
<220> FEATURE:
<221> NAME/KEY: CDS
<222> LOCATION: (1)..(1062)
<223> OTHER INFORMATION: coding for Zea mays lactate dehydrogenase

<400> SEQUENCE: 25
```

```
atg aag aag gcc act tcg ctc tcc gag ctg ggc ttc gac gcc ggc gac     48
Met Lys Lys Ala Thr Ser Leu Ser Glu Leu Gly Phe Asp Ala Gly Asp
1               5                   10                  15 gcg tcg tcg ggc ttc ttc cgc cct gtg tcc ggc gac tcg tcg acg ccg     96
Ala Ser Ser Gly Phe Phe Arg Pro Val Ser Gly Asp Ser Ser Thr Pro
            20                  25                  30 acg tcg cag cac cac cgg cgg agg ctg acc aag gtg tcg gtc atc ggc    144
Thr Ser Gln His His Arg Arg Arg Leu Thr Lys Val Ser Val Ile Gly
        35                  40                  45 gcg ggc aac gtg ggg atg gcc atc gcg cag acc atc ctc acg cgc gac    192
Ala Gly Asn Val Gly Met Ala Ile Ala Gln Thr Ile Leu Thr Arg Asp
    50                  55                  60 ctg gcc gac gag atc gcg ctg gtg gac gcg gtc ccg gac aag ctc cgc    240
Leu Ala Asp Glu Ile Ala Leu Val Asp Ala Val Pro Asp Lys Leu Arg
65                  70                  75                  80 ggg gag atg ctg gac ctg cag cac gcg gcg gcg ttc ctg ccg cgc acg    288
Gly Glu Met Leu Asp Leu Gln His Ala Ala Ala Phe Leu Pro Arg Thr
                85                  90                  95 cgc ctc gtg tcc ggc acc gac atg tcc gtg acc agg ggc tcg gac ctg    336
Arg Leu Val Ser Gly Thr Asp Met Ser Val Thr Arg Gly Ser Asp Leu
            100                 105                 110 gtc atc gtg acg gcc ggg gcg cgg cag atc cag ggc gag acg agg ctc    384
Val Ile Val Thr Ala Gly Ala Arg Gln Ile Gln Gly Glu Thr Arg Leu
        115                 120                 125
```

```
gac ctg ctc cag cgg aac gtg gcg ctg ttc cgc aag atc gtg ccg ccg       432
Asp Leu Leu Gln Arg Asn Val Ala Leu Phe Arg Lys Ile Val Pro Pro
    130                 135                 140 ctg gcg gag cag tcc cac gac gcg ctg ctc gtc gtg tcc aac ccc           480
Leu Ala Glu Gln Ser His Asp Ala Leu Leu Val Val Ser Asn Pro
145                 150                 155                 160 gtg gac gtg ctc acc tac gtc gcc tgg aag ctt tcg ggc ttc ccg gcc       528
Val Asp Val Leu Thr Tyr Val Ala Trp Lys Leu Ser Gly Phe Pro Ala
                165                 170                 175 agc cgc gtc atc gga tcc ggc acc aac ctc gac tcg tcc agg ttc agg       576
Ser Arg Val Ile Gly Ser Gly Thr Asn Leu Asp Ser Ser Arg Phe Arg
            180                 185                 190 ttc ctt ctc gcc gag cac ctc gac gtc aac gcc cag gac gta cag gcg       624
Phe Leu Leu Ala Glu His Leu Asp Val Asn Ala Gln Asp Val Gln Ala
        195                 200                 205 tac atg gtc ggc gag cac ggc gac agc tcg gtg gcg gtg tgg tcg agc       672
Tyr Met Val Gly Glu His Gly Asp Ser Ser Val Ala Val Trp Ser Ser
    210                 215                 220 gtg agc gtg gcg ggg atg ccg gtg ctc aag tcg ctg cag gag agc cac       720
Val Ser Val Ala Gly Met Pro Val Leu Lys Ser Leu Gln Glu Ser His
225                 230                 235                 240 cgc tgc ttc gac gag gag gcg ctg gag ggc atc cgc cgc gcc gtc gtc       768
Arg Cys Phe Asp Glu Glu Ala Leu Glu Gly Ile Arg Arg Ala Val Val
                245                 250                 255 gac agc gcc tac gag gtc atc agc ctc aag ggc tac acc tcc tgg gcc       816
Asp Ser Ala Tyr Glu Val Ile Ser Leu Lys Gly Tyr Thr Ser Trp Ala
            260                 265                 270 atc ggc tac tcc gtc gcc agc ctc gcc gcg tcg ctg ctc cgg gac cag       864
Ile Gly Tyr Ser Val Ala Ser Leu Ala Ala Ser Leu Leu Arg Asp Gln
        275                 280                 285 cgc cgc atc cac ccg gtc tcc gtc ctc gcc agg ggg ttc cac ggc atc       912
Arg Arg Ile His Pro Val Ser Val Leu Ala Arg Gly Phe His Gly Ile
    290                 295                 300 ccc gac gga acg acg tct tcc tca gcc tgc ccg cca cgt cgg ccg cgc       960
Pro Asp Gly Thr Thr Ser Ser Ser Ala Cys Pro Pro Arg Arg Pro Arg
305                 310                 315                 320 cgg cgt cca ggg cgt cgc gag atg gag ctc acc gag gag gag gcc aaa      1008
Arg Arg Pro Gly Arg Arg Glu Met Glu Leu Thr Glu Glu Glu Ala Lys
                325                 330                 335 cga ctg cgc cgc tcc gcc aag acc atc tgg gag aac tgc cag ctc ctc      1056
Arg Leu Arg Arg Ser Ala Lys Thr Ile Trp Glu Asn Cys Gln Leu Leu
            340                 345                 350 ggc ctc tga                                                          1065
Gly Leu <210> SEQ ID NO 26
<211> LENGTH: 354
<212> TYPE: PRT
<213> ORGANISM: Zea mays

<400> SEQUENCE: 26

Met Lys Lys Ala Thr Ser Leu Ser Glu Leu Gly Phe Asp Ala Gly Asp
1               5                   10                  15

Ala Ser Ser Gly Phe Phe Arg Pro Val Ser Gly Asp Ser Ser Thr Pro
            20                  25                  30

Thr Ser Gln His His Arg Arg Arg Leu Thr Lys Val Ser Val Ile Gly
        35                  40                  45

Ala Gly Asn Val Gly Met Ala Ile Ala Gln Thr Ile Leu Thr Arg Asp
    50                  55                  60
```

```
Leu Ala Asp Glu Ile Ala Leu Val Asp Ala Val Pro Asp Lys Leu Arg
 65                  70                  75                  80

Gly Glu Met Leu Asp Leu Gln His Ala Ala Phe Leu Pro Arg Thr
             85                  90                  95

Arg Leu Val Ser Gly Thr Asp Met Ser Val Thr Arg Gly Ser Asp Leu
            100                 105                 110

Val Ile Val Thr Ala Gly Ala Arg Gln Ile Gln Gly Glu Thr Arg Leu
            115                 120                 125

Asp Leu Leu Gln Arg Asn Val Ala Leu Phe Arg Lys Ile Val Pro Pro
            130                 135             140

Leu Ala Glu Gln Ser His Asp Ala Leu Leu Val Ser Asn Pro
145                 150                 155                 160

Val Asp Val Leu Thr Tyr Val Ala Trp Lys Leu Ser Gly Phe Pro Ala
                165                 170                 175

Ser Arg Val Ile Gly Ser Gly Thr Asn Leu Asp Ser Ser Arg Phe Arg
                180                 185                 190

Phe Leu Leu Ala Glu His Leu Asp Val Asn Ala Gln Asp Val Gln Ala
            195                 200                 205

Tyr Met Val Gly Glu His Gly Asp Ser Ser Val Ala Val Trp Ser Ser
210                 215                 220

Val Ser Val Ala Gly Met Pro Val Leu Lys Ser Leu Gln Glu Ser His
225                 230                 235                 240

Arg Cys Phe Asp Glu Glu Ala Leu Glu Gly Ile Arg Arg Ala Val Val
                245                 250                 255

Asp Ser Ala Tyr Glu Val Ile Ser Leu Lys Gly Tyr Thr Ser Trp Ala
            260                 265                 270

Ile Gly Tyr Ser Val Ala Ser Leu Ala Ala Ser Leu Leu Arg Asp Gln
            275                 280                 285

Arg Arg Ile His Pro Val Ser Val Leu Ala Arg Gly Phe His Gly Ile
            290                 295                 300

Pro Asp Gly Thr Thr Ser Ser Ser Ala Cys Pro Pro Arg Arg Pro Arg
305                 310                 315                 320

Arg Arg Pro Gly Arg Arg Glu Met Glu Leu Thr Glu Glu Glu Ala Lys
                325                 330                 335

Arg Leu Arg Arg Ser Ala Lys Thr Ile Trp Glu Asn Cys Gln Leu Leu
            340                 345                 350

Gly Leu

<210> SEQ ID NO 27
<211> LENGTH: 998
<212> TYPE: DNA
<213> ORGANISM: Oryza sativa
<220> FEATURE:
<221> NAME/KEY: promoter
<222> LOCATION: (1)..(998)
<223> OTHER INFORMATION: transcription regulating sequence of
      chloroplast protein 12 gene including 5'-untranslated region
<220> FEATURE:
<221> NAME/KEY: misc_feature
<222> LOCATION: (648)..(948)
<223> OTHER INFORMATION: Potential core region of the promoter
      comprising clusters of promoter elements
<220> FEATURE:
<221> NAME/KEY: TATA_signal
<222> LOCATION: (908)..(914)
<220> FEATURE:
<221> NAME/KEY: 5'UTR
<222> LOCATION: (949)..(998)
<223> OTHER INFORMATION: potential 5'UTR
```

-continued

```
<400> SEQUENCE: 27
tttgtattta ggtccctaac gccctctgga agggtgattt gaaaaaagcc ctctaggagg      60
acgtgaggca cgactagatt tgtaaatttt cggaatgaaa aattattttt aaatatttta     120
atcaaaaaat gtaaaaataa aaaaaattct cggcagggtg gcagcatggg cctaaggccc     180
agtcaactgt gggcctataa gcgactaatc cggctgtaac tgggccttgc aagaggcttg     240
tcttgttggt ccgaactcag gaagtccagg ttgcggggac aacttcaagg ccatctggtt     300
tccacttctc ttaccacctc aattccgctc ttgatccgag ctagcttagt cccaatctaa     360
aaactttaca agaaagaac catacgcacc tattgggcaa aatgaaaaat aatttgctac     420
tcaccaaata atttgagcac ctctgcacct gtacactaaa taactctgtt ccaccaaaat     480
agttgagata tctaggacgt ttcattttgt ccgttcttca ccaaactttt ccatagtatc     540
tcagatattt tcgagaccga aagtgatctt tctggcctta gaccgagttc acttccctac     600
aagccattct ttgctggcac aacacgaacc tctacatcaa tttcgtatcc aacctgaact     660
tctgcataca tgtacacacc cacagtcatc tgctcatgtt ttcacggtca aattaaaact     720
gcttctctca ccttagattc acccaaggga aaagaaaaag atctcctttg ccaagtcccc     780
atttcgcatg aaatatctca aaatacagcc cacgtggcac acgacgattg gctgaggagg     840
cgataagaaa cgagtgcacg tcgtcgaatc ctctctcccc ttctccccca ccccacggag     900
ctatatatat ataaacccca tctcttcaat ccgtgcaacg aacgcctcgt cgcaacagct     960
acaaacgccc acatcacacg cagaaatccg catcaaca                             998

<210> SEQ ID NO 28
<211> LENGTH: 948
<212> TYPE: DNA
<213> ORGANISM: Oryza sativa
<220> FEATURE:
<221> NAME/KEY: promoter
<222> LOCATION: (1)..(948)
<223> OTHER INFORMATION: transcription regulating sequence of
      chloroplast protein 12 gene
<220> FEATURE:
<221> NAME/KEY: misc_feature
<222> LOCATION: (648)..(948)
<223> OTHER INFORMATION: Potential core region of the promoter
      comprising clusters of promoter elements
<220> FEATURE:
<221> NAME/KEY: TATA_signal
<222> LOCATION: (908)..(914)

<400> SEQUENCE: 28
tttgtattta ggtccctaac gccctctgga agggtgattt gaaaaaagcc ctctaggagg      60
acgtgaggca cgactagatt tgtaaatttt cggaatgaaa aattattttt aaatatttta     120
atcaaaaaat gtaaaaataa aaaaaattct cggcagggtg gcagcatggg cctaaggccc     180
agtcaactgt gggcctataa gcgactaatc cggctgtaac tgggccttgc aagaggcttg     240
tcttgttggt ccgaactcag gaagtccagg ttgcggggac aacttcaagg ccatctggtt     300
tccacttctc ttaccacctc aattccgctc ttgatccgag ctagcttagt cccaatctaa     360
aaactttaca agaaagaac catacgcacc tattgggcaa aatgaaaaat aatttgctac     420
tcaccaaata atttgagcac ctctgcacct gtacactaaa taactctgtt ccaccaaaat     480
agttgagata tctaggacgt ttcattttgt ccgttcttca ccaaactttt ccatagtatc     540
tcagatattt tcgagaccga aagtgatctt tctggcctta gaccgagttc acttccctac     600
aagccattct ttgctggcac aacacgaacc tctacatcaa tttcgtatcc aacctgaact     660
```

```
tctgcataca tgtacacacc cacagtcatc tgctcatgtt ttcacggtca aattaaaact    720
gcttctctca ccttagattc acccaaggga aagaaaaag atctcctttg ccaagtcccc     780
atttcgcatg aaatatctca aaatacagcc cacgtggcac acgacgattg gctgaggagg    840
cgataagaaa cgagtgcacg tcgtcgaatc ctctctcccc ttctccccca ccccacggag    900
ctatatatat ataaacccca tctcttcaat ccgtgcaacg aacgcctc                 948
```

<210> SEQ ID NO 29
<211> LENGTH: 301
<212> TYPE: DNA
<213> ORGANISM: Oryza sativa
<220> FEATURE:
<221> NAME/KEY: promoter
<222> LOCATION: (1)..(301)
<223> OTHER INFORMATION: Potential core region of the promoter of
      chloroplast protein 12 gene comprising clusters of promoter
      elements
<220> FEATURE:
<221> NAME/KEY: TATA_signal
<222> LOCATION: (261)..(267)

<400> SEQUENCE: 29

```
tccaacctga acttctgcat acatgtacac acccacagtc atctgctcat gttttcacgg    60
tcaaattaaa actgcttctc tcaccttaga ttcacccaag ggaaaagaaa aagatctcct   120
ttgccaagtc cccatttcgc atgaaatatc tcaaaataca gccacgtgg cacacgacga    180 ttggctgagg aggcgataag aaacgagtgc acgtcgtcga atcctctctc ccttctccc    240 ccaccccacg gagctatata tatataaacc ccatctcttc aatccgtgca acgaacgcct   300
c                                                                   301
```

<210> SEQ ID NO 30
<211> LENGTH: 375
<212> TYPE: DNA
<213> ORGANISM: Oryza sativa
<220> FEATURE:
<221> NAME/KEY: CDS
<222> LOCATION: (1)..(372)
<223> OTHER INFORMATION: coding for putative Choroplast 12 (CP12)
      protein

<400> SEQUENCE: 30

```
atg gcg tcc acg ctg acc aac gtc ggc ctg tct acc ccg gcg gcg gcg    48
Met Ala Ser Thr Leu Thr Asn Val Gly Leu Ser Thr Pro Ala Ala Ala
1               5                  10                  15 gcg tcg tcc ctc gtt agg ccg gtc gcc gga gct gga cgc gtg gtg ttt    96
Ala Ser Ser Leu Val Arg Pro Val Ala Gly Ala Gly Arg Val Val Phe
            20                  25                  30 ccc cgt gtt ggc cgc ggc ggg ttc gcg gcg gtg agg gcg agc ggg ccg   144
Pro Arg Val Gly Arg Gly Gly Phe Ala Ala Val Arg Ala Ser Gly Pro
        35                  40                  45 gcg acg ccg ccg gac atc tcg gac aag atg tcg gag agc atc gac aag   192
Ala Thr Pro Pro Asp Ile Ser Asp Lys Met Ser Glu Ser Ile Asp Lys
    50                  55                  60 gcg aag gag gcg tgc gcg gag gac acg gcg agc ggc gag tgc gcg gcg   240
Ala Lys Glu Ala Cys Ala Glu Asp Thr Ala Ser Gly Glu Cys Ala Ala
65                  70                  75                  80 gcg tgg gac gag gtg gag gag ctg agc gcg gcg gcg agc cac gcg cgc   288
Ala Trp Asp Glu Val Glu Glu Leu Ser Ala Ala Ala Ser His Ala Arg
                85                  90                  95 gac aag ctc aag gag acc tcc gac ccg ctc gag gcc tac tgc aag gac   336
Asp Lys Leu Lys Glu Thr Ser Asp Pro Leu Glu Ala Tyr Cys Lys Asp
```

```
                100             105             110
aac ccg gag acc gac gag tgc cgc acc tac gac aac tga                375
Asn Pro Glu Thr Asp Glu Cys Arg Thr Tyr Asp Asn
        115                 120

<210> SEQ ID NO 31
<211> LENGTH: 124
<212> TYPE: PRT
<213> ORGANISM: Oryza sativa

<400> SEQUENCE: 31

Met Ala Ser Thr Leu Thr Asn Val Gly Leu Ser Thr Pro Ala Ala Ala
1               5                   10                  15

Ala Ser Ser Leu Val Arg Pro Val Ala Gly Ala Gly Arg Val Val Phe
            20                  25                  30

Pro Arg Val Gly Arg Gly Gly Phe Ala Ala Val Arg Ala Ser Gly Pro
        35                  40                  45

Ala Thr Pro Pro Asp Ile Ser Asp Lys Met Ser Glu Ser Ile Asp Lys
    50                  55                  60

Ala Lys Glu Ala Cys Ala Glu Asp Thr Ala Ser Gly Glu Cys Ala Ala
65                  70                  75                  80

Ala Trp Asp Glu Val Glu Glu Leu Ser Ala Ala Ser His Ala Arg
                85                  90                  95

Asp Lys Leu Lys Glu Thr Ser Asp Pro Leu Gly Ala Tyr Cys Lys Asp
            100                 105                 110

Asn Pro Glu Thr Asp Glu Cys Arg Thr Tyr Asp Asn
        115                 120

<210> SEQ ID NO 32
<211> LENGTH: 479
<212> TYPE: DNA
<213> ORGANISM: Zea mays
<220> FEATURE:
<221> NAME/KEY: terminator
<222> LOCATION: (1)..(473)
<223> OTHER INFORMATION: Intergenic sequence comprising 3'-untranslated
      region of Zea mays lactate dehydrogenase gene
<220> FEATURE:
<221> NAME/KEY: polyA_signal
<222> LOCATION: (83)..(90)

<400> SEQUENCE: 32
gatgatcaca tcaccgtctc tcttcattaa ttaattattg tatcaatttc cacaacctag     60
cagcagcatc cggtacccgt gttcaataaa aacaaaccgc tacaatgtgt gctttctagc    120
tgcattaagc tgcttactac gagtatttgg gctgcggctt tcttttcat gtatctcacc     180 aaatcgttat tgttgtgaga gctatactac acggtggtat caagagtatc acaatgccca    240
acaggcgatg gattgagctt tcctaatttt ttcatgataa attaagttct actccctccg    300
tccacataaa tttgtctttc tagatttttt cgtaagtcaa aatatttaaa ctttgatcaa    360
cgatatatat aaaagaataa attgttttaa actaaaaaat ttattccctc agttctttt     420 tatttgtcgc agtttagttc aaaaataaac tagcggatga caatatcgag actgggata    479

<210> SEQ ID NO 33
<211> LENGTH: 2088
<212> TYPE: DNA
<213> ORGANISM: Artificial
<220> FEATURE:
<223> OTHER INFORMATION: construct pBPSMM304 [Os.CP12
      promoter::Zm.ubiquitin intron]
```

<400> SEQUENCE: 33

```
tttgtattta ggtccctaac gccctctgga agggtgattt gaaaaaagcc ctctaggagg      60
acgtgaggca cgactagatt tgtaaatttt cggaatgaaa aattattttt aaatatttta     120
atcaaaaaat gtaaaaataa aaaaaattct cggcagggtg gcagcatggg cctaaggccc     180
agtcaactgt gggcctataa gcgactaatc cggctgtaac tgggccttgc aagaggcttg     240
tcttgttggt ccgaactcag gaagtccagg ttgcggggac aacttcaagg ccatctggtt     300
tccacttctc ttaccacctc aattccgctc ttgatccgag ctagcttagt cccaatctaa     360
aaactttaca agaaagaac catacgcacc tattgggcaa aatgaaaaat aatttgctac      420
tcaccaaata atttgagcac ctctgcacct gtacactaaa taactctgtt ccaccaaaat     480
agttgagata tctaggacgt ttcattttgt ccgttcttca ccaaacttt ccatagtatc      540
tcagatattt tcgagaccga aagtgatctt tctggcctta gaccgagttc acttccctac     600
aagccattct ttgctggcac aacacgaacc tctacatcaa tttcgtatcc aacctgaact     660
tctgcataca tgtacacacc cacagtcatc tgctcatgtt ttcacggtca aattaaaact     720
gcttctctca ccttagattc acccaaggga aagaaaaag atctcctttg ccaagtcccc      780
atttcgcatg aaatatctca aaatacagcc cacgtggcac acgacgattg gctgaggagg     840
cgataagaaa cgagtgcacg tcgtcgaatc ctctctcccc ttctccccca ccccacggag     900
ctatatatat ataaacccca tctcttcaat ccgtgcaacg aacgcctcgt cgcaacagct     960
acaaacgccc acatcacacg cagaaatccg catcaacagg cgcgccaagc ttgcatgcct    1020
gcaggtcgac tctagaggat ctcccccaaa tccacccgtc ggcacctccg cttcaaggta    1080
cgccgctcgt cctccccccc ccccctctc taccttctct agatcggcgt tccggtccat     1140
ggttagggcc cggtagttct acttctgttc atgtttgtgt tagatccgtg tttgtgttag    1200
atccgtgctg ctagcgttcg tacacggatg cgacctgtac gtcagacacg ttctgattgc    1260
taacttgcca gtgtttctct ttggggaatc ctgggatggc tctagccgtt ccgcagacgg    1320
gatcgatttc atgatttttt ttgtttcgtt gcatagggtt tggtttgccc ttttccttta    1380
tttcaatata tgccgtgcac ttgtttgtcg ggtcatcttt tcatgctttt ttttgtcttg    1440
gttgtgatga tgtggtctgg ttgggcggtc gttctagatc ggagtagaat tctgtttcaa    1500
actacctggt ggatttatta attttggatc tgtatgtgtg tgccatacat attcatagtt    1560
acgaattgaa gatgatggat ggaaatatcg atctaggata ggtatacatg ttgatgcggg    1620
ttttactgat gcatatacag agatgctttt tgttcgcttg gttgtgatga tgtggtgtgg    1680
ttgggcggtc gttcattcgt tctagatcgg agtagaatac tgtttcaaac tacctggtgt    1740
atttattaat tttggaactg tatgtgtgtg tcatacatct tcatagttac gagtttaaga    1800
tggatggaaa tatcgatcta ggataggtat acatgttgat gtgggtttta ctgatgcata    1860
tacatgatgg catatgcagc atcattcat atgctctaac cttgagtacc tatctattat     1920
aataaacaag tatgttttat aattattttg atcttgatat acttggatga tggcatatgc    1980
agcagctata tgtggatttt tttagccctg ccttcatacg ctatttattt gcttggtact    2040
gtttcttttg tcgatgctca ccctgttgtt tggtgttact tctgcagc                 2088
```

<210> SEQ ID NO 34
<211> LENGTH: 1093
<212> TYPE: DNA
<213> ORGANISM: Oryza sativa
<220> FEATURE:
<221> NAME/KEY: terminator

```
<222> LOCATION: (1)..(1093)
<223> OTHER INFORMATION: Intergenic sequence including the 3'
      untranslated region of caffeoyl CoA-O-methyltransferase functional
      as transcription terminator
<220> FEATURE:
<221> NAME/KEY: 3'UTR
<222> LOCATION: (1)..(171)
<223> OTHER INFORMATION: potential 3'-untranslated region

<400> SEQUENCE: 34
gccgatgccc aagaactagt cattttaaat ttataaatta taactaaatt gtataatttt      60 tgccttttt ttttaatttg caagctactg gaaaatgtta tttaatatat gtataaatgt     120
cgagacaata atattattgc attataaatt gacctggttt ttgttagctt tcgttgcgcg    180
tgagaatggt gagtgtgtgc tgctgatgaa actcgaatgt tcacttttgt tgtcttgtcc    240
agctttgcta aactttggca gcattagcaa agctgttttg ttctgtttct gaattgttct    300
tggattgaaa tctctaatat tgacttgata attaaatttg accggttttt ggcagtaaat    360
tccttcagta ttggcagctc aaactgaatt cttctactaa tagtttagtg cttgtggaga    420
gtgtagtcgt gtagagtgga ctggactaat tcagatcttt acttggttag ctgaagatgg    480
catccgttat ctgaattctt cagtagttgg tggataatga caactcgatg tagagagata    540
atttgctgca tgttagtttg gaagtagctt caaaggattt aattctcagc gtccgaagtc    600
ttaagtacag ttggtttgga gagctgttcc tgtgaagact tttatgattt gtgctagtta    660
tgtcatcaca tgatcacttc aattatcact tatcgatcta gtgagaccaa ccatacatac    720
catacaaagg taaaaagtgt tcaaactgga ttgaacaagt tctgtctcca tatagatcct    780
actaaaatgc atacatgttg tagcaatccc atttcatcca aaccaaacaa aatctctttc    840
attcggctct aaccaatcaa acagagccat ttgtatcccc cgaaccaaac cagccgagca    900
tggatgaggg atcgagggca tccgagcaac caaacaggcc caaagtgaat gctttggtcg    960 atttcgatt tgttccctac gaatccaatt ttagtcctttc agccagaaga ccagatacaa   1020
ttgatccctc aactatcaaa acaagtgcag atgagctccc tcgacagttt ggacggcggt   1080
ttggttgacg tgg                                                      1093

<210> SEQ ID NO 35
<211> LENGTH: 558
<212> TYPE: DNA
<213> ORGANISM: Zea mays
<220> FEATURE:
<221> NAME/KEY: terminator
<222> LOCATION: (1)..(558)
<223> OTHER INFORMATION: Intergenic sequence including the 3'
      untranslated region of hydroxyproline-rich glyco-protein gene
      functional as transcription terminator sequence

<400> SEQUENCE: 35
gccaccatac tactagaaag cgatgcctac cataccacac tgctgtcagt ctctggagca     60
tttaggtacg tactaatact acgtacaacg gtacaagaat ggagcatgca atatgcatgc    120
acactacata catttagtat gcttgtgtca aatgtatcgt cagtatcata ctgatctcct    180
ggcatagtct ggcactaacc ataggctctc cttttctttt gtgttgggac aggtggtctc    240
gatcgatgga agaattgtgt cctagccagc cggcaaaggt gacctgctga tgatgatgat    300
gagaggcgag tcctacgccc tagtcctact actaccctct tgtgtgctg ccatccatcc    360 gtccccgcta gacgatcgag gagagaataa cgcagagctc tgtgctcccg gcctctgtct    420
tctgccgtcc cggccgttta atttatagtc tctactgtgt gttcgtccca tgtgtttagc    480
```

```
agcagcagca ggtgtattgt gcgggtatgt aatggtattg caactatatt gggtgtaaaa    540
ccataataaa tgtgggca                                                  558

<210> SEQ ID NO 36
<211> LENGTH: 5238
<212> TYPE: DNA
<213> ORGANISM: Artificial
<220> FEATURE:
<223> OTHER INFORMATION: construct pBPSMM325 [Os.CCoAMT1
      promoter::Zm.ubiquitin intron::GUS::Os.CCoAMT1 terminator]

<400> SEQUENCE: 36
gcaactactg cacggtaaaa gtgataggaa tcggtcggaa acagtattaa tgttttatt      60 attttacaa aaacgaattg aaataattgg aaattttcat atttatatat taaactattc    120
agtatcaact tcaattcgac gtcaatagaa attagaaaag cataattata cacagtaata   180
ggcgttcaag atattattgt tattatttag ttttgtggaa atggtatcaa cgtgatcgga   240
aaattttgta catgttttca ccctgcggga tatctcaatt ccttctcctc cctctaccgc   300
catatcagca cacgttttag agcaccaatc ataacccata aatccgtggg ctactcactt   360
atttaattta tatgtgaatt cgtgacctga ctcactcaca tactatcaaa aatttgtctc   420
agtcacccat ctccttcttt cctggtccga taagggttta tcctacggtt cgacggttat   480
cacgatagtc gtgcggttac tgaggtatac cgtgatttaa aaatatgata aagttaccgc   540
aggttttaac tgcgcggttt ggtaaacctg ttcctcctca ccaaccttct cctccggtct   600
ccttatgtgt ctcaccgagg cgagccgccg cgagaccgca tggacgcggt ccacgcacct   660
ggcggtgcac ctcctcctcc ccggcgaaga agacgtggag gagagtaaat gagcaatcag   720
gcccacggcc caatcgccgt ccaccaccca ccacccctcag cgacccaaaa ccacctcacc   780
aacccaactc tgtaccgtac tgtacccgcc ctcccctccc actgacactc cgggcccacc   840
tgtcggcgcg actcttccac ggtcccctcc tctcctcaga gatttttttcc acgcattttt   900 taatttttttt ttctgcagtt cacatgctct tctcccactc ttccgccgcg ctatataaac   960
cgcgcgaggc gtcgttgcct cgtcggcgaa gtcaatccgg cgatccccgg cgagcgagag  1020
atcgaagcaa gctgcgagct cgatctcccc caaatccacc cgtcggcacc tccgcttcaa  1080
ggtacgccgc tcgtcctccc ccccccccccc tctctacctt ctctagatcg gcgttccggt  1140
ccatggttag ggcccggtag ttctacttct gttcatgttt gtgttagatc cgtgtttgtg  1200
ttagatccgt gctgctagcg ttcgtacacg gatgcgacct gtacgtcaga cacgttctga  1260
ttgctaactt gccagtgttt ctctttgggg aatcctggga tggctctagc cgttccgcag  1320
acgggatcga tttcatgatt ttttttgttt cgttgcatag ggtttggttt gcccttttcc  1380
tttatttcaa tatatgccgt gcacttgttt gtcgggtcat cttttcatgc tttttttttgt  1440 cttggttgtg atgatgtggt ctggttgggc ggtcgttcta gatcggagta gaattctgtt  1500
tcaaactacc tggtggattt attaattttg gatctgtatg tgtgtgccat acatattcat   1560
agttacgaat tgaagatgat ggatggaaat atcgatctag gataggtata catgttgatg   1620
cgggttttac tgatgcatat acagagatgc ttttttgttcg cttggttgtg atgatgtggt   1680
gtggttgggc ggtcgttcat tcgttctaga tcggagtaga atactgtttc aaactacctg   1740
gtgtatttat taattttgga actgtatgtg tgtgtcatac atcttcatag ttacgagttt   1800
aagatggatg gaaatatcga tctaggatag gtatacatgt tgatgtgggt tttactgatg   1860
catatacatg atggcatatg cagcatctat tcatatgctc taaccttgag tacctatcta   1920
```

```
ttataataaa caagtatgtt ttataattat tttgatcttg atatacttgg atgatggcat    1980
atgcagcagc tatatgtgga ttttttttagc cctgccttca tacgctattt atttgcttgg    2040
tactgtttct tttgtcgatg ctcaccctgt tgtttggtgt tacttctgca gccccgggga    2100
tccatgttac gtcctgtaga aaccccaacc cgtgaaatca aaaaactcga cggcctgtgg    2160
gcattcagtc tggatcgcga aaactgtgga attgatcagc gttggtggga agcgcgtta     2220 caagaaagcc gggcaattgc tgtgccaggc agttttaacg atcagttcgc cgatgcagat    2280
attcgtaatt atgcgggcaa cgtctggtat cagcgcgaag tctttatacc gaaaggttgg    2340
gcaggccagc gtatcgtgct gcgtttcgat gcggtcactc attacggcaa agtgtgggtc    2400
aataatcagg aagtgatgga gcatcagggc ggctatacgc catttgaagc cgatgtcacg    2460
ccgtatgtta ttgccgggaa aagtgtacgt aagtttctgc ttctaccttt gatatatata    2520
taataattat cattaattag tagtaatata atatttcaaa tattttttc aaaataaaag     2580 aatgtagtat atagcaattg cttttctgta gtttataagt gtgtatattt taatttataa    2640 ctttttctaat atatgaccaa aatttgttga tgtgcaggta tcaccgtttg tgtgaacaac   2700
gaactgaact ggcagactat cccgccggga atggtgatta ccgacgaaaa cggcaagaaa    2760
aagcagtctt acttccatga tttctttaac tatgccggaa tccatcgcag cgtaatgctc    2820
tacaccacgc cgaacacctg ggtggacgat atcaccgtgg tgacgcatgt cgcgcaagac    2880
tgtaaccacg cgtctgttga ctggcaggtg gtggccaatg gtgatgtcag cgttgaactg    2940
cgtgatgcgg atcaacaggt ggttgcaact ggacaaggca ctagcgggac tttgcaagtg    3000
gtgaatccgc acctctggca accgggtgaa ggttatctct atgaactgtg cgtcacagcc    3060
aaaagccaga cagagtgtga tatctacccg cttcgcgtcg gcatccggtc agtggcagtg    3120
aagggccaac agttcctgat taaccacaaa ccgttctact ttactggctt tggtcgtcat    3180
gaagatgcgg acttacgtgg caaaggattc gataacgtgc tgatggtgca cgaccacgca    3240
ttaatggact ggattggggc caactcctac cgtacctcgc attaccctta cgctgaagag    3300
atgctcgact gggcagatga acatggcatc gtggtgattg atgaaactgc tgctgtcggc    3360
tttaacctct ctttaggcat tggtttcgaa gcgggcaaca gccgaaaga actgtacagc     3420 gaagaggcag tcaacgggga aactcagcaa gcgcacttac aggcgattaa agagctgata    3480
gcgcgtgaca aaaaccaccc aagcgtggtg atgtggagta ttgccaacga accggatacc    3540
cgtccgcaag tgcacgggaa tatttcgcca ctggcggaag caacgcgtaa actcgacccg    3600
acgcgtccga tcacctgcgt caatgtaatg ttctgcgacg ctcacaccga taccatcagc    3660
gatctctttg atgtgctgtg cctgaaccgt tattacggat ggtatgtcca aagcggcgat    3720
ttggaaacgg cagagaaggt actggaaaaa gaacttctgg cctggcagga gaaactgcat    3780
cagccgatta tcatcaccga atacggcgtg gatacgttag ccgggctgca ctcaatgtac    3840
accgacatgt ggagtgaaga gtatcagtgt gcatggctgg atatgtatca ccgcgtcttt    3900
gatcgcgtca gcgccgtcgt cggtgaacag gtatggaatt tcgccgattt tgcgacctcg    3960
caaggcatat tgcgcgttgg cggtaacaag aaagggatct tcactcgcga ccgcaaaccg    4020
aagtcggcgc ttttctgct gcaaaaacgc tggactggca tgaacttcgg tgaaaaaccg    4080
cagcagggag gcaaacaatg aagatcctct agagtcgacc tgcaggcatg caagcttggc    4140
gcgccgccga tgcccaagaa ctagtcattt taaatttata aattataact aaattgtata    4200 attttttgcct ttttttttta atttgcaagc tactggaaaa tgttatttaa tatatgtata    4260
aatgtcgaga caataatatt attgcattat aaattgacct ggttttttgtt agctttcgtt    4320
```

```
gcgcgtgaga atggtgagtg tgtgctgctg atgaaactcg aatgttcact tttgttgtct    4380
tgtccagctt tgctaaactt tggcagcatt agcaaagctg ttttgttctg tttctgaatt    4440
gttcttggat tgaaatctct aatattgact tgataattaa atttgaccgg tttttggcag    4500
taaattcctt cagtattggc agctcaaact gaattcttct actaatagtt tagtgcttgt    4560
ggagagtgta gtcgtgtaga gtggactgga ctaattcaga tctttacttg gttagctgaa    4620
gatggcatcc gttatctgaa ttcttcagta gttggtggat aatgacaact cgatgtagag    4680
agataatttg ctgcatgtta gtttggaagt agcttcaaag gatttaattc tcagcgtccg    4740
aagtcttaag tacagttggt ttggagagct gttcctgtga agactttat gatttgtgct    4800 agttatgtca tcacatgatc acttcaatta tcacttatcg atctagtgag accaaccata    4860
cataccatac aaaggtaaaa agtgttcaaa ctggattgaa caagttctgt ctccatatag    4920
atcctactaa aatgcataca tgttgtagca atcccatttc atccaaacca aacaaaatct    4980
ctttcattcg gctctaacca atcaaacaga gccatttgta tccccgaac caaaccagcc    5040 gagcatggat gagggatcga gggcatccga gcaaccaaac aggcccaaag tgaatgcttt    5100
ggtcgatttt cgatttgttc cctacgaatc caatttttagt ccttcagcca gaagaccaga    5160
tacaattgat ccctcaacta tcaaaacaag tgcagatgag ctccctcgac agtttggacg    5220
gcggtttggt tgacgtgg                                                  5238

<210> SEQ ID NO 37
<211> LENGTH: 1891
<212> TYPE: DNA
<213> ORGANISM: Artificial
<220> FEATURE:
<223> OTHER INFORMATION: construct pBPSMM331 [Os.SI
      promoter::Zm.ubiquitin intron]

<400> SEQUENCE: 37
gcctcgattc gaccgtgtaa tggaatgaag gtggtgggcc cccaccccca caagccactc      60
tccacacttt ggtgttcctg gtatgtcacc tagaccaaca actatgttaa gccatatgtt     120
ccacagtgca aaatctacaa gaccacgata caagtaggta tggtggacta ccacatttc     180 acttctcttt cactttcccc tctctctccc ccctctcttc ctttcccccca ccgcagagag    240 cctggcgcgc ggagacggcg acggcgccgg accaagcagt ggtggagcga cggcagggcg    300
acagcgccga gcggcgggat gcgctcgccg gcgcaccacc ccctcctctc cccccgagc    360 ggcgggctg ctcggagcag cagggcgcg cggcatgtc ggcggcgggc agacgacttg       420
gagcgggaga cggcgacggg cggatgcgag gcggcggtcg gcgccctcct ccctggagt      480 tcggctgctt cgcccctct cctctctcct ctagcggtgg tgtgggtccc actgagctga      540
ggagggcgcg cggttggacg acgaggcaaa ggaatactag tcttcgcttt tttgggttga    600
ggctgaatgc cacgtcggcc cattgtgaat gccctttaac aaaacaaggg tttatggcta    660
tgggatctgg ctgaggcatt gacctacctt ggtccttggc agagagagag agagactccc    720
cctcactcct tccccgacga cctgctcgat ccgatccaat cagctcctct ccagtccaga    780
tcggaaggaa gccaggagtt aggcgcgcca agcttgcatg cctgcaggtc gactctagag    840
gatctccccc aaatccaccc gtcggcacct ccgcttcaag gtacgccgct cgtcctcccc    900 cccccccct ctctaccttc tctagatcgg cgttccggtc catggttagg gcccggtagt    960
tctacttctg ttcatgtttg tgttagatcc gtgtttgtgt tagatccgtg ctgctagcgt   1020
tcgtacacgg atgcgacctg tacgtcagac acgttctgat tgctaacttg ccagtgtttc   1080
```

```
tctttgggga atcctgggat ggctctagcc gttccgcaga cgggatcgat ttcatgattt    1140 ttttttgtttc gttgcatagg gtttggtttg ccctttttcct ttatttcaat atatgccgtg   1200
cacttgtttg tcgggtcatc ttttcatgct tttttttgtc ttggttgtga tgatgtggtc    1260
tggttgggcg gtcgttctag atcggagtag aattctgttt caaactacct ggtggattta   1320
ttaattttgg atctgtatgt gtgtgccata catattcata gttacgaatt gaagatgatg    1380
gatgaaaata tcgatctagg ataggtatac atgttgatgc gggttttact gatgcatata   1440
cagagatgct ttttgttcgc ttggttgtga tgatgtggtg tggttgggcg gtcgttcatt   1500
cgttctagat cggagtagaa tactgtttca aactacctgg tgtatttatt aattttggaa   1560
ctgtatgtgt gtgtcataca tcttcatagt tacgagttta agatggatgg aaatatcgat   1620
ctaggatagg tatacatgtt gatgtgggtt ttactgatgc atatacatga tggcatatgc    1680
agcatctatt catatgctct aaccttgagt acctatctat tataataaac aagtatgttt   1740
tataattatt ttgatcttga tacttggga tgatggcata tgcagcagct atatgtggat    1800
ttttttagcc ctgccttcat acgctattta tttgcttggt actgtttctt ttgtcgatgc   1860
tcaccctgtt gtttggtgtt acttctgcag c                                   1891
```

<210> SEQ ID NO 38
<211> LENGTH: 4835
<212> TYPE: DNA
<213> ORGANISM: Artificial
<220> FEATURE:
<223> OTHER INFORMATION: construct pBPSET003 [Zm.HRGP
      promoter::Zm.ubiquitin intron::GUS::Zm.HRGP terminator]

<400> SEQUENCE: 38

```
ggtgaccttc ttgcttcttc gatcgtctgg acgtcgagga gccccgcggc agcgcacgcg     60
tctgcaccgt tatggtggcc gcgctcgcga tggaatagaa ggggtaatga tggatccggc    120
caggaaggcc acgacatcga cggatccaac cggcaagacg gcgatccggt taaatagacg    180
acggatctag ctgggaaggt agactctaca ttaaatgagg ttgcacatgc cctaataact    240
ttataaatct aatttattca gaggcaaggt agtagtatta tctttcccaa cggatagtta    300
tctgatctgc cgttcagctt gatcgataac tttataaatc taatttattc agaggccggc    360
ggcagcgcac acgtctgcac cagtaatgtt agccgcgcct gtggcgtaat agaagggggta   420 acgatggatc cgaccagaaa ggcctcgaca ttgacggatc cagacggcga tccggtcaaa    480
gagacgacga atctagccga gaaggtagat ctctcgagag agttcatatt aaatgatgtt    540
gtacatgcca taataactct ataaatctaa tttattcata ggcgaaggta gtagtattat    600
ctttcccagc ggatcgttat ctgatctgcc gttcagcttg atcgatccac gtcgtttgat    660
ctcggcgagc agcacatggc ggctcttctt gtgtacaggt ctcactctct gctacttcag    720
tgcaaggcgg agtgaatgca cacaataacg tgagtattgt gggaactact tgtagatgca    780
aacgatgtaa atccacctgc tccaccaagt gcccgcccgg ctctatccat tccattcgtc    840
aacatgcagg ttcagactgg cccgtgctgg accagtgagc ggtgccggtg aaccccaatg    900
caagcgaagc gagtgaccat cggggaagcc tcccgtgctg cccccacatg gcttgcctga    960
atgcctctct ctcgccgcag tgccctctct ctcctcctcct cctctccgtc gaagggcgtc   1020
acgagagccc agagggcatc cgaggccccc accccacccc ttcctccgtg tatataagca   1080
gtggcagggt gagcgtctct cctcagacca ccactgcgcc attggccagc tagagccaac   1140
cagaagagct tgcagttact gagagtgtgt gtgagagaga gggagctcga tctcccccaa   1200
```

```
atccacccgt cggcacctcc gcttcaaggt acgccgctcg tcctccccccc ccccctctc    1260
tctaccttct ctagatcggc gttccggtcc atggttaggg cccggtagtt ctacttctgt    1320
tcatgtttgt gttagatccg tgtttgtgtt agatccgtgc tgctagcgtt cgtacacgga    1380
tgcgacctgt acgtcagaca cgttctgatt gctaacttgc cagtgtttct ctttggggaa    1440
tcctgggatg gctctagccg ttccgcagac gggatcgatt tcatgatttt ttttgtttcg    1500
ttgcataggg tttggtttgc ccttttcctt tatttcaata tatgccgtgc acttgtttgt    1560
cgggtcatct tttcatgctt ttttttgtct tggttgtgat gatgtggtct ggttgggcgg    1620
tcgttctaga tcgagtagaa attctgtttc aaactacctg gtggatttat taattttgga    1680
tctgtatgtg tgtgccatac atattcatag ttacgaattg aagatgatgg atggaaatat    1740
cgatctagga taggtataca tgttgatgcg ggttttactg atgcatatac agagatgctt    1800
tttgttcgct tggttgtgat gatgtggtgt ggttgggcgg tcgttcattc gttctagatc    1860
ggagtagaat actgtttcaa actacctggt gtatttatta attttggaac tgtatgtgtg    1920
tgtcatacat cttcatagtt acgagtttaa gatggatgga aatatcgatc taggataggt    1980
atacatgttg atgtgggttt tactgatgca tatacatgat ggcatatgca gcatctattc    2040
atatgctcta accttgagta cctatctatt ataataaaca agtatgtttt ataattattt    2100
tgatcttgat atacttggat gatggcatat gcagcagcta tatgtggatt ttttttagccc   2160
tgccttcata cgctatttat ttgcttggta ctgtttcttt tgtcgatgct caccctgttg    2220
tttggtgtta cttctgcagc cccggggatc catgttacgt cctgtagaaa ccccaacccg    2280
tgaaatcaaa aaactcgacg gcctgtgggc attcagtctg gatcgcgaaa actgtggaat    2340
tggtcagcgt tggtgggaaa gcgcgttaca agaaagccgg gcaattgctg tgccaggcag    2400
ttttaacgat cagttcgccg atgcagatat tcgtaattat gcgggcaacg tctggtatca    2460
gcgcgaagtc tttataccga aaggttgggc aggccagcgt atcgtgctgc gtttcgatgc    2520
ggtcactcat tacggcaaag tgtgggtcaa taatcaggaa gtgatggagc atcagggcgg    2580
ctatacgcca tttgaagccg atgtcacgcc gtatgttatt gccgggaaaa gtgtacgtaa    2640
gtttctgctt ctacctttga tatatatata ataattatca ttaattagta gtaatataat    2700
atttcaaata tttttttcaa aataaaagaa tgtagtatat agcaattgct tttctgtagt    2760
ttataagtgt gtatatttta atttataact tttctaatat atgaccaaaa tttgttgatg    2820
tgcaggtatc accgtttgtg tgaacaacga actgaactgg cagactatcc cgccgggaat    2880
ggtgattacc gacgaaaacg gcaagaaaaa gcagtcttac ttccatgatt tctttaacta    2940
tgccggaatc catcgcagcg taatgctcta caccacgccg aacacctggg tggacgatat    3000
caccgtggtg acgcatgtcg cgcaagactg taaccacgcg tctgttgact ggcaggtggt    3060
ggccaatggt gatgtcagcg ttgaactgcg tgatgcggat caacaggtgg ttgcaactgg    3120
acaaggcact agcgggactt tgcaagtggt gaatccgcac ctctggcaac cgggtgaagg    3180
ttatctctat gaactgtgcg tcacagccaa agccagaca gagtgtgata tctacccgct    3240
tcgcgtcggc atccggtcag tggcagtgaa gggcgaacag ttcctgatta accacaaacc    3300
gttctacttt actggctttg gtcgtcatga agatgcggac ttgcgtggca aaggattcga    3360
taacgtgctg atggtgcacg accacgcatt aatggactgg attggggcca actcctaccg    3420
tacctcgcat taccccttacg ctgaagagat gctcgactgg gcagatgaac atggcatcgt    3480
ggtgattgat gaaactgctg ctgtcggctt taacctctct ttaggcattg gtttcgaagc    3540
```

| | |
|---|---:|
| gggcaacaag ccgaaagaac tgtacagcga agaggcagtc aacggggaaa ctcagcaagc | 3600 |
| gcacttacag gcgattaaag agctgatagc gcgtgacaaa aaccacccaa gcgtggtgat | 3660 |
| gtggagtatt gccaacgaac cggatacccg tccgcaaggt gcacgggaat atttcgcgcc | 3720 |
| actggcggaa gcaacgcgta aactcgaccc gacgcgtccg atcacctgcg tcaatgtaat | 3780 |
| gttctgcgac gctcacaccg ataccatcag cgatctcttt gatgtgctgt gcctgaaccg | 3840 |
| ttattacgga tggtatgtcc aaagcggcga tttggaaacg gcagagaagg tactggaaaa | 3900 |
| agaacttctg gcctggcagg agaaaactgca tcagccgatt atcatcaccg aatacggcgt | 3960 |
| ggatacgtta gccgggctgc actcaatgta caccgacatg tggagtgaag agtatcagtg | 4020 |
| tgcatggctg gatatgtatc accgcgtctt tgatcgcgtc agcgccgtcg tcggtgaaca | 4080 |
| ggtatggaat ttcgccgatt ttgcgaccctc gcaaggcata ttgcgcgttg gcggtaacaa | 4140 |
| gaaagggatc ttcactcgcg accgcaaacc gaagtcggcg gcttttctgc tgcaaaaacg | 4200 |
| ctggactggc atgaacttcg gtgaaaaacc gcagcaggga ggcaaacaat gaagatcctc | 4260 |
| tagagtcgac ctgcagggcc accatactac tagaaagcga tgcctaccat accacactgc | 4320 |
| tgtcagtctc tggagcattt aggtacgtac taatactacg tacaacggta caagaatgga | 4380 |
| gcatgcaata tgcatgcaca ctacatacat ttagtatgct tgtgtcaaat gtatcgtcag | 4440 |
| tatcatactg atctcctggc atagtctggc actaaccata ggctctcctt ttcttttgtg | 4500 |
| ttgggacagg tggtctcgat cgatggaaga attgtgtcct agccagccgg caaaggtgac | 4560 |
| ctgctgatga tgatgatgag aggcgagtcc tacgccctag tcctactact accctctttg | 4620 |
| tgtgctgcca tccatccgtc cccgctagac gatcgaggag agaataacgc agagctctgt | 4680 |
| gctcccggcc tctgtcttct gccgtcccgg ccgtttaatt tatagtctct actgtgtgtt | 4740 |
| cgtcccatgt gtttagcagc agcagcaggt gtattgtgcg ggtatgtaat ggtattgcaa | 4800 |
| ctatattggg tgtaaaacca taataaatgt gggca | 4835 |

<210> SEQ ID NO 39
<211> LENGTH: 4632
<212> TYPE: DNA
<213> ORGANISM: Artificial
<220> FEATURE:
<223> OTHER INFORMATION: construct pBPSET007
    [Zm.LDH promoter::Zm.ubiquitin intron::GUS::Zm.LDH terminator]

<400> SEQUENCE: 39

| | |
|---|---:|
| aacaaatggc gtacttatat aaccacaatg tactggtgct gcgtcattat tttatactac | 60 |
| gcatatatta ttataagtag agaaagctca caaaaccatg cgcgcgcccc cctgtttgtt | 120 |
| tcggtcgcta attacaccct ttgtatcgtt ggttgatgat ggtctccacc ggccgtacga | 180 |
| gtcatcgatc gttgatttat ttttatcacc gacttgcacg cctttcgaac aaagacgcaa | 240 |
| caaaggaaag cgaaagcgtc acgaacgagg ttgttccctg acagttgttc gactaataca | 300 |
| actgcaagac actgaataag cagtaaaaat caatatagat taaagttaaa cgaacatgct | 360 |
| caacatcgaa tactactcat atgtgttatt attaagagaa taccaccaag gtagaaaagt | 420 |
| taaaggacct aaactgttgt gccgggagag ttgtgcgacg aacagatgta aatatgataa | 480 |
| aataagttca aagttcatat agatagcacg atcacactta gggctagttt gaagccataa | 540 |
| aaatggaaga gattaaatga gataaaattc acttatttaa ttttaaataa gaagagagtt | 600 |
| ttaacctcta attctctcca gtattttagc tcctaaacta gctcttacag cagtaaaaga | 660 |
| cccttgatgg tagcgtatgc aaagagaagg aactattcaa tgaattgttt ttttaatcac | 720 |

```
tagtagtatg gtgggtaact gtcgtcaacc ggccctatct acttcagttt agtgaagcac    780
taaaccgcac cttggtatgt tcaaatttaa gatttttttt gaaacgaaac aattttaacc    840
agcggctcca aaccggtgaa gtggtttggt ctttggtgtg gggccagggt attaatggaa    900
ttgaatatat aaagagcagg gtggtggacc ttteccctec cacgagtcga gtagccattg    960
cccattgcca ttccttcctt cctccacaga gaaatccgat ccgcggagat ttgacccaac   1020
cagatcatat cacacacgta atcccatccc attccgcccg gagctcgatc tcccccaaat   1080
ccacccgtcg gcacctccgc ttcaaggtac gccgctcgtc ctcccccccc ccctctctc    1140
taccttctct agatcggcgt tccggtccat ggttagggcc cggtagttct acttctgttc   1200
atgtttgtgt tagatccgtg tttgtgttag atccgtgctg ctagcgttcg tacacggatg   1260
cgacctgtac gtcagacacg ttctgattgc taacttgcca gtgtttctct ttggggaatc   1320
ctgggatggc tctagccgtt ccgcagacgg gatcgatttc atgatttttt ttgtttcgtt   1380
gcatagggtt tggtttgccc ttttcccttta tttcaatata tgccgtgcac ttgtttgtcg   1440
ggtcatcttt tcatgctttt ttttgtcttg gttgtgatga tgtggtctgg ttgggcggtc   1500
gttctagatc ggagtagaat tctgtttcaa actacctggt ggatttatta attttggatc   1560
tgtatgtgtg tgccatacat attcatagtt acgaattgaa gatgatggat ggaaatatcg   1620
atctaggata ggtatacatg ttgatgcggg ttttactgat gcatatacag agatgctttt   1680
tgttcgcttg gttgtgatga tgtggtgtgg ttgggcggtc gttcattcgt tctagatcgg   1740
agtagaatac tgtttcaaac tacctggtgt atttattaat tttggaactg tatgtgtgtg   1800
tcatacatct tcatagttac gagtttaaga tggatgaaaa tatcgatcta ggataggtat   1860
acatgttgat gtgggtttta ctgatgcata tacatgatgg catatgcagc atctattcat   1920
atgctctaac cttgagtacc tatctattat aataaacaag tatgttttat aattattttg   1980
atcttgatat acttggatga tggcatatgc agcagctata tgtggatttt tttagccctg   2040
ccttcatacg ctatttattt gcttggtact gtttcttttg tcgatgctca ccctgttgtt   2100
tggtgttact tctgcagccc ggggatccat gttacgtcct gtagaaaccc caacccgtga   2160
aatcaaaaaa ctcgacggcc tgtgggcatt cagtctggat cgcgaaaact gtggaattgg   2220
tcagcgttgg tgggaaagcg cgttacaaga aagccgggca attgctgtgc caggcagttt   2280
taacgatcag ttcgccgatg cagatattcg taattatgcg gcaacgtct ggtatcagcg   2340
cgaagtcttt ataccgaaag gttgggcagg ccagcgtatc gtgctgcgtt tcgatgcggt   2400
cactcattac ggcaaagtgt gggtcaataa tcaggaagtg atggagcatc agggcggcta   2460
tacgccattt gaagccgatg tcacgccgta tgttattgcc gggaaaagtg tacgtaagtt   2520
tctgcttcta ccttttgatat atatataata attatcatta attagtagta atataatatt   2580
tcaaatattt ttttcaaaat aaaagaatgt agtatatagc aattgctttt ctgtagttta   2640
taagtgtgta tattttaatt tataaacttt ctaatatatg accaaaattt gttgatgtgc   2700
aggtatcacc gtttgtgtga acaacgaact gaactggcag actatcccgc cgggaatggt   2760
gattaccgac gaaaacggca agaaaaagca gtcttacttc catgatttct taactatgc    2820
cggaatccat cgcagcgtaa tgctctacac cacgccgaac acctgggtgg acgatatcac   2880
cgtggtgacg catgtcgcgc aagactgtaa ccacgcgtct gttgactggc aggtggtggc   2940
caatggtgat gtcagcgttg aactgcgtga tgcggatcaa caggtggttg caactggaca   3000
aggcactagc gggactttgc aagtggtgaa tccgcacctc tggcaaccgg gtgaaggtta   3060
tctctatgaa ctgtgcgtca cagccaaaag ccagacagag tgtgatatct acccgcttcg   3120
```

```
cgtcggcatc cggtcagtgg cagtgaaggg cgaacagttc ctgattaacc acaaaccgtt      3180
ctactttact ggctttggtc gtcatgaaga tgcggacttc cgtggcaaag gattcgataa      3240
cgtgctgatg gtgcacgacc acgcattaat ggactggatt ggggccaact cctaccgtac      3300
ctcgcattac ccttacgctg aagagatgct cgactgggca gatgaacatg gcatcgtggt      3360
gattgatgaa actgctgctg tcggctttaa cctctcttta ggcattggtt tcgaagcggg      3420
caacaagccg aaagaactgt acagcgaaga ggcagtcaac ggggaaactc agcaagcgca      3480
cttacaggcg attaaagagc tgatagcgcg tgacaaaaac cacccaagcg tggtgatgtg      3540
gagtattgcc aacgaaccgg ataccogtcc gcaaggtgca cggaatatt tcgcgccact       3600 ggcggaagca acgcgtaaac tcgacccgac gcgtccgatc acctgcgtca atgtaatgtt      3660
ctgcgacgct cacaccgata ccatcagcga tctctttgat gtgctgtgcc tgaaccgtta      3720
ttacggatgg tatgtccaaa gcggcgattt ggaaacggca gagaaggtac tggaaaaaga      3780
acttctggcc tggcaggaga aactgcatca gccgattatc atcaccgaat acggcgtgga      3840
tacgttagcc gggctgcact caatgtacac cgacatgtgg agtgaagagt atcagtgtgc      3900
atggctggat atgtatcacc gcgtctttga tcgcgtcagc gccgtcgtcg gtgaacaggt      3960
atggaatttc gccgattttg cgacctcgca aggcatattg cgcgttggcg gtaacaagaa      4020
agggatcttc actcgcgacc gcaaaccgaa gtcggcggct tttctgctgc aaaaacgctg      4080
gactggcatg aacttcggtg aaaaaccgca gcagggaggc aaacaatgaa gatcctctag      4140
agtcgacctg caggatgatc acatcaccgt ctctcttcat taattaatta ttgtatcaat      4200
ttccacaacc tagcagcagc atccggtacc cgtgttcaat aaaaacaaac cgctacaatg      4260
tgtgctttct agctgcatta agctgcttac tacgagtatt tgggctgcgg ctttcttttt      4320
catgtatctc accaaatcgt tattgttgtg agagctatac tacacggtgg tatcaagagt      4380
atcacaatgc caacaggcg atggattgag ctttcctaat ttttttcatga taaattaagt       4440 tctactccct ccgtccacat aaatttgtct ttctagattt tttcgtaagt caaaatattt      4500
aaactttgat caacgatata tataaaagaa taaattgttt taaactaaaa aatttattcc      4560
ctcagttctt ttttatttgt cgcagtttag ttcaaaaata aactagcgga tgacaatatc      4620
gagactggga ta                                                          4632
```

<210> SEQ ID NO 40
<211> LENGTH: 27
<212> TYPE: DNA
<213> ORGANISM: Artificial
<220> FEATURE:
<223> OTHER INFORMATION: oligonucleotide primer

<400> SEQUENCE: 40
caactactgc acggtaaaag tgatagg                                           27

<210> SEQ ID NO 41
<211> LENGTH: 27
<212> TYPE: DNA
<213> ORGANISM: Artificial
<220> FEATURE:
<223> OTHER INFORMATION: oligonucleotide primer

<400> SEQUENCE: 41
gcagcttgct tcgatctctc gctcgcc                                           27

<210> SEQ ID NO 42

```
<211> LENGTH: 28
<212> TYPE: DNA
<213> ORGANISM: Artificial
<220> FEATURE:
<223> OTHER INFORMATION: oligonucleotide primer

<400> SEQUENCE: 42
gccgatgccc aagaactagt cattttaa                                          28

<210> SEQ ID NO 43
<211> LENGTH: 27
<212> TYPE: DNA
<213> ORGANISM: Artificial
<220> FEATURE:
<223> OTHER INFORMATION: oligonucleotide primer

<400> SEQUENCE: 43
attaacacgt caaccaaacc gccgtcc                                           27

<210> SEQ ID NO 44
<211> LENGTH: 27
<212> TYPE: DNA
<213> ORGANISM: Artificial
<220> FEATURE:
<223> OTHER INFORMATION: oligonucleotide primer

<400> SEQUENCE: 44
tgcctcgatt cgaccgtgta atggaat                                           27

<210> SEQ ID NO 45
<211> LENGTH: 27
<212> TYPE: DNA
<213> ORGANISM: Artificial
<220> FEATURE:
<223> OTHER INFORMATION: oligonucleotide primer

<400> SEQUENCE: 45
actcctggct tccttccgat ctggact                                           27

<210> SEQ ID NO 46
<211> LENGTH: 27
<212> TYPE: DNA
<213> ORGANISM: Artificial
<220> FEATURE:
<223> OTHER INFORMATION: oligonucleotide primer

<400> SEQUENCE: 46
ccggtgacct tcttgcttct tcgatcg                                           27

<210> SEQ ID NO 47
<211> LENGTH: 27
<212> TYPE: DNA
<213> ORGANISM: Artificial
<220> FEATURE:
<223> OTHER INFORMATION: oligonucleotide primer

<400> SEQUENCE: 47
cctctctctc acacacactc tcagtaa                                           27

<210> SEQ ID NO 48
<211> LENGTH: 27
<212> TYPE: DNA
<213> ORGANISM: Artificial
<220> FEATURE:
<223> OTHER INFORMATION: oligonucleotide primer

<400> SEQUENCE: 48
```

-continued

```
aacaaatggc gtacttatat aaccaca                                              27

<210> SEQ ID NO 49
<211> LENGTH: 27
<212> TYPE: DNA
<213> ORGANISM: Artificial
<220> FEATURE:
<223> OTHER INFORMATION: oligonucleotide primer

<400> SEQUENCE: 49
cgggcggaat gggatgggat tacgtgt                                              27

<210> SEQ ID NO 50
<211> LENGTH: 27
<212> TYPE: DNA
<213> ORGANISM: Artificial
<220> FEATURE:
<223> OTHER INFORMATION: oligonucleotide primer

<400> SEQUENCE: 50
aaagcgatgc ctaccatacc acactgc                                              27

<210> SEQ ID NO 51
<211> LENGTH: 28
<212> TYPE: DNA
<213> ORGANISM: Artificial
<220> FEATURE:
<223> OTHER INFORMATION: oligonucleotide primer

<400> SEQUENCE: 51
tgcccacatt tattatggtt ttacaccc                                             28

<210> SEQ ID NO 52
<211> LENGTH: 28
<212> TYPE: DNA
<213> ORGANISM: Artificial
<220> FEATURE:
<223> OTHER INFORMATION: oligonucleotide primer

<400> SEQUENCE: 52
tgatcacatc accgtctctc ttcattaa                                             28

<210> SEQ ID NO 53
<211> LENGTH: 28
<212> TYPE: DNA
<213> ORGANISM: Artificial
<220> FEATURE:
<223> OTHER INFORMATION: oligonucleotide primer

<400> SEQUENCE: 53
tatcccagtc tcgatattgt catccgct                                             28

<210> SEQ ID NO 54
<211> LENGTH: 26
<212> TYPE: DNA
<213> ORGANISM: Artificial
<220> FEATURE:
<223> OTHER INFORMATION: Oligonucleotide primer

<400> SEQUENCE: 54
tttgtattta ggtccctaac gccctc                                               26

<210> SEQ ID NO 55
<211> LENGTH: 26
<212> TYPE: DNA
```

-continued

```
<213> ORGANISM: Artificial
<220> FEATURE:
<223> OTHER INFORMATION: Oligonucleotide primer

<400> SEQUENCE: 55
tgttgatgcg gatttctgcg tgtgat                                              26

<210> SEQ ID NO 56
<211> LENGTH: 1000
<212> TYPE: DNA
<213> ORGANISM: Oryza sativa
<220> FEATURE:
<221> NAME/KEY: promoter
<222> LOCATION: (1)..(1000)
<223> OTHER INFORMATION: transcription regulating sequence from Oryza
      sativa Lactate-dehydrogenase gene comprising 5'-untranslated
      region
<220> FEATURE:
<221> NAME/KEY: misc_feature
<222> LOCATION: (645)..(945)
<223> OTHER INFORMATION: potential core promoter region comprising
      cluster of promoter elements
<220> FEATURE:
<221> NAME/KEY: TATA_signal
<222> LOCATION: (905)..(911)
<223> OTHER INFORMATION: potential TATA box
<220> FEATURE:
<221> NAME/KEY: 5'UTR
<222> LOCATION: (946)..(1000)
<223> OTHER INFORMATION: 5'-untranslated region

<400> SEQUENCE: 56
aaccgtgcgc gctctcaaat taaaccagcg gcagctcgta gtacctagga tcatgcttgg         60
ccacgaactt ataattactg tgttaagtag tggcccctac agctacttgt agcttgtttc        120
gcaaggccct tcatgcattt acttagtagt actactgatt atcatatcaa gggtgtctct        180
gtcaaggatg atctgagctt gaatcgatct atgtaatcag cagtcatgca tgatgtttct        240
gtgttggtgg acgccacggt tttctccctc agctcatcgt ttcaaaccga aaaaaaagaa        300
tggaatcttg atcaagattc ttaagaccta attaccacta cagccgcgac ctcgattttg        360
ttttcttccg gcctgatcca acaggcatcg caagttaagt acgtggtttt catccccatc        420
aattcaattc tacccaaatc aagtcttatg ttaacggcat gcgttggtcg tctaattcat        480
gctgaccact aattaagtta ctggctagta gcttagctac tgacaacatt ctttcttaaa        540
aagggagatc tatatacatt catatatatg tacatgtgtg tgtcgcttta ttaaagtgga        600
tcgatgaacc gacgaagaaa ttaggtacca caaattaaag gtagcagtac tgccgccatt        660
gtgccaaaaa ccagctaatt aaccatcggt tttcactaat caagcacaat catgctacta        720
attacccttt tcaacctata aatttatcac ggtcagatca atttttctaa ttactttaaa        780
gataatataa tagtagtaat caaccctata aatacacaag gggtgcaacg accatgcatg        840
tatagcaaaa acacatttcc aacattcggt cttcactact agctagtagt gttttttttcc       900 tacatatata aacaataatt attcattgac aggcatcaag ctagctagct agccaactgt        960
ctgcaagaag aagaagaaga agaaggtgca ggataaatcg                             1000

<210> SEQ ID NO 57
<211> LENGTH: 945
<212> TYPE: DNA
<213> ORGANISM: Oryza sativa
<220> FEATURE:
<221> NAME/KEY: promoter
<222> LOCATION: (1)..(945)
<223> OTHER INFORMATION: transcription regulating sequence from Oryza
      sativa Lactate-dehydrogenase gene
```

```
<220> FEATURE:
<221> NAME/KEY: misc_feature
<222> LOCATION: (645)..(945)
<223> OTHER INFORMATION: potential core promoter region comprising
      clusters of promoter elements
<220> FEATURE:
<221> NAME/KEY: TATA_signal
<222> LOCATION: (905)..(911)
<223> OTHER INFORMATION: potentail TATA box

<400> SEQUENCE: 57
aaccgtgcgc gctctcaaat taaaccagcg gcagctcgta gtacctagga tcatgcttgg      60
ccacgaactt ataattactg tgttaagtag tggcccctac agctacttgt agcttgtttc     120
gcaaggccct tcatgcattt acttagtagt actactgatt atcatatcaa gggtgtctct     180
gtcaaggatg atctgagctt gaatcgatct atgtaatcag cagtcatgca tgatgtttct     240
gtgttggtgg acgccacggt tttctccctc agctcatcgt ttcaaaccga aaaaaagaa      300 tggaatcttg atcaagattc ttaagaccta attccacta cagccgcgac ctcgattttg      360
ttttcttccg gcctgatcca acaggcatcg caagttaagt acgtggtttt catccccatc     420
aattcaattc tacccaaatc aagtcttatg ttaacggcat gcgttggtcg tctaattcat     480
gctgaccact aattaagtta ctggctagta gcttagctac tgacaacatt ctttcttaaa     540
aagggagatc tatatacatt catatatatg tacatgtgtg tgtcgcttta ttaaagtgga     600
tcgatgaacc gacgaagaaa ttaggtacca caaattaaag gtagcagtac tgccgccatt     660
gtgccaaaaa ccagctaatt aaccatcggt tttcactaat caagcacaat catgctacta     720
attacccttt tcaacctata aatttatcac ggtcagatca atttttctaa ttactttaaa     780
gataatataa tagtagtaat caaccctata aatacacaag gggtgcaacg accatgcatg     840
tatagcaaaa acacatttcc aacattcggt cttcactact agctagtagt gttttttcc      900 tacatatata aacaataatt attcattgac aggcatcaag ctagc                     945

<210> SEQ ID NO 58
<211> LENGTH: 301
<212> TYPE: DNA
<213> ORGANISM: Oryza sativa
<220> FEATURE:
<221> NAME/KEY: promoter
<222> LOCATION: (1)..(301)
<223> OTHER INFORMATION: core transcription regulating sequence from
      Oryza sativa Lactate-dehydrogenase gene comprising clusters of
      promoter elements
<220> FEATURE:
<221> NAME/KEY: TATA_signal
<222> LOCATION: (261)..(267)
<223> OTHER INFORMATION: potential TATA box

<400> SEQUENCE: 58
cagtactgcc gccattgtgc caaaaaccag ctaattaacc atcggttttc actaatcaag      60
cacaatcatg ctactaatta ccctttttcaa cctataaatt tatcacggtc agatcaattt    120
ttctaattac tttaaagata atataatagt agtaatcaac cctataaata cacaaggggt    180
gcaacgacca tgcatgtata gcaaaaacac atttccaaca ttcggtcttc actactagct    240
agtagtgttt ttttcctaca tatataaaca ataattattc attgacaggc atcaagctag    300
c                                                                      301

<210> SEQ ID NO 59
<211> LENGTH: 1083
<212> TYPE: DNA
<213> ORGANISM: Oryza sativa
```

```
<220> FEATURE:
<221> NAME/KEY: CDS
<222> LOCATION: (1)..(1080)
<223> OTHER INFORMATION: coding for Oryza sativa Lactate-dehydrogenase

<400> SEQUENCE: 59 atg aag aag gcg tcg tcg ctg tct gag ctg ggg ttc gac gcc gat ggc      48
Met Lys Lys Ala Ser Ser Leu Ser Glu Leu Gly Phe Asp Ala Asp Gly
1               5                   10                  15 ccg tca ttc ttc cgg cac ctg acg ctg acc gat ggc gac gac ggc acg      96
Pro Ser Phe Phe Arg His Leu Thr Leu Thr Asp Gly Asp Asp Gly Thr
            20                  25                  30 ctg ccc cgg cgg cgg ctg atc aag atc tcg gtg atc ggc gcg ggc aac     144
Leu Pro Arg Arg Arg Leu Ile Lys Ile Ser Val Ile Gly Ala Gly Asn
        35                  40                  45 gtg ggc atg gcc atc gcg cag acg atc ctg acg cag gac ctc gcc gac     192
Val Gly Met Ala Ile Ala Gln Thr Ile Leu Thr Gln Asp Leu Ala Asp
    50                  55                  60 gag atc gtg ctg atc gac gcg gtg gcg gac aag gtg cgg ggc gag atg     240
Glu Ile Val Leu Ile Asp Ala Val Ala Asp Lys Val Arg Gly Glu Met
65                  70                  75                  80 ctg gac ctg cag cac gcg gcg gcg ttc ctc ccc cgc gtg aac atc gtg     288
Leu Asp Leu Gln His Ala Ala Ala Phe Leu Pro Arg Val Asn Ile Val
                85                  90                  95 tcc ggc acg gag gtg tcg ctg acg agg agc tcg gac ctg gtg atc gtg     336
Ser Gly Thr Glu Val Ser Leu Thr Arg Ser Ser Asp Leu Val Ile Val
            100                 105                 110 acg gcg ggg gct cgg cag atc ccg ggg gag acg cgg ctg aac ctg ctg     384
Thr Ala Gly Ala Arg Gln Ile Pro Gly Glu Thr Arg Leu Asn Leu Leu
        115                 120                 125 cag cgg aac gtg tcg ctg ttc cgg aag atc gtg ccg gcg gcg gcg gag     432
Gln Arg Asn Val Ser Leu Phe Arg Lys Ile Val Pro Ala Ala Ala Glu
    130                 135                 140 gcg tcg ccg gag tcg gtg ctg gtg atc gtg tcg aac ccg gtg gac gtg     480
Ala Ser Pro Glu Ser Val Leu Val Ile Val Ser Asn Pro Val Asp Val
145                 150                 155                 160 ctg acg tac gtg gcg tgg aag ctg tcg ggg ttc ccg gcg agc agg gtg     528
Leu Thr Tyr Val Ala Trp Lys Leu Ser Gly Phe Pro Ala Ser Arg Val
                165                 170                 175 atc ggg tcg ggg acg aac ctg gac tcg tct cgg ttc agg ttc ctc ctc     576
Ile Gly Ser Gly Thr Asn Leu Asp Ser Ser Arg Phe Arg Phe Leu Leu
            180                 185                 190 gcc gag cac ctg gag gtg agc gcg cag gac gtg cag gcg tac atg gtg     624
Ala Glu His Leu Glu Val Ser Ala Gln Asp Val Gln Ala Tyr Met Val
        195                 200                 205 ggg gag cac ggg gac agc tcg gtg gcg ctg tgg tcg agc atc agc gtg     672
Gly Glu His Gly Asp Ser Ser Val Ala Leu Trp Ser Ser Ile Ser Val
    210                 215                 220 ggg ggg atg ccg gtg ctg gcg cac ctg cag aag aac cac cgg tcg gcg     720
Gly Gly Met Pro Val Leu Ala His Leu Gln Lys Asn His Arg Ser Ala
225                 230                 235                 240 gcg acg gcg aag aag ttc gac gag gcg gcg ctg gag ggg atc cgg cgg     768
Ala Thr Ala Lys Lys Phe Asp Glu Ala Ala Leu Glu Gly Ile Arg Arg
                245                 250                 255 gcg gtg gtg ggg agc gcg tac gag gtg atc aag ctc aag ggg tac acg     816
Ala Val Val Gly Ser Ala Tyr Glu Val Ile Lys Leu Lys Gly Tyr Thr
            260                 265                 270 tcg tgg gcc atc ggc tac tcc gtc gcc agc atc gcc tgg tcg ctg ctc     864
Ser Trp Ala Ile Gly Tyr Ser Val Ala Ser Ile Ala Trp Ser Leu Leu
        275                 280                 285
```

| | | | | | | | | | | | | | | | | |
|---|---|---|---|---|---|---|---|---|---|---|---|---|---|---|---|---|
| cgt | gac | cag | cgc | cgc | atc | cac | ccg | gtc | tcc | gtc | ctc | gcc | aag | ggc | ctt | 912 |
| Arg | Asp | Gln | Arg | Arg | Ile | His | Pro | Val | Ser | Val | Leu | Ala | Lys | Gly | Leu | |
| | 290 | | | | 295 | | | | 300 | | | | | | | |
| gtc | cgt | ggc | gtc | ccc | gcc | gac | cgc | gag | ctc | ttc | ctc | agc | ctg | ccc | gct | 960 |
| Val | Arg | Gly | Val | Pro | Ala | Asp | Arg | Glu | Leu | Phe | Leu | Ser | Leu | Pro | Ala | |
| 305 | | | | | 310 | | | | | 315 | | | | | 320 | |
| cgc | ctc | ggc | cgc | gcc | ggc | gtg | ctt | ggc | gtc | gcc | gcc | gag | ctg | gtg | ctc | 1008 |
| Arg | Leu | Gly | Arg | Ala | Gly | Val | Leu | Gly | Val | Ala | Ala | Glu | Leu | Val | Leu | |
| | | | 325 | | | | | 330 | | | | | 335 | | | |
| acc | gac | gag | gag | gag | agg | agg | ctt | cgc | atc | tcc | gcc | gaa | acc | ctc | tgg | 1056 |
| Thr | Asp | Glu | Glu | Glu | Arg | Arg | Leu | Arg | Ile | Ser | Ala | Glu | Thr | Leu | Trp | |
| | | 340 | | | | | 345 | | | | | 350 | | | | |
| gga | tac | tgc | cac | gcc | ctc | ggc | ctc | taa | | | | | | | | 1083 |
| Gly | Tyr | Cys | His | Ala | Leu | Gly | Leu | | | | | | | | | |
| | 355 | | | | 360 | | | | | | | | | | | |

<210> SEQ ID NO 60
<211> LENGTH: 360
<212> TYPE: PRT
<213> ORGANISM: Oryza sativa

<400> SEQUENCE: 60

Met Lys Lys Ala Ser Ser Leu Ser Glu Leu Gly Phe Asp Ala Asp Gly
1               5                   10                  15

Pro Ser Phe Phe Arg His Leu Thr Leu Thr Asp Gly Asp Asp Gly Thr
            20                  25                  30

Leu Pro Arg Arg Leu Ile Lys Ile Ser Val Ile Gly Ala Gly Asn
        35                  40                  45

Val Gly Met Ala Ile Ala Gln Thr Ile Leu Thr Gln Asp Leu Ala Asp
50                  55                  60

Glu Ile Val Leu Ile Asp Ala Val Ala Asp Lys Val Arg Gly Glu Met
65                  70                  75                  80

Leu Asp Leu Gln His Ala Ala Phe Leu Pro Arg Val Asn Ile Val
            85                  90                  95

Ser Gly Thr Glu Val Ser Leu Thr Arg Ser Ser Asp Leu Val Ile Val
            100                 105                 110

Thr Ala Gly Ala Arg Gln Ile Pro Gly Glu Thr Arg Leu Asn Leu Leu
        115                 120                 125

Gln Arg Asn Val Ser Leu Phe Arg Lys Ile Val Pro Ala Ala Ala Glu
130                 135                 140

Ala Ser Pro Glu Ser Val Leu Val Ile Val Ser Asn Pro Val Asp Val
145                 150                 155                 160

Leu Thr Tyr Val Ala Trp Lys Leu Ser Gly Phe Pro Ala Ser Arg Val
            165                 170                 175

Ile Gly Ser Gly Thr Asn Leu Asp Ser Ser Arg Phe Arg Phe Leu Leu
        180                 185                 190

Ala Glu His Leu Glu Val Ser Ala Gln Asp Val Gln Ala Tyr Met Val
    195                 200                 205

Gly Glu His Gly Asp Ser Ser Val Ala Leu Trp Ser Ser Ile Ser Val
210                 215                 220

Gly Gly Met Pro Val Leu Ala His Leu Gln Lys Asn His Arg Ser Ala
225                 230                 235                 240

Ala Thr Ala Lys Lys Phe Asp Glu Ala Leu Glu Gly Ile Arg Arg
            245                 250                 255

Ala Val Val Gly Ser Ala Tyr Glu Val Ile Lys Leu Lys Gly Tyr Thr
        260                 265                 270

```
Ser Trp Ala Ile Gly Tyr Ser Val Ala Ser Ile Ala Trp Ser Leu Leu
        275                 280                 285

Arg Asp Gln Arg Arg Ile His Pro Val Ser Val Leu Ala Lys Gly Leu
290                 295                 300

Val Arg Gly Val Pro Ala Asp Arg Glu Leu Phe Leu Ser Leu Pro Ala
305                 310                 315                 320

Arg Leu Gly Arg Ala Gly Val Leu Gly Val Ala Ala Glu Leu Val Leu
                325                 330                 335

Thr Asp Glu Glu Arg Arg Leu Arg Ile Ser Ala Glu Thr Leu Trp
            340                 345                 350

Gly Tyr Cys His Ala Leu Gly Leu
        355                 360

<210> SEQ ID NO 61
<211> LENGTH: 1000
<212> TYPE: DNA
<213> ORGANISM: Oryza sativa
<220> FEATURE:
<221> NAME/KEY: promoter
<222> LOCATION: (1)..(1000)
<223> OTHER INFORMATION: transcription regulating sequence from Oryza
      sativa Lactate-dehydrogenase gene comprising 5'-untranslated
      region
<220> FEATURE:
<221> NAME/KEY: misc_feature
<222> LOCATION: (419)..(719)
<223> OTHER INFORMATION: potential core promoter region comprising
      clusters of promoter elements
<220> FEATURE:
<221> NAME/KEY: TATA_signal
<222> LOCATION: (679)..(685)
<223> OTHER INFORMATION: potential TATA box
<220> FEATURE:
<221> NAME/KEY: 5'UTR
<222> LOCATION: (720)..(1000)
<223> OTHER INFORMATION: 5'-untranslated region

<400> SEQUENCE: 61
atcaacatcc gtaccaaatt aagtgtttct ttgacagcgt gccagatttg gatcggtcat      60
tcgttgcgga aagtagtacc aatgacttac tgctactatt aatctactac tgtttcgctt     120
aagtataggt aaaggaaatg taaccctatt tcgagaaaat atattagtgg tagataggat     180
agctaggaga tccaaagagc agaatggtat actgcattag atatatccaa tgtgccacga     240
tgagtggttt ttctttatct gtttgtacta atttgcgcac ttttgaccga taagcgggcc     300
ggcatctttt taaatagaga aacacgcgat atgatgatag gcagtgagat ttcttcacaa     360
atactgtaca gaacagtaga gcagtagtag tagggcacaa attgatggaa tcaacttagc     420
aacctttgta gaccgtcgtc aattttacaa gggagagata tagtagaatg cgggtacaac     480
agttcatgct gtgttgagtt atatattgtt tttgggtttg tgattaaaca gtgtaacaac     540
acggaaaggt tcaagacgag caaacacgtc agcatgtaca aacgcagtgt atgagttaat     600
taattatatg gttagcgtgt atcgacattc tcgataccag tttaaaatat gtgatgatat     660
tattagacct tgcaccccta taaattaggg ccggtgaaca aaaccatcaa cgccttagtt     720
tttgattttg aagaagaaat tgttgtcagc atcattagat cttgtgtgag tatatttgag     780
agtcaaatca gcatgagcgg tttggaaaac cgccgtctgt agtgtagcgg ttttgtctcc     840
agagcgacct cttctctata aagaggagga gaacttccat ggaatgagcc acaaaaccac     900
catcgatcat ttccatttcc attttcagga gagatccaca tcgccgttgg cctttcatcc     960
agtgagtgag ggagggagat ctcgatctcg gtctcgcgac                          1000
```

<210> SEQ ID NO 62
<211> LENGTH: 719
<212> TYPE: DNA
<213> ORGANISM: Oryza sativa
<220> FEATURE:
<221> NAME/KEY: promoter
<222> LOCATION: (1)..(719)
<223> OTHER INFORMATION: transcription regulating sequence from Oryza sativa Lactate-dehydrogenase gene
<220> FEATURE:
<221> NAME/KEY: misc_feature
<222> LOCATION: (419)..(719)
<223> OTHER INFORMATION: potential core promoter region comprising clusters of promoter elements
<220> FEATURE:
<221> NAME/KEY: TATA_signal
<222> LOCATION: (679)..(685)
<223> OTHER INFORMATION: potential TATA box

<400> SEQUENCE: 62

```
atcaacatcc gtaccaaatt aagtgtttct ttgacagcgt gccagatttg gatcggtcat    60
tcgttgcgga aagtagtacc aatgacttac tgctactatt aatctactac tgtttcgctt   120
aagtataggt aaaggaaatg taaccctatt tcgagaaaat atattagtgg tagataggat   180
agctaggaga tccaaagagc agaatggtat actgcattag atatatccaa tgtgccacga   240
tgagtggttt ttctttatct gtttgtacta atttgcgcac ttttgaccga taagcgggcc   300
ggcatctttt taaatagaga aacacgcgat atgatgatag gcagtgagat ttcttcacaa   360
atactgtaca gaacagtaga gcagtagtag tagggcacaa attgatggaa tcaacttagc   420
aacctttgta gaccgtcgtc aattttacaa gggagagata tagtagaatg cgggtacaac   480
agttcatgct gtgttgagtt atatattgtt tttgggtttg tgattaaaca gtgtaacaac   540
acggaaaggt tcaagacgag caaacacgtc agcatgtaca aacgcagtgt atgagttaat   600
taattatatg gttagcgtgt atcgacattc tcgataccag tttaaaatat gtgatgatat   660
tattagacct tgcaccccta taaattaggg ccggtgaaca aaaccatcaa cgccttagt   719
```

<210> SEQ ID NO 63
<211> LENGTH: 301
<212> TYPE: DNA
<213> ORGANISM: Oryza sativa
<220> FEATURE:
<221> NAME/KEY: promoter
<222> LOCATION: (1)..(301)
<223> OTHER INFORMATION: core transcription regulating sequence from Oryza sativa Lactate-dehydrogenase gene comprising clusters of promoter elements
<220> FEATURE:
<221> NAME/KEY: TATA_signal
<222> LOCATION: (261)..(267)
<223> OTHER INFORMATION: potential TATA box

<400> SEQUENCE: 63

```
gcaacctttg tagaccgtcg tcaattttac aagggagaga tatagtagaa tgcgggtaca    60
acagttcatg ctgtgttgag ttatatattg tttttgggtt tgtgattaaa cagtgtaaca   120
acacggaaag gttcaagacg agcaaacacg tcagcatgta caaacgcagt gtatgagtta   180
attaattata tggttagcgt gtatcgacat tctcgatacc agtttaaaat atgtgatgat   240
attattagac cttgcaccccc tataaattag ggccggtgaa caaaaccatc aacgccttag   300
t                                                                   301
```

<210> SEQ ID NO 64
<211> LENGTH: 1062

<212> TYPE: DNA
<213> ORGANISM: Oryza sativa
<220> FEATURE:
<221> NAME/KEY: CDS
<222> LOCATION: (1)..(1059)
<223> OTHER INFORMATION: coding for Oryza sativa Lactate-dehydrogenase

<400> SEQUENCE: 64

```
atg aag aag gct tcg tct ctg tcg gag ctg ggg ttc gac gcg gag ggc      48
Met Lys Lys Ala Ser Ser Leu Ser Glu Leu Gly Phe Asp Ala Glu Gly
1               5                   10                  15 gcg tcg tcg ggg ttc ttc cgt ccg gtg gcg gac ggc ggg tcg acg ccg      96
Ala Ser Ser Gly Phe Phe Arg Pro Val Ala Asp Gly Gly Ser Thr Pro
                20                  25                  30 acg tcg cac cgg cgt cgg ctg acg aag ata tcg gtg atc ggc gcg ggc     144
Thr Ser His Arg Arg Arg Leu Thr Lys Ile Ser Val Ile Gly Ala Gly
            35                  40                  45 aac gtg ggg atg gcg atc gcg cag acc atc ctg acc cgg gac atg gcg     192
Asn Val Gly Met Ala Ile Ala Gln Thr Ile Leu Thr Arg Asp Met Ala
        50                  55                  60 gac gag atc gcg ctg gtg gac gcg gtg ccg gac aag ctg cgc ggg gag     240
Asp Glu Ile Ala Leu Val Asp Ala Val Pro Asp Lys Leu Arg Gly Glu
65                  70                  75                  80 atg ctg gac ctg cag cac gcg gcg gcg ttc ctc ccc cgc gtc cgc ctc     288
Met Leu Asp Leu Gln His Ala Ala Ala Phe Leu Pro Arg Val Arg Leu
                85                  90                  95 gtc tcc gac acc gac ctg gcc gtc acg cgc ggc tcc gac ctg gcc atc     336
Val Ser Asp Thr Asp Leu Ala Val Thr Arg Gly Ser Asp Leu Ala Ile
            100                 105                 110 gtc acg gcc ggc gcg cgc cag atc ccc ggg gag agc cgc ctg aac ctg     384
Val Thr Ala Gly Ala Arg Gln Ile Pro Gly Glu Ser Arg Leu Asn Leu
        115                 120                 125 ctg cag cgg aac gtg gcg ctg ttc cgg aag atc gtg ccg gcg ctg gcg     432
Leu Gln Arg Asn Val Ala Leu Phe Arg Lys Ile Val Pro Ala Leu Ala
130                 135                 140 gag cac tcg ccg gag gcg ctg ctg ctg atc gtc tcc aac ccc gtc gac     480
Glu His Ser Pro Glu Ala Leu Leu Leu Ile Val Ser Asn Pro Val Asp
145                 150                 155                 160 gtg ctg acg tac gtg gcg tgg aag ctg tcg ggg ttc ccg gcg agc cgc     528
Val Leu Thr Tyr Val Ala Trp Lys Leu Ser Gly Phe Pro Ala Ser Arg
                165                 170                 175 gtc atc ggc tcc ggc acc aac ctc gac tcc tcc agg ttc cgc ttc ctc     576
Val Ile Gly Ser Gly Thr Asn Leu Asp Ser Ser Arg Phe Arg Phe Leu
            180                 185                 190 ctc gcc gag cac ctc cag gtc aac gcc cag gat gtc cag gcg tac atg     624
Leu Ala Glu His Leu Gln Val Asn Ala Gln Asp Val Gln Ala Tyr Met
        195                 200                 205 gtg gga gag cac ggg gac agc tcg gtg gcg ata tgg tcg agc atg agc     672
Val Gly Glu His Gly Asp Ser Ser Val Ala Ile Trp Ser Ser Met Ser
210                 215                 220 gtg gcc ggg atg ccg gtg ctc aag tcg ctg cgg gag agc cac cag agc     720
Val Ala Gly Met Pro Val Leu Lys Ser Leu Arg Glu Ser His Gln Ser
225                 230                 235                 240 ttc gac gag gag gcc ctg gag gga atc cgg cga gcg gtg gtg gac agc     768
Phe Asp Glu Glu Ala Leu Glu Gly Ile Arg Arg Ala Val Val Asp Ser
                245                 250                 255 gcg tac gag gtg atc agc ctc aag ggc tac acc tcc tgg gcc atc ggc     816
Ala Tyr Glu Val Ile Ser Leu Lys Gly Tyr Thr Ser Trp Ala Ile Gly
            260                 265                 270 tac tcc gtc gcc agc ctc gcc gcc tcc ctc ctc cgc gac cag cac cgc     864
Tyr Ser Val Ala Ser Leu Ala Ala Ser Leu Leu Arg Asp Gln His Arg
```

```
                   275                 280                 285
atc cac ccc gtc tcc gtc ctc gcc tcc ggc ttc cac ggc atc ccc caa       912
Ile His Pro Val Ser Val Leu Ala Ser Gly Phe His Gly Ile Pro Gln
    290                 295                 300 gac cac gag gtc ttc ctc agc ctc ccc gcc cgc ctc ggc cgc gcc ggc       960
Asp His Glu Val Phe Leu Ser Leu Pro Ala Arg Leu Gly Arg Ala Gly
305                 310                 315                 320 gtc ctc ggc gtc gcc gag atg gag ctc acc gag gag gag gcc cgc cgc      1008
Val Leu Gly Val Ala Glu Met Glu Leu Thr Glu Glu Glu Ala Arg Arg
                325                 330                 335 ctc cgc cgc tcc gcc aag acg ctc tgg gag aac tgc cag ctg ctc gac      1056
Leu Arg Arg Ser Ala Lys Thr Leu Trp Glu Asn Cys Gln Leu Leu Asp
            340                 345                 350 ctc taa                                                               1062
Leu

<210> SEQ ID NO 65
<211> LENGTH: 353
<212> TYPE: PRT
<213> ORGANISM: Oryza sativa

<400> SEQUENCE: 65

Met Lys Lys Ala Ser Ser Leu Ser Glu Leu Gly Phe Asp Ala Glu Gly
1               5                   10                  15

Ala Ser Ser Gly Phe Phe Arg Pro Val Ala Asp Gly Gly Ser Thr Pro
            20                  25                  30

Thr Ser His Arg Arg Leu Thr Lys Ile Ser Val Ile Gly Ala Gly
        35                  40                  45

Asn Val Gly Met Ala Ile Ala Gln Thr Ile Leu Thr Arg Asp Met Ala
    50                  55                  60

Asp Glu Ile Ala Leu Val Asp Ala Val Pro Asp Lys Leu Arg Gly Glu
65                  70                  75                  80

Met Leu Asp Leu Gln His Ala Ala Ala Phe Leu Pro Arg Val Arg Leu
                85                  90                  95

Val Ser Asp Thr Asp Leu Ala Val Thr Arg Gly Ser Asp Leu Ala Ile
            100                 105                 110

Val Thr Ala Gly Ala Arg Gln Ile Pro Gly Glu Ser Arg Leu Asn Leu
        115                 120                 125

Leu Gln Arg Asn Val Ala Leu Phe Arg Lys Ile Val Pro Ala Leu Ala
    130                 135                 140

Glu His Ser Pro Glu Ala Leu Leu Leu Ile Val Ser Asn Pro Val Asp
145                 150                 155                 160

Val Leu Thr Tyr Val Ala Trp Lys Leu Ser Gly Phe Pro Ala Ser Arg
                165                 170                 175

Val Ile Gly Ser Gly Thr Asn Leu Asp Ser Ser Arg Phe Arg Phe Leu
            180                 185                 190

Leu Ala Glu His Leu Gln Val Asn Ala Gln Asp Val Gln Ala Tyr Met
        195                 200                 205

Val Gly Glu His Gly Asp Ser Ser Val Ala Ile Trp Ser Ser Met Ser
    210                 215                 220

Val Ala Gly Met Pro Val Leu Lys Ser Leu Arg Glu Ser His Gln Ser
225                 230                 235                 240

Phe Asp Glu Glu Ala Leu Glu Gly Ile Arg Arg Ala Val Val Asp Ser
                245                 250                 255

Ala Tyr Glu Val Ile Ser Leu Lys Gly Tyr Thr Ser Trp Ala Ile Gly
            260                 265                 270
```

```
Tyr Ser Val Ala Ser Leu Ala Ala Ser Leu Leu Arg Asp Gln His Arg
        275                 280                 285

Ile His Pro Val Ser Val Leu Ala Ser Gly Phe His Gly Ile Pro Gln
        290                 295                 300

Asp His Glu Val Phe Leu Ser Leu Pro Ala Arg Leu Gly Arg Ala Gly
305                 310                 315                 320

Val Leu Gly Val Ala Glu Met Glu Leu Thr Glu Glu Ala Arg Arg
                325                 330                 335

Leu Arg Arg Ser Ala Lys Thr Leu Trp Glu Asn Cys Gln Leu Leu Asp
        340                 345                 350

Leu

<210> SEQ ID NO 66
<211> LENGTH: 997
<212> TYPE: DNA
<213> ORGANISM: Zea mays
<220> FEATURE:
<221> NAME/KEY: promoter
<222> LOCATION: (1)..(997)
<223> OTHER INFORMATION: transcription regulating sequence from Zea mays
      Caffeoyl-CoA-O-methyltransferase gene comprising 5'-untranslated
      region
<220> FEATURE:
<221> NAME/KEY: misc_feature
<222> LOCATION: (600)..(900)
<223> OTHER INFORMATION: putative core promoter region comprising
      clusters of promoter elements
<220> FEATURE:
<221> NAME/KEY: TATA_signal
<222> LOCATION: (860)..(866)
<223> OTHER INFORMATION: potential TATA box
<220> FEATURE:
<221> NAME/KEY: 5'UTR
<222> LOCATION: (901)..(997)
<223> OTHER INFORMATION: 5'-untranslated region

<400> SEQUENCE: 66
cagcccgtac caggtgtcgc tcttgggccg tgttgttgcc gtccaaccaa gcaaggcaag      60
cgtgtagata gataagaaga tagcgtgagt gagtggcatc cagacatcca gtacgttagc     120
ctggcttacg ttacggacac gggcgtggcg cctttgtcgt gctgcgcacc cgccagccag     180
cagccatcca gcagggcctc cgtttgtccg tctcctctct ctacaggctg tttgtgcccc     240
caagcaagca ctacgcgcgc gaaaaaaaat aaaaaaaaaa ggcacgtcat ctggatctct     300
tgctctagct cactcaacct caccaaaatg tgcaggctgc tccgactccg agaacaggac     360
ggtcatgccg cgcgcaccgg tttcccttcc catgccgcta ccacctcccg actcccgagt     420
cacgactggg ggaccacccg atggacgatg attgatgcac tgaaagcaag agtgggttgg     480
tggtggaccg tggcagtcta ccaaatgtcg ctgctctccc cgcccggccg gaacgaggaa     540
ggaaggcgac caccactcca cgccggtcgt gccaggtcgg cagtcagagt cagccgcgcc     600
tgcgcgcgtc ccttccccac caaccccttct ccctccccgc actcgacagc cacggccgcg     660
acggcgtccg cgtgcaccgg acaccacggc cagacccgag gccacacagc cctctgacca     720
aacgcacgga tccggccagc cacccacccc gcccccctag cggccgccac ccacccgtgc     780
gcgcggcgca ccaaggcctg gcccggcagt ggcagccagg ctctcacacg cctcgcctag     840
tcgccttgcc gccgcgcgtt atataagagc cgccccggca ggcacggtcg gtcaatccag     900
caatacccga cgcgcaagcc agtgccgcac ccagaccaga tctccgcgac atatcagtcg     960
ttcgtccagc taactgcact gcactgcact gcacgca                              997
```

<210> SEQ ID NO 67
<211> LENGTH: 900
<212> TYPE: DNA
<213> ORGANISM: Zea mays
<220> FEATURE:
<221> NAME/KEY: promoter
<222> LOCATION: (1)..(900)
<223> OTHER INFORMATION: transcription regulating sequence from Zea mays Caffeoyl-CoA-O-methyltransferase gene
<220> FEATURE:
<221> NAME/KEY: misc_feature
<222> LOCATION: (600)..(900)
<223> OTHER INFORMATION: putative core promoter region comprising clusters of promotere elements
<220> FEATURE:
<221> NAME/KEY: TATA_signal
<222> LOCATION: (860)..(866)
<223> OTHER INFORMATION: potential TATA box

<400> SEQUENCE: 67

```
cagcccgtac caggtgtcgc tcttgggccg tgttgttgcc gtccaaccaa gcaaggcaag      60
cgtgtagata gataagaaga tagcgtgagt gagtggcatc cagacatcca gtacgttagc     120
ctggcttacg ttacggacac gggcgtggcg cctttgtcgt gctgcgcacc cgccagccag     180
cagccatcca gcaggcctc cgtttgtccg tctcctctct ctacaggctg tttgtgcccc     240
caagcaagca ctacgcgcgc gaaaaaaaat aaaaaaaaaa ggcacgtcat ctggatctct     300
tgctctagct cactcaacct caccaaaatg tgcaggctgc tccgactccg agaacaggac     360
ggtcatgccg cgcgcaccgg tttcccttcc catgccgcta ccacctcccg actcccgagt     420
cacgactggg ggaccacccg atggacgatg attgatgcac tgaaagcaag agtgggttgg     480
tggtggaccg tggcagtcta ccaaatgtcg ctgctctccc cgcccggccg gaacgaggaa     540
ggaaggcgac caccactcca cgccggtcgt gccaggtcgg cagtcagagt cagccgcgcc     600
tgcgcgcgtc cctttcccac caacccctct ccctccccgc actcgacagc cacggccgcg     660
acggcgtccg cgtgcaccgg acaccacggc cagacccgag gccacacagc cctctgacca     720
aacgcacgga tccggccagc cacccacccc gccccctag cggccgccac ccacccgtgc     780
gcgcggcgca ccaaggcctg gcccggcagt ggcagccagg ctctcacacg cctcgcctag     840
tcgccttgcc gccgcgcgtt atataagagc cgccccggca ggcacggtcg gtcaatccag     900
```

<210> SEQ ID NO 68
<211> LENGTH: 301
<212> TYPE: DNA
<213> ORGANISM: Zea mays
<220> FEATURE:
<221> NAME/KEY: promoter
<222> LOCATION: (1)..(301)
<223> OTHER INFORMATION: core transcription regulating sequence from Zea mays Caffeoyl-CoA-O-methyltransferase gene comprising clusters of promoter elements
<220> FEATURE:
<221> NAME/KEY: TATA_signal
<222> LOCATION: (261)..(267)
<223> OTHER INFORMATION: potential TATA box

<400> SEQUENCE: 68

```
ctgcgcgcgt ccctttccca ccaacccctc tccctccccg cactcgacag ccacggccgc      60
gacggcgtcc gcgtgcaccg gacaccacgg ccagacccga ggccacacag ccctctgacc     120
aaacgcacgg atccggccag ccacccaccc cgccccccta gcggccgcca cccacccgtg     180
cgcgcggcgc accaaggcct ggcccggcag tggcagccag gctctcacac gcctcgccta     240
gtcgccttgc cgccgcgcgt tatataagag ccgccccggc aggcacggtc ggtcaatcca     300
``` g                                                                                                              301

<210> SEQ ID NO 69
<211> LENGTH: 801
<212> TYPE: DNA
<213> ORGANISM: Zea mays
<220> FEATURE:
<221> NAME/KEY: CDS
<222> LOCATION: (1)..(798)
<223> OTHER INFORMATION: encoding Zea mays Caffeoyl-CoA-O-
      methyltransferase

<400> SEQUENCE: 69

```
atg gcc acc acg gcg acc gag gcg acc aag acg act gca ccg gcg cag        48
Met Ala Thr Thr Ala Thr Glu Ala Thr Lys Thr Thr Ala Pro Ala Gln
1               5                   10                  15 gag cag cag gcc aac ggc aac ggc aac ggc aac ggc gag cag aag acg        96
Glu Gln Gln Ala Asn Gly Asn Gly Asn Gly Asn Gly Glu Gln Lys Thr
            20                  25                  30 cgc cac tcc gag gtc ggg cac aag agc ctg ctc aag agc gac gac ctc       144
Arg His Ser Glu Val Gly His Lys Ser Leu Leu Lys Ser Asp Asp Leu
        35                  40                  45 tac cag tac atc ctg gac acg agc gtg tac ccg cgg gag ccg gag agc       192
Tyr Gln Tyr Ile Leu Asp Thr Ser Val Tyr Pro Arg Glu Pro Glu Ser
50                  55                  60 atg aag gag ctg cgc gag atc acc gcc aag cac cca tgg aac ctg atg       240
Met Lys Glu Leu Arg Glu Ile Thr Ala Lys His Pro Trp Asn Leu Met
65                  70                  75                  80 acc acc tcc gcc gac gag ggc cag ttc ctc aac atg ctc atc aag ctc       288
Thr Thr Ser Ala Asp Glu Gly Gln Phe Leu Asn Met Leu Ile Lys Leu
                85                  90                  95 atc ggc gcc aag aag acc atg gag atc ggc gtc tac acc ggc tac tcg       336
Ile Gly Ala Lys Lys Thr Met Glu Ile Gly Val Tyr Thr Gly Tyr Ser
            100                 105                 110 ctc ctc gcc acc gcg ctc gca ctc ccg gag gac ggc acg atc ttg gcc       384
Leu Leu Ala Thr Ala Leu Ala Leu Pro Glu Asp Gly Thr Ile Leu Ala
        115                 120                 125 atg gac atc aac cgc gag aac tac gag cta ggc ctt ccc tgc atc aac       432
Met Asp Ile Asn Arg Glu Asn Tyr Glu Leu Gly Leu Pro Cys Ile Asn
    130                 135                 140 aag gcc ggc gtg gcc cac aag atc gac ttc cgc gag ggc ccc gcg ctc       480
Lys Ala Gly Val Ala His Lys Ile Asp Phe Arg Glu Gly Pro Ala Leu
145                 150                 155                 160 ccc gtc ctg gac gac ctc gtg gcg gac aag gag cag cac ggg tcg ttc       528
Pro Val Leu Asp Asp Leu Val Ala Asp Lys Glu Gln His Gly Ser Phe
                165                 170                 175 gac ttc gcc ttc gtg gac gcc gac aag gac aac tac ctc agc tac cac       576
Asp Phe Ala Phe Val Asp Ala Asp Lys Asp Asn Tyr Leu Ser Tyr His
            180                 185                 190 gag cgg ctc ctg aag ctg gtg agg ccc ggc ggc ctc atc ggc tac gac       624
Glu Arg Leu Leu Lys Leu Val Arg Pro Gly Gly Leu Ile Gly Tyr Asp
        195                 200                 205 aac acg ctg tgg aac ggc tcc gtc gtg ctc ccc gac gac gcg ccc atg       672
Asn Thr Leu Trp Asn Gly Ser Val Val Leu Pro Asp Asp Ala Pro Met
    210                 215                 220 cgc aag tac atc cgc ttc tac cgc gac ttc gtc ctc gcc ctc aac agc       720
Arg Lys Tyr Ile Arg Phe Tyr Arg Asp Phe Val Leu Ala Leu Asn Ser
225                 230                 235                 240 gcg ctc gcc gcc gac gac cgc gtc gag atc tgc cag ctc ccc gtc ggc       768
Ala Leu Ala Ala Asp Asp Arg Val Glu Ile Cys Gln Leu Pro Val Gly
                245                 250                 255
```

```
gac ggc gtc acg ctc tgc cgc cgc gtc aag tga                              801
Asp Gly Val Thr Leu Cys Arg Arg Val Lys
            260                 265

<210> SEQ ID NO 70
<211> LENGTH: 266
<212> TYPE: PRT
<213> ORGANISM: Zea mays

<400> SEQUENCE: 70

Met Ala Thr Thr Ala Thr Glu Ala Thr Lys Thr Thr Ala Pro Ala Gln
1               5                   10                  15

Glu Gln Gln Ala Asn Gly Asn Gly Asn Gly Asn Gly Glu Gln Lys Thr
            20                  25                  30

Arg His Ser Glu Val Gly His Lys Ser Leu Leu Lys Ser Asp Asp Leu
        35                  40                  45

Tyr Gln Tyr Ile Leu Asp Thr Ser Val Tyr Pro Arg Glu Pro Glu Ser
    50                  55                  60

Met Lys Glu Leu Arg Glu Ile Thr Ala Lys His Pro Trp Asn Leu Met
65                  70                  75                  80

Thr Thr Ser Ala Asp Glu Gly Gln Phe Leu Asn Met Leu Ile Lys Leu
                85                  90                  95

Ile Gly Ala Lys Lys Thr Met Glu Ile Gly Val Tyr Thr Gly Tyr Ser
            100                 105                 110

Leu Leu Ala Thr Ala Leu Ala Leu Pro Glu Asp Gly Thr Ile Leu Ala
        115                 120                 125

Met Asp Ile Asn Arg Glu Asn Tyr Glu Leu Gly Leu Pro Cys Ile Asn
    130                 135                 140

Lys Ala Gly Val Ala His Lys Ile Asp Phe Arg Glu Gly Pro Ala Leu
145                 150                 155                 160

Pro Val Leu Asp Asp Leu Val Ala Asp Lys Glu Gln His Gly Ser Phe
                165                 170                 175

Asp Phe Ala Phe Val Asp Ala Asp Lys Asp Asn Tyr Leu Ser Tyr His
            180                 185                 190

Glu Arg Leu Leu Lys Leu Val Arg Pro Gly Gly Leu Ile Gly Tyr Asp
        195                 200                 205

Asn Thr Leu Trp Asn Gly Ser Val Val Leu Pro Asp Asp Ala Pro Met
    210                 215                 220

Arg Lys Tyr Ile Arg Phe Tyr Arg Asp Phe Val Leu Ala Leu Asn Ser
225                 230                 235                 240

Ala Leu Ala Ala Asp Arg Val Glu Ile Cys Gln Leu Pro Val Gly
                245                 250                 255

Asp Gly Val Thr Leu Cys Arg Arg Val Lys
            260                 265

<210> SEQ ID NO 71
<211> LENGTH: 1028
<212> TYPE: DNA
<213> ORGANISM: Zea diploperennis
<220> FEATURE:
<221> NAME/KEY: promoter
<222> LOCATION: (1)..(1028)
<223> OTHER INFORMATION: transcription regulating region from Zea
      diploperennis hydroxyproline-rich glycoprotein gene comprising 5'-
      untranslated region
<220> FEATURE:
<221> NAME/KEY: misc_feature
<222> LOCATION: (654)..(954)
<223> OTHER INFORMATION: potential core promoter region comprising
```

```
        clusters of promoter elements
<220> FEATURE:
<221> NAME/KEY: TATA_signal
<222> LOCATION: (914)..(920)
<223> OTHER INFORMATION: potential TATA bos
<220> FEATURE:
<221> NAME/KEY: 5'UTR
<222> LOCATION: (955)..(1028)
<223> OTHER INFORMATION: potential 5'-untranslated region

<400> SEQUENCE: 71
atggacttcg aggaaacgat aacccctgga tgtcgagata gccgaagtcg aggtggtcat      60
ggtcgggaga cacgcggcag tagcatattc ttcggtaggg ctcgatgttc aagcgacaac     120
ggtcggcggg gcgacacaaa aatttagcac cagcagacct tcttgcttct tcgaccgtct     180
ggacatcgag gagcccagcc agggaggccg gcagcagcgc acacgtctgc accagtaatg     240
ttagccgcgc ccgcgacgta atagaagggg caacgataga tccggtcagg aaggccacga     300
catcgacgga tctagacagc gatcaggtca aagagacgac gaatctagcc gggaaggtag     360
atccctcgag agagttcata ttaaatgatg ttgtacatgc cataataact ctataaatct     420
aatttattca taggcgaagg taattgtatt atctttccca gcggagcatt atctgatctg     480
ccgttcagct tgatcgatcc acgtcgtttg atctcggcga gcagcacatg gcggctcttc     540
ttgtgtacag ggctcactct ctgctacttc agtgcaaggc ggagtgaatg cacaataacg     600
tgagtattgt gggaactact tgtagatgca aacgatgtaa atccacctgc tccaccaagt     660
gcccgcccgg ctctatccat tacattcgtc aacacgcagg ttcagactgg cccgtgctgg     720
accagtgagc ggtgaaccca gcccaagcga gtgaccatcg gggaagcctc ccgcccgtgc     780
tgcccccaca tggcttgcct gaatgcctct cgccgcagtg ccctctctcc tcctcctccc     840 cctccoctcc gtcgaagggc gtcacgagag cccagagggt atccgaggcc cccaccccac     900 ccottcctcc gtgtatataa gcagtggcag ggtgaacgtc tctcctcaga ccacccactg     960
cgccattggc cagctagagc caaccagaag agcttgcagt tactgggaga gtgtgtgtga    1020
gagagagg                                                             1028

<210> SEQ ID NO 72
<211> LENGTH: 954
<212> TYPE: DNA
<213> ORGANISM: Zea diploperennis
<220> FEATURE:
<221> NAME/KEY: promoter
<222> LOCATION: (1)..(954)
<223> OTHER INFORMATION: transcription regulating region from Zea
      diploperennis hydroxyproline-rich glycoprotein gene
<220> FEATURE:
<221> NAME/KEY: misc_feature
<222> LOCATION: (654)..(954)
<223> OTHER INFORMATION: putative core promoter region comprising
      clusters of promoter elements
<220> FEATURE:
<221> NAME/KEY: TATA_signal
<222> LOCATION: (914)..(920)
<223> OTHER INFORMATION: potential TATA box

<400> SEQUENCE: 72
atggacttcg aggaaacgat aacccctgga tgtcgagata gccgaagtcg aggtggtcat      60
ggtcgggaga cacgcggcag tagcatattc ttcggtaggg ctcgatgttc aagcgacaac     120
ggtcggcggg gcgacacaaa aatttagcac cagcagacct tcttgcttct tcgaccgtct     180
ggacatcgag gagcccagcc agggaggccg gcagcagcgc acacgtctgc accagtaatg     240
ttagccgcgc ccgcgacgta atagaagggg caacgataga tccggtcagg aaggccacga     300
```

```
catcgacgga tctagacagc gatcaggtca aagagacgac gaatctagcc gggaaggtag    360
atccctcgag agagttcata ttaaatgatg ttgtacatgc cataataact ctataaatct    420
aatttattca taggcgaagg taattgtatt atctttccca gcggagcatt atctgatctg    480
ccgttcagct tgatcgatcc acgtcgtttg atctcggcga gcagcacatg gcggctcttc    540
ttgtgtacag gctcactct ctgctacttc agtgcaaggc ggagtgaatg cacaataacg    600
tgagtattgt gggaactact tgtagatgca aacgatgtaa atccacctgc tccaccaagt    660
gcccgcccgg ctctatccat tacattcgtc aacacgcagg ttcagactgg cccgtgctgg    720
accagtgagc ggtgaaccca gcccaagcga gtgaccatcg gggaagcctc ccgcccgtgc    780
tgcccccaca tggcttgcct gaatgcctct cgccgcagtg ccctctctcc tcctcctccc    840
cctcccctcc gtcgaagggc gtcacgagag cccagagggt atccgaggcc ccacccccac    900
cccttcctcc gtgtatataa gcagtggcag ggtgaacgtc tctcctcaga ccac          954

<210> SEQ ID NO 73
<211> LENGTH: 301
<212> TYPE: DNA
<213> ORGANISM: Zea diploperennis
<220> FEATURE:
<221> NAME/KEY: promoter
<222> LOCATION: (1)..(301)
<223> OTHER INFORMATION: core transcription regulating region from Zea
      diploperennis hydroxyproline-rich glycoprotein gene comprising
      clusters of promoter elements
<220> FEATURE:
<221> NAME/KEY: TATA_signal
<222> LOCATION: (261)..(267)
<223> OTHER INFORMATION: potential TATA box

<400> SEQUENCE: 73
accaagtgcc cgcccggctc tatccattac attcgtcaac acgcaggttc agactggccc    60
gtgctggacc agtgagcggt gaacccagcc caagcgagtg accatcgggg aagcctcccg    120
cccgtgctgc ccccacatgg cttgcctgaa tgcctctcgc cgcagtgccc tctctcctcc    180 tcctcccct cccctccgtc gaagggcgtc acgagagccc agagggtatc cgaggccccc    240
accccacccc ttcctccgtg tatataagca gtggcagggt gaacgtctct cctcagacca    300
c                                                                    301

<210> SEQ ID NO 74
<211> LENGTH: 1053
<212> TYPE: DNA
<213> ORGANISM: Zea diploperennis
<220> FEATURE:
<221> NAME/KEY: CDS
<222> LOCATION: (1)..(1050)
<223> OTHER INFORMATION: encoding Zea diploperennis hydroxyproline-rich
      glycoprotein

<400> SEQUENCE: 74 atg ggt ggc agc ggc acg gct gct ctg ctg ctg gcc ctg gtg gcc gtg    48
Met Gly Gly Ser Gly Thr Ala Ala Leu Leu Leu Ala Leu Val Ala Val
1               5                   10                  15 agc ctg gcc gtg gag atc cag gcc gac gcc ggg tac ggg tac acc ccg    96
Ser Leu Ala Val Glu Ile Gln Ala Asp Ala Gly Tyr Gly Tyr Thr Pro
            20                  25                  30 aca ccg acg ccg gcc acc ccg acc ccg aag ccg gag aag ccc ccc acc    144
Thr Pro Thr Pro Ala Thr Pro Thr Pro Lys Pro Glu Lys Pro Pro Thr
        35                  40                  45 aag ggg ccc aag ccg gag aag ccg cca aag gag cac aag ccg ccc aag    192
```

```
              Lys Gly Pro Lys Pro Glu Lys Pro Pro Lys Glu His Lys Pro Pro Lys
                  50                  55                  60 gag cac ggg ccc aag ccg gag aag ccg ccc aag gag cac aag ccg acg           240
Glu His Gly Pro Lys Pro Glu Lys Pro Pro Lys Glu His Lys Pro Thr
 65                  70                  75                  80 ccg ccc acg tac acc ccg agc ccc aaa ccc acg ccg acg tac act               288
Pro Pro Thr Tyr Thr Pro Ser Pro Lys Pro Thr Pro Pro Thr Tyr Thr
                     85                  90                  95 ccc acc ccg acg ccg ccg act ccc aag ccg acg cca ccc aca tac acc           336
Pro Thr Pro Thr Pro Pro Thr Pro Lys Pro Thr Pro Pro Thr Tyr Thr
                    100                 105                 110 cca gcc cct acg ccc cac aaa ccc aca ccc aca cca aaa ccc act ccc           384
Pro Ala Pro Thr Pro His Lys Pro Thr Pro Thr Pro Lys Pro Thr Pro
                    115                 120                 125 act cct ccg acg tac acc cct tcc ccc aag cct ccg aca cct aag ccg           432
Thr Pro Pro Thr Tyr Thr Pro Ser Pro Lys Pro Pro Thr Pro Lys Pro
                    130                 135                 140 acc ccg ccg acg tac gct cca agc ccc aag cca ccg gct acc aag cct           480
Thr Pro Pro Thr Tyr Ala Pro Ser Pro Lys Pro Pro Ala Thr Lys Pro
145                 150                 155                 160 ccc acg ccc aag ccg acc ccg acg tac acc cct tcc ccc aaa cct               528
Pro Thr Pro Lys Pro Thr Pro Pro Thr Tyr Thr Pro Ser Pro Lys Pro
                    165                 170                 175 ccg aca ccc aag ccg acc ccg acg tac acc cca agc ccc aag ccg               576
Pro Thr Pro Lys Pro Thr Pro Pro Thr Tyr Thr Pro Ser Pro Lys Pro
                    180                 185                 190 acc ccg ccg acg tac acc cct tct ccc aag cct ccg aca cct aag ccg           624
Thr Pro Pro Thr Tyr Thr Pro Ser Pro Lys Pro Pro Thr Pro Lys Pro
                    195                 200                 205 acc ccg cct acg tac act cca agc cct aag cca ccg gct acc aag cct           672
Thr Pro Pro Thr Tyr Thr Pro Ser Pro Lys Pro Pro Ala Thr Lys Pro
210                 215                 220 ccc acg ccc aag ccg acc ccg cca acg tac acc cct tcc cca aag cct           720
Pro Thr Pro Lys Pro Thr Pro Pro Thr Tyr Thr Pro Ser Pro Lys Pro
225                 230                 235                 240 ccg aca ccc aag ccg acc ccg acg tac acc cct tcc ccc aag cca               768
Pro Thr Pro Lys Pro Thr Pro Pro Thr Tyr Thr Pro Ser Pro Lys Pro
                    245                 250                 255 ccg gct acc aag ccg acc cca acg tac acc cct tcc cca aag cct               816
Pro Ala Thr Lys Pro Thr Pro Pro Thr Tyr Thr Pro Ser Pro Lys Pro
                    260                 265                 270 ccg aca cct aag ccg acc ccg acg tac acc cct tcc ccc aag cct               864
Pro Thr Pro Lys Pro Thr Pro Pro Thr Tyr Thr Pro Ser Pro Lys Pro
                    275                 280                 285 ccg aca ccc aag ccg acc cca ccg tac acc act cca agc ccc aaa cca           912
Pro Thr Pro Lys Pro Thr Pro Pro Tyr Thr Pro Ser Pro Lys Pro
                    290                 295                 300 ccg gct acc aag cct ccc acg ccc aag ccg acc cca acg tac act               960
Pro Ala Thr Lys Pro Pro Thr Pro Lys Pro Thr Pro Pro Thr Tyr Thr
305                 310                 315                 320 ccc aca ccg aag ccg ccg gcc acc aag ccg ccc acc tac act ccg acg          1008
Pro Thr Pro Lys Pro Pro Ala Thr Lys Pro Pro Thr Tyr Thr Pro Thr
                    325                 330                 335 ccg ccg gtg tct cac acc ccc agc ccg ccg cca cct tac tac tag              1053
Pro Pro Val Ser His Thr Pro Ser Pro Pro Pro Pro Tyr Tyr
                    340                 345                 350

<210> SEQ ID NO 75
<211> LENGTH: 350
<212> TYPE: PRT
```

<213> ORGANISM: Zea diploperennis

<400> SEQUENCE: 75

```
Met Gly Gly Ser Gly Thr Ala Ala Leu Leu Ala Leu Val Ala Val
1               5                   10                  15

Ser Leu Ala Val Glu Ile Gln Ala Asp Ala Gly Tyr Gly Tyr Thr Pro
                20                  25                  30

Thr Pro Thr Pro Ala Thr Pro Thr Pro Lys Pro Glu Lys Pro Pro Thr
            35                  40                  45

Lys Gly Pro Lys Pro Glu Lys Pro Pro Lys Glu His Lys Pro Pro Lys
        50                  55                  60

Glu His Gly Pro Lys Pro Glu Lys Pro Pro Lys Glu His Lys Pro Thr
65                  70                  75                  80

Pro Pro Thr Tyr Thr Pro Ser Pro Lys Pro Thr Pro Thr Tyr Thr
                85                  90                  95

Pro Thr Pro Thr Pro Pro Thr Pro Lys Pro Thr Pro Thr Pro Tyr Thr
                100                 105                 110

Pro Ala Pro Thr Pro His Lys Pro Thr Pro Thr Pro Lys Pro Thr Pro
                115                 120                 125

Thr Pro Pro Thr Tyr Thr Pro Ser Pro Lys Pro Pro Thr Pro Lys Pro
                130                 135                 140

Thr Pro Pro Thr Tyr Ala Pro Ser Pro Lys Pro Ala Thr Lys Pro
145                 150                 155                 160

Pro Thr Pro Lys Pro Thr Pro Pro Thr Tyr Thr Pro Ser Pro Lys Pro
                165                 170                 175

Pro Thr Pro Lys Pro Thr Pro Pro Thr Tyr Thr Pro Ser Pro Lys Pro
                180                 185                 190

Thr Pro Pro Thr Tyr Thr Pro Ser Pro Lys Pro Pro Thr Pro Lys Pro
                195                 200                 205

Thr Pro Pro Thr Tyr Thr Pro Ser Pro Lys Pro Ala Thr Lys Pro
                210                 215                 220

Pro Thr Pro Lys Pro Thr Pro Pro Thr Tyr Thr Pro Ser Pro Lys Pro
225                 230                 235                 240

Pro Thr Pro Lys Pro Thr Pro Pro Thr Tyr Thr Pro Ser Pro Lys Pro
                245                 250                 255

Pro Ala Thr Lys Pro Thr Pro Pro Thr Tyr Thr Pro Ser Pro Lys Pro
                260                 265                 270

Pro Thr Pro Lys Pro Thr Pro Pro Thr Tyr Thr Pro Ser Pro Lys Pro
                275                 280                 285

Pro Thr Pro Lys Pro Thr Pro Pro Thr Tyr Thr Pro Ser Pro Lys Pro
                290                 295                 300

Pro Ala Thr Lys Pro Pro Thr Pro Lys Pro Thr Pro Pro Thr Tyr Thr
305                 310                 315                 320

Pro Thr Pro Lys Pro Pro Ala Thr Lys Pro Pro Thr Tyr Thr Pro Thr
                325                 330                 335

Pro Pro Val Ser His Thr Pro Ser Pro Pro Pro Tyr Tyr
                340                 345                 350
```

<210> SEQ ID NO 76
<211> LENGTH: 9
<212> TYPE: PRT
<213> ORGANISM: Artificial
<220> FEATURE:
<223> OTHER INFORMATION: amino acid motif for monocotyledonous lactate dehydrogenases

```
<400> SEQUENCE: 76

Ser Leu Ser Glu Leu Gly Phe Asp Ala
1               5

<210> SEQ ID NO 77
<211> LENGTH: 10
<212> TYPE: PRT
<213> ORGANISM: Artificial
<220> FEATURE:
<223> OTHER INFORMATION: amino acid motif for monocotyledonous lactate
      dehydrogenases

<400> SEQUENCE: 77

Val Ile Gly Ala Gly Asn Val Gly Met Ala
1               5                   10

<210> SEQ ID NO 78
<211> LENGTH: 9
<212> TYPE: PRT
<213> ORGANISM: Artificial
<220> FEATURE:
<223> OTHER INFORMATION: amino acid motif for monocotyledonous lactate
      dehydrogenases

<400> SEQUENCE: 78

Ile Val Thr Ala Gly Ala Arg Gln Ile
1               5

<210> SEQ ID NO 79
<211> LENGTH: 7
<212> TYPE: PRT
<213> ORGANISM: Artificial
<220> FEATURE:
<223> OTHER INFORMATION: amino acid motif for monocotyledonous lactate
      dehydrogenases
<220> FEATURE:
<221> NAME/KEY: VARIANT
<222> LOCATION: (2)..(2)
<223> OTHER INFORMATION: (F/Y) variation

<400> SEQUENCE: 79

Leu Phe Arg Lys Ile Val Pro
1               5

<210> SEQ ID NO 80
<211> LENGTH: 7
<212> TYPE: PRT
<213> ORGANISM: Artificial
<220> FEATURE:
<223> OTHER INFORMATION: amino acid motif for monocotyledonous lactate
      dehydrogenases

<400> SEQUENCE: 80

Gly Phe Pro Ala Ser Arg Val
1               5

<210> SEQ ID NO 81
<211> LENGTH: 8
<212> TYPE: PRT
<213> ORGANISM: Artificial
<220> FEATURE:
<223> OTHER INFORMATION: amino acid motif for monocotyledonous lactate
      dehydrogenases
<220> FEATURE:
<221> NAME/KEY: VARIANT
<222> LOCATION: (3)..(3)
<223> OTHER INFORMATION: (L/I) variation

<400> SEQUENCE: 81
```

```
Arg Phe Leu Leu Ala Glu His Leu
1               5

<210> SEQ ID NO 82
<211> LENGTH: 8
<212> TYPE: PRT
<213> ORGANISM: Artificial
<220> FEATURE:
<223> OTHER INFORMATION: amino acid motif for monocotyledonous lactate
      dehydrogenases

<400> SEQUENCE: 82

Gln Ala Tyr Met Val Gly Glu His
1               5

<210> SEQ ID NO 83
<211> LENGTH: 9
<212> TYPE: PRT
<213> ORGANISM: Artificial
<220> FEATURE:
<223> OTHER INFORMATION: amino acid motif for monocotyledonous lactate
      dehydrogenases

<400> SEQUENCE: 83

Ala Leu Glu Gly Ile Arg Arg Ala Val
1               5

<210> SEQ ID NO 84
<211> LENGTH: 8
<212> TYPE: PRT
<213> ORGANISM: Artificial
<220> FEATURE:
<223> OTHER INFORMATION: amino acid motif for monocotyledonous lactate
      dehydrogenases
<220> FEATURE:
<221> NAME/KEY: VARIANT
<222> LOCATION: (7)..(7)
<223> OTHER INFORMATION: (L/I) variation

<400> SEQUENCE: 84

Gly Tyr Ser Val Ala Ser Leu Ala
1               5

<210> SEQ ID NO 85
<211> LENGTH: 8
<212> TYPE: PRT
<213> ORGANISM: Artificial
<220> FEATURE:
<223> OTHER INFORMATION: amino acid motif for monocotyledonous Caffeoyl
      CoA-O-methyltransferases

<400> SEQUENCE: 85

Glu Gln Lys Thr Arg His Ser Glu
1               5

<210> SEQ ID NO 86
<211> LENGTH: 8
<212> TYPE: PRT
<213> ORGANISM: Artificial
<220> FEATURE:
<223> OTHER INFORMATION: amino acid motif for monocotyledonous Caffeoyl
      CoA-O-methyltransferases
<220> FEATURE:
<221> NAME/KEY: VARIANT
<222> LOCATION: (2)..(2)
<223> OTHER INFORMATION: (I/L) variation

<400> SEQUENCE: 86
```

-continued

```
Leu Ile Lys Leu Ile Gly Ala Lys
1               5

<210> SEQ ID NO 87
<211> LENGTH: 8
<212> TYPE: PRT
<213> ORGANISM: Artificial
<220> FEATURE:
<223> OTHER INFORMATION: amino acid motif for monocotyledonous Caffeoyl
      CoA-O-methyltransferases

<400> SEQUENCE: 87

Lys Thr Met Glu Ile Gly Val Tyr
1               5

<210> SEQ ID NO 88
<211> LENGTH: 8
<212> TYPE: PRT
<213> ORGANISM: Artificial
<220> FEATURE:
<223> OTHER INFORMATION: amino acid motif for monocotyledonous Caffeoyl
      CoA-O-methyltransferases
<220> FEATURE:
<221> NAME/KEY: VARIANT
<222> LOCATION: (5)..(5)
<223> OTHER INFORMATION: (L/M) variation

<400> SEQUENCE: 88

His Glu Arg Leu Leu Lys Leu Val
1               5

<210> SEQ ID NO 89
<211> LENGTH: 8
<212> TYPE: PRT
<213> ORGANISM: Artificial
<220> FEATURE:
<223> OTHER INFORMATION: amino acid motif for monocotyledonous Caffeoyl
      CoA-O-methyltransferases

<400> SEQUENCE: 89

Cys Gln Leu Pro Val Gly Asp Gly
1               5

<210> SEQ ID NO 90
<211> LENGTH: 7
<212> TYPE: PRT
<213> ORGANISM: Artificial
<220> FEATURE:
<223> OTHER INFORMATION: amino acid motif for monocotyledonous Caffeoyl
      CoA-O-methyltransferases

<400> SEQUENCE: 90

Thr Leu Cys Arg Arg Val Lys
1               5

<210> SEQ ID NO 91
<211> LENGTH: 21
<212> TYPE: DNA
<213> ORGANISM: Artificial
<220> FEATURE:
<223> OTHER INFORMATION: oligonucleotide primer

<400> SEQUENCE: 91
ttacgtggca aaggattcga t                                              21

<210> SEQ ID NO 92
<211> LENGTH: 20
<212> TYPE: DNA
```

<213> ORGANISM: Artificial
<220> FEATURE:
<223> OTHER INFORMATION: oligonucleotide primer

<400> SEQUENCE: 92
gccccaatcc agtccattaa							20

<210> SEQ ID NO 93
<211> LENGTH: 18
<212> TYPE: DNA
<213> ORGANISM: Artificial
<220> FEATURE:
<223> OTHER INFORMATION: oligonucleotide primer

<400> SEQUENCE: 93
tctgccttgc ccttgctt							18

<210> SEQ ID NO 94
<211> LENGTH: 23
<212> TYPE: DNA
<213> ORGANISM: Artificial
<220> FEATURE:
<223> OTHER INFORMATION: oligonucleotide primer

<400> SEQUENCE: 94
caattgcttg gcaggtctta ttt						23

<210> SEQ ID NO 95
<211> LENGTH: 356
<212> TYPE: PRT
<213> ORGANISM: Hordeum vulgare

<400> SEQUENCE: 95

Met His Lys Ala Ser Ser Leu Ser Glu Leu Gly Phe Asp Ala Gly Gly
1               5                   10                  15

Ala Ser Ser Gly Phe Phe Arg Pro Val Ala Asp Gly Cys Pro Ala Thr
            20                  25                  30

Pro Thr Ser Ser Ala Val Pro His Arg Arg Leu Thr Lys Ile Ser Val
        35                  40                  45

Ile Gly Ala Gly Asn Val Gly Met Ala Ile Ala Gln Thr Ile Leu Thr
    50                  55                  60

Gln Asn Leu Ala Asp Glu Ile Ala Leu Val Asp Ala Leu Pro Asp Lys
65                  70                  75                  80

Leu Arg Gly Glu Ala Leu Asp Leu Gln His Ala Ala Phe Leu Pro
                85                  90                  95

Arg Val Arg Ile Ser Gly Thr Asp Ala Ala Val Thr Lys Asn Ser Asp
            100                 105                 110

Leu Val Ile Val Thr Ala Gly Ala Arg Gln Ile Pro Gly Glu Thr Arg
        115                 120                 125

Leu Asn Leu Leu Gln Arg Asn Val Ala Leu Tyr Arg Lys Ile Val Pro
    130                 135                 140

Pro Val Ala Glu His Ser Pro Asp Ala Leu Leu Leu Val Val Ser Asn
145                 150                 155                 160

Pro Val Asp Val Leu Thr Tyr Val Ala Trp Lys Leu Ser Gly Phe Pro
                165                 170                 175

Ala Ser Arg Val Ile Gly Ser Gly Thr Asn Leu Asp Ser Ser Arg Phe
            180                 185                 190

Arg Phe Leu Ile Ala Glu His Leu Asp Val Asn Ala Gln Asp Val Gln
        195                 200                 205

Ala Tyr Met Val Gly Glu His Gly Asp Ser Ser Val Ala Ile Trp Ser
210                 215                 220

Ser Ile Ser Val Gly Gly Met Pro Ala Phe Lys Ser Leu Arg Asp Ser
225                 230                 235                 240

His Arg Ser Phe Asp Glu Ala Ala Leu Glu Gly Ile Arg Arg Ala Val
            245                 250                 255

Val Gly Gly Ala Tyr Glu Val Ile Gly Leu Lys Gly Tyr Thr Ser Trp
            260                 265                 270

Ala Ile Gly Tyr Ser Val Ala Ser Leu Ala Ala Ser Leu Leu Arg Asp
            275                 280                 285

Gln Arg Arg Val His Pro Val Ser Val Leu Ala Ser Gly Phe His Gly
290                 295                 300

Ile Ser Asp Gly His Glu Val Phe Leu Ser Leu Pro Ala Arg Leu Gly
305                 310                 315                 320

Arg Gly Gly Ile Leu Gly Val Ala Glu Met Asp Leu Thr Glu Ala Glu
            325                 330                 335

Ala Ala Gln Leu Arg Arg Ser Ala Lys Thr Leu Trp Glu Asn Cys Gln
            340                 345                 350

Leu Leu Asp Leu
            355

<210> SEQ ID NO 96
<211> LENGTH: 353
<212> TYPE: PRT
<213> ORGANISM: Arabidopsis thaliana

<400> SEQUENCE: 96

Met Glu Lys Asn Ala Ser Thr Ser Ser Leu Lys Asp Leu Gly Pro Ser
1               5                   10                  15

Gly Leu Asp Leu Thr Ser Ala Phe Phe Lys Pro Ile His Asn Ser Asp
            20                  25                  30

Pro Ser Leu Pro Ser Asn Arg Arg Thr Lys Val Ser Val Val Gly Val
        35                  40                  45

Gly Asn Val Gly Met Ala Ile Ala Gln Thr Ile Leu Thr Gln Asp Leu
50                  55                  60

Ala Asp Glu Ile Ala Leu Val Asp Ala Lys Pro Asp Lys Leu Arg Gly
65                  70                  75                  80

Glu Met Leu Asp Leu Gln His Ala Ala Phe Leu Pro Arg Thr Lys
                85                  90                  95

Ile Thr Ala Ser Val Asp Tyr Glu Val Thr Ala Gly Ser Asp Leu Cys
            100                 105                 110

Ile Val Thr Ala Gly Ala Arg Gln Asn Pro Gly Glu Ser Arg Leu Asn
            115                 120                 125

Leu Leu Gln Arg Asn Val Ala Leu Phe Arg His Ile Ile Pro Pro Leu
130                 135                 140

Ala Lys Ala Ser Pro Asp Ser Ile Leu Ile Val Val Ser Asn Pro Val
145                 150                 155                 160

Asp Val Leu Thr Tyr Val Ala Trp Lys Leu Ser Gly Phe Pro Val Asn
            165                 170                 175

Arg Val Leu Gly Ser Gly Thr Asn Leu Asp Ser Ser Arg Phe Arg Phe
            180                 185                 190

Leu Ile Ala Asp His Leu Asp Val Asn Ala Gln Asp Val Gln Ala Phe
            195                 200                 205

Ile Val Gly Glu His Gly Asp Ser Ser Val Ala Leu Trp Ser Ser Ile
210                 215                 220

```
Ser Val Gly Gly Ile Pro Val Leu Ser Phe Leu Glu Lys Asn Gln Ile
225                 230                 235                 240

Ala Tyr Glu Lys Gln Thr Leu Glu Asp Ile His Gln Ala Val Val Gly
                245                 250                 255

Ser Ala Tyr Glu Val Ile Gly Leu Lys Gly Tyr Thr Ser Trp Ala Ile
                260                 265                 270

Gly Tyr Ser Val Ala Asn Leu Ala Arg Thr Ile Leu Arg Asp Gln Arg
            275                 280                 285

Lys Ile His Pro Val Thr Val Leu Ala Arg Gly Phe Tyr Gly Val Asp
            290                 295                 300

Gly Gly Asp Val Phe Leu Ser Leu Pro Ala Leu Leu Gly Arg Asn Gly
305                 310                 315                 320

Val Val Ala Val Thr Asn Val His Met Thr Asp Glu Glu Ala Glu Lys
                325                 330                 335

Leu Gln Lys Ser Ala Lys Thr Ile Leu Glu Met Gln Ser Gln Leu Gly
                340                 345                 350

Leu
```

<210> SEQ ID NO 97
<211> LENGTH: 353
<212> TYPE: PRT
<213> ORGANISM: Arabidopsis thaliana

<400> SEQUENCE: 97

```
Met Glu Lys Asn Ala Ser Thr Ser Leu Lys Asp Leu Gly Pro Ser
1               5                   10                  15

Gly Leu Asp Leu Thr Ser Ala Phe Phe Lys Pro Ile His Asn Ser Asp
                20                  25                  30

Pro Ser Leu Pro Ser Asn Arg Arg Thr Lys Val Ser Val Gly Val
            35                  40                  45

Gly Asn Val Gly Met Ala Ile Ala Gln Thr Ile Leu Thr Gln Asp Leu
        50                  55                  60

Ala Asp Glu Ile Ala Leu Val Asp Ala Lys Pro Asp Lys Leu Arg Gly
65                  70                  75                  80

Glu Met Leu Asp Leu Gln His Ala Ala Phe Leu Pro Arg Thr Lys
                85                  90                  95

Ile Thr Ala Ser Val Asp Tyr Glu Val Thr Ala Gly Ser Asp Leu Cys
                100                 105                 110

Ile Val Thr Ala Gly Ala Arg Gln Asn Pro Gly Glu Ser Arg Leu Asn
            115                 120                 125

Leu Leu Gln Arg Asn Val Ala Leu Phe Arg His Ile Ile Pro Pro Leu
130                 135                 140

Ala Lys Ala Ser Pro Asp Ser Ile Leu Ile Ile Val Ser Asn Pro Val
145                 150                 155                 160

Asp Val Leu Thr Tyr Val Ala Trp Lys Leu Ser Gly Phe Pro Val Asn
                165                 170                 175

Arg Val Leu Gly Ser Gly Thr Asn Leu Asp Ser Ser Arg Phe Arg Phe
            180                 185                 190

Leu Ile Ala Asp His Leu Asp Val Asn Ala Gln Asp Val Gln Ala Phe
        195                 200                 205

Ile Val Gly Glu His Gly Asp Ser Ser Val Ala Leu Trp Ser Ser Ile
    210                 215                 220

Ser Val Gly Gly Ile Pro Val Leu Ser Phe Leu Glu Lys Asn Gln Ile
225                 230                 235                 240
```

Ala Tyr Glu Lys Gln Thr Leu Glu Asp Ile His Gln Ala Val Val Gly
                245                 250                 255

Ser Ala Tyr Glu Val Ile Gly Leu Lys Gly Tyr Thr Ser Trp Ala Ile
            260                 265                 270

Gly Tyr Ser Val Ala Asn Leu Ala Arg Thr Ile Leu Arg Asp Gln Arg
        275                 280                 285

Lys Ile His Pro Val Thr Val Leu Ala Arg Gly Phe Tyr Gly Val Asp
    290                 295                 300

Gly Gly Asp Val Phe Leu Ser Leu Pro Ala Leu Leu Gly Arg Asn Gly
305                 310                 315                 320

Val Val Ala Val Thr Asn Val His Met Thr Asp Glu Glu Ala Glu Lys
                325                 330                 335

Leu Gln Lys Ser Ala Lys Thr Ile Leu Glu Met Gln Ser Gln Leu Gly
            340                 345                 350

Leu

<210> SEQ ID NO 98
<211> LENGTH: 350
<212> TYPE: PRT
<213> ORGANISM: Lycopersicon esculentum

<400> SEQUENCE: 98

Met Gln Asn Ser Ser Ser Ser Ser Leu Gly Pro Gly Gly Leu Asp
1               5                   10                  15

Leu Thr Gln Ala Phe Phe Lys Ser Ile Ser Asn Ala Ala Pro Pro Ser
            20                  25                  30

Pro Thr Lys Arg His Thr Lys Ile Ser Val Ile Gly Val Gly Asn Val
        35                  40                  45

Gly Met Ala Ile Ala Gln Thr Ile Leu Thr Gln Asp Leu Val Asp Glu
    50                  55                  60

Leu Ala Leu Val Asp Ala Lys Ser Asp Lys Leu Arg Gly Glu Met Leu
65                  70                  75                  80

Asp Leu Gln His Ala Ala Ala Phe Leu Pro Arg Thr Lys Ile His Ala
                85                  90                  95

Ser Ile Asp Tyr Ser Val Thr Ala Gly Ser Asp Leu Cys Ile Val Thr
            100                 105                 110

Ala Gly Ala Arg Gln Asn Pro Gly Glu Ser Arg Leu Asn Leu Leu Gln
        115                 120                 125

Arg Asn Met Ala Leu Phe Arg Ser Ile Ile Pro Pro Leu Val Lys Tyr
    130                 135                 140

Ser Pro Glu Thr Thr Leu Leu Val Val Ser Asn Pro Val Asp Val Leu
145                 150                 155                 160

Thr Tyr Val Ala Trp Lys Leu Ser Gly Phe Pro Ala Asn Arg Val Ile
                165                 170                 175

Gly Ser Gly Thr Asn Leu Asp Ser Ser Arg Phe Arg Phe Leu Ile Ala
            180                 185                 190

Asp His Leu Asp Val Asn Ala Gln Asp Val Gln Ala Tyr Ile Val Gly
        195                 200                 205

Glu His Gly Asp Ser Ser Val Ala Leu Trp Ser Gly Ile Ser Val Gly
    210                 215                 220

Gly Val Pro Val Leu Ser Phe Leu Glu Arg Gln Gln Ile Ala Leu Glu
225                 230                 235                 240

Lys Glu Thr Leu Glu Lys Ile His Gln Glu Val Val His Ser Ala Tyr
                245                 250                 255

```
Glu Val Ile Ser Leu Lys Gly Tyr Thr Ser Trp Ala Ile Gly Tyr Ser
            260                 265                 270

Val Ala Asn Leu Ala Arg Thr Ile Leu Arg Asp Gln Arg Arg Ile His
            275                 280                 285

Pro Val Ser Val Leu Ala Lys Gly Phe Tyr Gly Ile Asp Gly Gly Asp
290                 295                 300

Val Phe Leu Ser Leu Pro Ala Gln Leu Gly Arg Ser Gly Val Leu Gly
305                 310                 315                 320

Val Thr Asn Val His Leu Thr Asp Glu Glu Ile Glu Gln Leu Arg Asn
                325                 330                 335

Ser Ala Lys Thr Ile Leu Glu Val Gln Ser Gln Leu Gly Ile
            340                 345                 350

<210> SEQ ID NO 99
<211> LENGTH: 346
<212> TYPE: PRT
<213> ORGANISM: Solanum tuberosum

<400> SEQUENCE: 99

Met Ser Ser Ser Ser Pro Leu Ser Leu Asp Gly Leu Asp Leu Asn Gln
1               5                   10                  15

Val Phe Phe Lys Ser Ile Ser Asn Ala Asp Pro Pro Ser Gln Thr Asn
            20                  25                  30

His His Thr Lys Ile Ser Val Ile Gly Val Gly Asn Val Gly Met Ala
            35                  40                  45

Ile Ala Gln Thr Ile Leu Thr Gln Asp Leu Val Asp Glu Leu Ala Leu
    50                  55                  60

Val Asp Val Asn Ser Asp Lys Leu Arg Gly Glu Met Leu Asp Leu Gln
65                  70                  75                  80

His Ala Ala Ala Phe Leu Pro Arg Thr Lys Ile Val Ala Ser Val Asp
                85                  90                  95

Tyr Thr Val Thr Ala Gly Ser Asp Leu Cys Ile Val Thr Ala Gly Ala
            100                 105                 110

Arg Gln Asn Pro Gly Glu Ser Arg Leu Asn Leu Leu Gln Arg Asn Leu
            115                 120                 125

Ala Met Tyr Lys Ser Ile Val Pro Glu Leu Val Lys Tyr Ser Pro Glu
    130                 135                 140

Cys Ile Leu Leu Ile Val Ser Asn Pro Val Asp Val Leu Thr Tyr Val
145                 150                 155                 160

Ala Trp Lys Ser Gly Phe Pro Val Asn Arg Val Ile Gly Ser Gly Thr
                165                 170                 175

Asn Leu Asp Ser Ser Arg Phe Arg Phe Leu Ile Ala Asp His Leu Asp
            180                 185                 190

Val Asn Ala Gln Asp Val Gln Ala Tyr Ile Val Gly Glu His Gly Asp
            195                 200                 205

Ser Ser Val Ala Leu Trp Ser Ser Ile Ser Val Gly Gly Ile Pro Val
    210                 215                 220

Leu Ser Phe Leu Glu Arg Gln Gln Ile Ala Phe Glu Lys Asp Thr Leu
225                 230                 235                 240

Glu Lys Ile His Lys Gln Val Val Gln Ser Ala Tyr Glu Val Ile Asn
                245                 250                 255

Leu Lys Gly Tyr Thr Ser Trp Ala Ile Gly Tyr Ser Val Ala Asn Leu
            260                 265                 270

Ala Phe Ser Ile Ile Arg Asp Gln Arg Arg Ile His Pro Val Ser Ile
```

```
                275                 280                 285
Leu Val Lys Gly Phe Tyr Gly Ile Asp Gly Asp Val Phe Leu Ser
        290                 295                 300
Leu Pro Ala Gln Leu Gly Arg Ser Gly Val Leu Gly Val Thr Asn Val
305                 310                 315                 320
His Leu Thr Asp Glu Glu Ile Gln Gln Leu Arg Asn Ser Ala Glu Thr
                325                 330                 335
Ile Leu Glu Val Gln Asn Gln Leu Gly Ile
        340                 345

<210> SEQ ID NO 100
<211> LENGTH: 223
<212> TYPE: PRT
<213> ORGANISM: Arabidopsis thaliana

<400> SEQUENCE: 100

Met Glu Glu Leu Ala His Pro Tyr Val Pro Arg Asp Leu Asn Leu Pro
1               5                   10                  15
Gly Tyr Val Pro Ile Ser Met Ser Met Ser Ser Ile Val Ser Ile Tyr
                20                  25                  30
Leu Gly Ser Ser Leu Leu Val Val Ser Leu Val Trp Leu Leu Phe Gly
            35                  40                  45
Arg Lys Lys Ala Lys Leu Asp Lys Leu Leu Met Cys Trp Trp Thr Phe
50                  55                  60
Thr Gly Leu Thr His Val Ile Leu Glu Gly Tyr Phe Val Phe Ser Pro
65                  70                  75                  80
Glu Phe Phe Lys Asp Asn Thr Ser Ala Tyr Leu Ala Glu Val Trp Lys
                85                  90                  95
Glu Tyr Ser Lys Gly Asp Ser Arg Tyr Val Gly Arg Asp Ser Ala Val
                100                 105                 110
Val Ser Val Glu Gly Ile Thr Ala Val Ile Val Gly Pro Ala Ser Leu
            115                 120                 125
Leu Ala Ile Tyr Ala Ile Ala Lys Glu Lys Ser Tyr Ser Tyr Val Leu
    130                 135                 140
Gln Leu Ala Ile Ser Val Cys Gln Leu Tyr Gly Cys Leu Val Tyr Phe
145                 150                 155                 160
Ile Thr Ala Ile Leu Glu Gly Asp Asn Phe Ala Thr Asn Ser Phe Tyr
                165                 170                 175
Tyr Tyr Ser Tyr Tyr Ile Gly Ala Asn Cys Trp Trp Val Leu Ile Pro
                180                 185                 190
Ser Leu Ile Ser Phe Arg Cys Trp Lys Lys Ile Cys Ala Ala Ala Ala
            195                 200                 205
Ile Ala Asn Asn Asn Val Glu Thr Lys Thr Lys Lys Thr Arg
    210                 215                 220

<210> SEQ ID NO 101
<211> LENGTH: 223
<212> TYPE: PRT
<213> ORGANISM: Arabidopsis thaliana

<400> SEQUENCE: 101

Met Lys Glu Leu Ala His Pro Tyr Val Pro Arg Asp Leu Asn Leu Pro
1               5                   10                  15
Gly Tyr Val Pro Ile Ser Met Ser Met Ser Ser Ile Val Ser Ile Tyr
                20                  25                  30
Leu Gly Ser Ser Leu Leu Val Val Ser Leu Val Trp Leu Leu Phe Gly
```

```
                35                  40                  45
Arg Lys Lys Ala Lys Leu Asp Lys Leu Leu Met Cys Trp Trp Thr Phe
 50                  55                  60

Thr Gly Leu Thr His Val Ile Leu Glu Gly Tyr Phe Val Phe Ser Pro
 65                  70                  75                  80

Glu Phe Phe Lys Asp Asn Thr Ser Ala Tyr Leu Ala Glu Val Trp Lys
                 85                  90                  95

Glu Tyr Ser Lys Gly Asp Ser Arg Tyr Val Gly Arg Asp Ser Ala Val
                100                 105                 110

Val Ser Val Glu Gly Ile Thr Ala Val Ile Val Gly Pro Ala Ser Leu
            115                 120                 125

Leu Ala Ile Tyr Ala Ile Ala Lys Glu Lys Ser Tyr Ser Tyr Val Leu
            130                 135                 140

Gln Leu Ala Ile Ser Val Cys Gln Leu Tyr Gly Cys Leu Val Tyr Phe
145                 150                 155                 160

Ile Thr Ala Ile Leu Glu Gly Asp Asn Phe Ala Thr Asn Ser Phe Tyr
                165                 170                 175

Tyr Tyr Ser Tyr Tyr Ile Gly Ala Asn Cys Trp Trp Val Leu Ile Pro
                180                 185                 190

Ser Leu Ile Ser Phe Arg Cys Trp Lys Lys Ile Cys Ala Ala Ala
            195                 200                 205

Ile Ala Asn Asn Asn Val Glu Thr Lys Thr Lys Lys Thr Arg
            210                 215                 220

<210> SEQ ID NO 102
<211> LENGTH: 223
<212> TYPE: PRT
<213> ORGANISM: Arabidopsis thaliana

<400> SEQUENCE: 102

Met Glu Glu Leu Ala His Pro Tyr Val Pro Arg Asp Leu Asn Leu Pro
 1               5                  10                  15

Gly Tyr Val Pro Ile Ser Met Ser Met Ser Ser Ile Val Ser Ile Tyr
                20                  25                  30

Leu Gly Ser Ser Leu Leu Val Val Ser Leu Val Trp Leu Leu Phe Gly
            35                  40                  45

Arg Lys Lys Ala Lys Leu Asp Lys Leu Leu Met Cys Trp Trp Thr Phe
 50                  55                  60

Thr Gly Leu Thr His Val Ile Leu Glu Gly Tyr Phe Val Phe Ser Pro
 65                  70                  75                  80

Glu Phe Phe Lys Asp Asn Thr Ser Ala Tyr Leu Ala Glu Val Trp Lys
                 85                  90                  95

Glu Tyr Ser Lys Gly Asp Ser Arg Tyr Val Gly Arg Asp Ser Ala Val
                100                 105                 110

Val Ser Val Glu Gly Ile Thr Ala Val Ile Val Gly Pro Ala Ser Leu
            115                 120                 125

Leu Ala Ile Tyr Ala Ile Ala Lys Glu Lys Ser Tyr Ser Tyr Val Leu
            130                 135                 140

Gln Leu Ala Ile Ser Val Cys Gln Leu Tyr Gly Cys Val Val Tyr Phe
145                 150                 155                 160

Ile Thr Ala Ile Leu Glu Gly Asp Asn Phe Ala Thr Asn Ser Phe Tyr
                165                 170                 175

Tyr Tyr Ser Tyr Tyr Ile Gly Ala Asn Cys Trp Trp Val Leu Ile Pro
                180                 185                 190
```

Ser Leu Ile Ser Phe Arg Cys Trp Lys Lys Ile Cys Ala Ala Ala
            195                 200                 205

Ile Ala Asn Asn Asn Val Glu Thr Lys Thr Lys Lys Thr Arg
    210                 215                 220

<210> SEQ ID NO 103
<211> LENGTH: 240
<212> TYPE: PRT
<213> ORGANISM: Nicotiana tabacum

<400> SEQUENCE: 103

Met Ala Glu Asn Gly Ile Lys His Gln Glu Val Gly His Lys Ser Leu
1               5                   10                  15

Leu Gln Ser Asp Ala Leu Tyr Gln Tyr Ile Leu Glu Thr Ser Val Tyr
            20                  25                  30

Pro Arg Glu Pro Glu Ser Met Lys Glu Leu Arg Glu Val Thr Ala Lys
        35                  40                  45

His Pro Trp Asn Leu Met Thr Thr Ser Ala Asp Glu Gly Gln Phe Leu
    50                  55                  60

Asn Met Leu Leu Lys Leu Ile Asn Ala Lys Asn Thr Met Glu Ile Gly
65                  70                  75                  80

Val Tyr Thr Gly Tyr Ser Leu Leu Ala Thr Ala Leu Ala Ile Pro Asp
                85                  90                  95

Asp Gly Lys Ile Leu Ala Met Asp Ile Asn Arg Glu Asn Tyr Glu Ile
            100                 105                 110

Gly Leu Pro Ile Ile Glu Lys Ala Gly Val Ala His Lys Ile Glu Phe
        115                 120                 125

Arg Glu Gly Pro Ala Leu Pro Val Leu Asp Gln Leu Val Glu Asp Lys
    130                 135                 140

Lys Asn His Gly Thr Tyr Asp Phe Ile Phe Val Asp Ala Asp Lys Asp
145                 150                 155                 160

Asn Tyr Ile Asn Tyr His Lys Arg Ile Ile Asp Leu Val Lys Val Gly
                165                 170                 175

Gly Leu Ile Gly Tyr Asp Asn Thr Leu Trp Asn Gly Ser Val Val Ala
            180                 185                 190

Pro Pro Asp Ala Pro Met Arg Lys Tyr Val Arg Tyr Arg Asp Phe
        195                 200                 205

Val Leu Glu Leu Asn Lys Ala Leu Ala Ala Asp Pro Arg Ile Glu Ile
    210                 215                 220

Cys Met Leu Pro Val Gly Asp Gly Ile Thr Leu Cys Arg Arg Ile Thr
225                 230                 235                 240

<210> SEQ ID NO 104
<211> LENGTH: 247
<212> TYPE: PRT
<213> ORGANISM: Eucalyptus species

<400> SEQUENCE: 104

Met Ala Ala Asn Ala Glu Pro Gln Gln Thr Gln Pro Ala Lys His Ser
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Ser Met Lys Glu
        35                  40                  45

Leu Arg Glu Ile Thr Ala Lys His Pro Trp Asn Leu Met Thr Thr Ser
    50                  55                  60

Ala Asp Glu Gly Gln Phe Leu Asn Met Leu Leu Lys Leu Ile Asn Ala
65                  70                  75                  80

Lys Asn Thr Met Glu Ile Gly Val Tyr Thr Gly Tyr Ser Leu Leu Ala
            85                  90                  95

Thr Ala Leu Ala Leu Pro Asp Asp Gly Lys Ile Leu Ala Met Asp Ile
            100                 105                 110

Asn Arg Glu Asn Phe Glu Ile Gly Leu Pro Val Ile Glu Lys Ala Gly
            115                 120                 125

Leu Ala His Lys Ile Asp Phe Arg Glu Gly Pro Ala Leu Pro Leu Leu
            130                 135                 140

Asp Gln Leu Val Gln Asp Glu Lys Asn His Gly Thr Tyr Asp Phe Ile
145                 150                 155                 160

Phe Val Asp Ala Asp Lys Asp Asn Tyr Ile Asn Tyr His Lys Arg Leu
            165                 170                 175

Ile Asp Leu Val Lys Val Gly Gly Leu Ile Gly Tyr Asp Asn Thr Leu
            180                 185                 190

Trp Asn Gly Ser Val Val Ala Pro Ala Asp Ala Pro Leu Arg Lys Tyr
            195                 200                 205

Val Arg Tyr Tyr Arg Asp Phe Val Leu Glu Leu Asn Lys Ala Leu Ala
210                 215                 220

Val Asp Pro Arg Val Glu Ile Cys Met Leu Pro Val Gly Asp Gly Ile
225                 230                 235                 240

Thr Leu Cys Arg Arg Val Ser
            245

<210> SEQ ID NO 105
<211> LENGTH: 247
<212> TYPE: PRT
<213> ORGANISM: Populus species

<400> SEQUENCE: 105

Met Ala Thr Asn Gly Glu Glu Gln Ser Gln Ala Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Cys Met Lys Glu
            35                  40                  45

Leu Arg Glu Val Thr Ala Lys His Pro Trp Asn Ile Met Thr Thr Ser
            50                  55                  60

Ala Asp Glu Gly Gln Phe Leu Asn Met Leu Leu Lys Leu Val Asn Ala
65                  70                  75                  80

Lys Asn Thr Met Glu Ile Gly Val Tyr Thr Gly Tyr Ser Leu Leu Ala
            85                  90                  95

Thr Ala Leu Ala Ile Pro Glu Asp Gly Lys Ile Leu Ala Met Asp Ile
            100                 105                 110

Asn Arg Glu Asn Tyr Glu Leu Gly Leu Pro Val Ile Gln Lys Ala Gly
            115                 120                 125

Val Ala His Lys Ile Asp Phe Lys Glu Gly Pro Ala Leu Pro Val Leu
            130                 135                 140

Asp Gln Met Ile Glu Asp Gly Lys Cys His Gly Ser Phe Asp Phe Ile
145                 150                 155                 160

Phe Val Asp Ala Asp Lys Asp Asn Tyr Ile Asn Tyr His Lys Arg Leu
            165                 170                 175

Ile Glu Leu Val Lys Val Gly Gly Leu Ile Gly Tyr Asp Asn Thr Leu
            180                 185                 190

Trp Asn Gly Ser Val Val Ala Pro Pro Asp Ala Pro Met Arg Lys Tyr
                195                 200                 205

Val Arg Tyr Tyr Arg Asp Phe Val Leu Glu Leu Asn Lys Ala Leu Ala
210                 215                 220

Ala Asp Pro Arg Ile Glu Ile Cys Met Leu Pro Val Gly Asp Gly Ile
225                 230                 235                 240

Thr Leu Cys Arg Arg Ile Gln
                245

<210> SEQ ID NO 106
<211> LENGTH: 258
<212> TYPE: PRT
<213> ORGANISM: Zea mays

<400> SEQUENCE: 106

Met Ala Thr Thr Ala Thr Glu Ala Ala Pro Ala Gln Glu Gln Gln Ala
1               5                   10                  15

Asn Gly Asn Gly Glu Gln Lys Thr Arg His Ser Glu Val Gly His Lys
            20                  25                  30

Ser Leu Leu Lys Ser Asp Asp Leu Tyr Gln Tyr Ile Leu Asp Thr Ser
        35                  40                  45

Val Tyr Pro Arg Glu Pro Glu Ser Met Lys Glu Leu Arg Glu Val Thr
50                  55                  60

Ala Lys His Pro Trp Asn Leu Met Thr Thr Ser Ala Asp Glu Gly Gln
65                  70                  75                  80

Phe Leu Asn Met Leu Ile Lys Leu Ile Gly Ala Lys Lys Thr Met Glu
                85                  90                  95

Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
        115                 120                 125

Glu Leu Gly Leu Pro Cys Ile Glu Lys Ala Gly Val Ala His Lys Ile
130                 135                 140

Asp Phe Arg Glu Gly Pro Ala Leu Pro Val Leu Asp Asp Leu Ile Ala
145                 150                 155                 160

Glu Glu Lys Asn His Gly Ser Phe Asp Phe Val Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
210                 215                 220

Asp Phe Val Leu Val Leu Asn Lys Ala Leu Ala Ala Asp Asp Arg Val
225                 230                 235                 240

Glu Ile Cys Gln Leu Pro Val Gly Asp Gly Val Thr Leu Cys Arg Arg
                245                 250                 255

Val Lys

<210> SEQ ID NO 107
<211> LENGTH: 264
<212> TYPE: PRT
<213> ORGANISM: Zea mays

<400> SEQUENCE: 107

-continued

```
Met Ala Thr Thr Ala Thr Glu Ala Thr Lys Thr Thr Ala Pro Ala Gln
1               5                   10                  15

Glu Gln Gln Ala Asn Gly Asn Gly Asn Gly Glu Gln Lys Thr Arg His
            20                  25                  30

Ser Glu Val Gly His Lys Ser Leu Leu Lys Ser Asp Asp Leu Tyr Gln
        35                  40                  45

Tyr Ile Leu Asp Thr Ser Val Tyr Pro Arg Glu Pro Glu Ser Met Lys
    50                  55                  60

Glu Leu Arg Glu Ile Thr Ala Lys His Pro Trp Asn Leu Met Thr Thr
65                  70                  75                  80

Ser Ala Asp Glu Gly Gln Phe Leu Asn Met Leu Ile Lys Leu Ile Gly
                85                  90                  95

Ala Lys Lys Thr Met Glu Ile Gly Val Tyr Thr Gly Tyr Ser Leu Leu
                100                 105                 110

Ala Thr Ala Leu Ala Leu Pro Glu Asp Gly Thr Ile Leu Ala Met Asp
            115                 120                 125

Ile Asn Arg Glu Asn Tyr Glu Leu Gly Leu Pro Cys Ile Asn Lys Ala
        130                 135                 140

Gly Val Gly His Lys Ile Asp Phe Arg Glu Gly Pro Ala Leu Pro Val
145                 150                 155                 160

Leu Asp Asp Leu Val Ala Asp Lys Glu Gln His Gly Ser Phe Asp Phe
            165                 170                 175

Ala Phe Val Asp Ala Asp Lys Asp Asn Tyr Leu Asn Tyr His Glu Arg
            180                 185                 190

Leu Leu Lys Leu Val Arg Pro Gly Gly Leu Ile Gly Tyr Asp Asn Thr
        195                 200                 205

Leu Trp Asn Gly Ser Val Val Leu Pro Asp Asp Ala Pro Met Arg Lys
    210                 215                 220

Tyr Ile Arg Phe Tyr Arg Asp Phe Val Leu Ala Leu Asn Ser Ala Leu
225                 230                 235                 240

Ala Ala Asp Asp Arg Val Glu Ile Cys Gln Leu Pro Val Gly Asp Gly
            245                 250                 255

Val Thr Leu Cys Arg Arg Val Lys
            260
```